US012616510B2

(12) United States Patent
Russell et al.

(10) Patent No.: US 12,616,510 B2
(45) Date of Patent: May 5, 2026

(54) DEVICES, SYSTEMS, AND METHODS FOR BONE REPAIR OR IMPLANT FIXATION

(71) Applicant: Biomimetic Innovations Limited, Shannon (IE)

(72) Inventors: Thomas A Russell, Eads, TN (US); Gerard Insley, Shannon (IE); Daniel Bichard, Shannon (IE); Ivana Ivankovic, Shannon (IE); Christophe Geisert, Donaueschingen (DE); Tanja Limberger, Donaueschingen (DE)

(73) Assignee: BIOMIMETIC INNOVATIONS LIMITED, Shannon (IE)

( * ) Notice: Subject to any disclaimer, the term of this patent is extended or adjusted under 35 U.S.C. 154(b) by 0 days.

(21) Appl. No.: 18/696,682

(22) PCT Filed: Sep. 28, 2022

(86) PCT No.: PCT/IB2022/000563
§ 371 (c)(1),
(2) Date: Mar. 28, 2024

(87) PCT Pub. No.: WO2023/052844
PCT Pub. Date: Apr. 6, 2023

(65) Prior Publication Data
US 2024/0390048 A1 Nov. 28, 2024

Related U.S. Application Data

(60) Provisional application No. 63/249,434, filed on Sep. 28, 2021.

(51) Int. Cl.
*A61B 17/86* (2006.01)
*A61B 17/34* (2006.01)
(Continued)

(52) U.S. Cl.
CPC ........ *A61B 17/864* (2013.01); *A61B 17/3472* (2013.01); *A61B 17/8014* (2013.01);
(Continued)

(58) Field of Classification Search
CPC . A61B 17/844; A61B 17/864; A61B 17/8685; A61B 2017/8655
See application file for complete search history.

(56) References Cited

U.S. PATENT DOCUMENTS 2,018,251 A 10/1935 Croessant
D321,560 S 11/1991 Miller
(Continued)

FOREIGN PATENT DOCUMENTS

CN 308252054 9/2023
EP 2745790 A1 6/2014
(Continued)

OTHER PUBLICATIONS

Bottlang et al., "Dynamic Stabilization with Active Locking Plates, Delivers Faster, Stronger, and More Symmetric, Fracture-Healing", Journal of Bone and Joint Therapy, 98:6 (Mar. 2016) (9 pages).
(Continued)

*Primary Examiner* — Olivia C Chang
(74) *Attorney, Agent, or Firm* — Clark & Elbing LLP

(57) ABSTRACT

The devices, systems, and methods herein described provide uniform biomaterial delivery to produce robust adhesion between an implant (e.g., an implantable screw) and a bone tissue. Furthermore, the devices, systems, and methods of the disclosure overcome challenges associated with the repair of weak or deficient bone and augmentation using injected biomaterials.

47 Claims, 95 Drawing Sheets

(51) Int. Cl.

| | |
|---|---|
| *A61B 17/80* | (2006.01) |
| *A61B 17/84* | (2006.01) |
| *A61B 17/88* | (2006.01) |
| *A61B 17/00* | (2006.01) |
| *A61B 17/68* | (2006.01) |
| *A61B 17/70* | (2006.01) |

(52) U.S. Cl.
    CPC .......... *A61B 17/844* (2013.01); *A61B 17/863* (2013.01); *A61B 17/8695* (2013.01); *A61B 17/8811* (2013.01); *A61B 17/8872* (2013.01); *A61B 2017/00477* (2013.01); *A61B 2017/00893* (2013.01); *A61B 2017/00951* (2013.01); *A61B 2017/681* (2013.01); *A61B 17/7059* (2013.01); *A61B 17/8061* (2013.01)

(56) References Cited

U.S. PATENT DOCUMENTS

| | | | |
|---|---|---|---|
| D331,626 | S | 12/1992 | Hayhurst et al. |
| D366,115 | S | 1/1996 | Sullivan |
| 5,509,765 | A | 4/1996 | Albin |
| D385,352 | S | 10/1997 | Bales et al. |
| 5,676,545 | A | 10/1997 | Jones |
| D403,069 | S | 12/1998 | Drewry et al. |
| D524,942 | S | 7/2006 | Felix |
| D574,958 | S | 8/2008 | Schendel et al. |
| D616,094 | S | 5/2010 | Boone, III et al. |
| 8,636,784 | B2 | 1/2014 | Greenhalgh et al. |
| 9,333,018 | B2 | 5/2016 | Russell et al. |
| 9,353,782 | B2 | 5/2016 | McDuff et al. |
| D775,735 | S | 1/2017 | Faux et al. |
| D783,821 | S | 4/2017 | Folsom et al. |
| D840,035 | S | 2/2019 | Weiner et al. |
| D841,811 | S | 2/2019 | Levy et al. |
| 10,251,688 | B2 | 4/2019 | Asfora |
| D847,994 | S | 5/2019 | Asfora et al. |
| D857,897 | S | 8/2019 | Loftus |
| D857,898 | S | 8/2019 | Loftus |
| D870,889 | S | 12/2019 | Miller |
| 10,993,754 | B2 | 5/2021 | Kuntz et al. |
| D952,855 | S | 5/2022 | Robbins |
| 11,446,070 | B2 | 9/2022 | Kuntz et al. |
| 11,771,482 | B2 | 10/2023 | Kuntz et al. |
| D1,010,819 | S | 1/2024 | Sweitzer et al. |
| 11,883,077 | B2 | 1/2024 | Kaufmann et al. |
| D1,019,954 | S | 3/2024 | O'Flaherty et al. |
| D1,032,841 | S | 6/2024 | Duarte et al. |
| 12,239,350 | B2 | 3/2025 | Kuntz et al. |
| D1,069,122 | S | 4/2025 | Linder et al. |
| D1,083,099 | S | 7/2025 | Russell et al. |
| 12,376,895 | B2 | 8/2025 | Kuntz et al. |
| 2001/0021852 | A1 | 9/2001 | Chappius |
| 2003/0000350 | A1 | 1/2003 | Zhao et al. |
| 2007/0270855 | A1 | 11/2007 | Partin |
| 2009/0131992 | A1 | 5/2009 | Greenhalgh et al. |
| 2010/0069913 | A1 | 3/2010 | Chirico et al. |
| 2010/0228301 | A1 | 9/2010 | Greenhalgh et al. |
| 2010/0239384 | A1 | 9/2010 | Lu |
| 2010/0303574 | A1 | 12/2010 | Mcduff et al. |
| 2011/0137354 | A1 | 6/2011 | Biedermann et al. |
| 2011/0144766 | A1 | 6/2011 | Kale et al. |
| 2011/0301653 | A1 | 12/2011 | Reed et al. |
| 2011/0319946 | A1 | 12/2011 | Levy et al. |
| 2014/0066758 | A1 | 3/2014 | Marik et al. |
| 2015/0005818 | A1 | 1/2015 | McDevitt et al. |
| 2015/0272646 | A1 | 10/2015 | Russell |
| 2020/0305938 | A1 | 10/2020 | Krumme et al. |
| 2020/0315678 | A1* | 10/2020 | Mazzio ................ A61B 17/808 |

FOREIGN PATENT DOCUMENTS

| | | | |
|---|---|---|---|
| EP | | 2848221 A1 | 3/2015 |
| WO | WO-2017/147537 A1 | | 8/2017 |
| WO | WO-2020/146684 A2 | | 7/2020 |
| WO | WO-2023/052844 A2 | | 4/2023 |

OTHER PUBLICATIONS

Dhandapani et al., "Additive manufacturing of biodegradable porous orthopaedic screw", Bioact. Mater. 5:458-467, (2020) (10 pages).
International Search Report and Written Opinion of the International Searching Authority for International Application No. PCT/IB2022/000563 mailed on Apr. 28, 2023 (25 pages).
Uhtoff et al., "Internal plate fixation of fractures: short history and recent developments.", J. Orthop. Sci.; 11(2): 118-126 (Mar. 2006) (9 pages).

\* cited by examiner

FIG. 2

Cross-sectional view

200

Cross-sectional view

280

Cross-sectional view

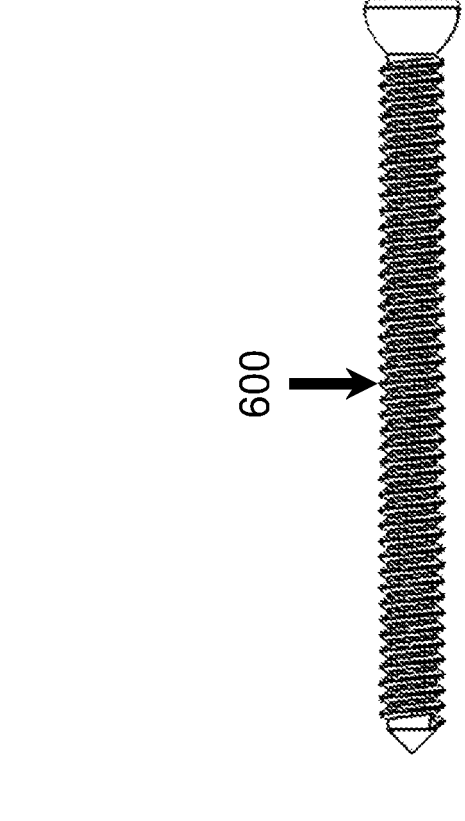
600
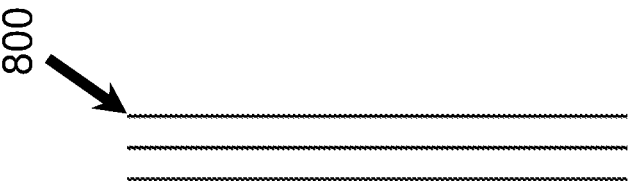
800
FIG. 10
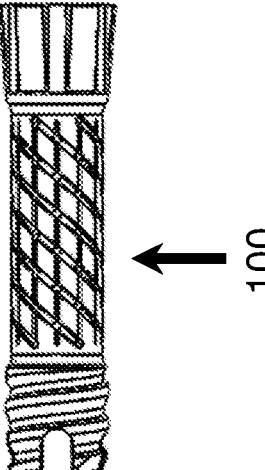
100

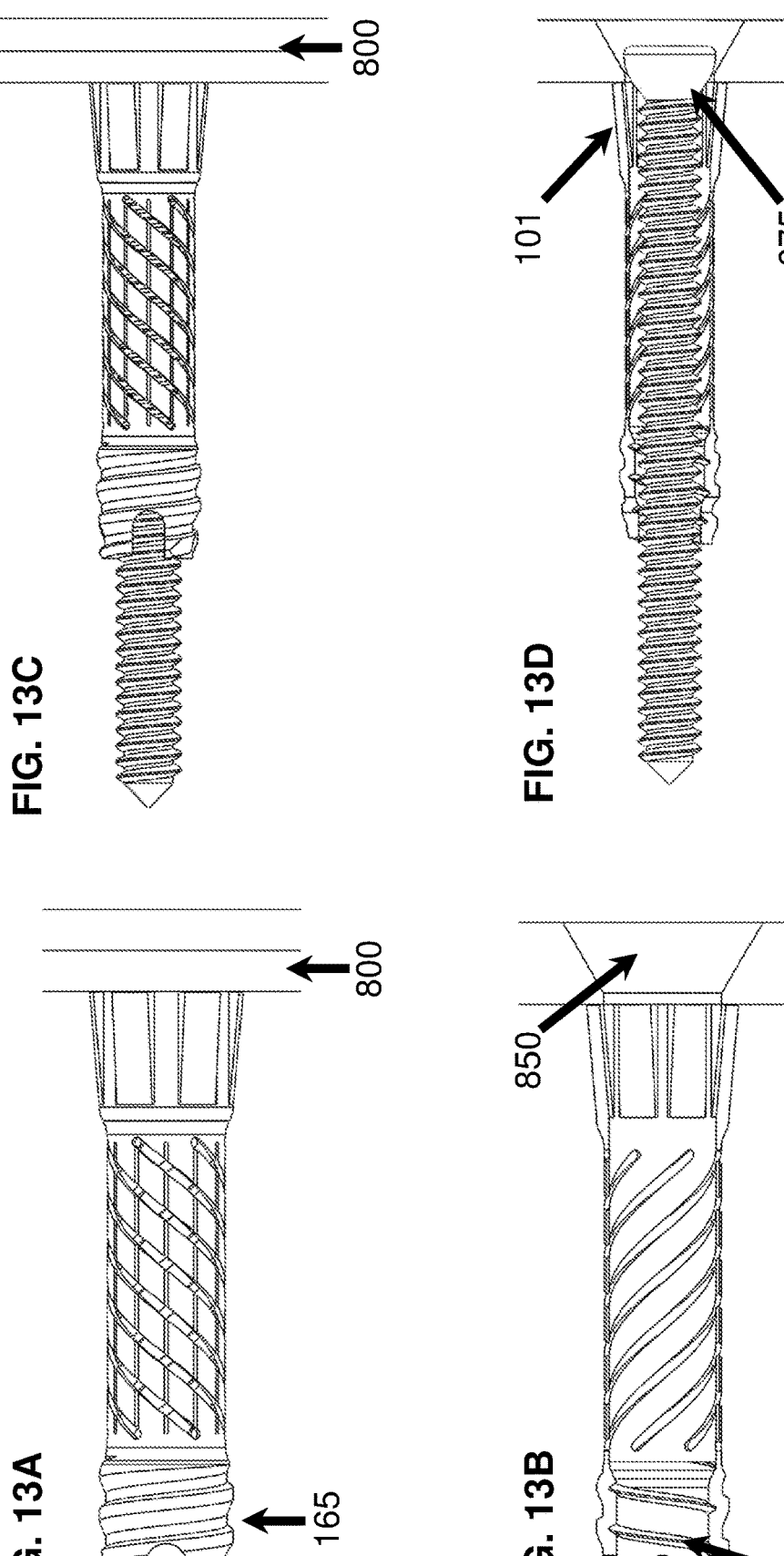

FIG. 14C
--→To bone
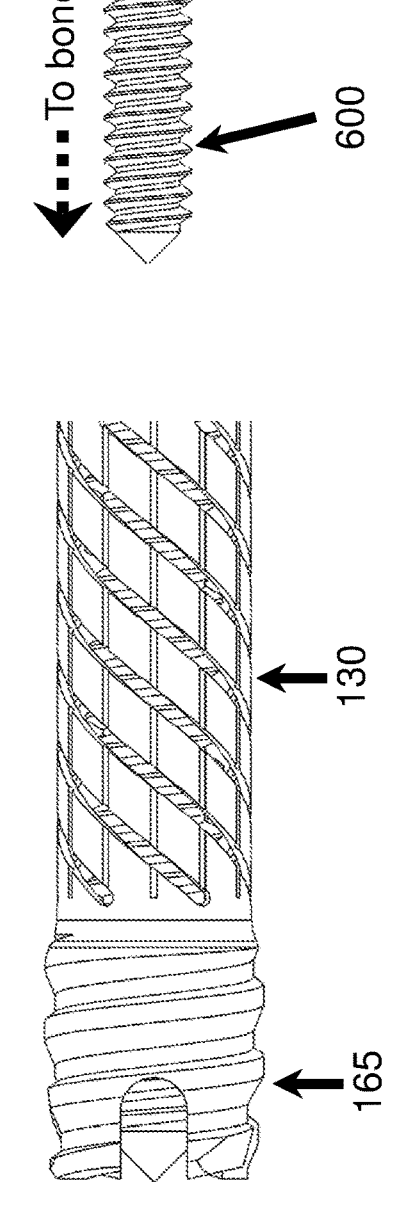
600
FIG. 14A
130
165
FIG. 14D
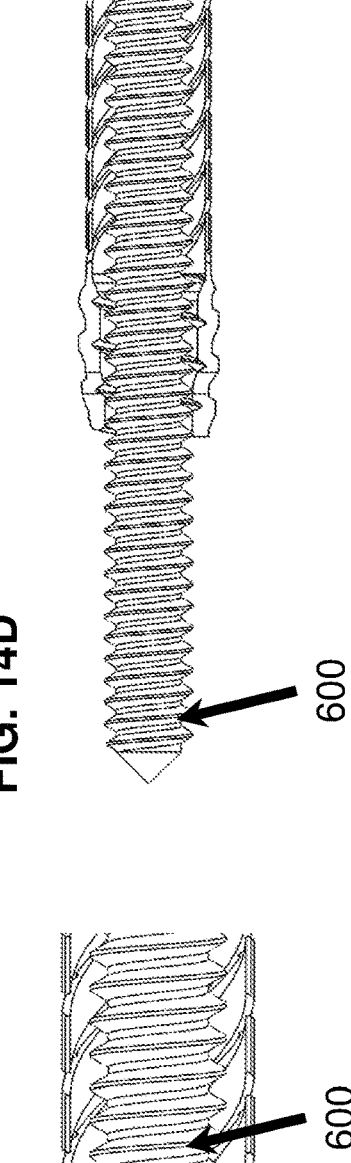
600
FIG. 14B
600
160
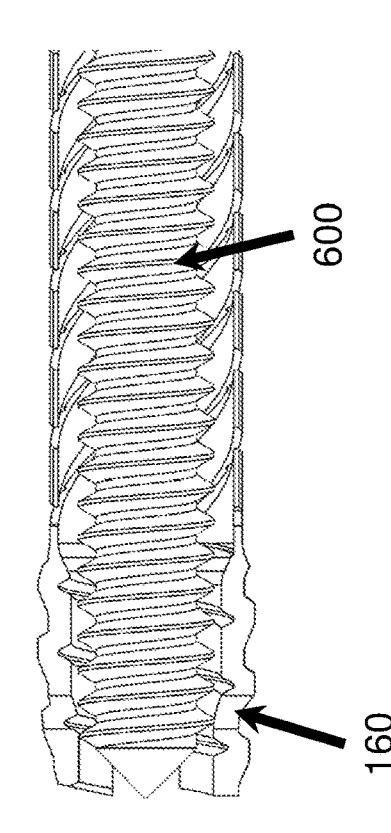

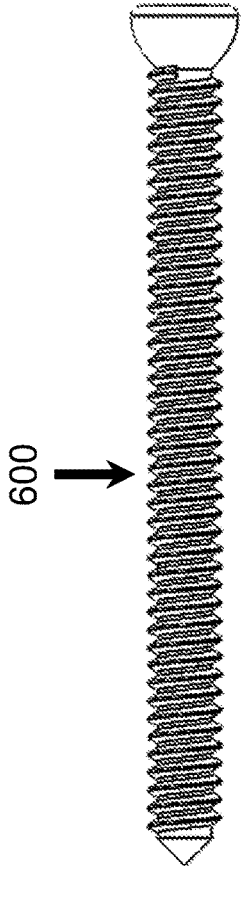
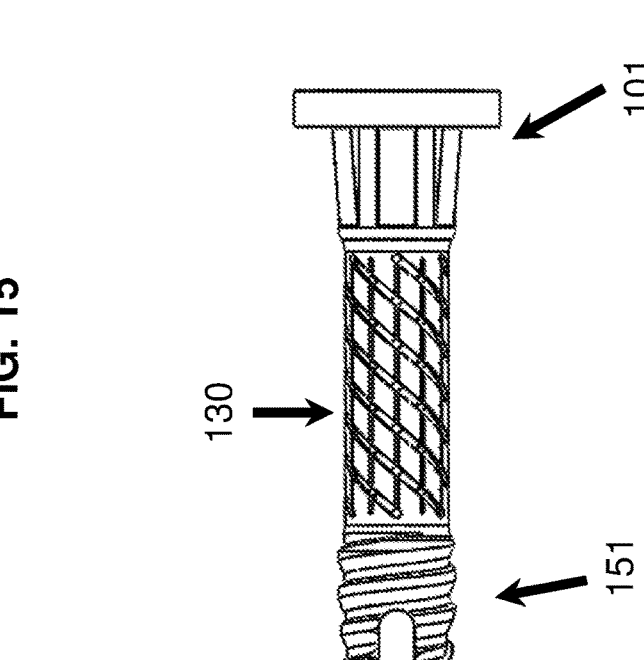
FIG. 15

Cross-sectional view

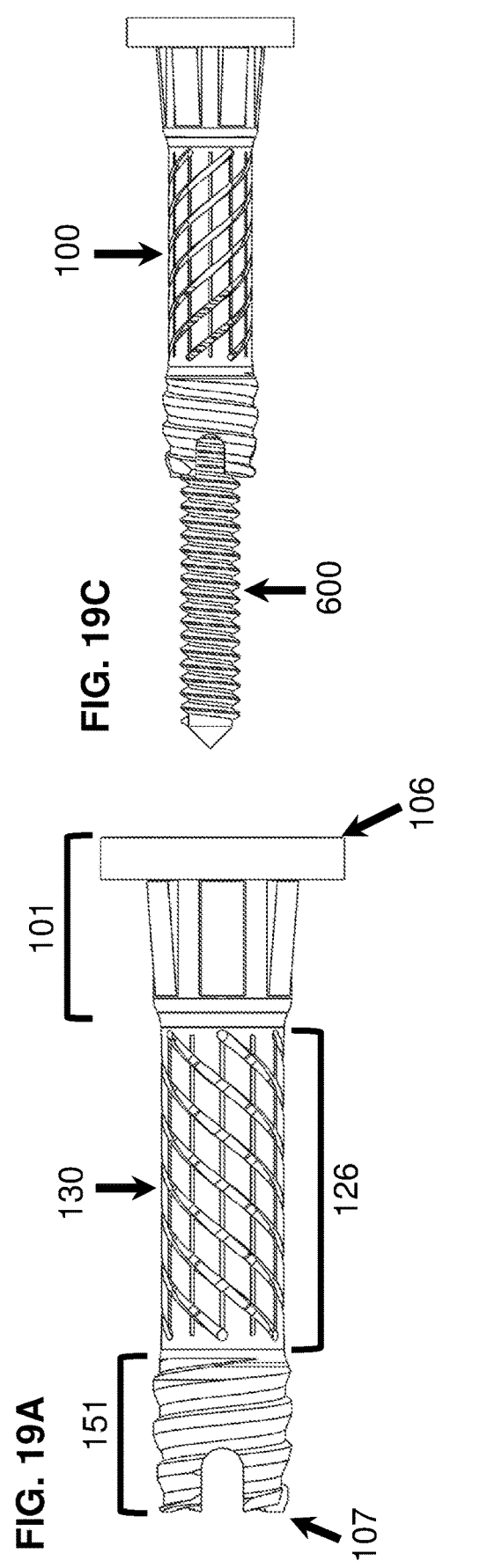
FIG. 19C
100
600
FIG. 19A
106
101
130
126
151
107
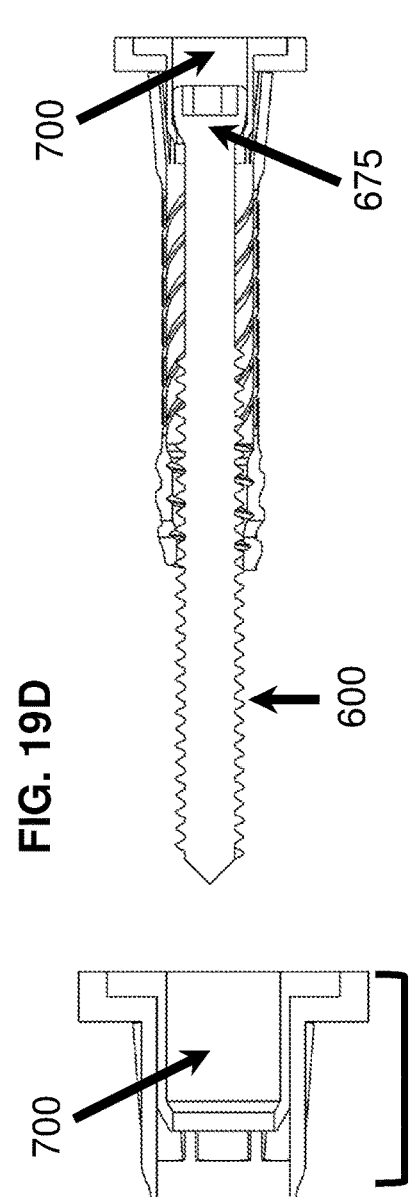
FIG. 19D
700
675
600
Cross-sectional view
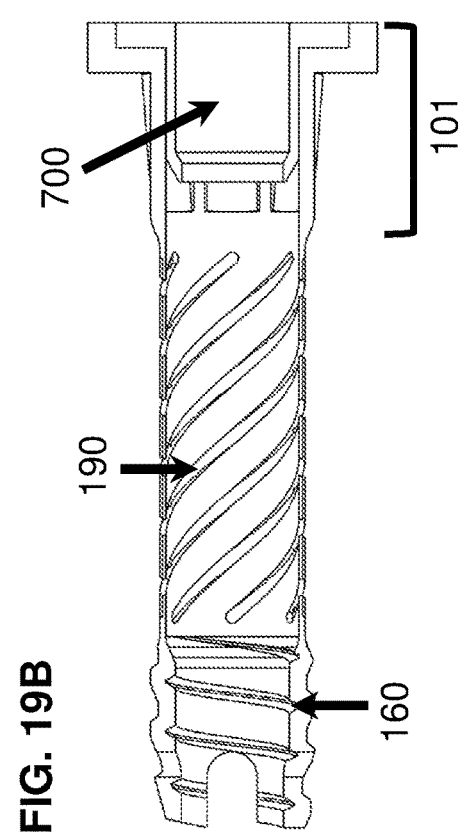
FIG. 19B
700
101
190
160
Cross-sectional view

101 width

140

Torque = 0 N·m
Displacement = 0 mm

101

140

Two helical openings
Opening width = 1.5 mm
Torque = 0.1 N·m
Displacement = 2.809 mm No longitudinal grooves

101

Torque = 5 N·m
Displacement = 5.048 mm

101

150

Torque = 5 N·m
Displacement = 5.092 mm

101

140

Four helical openings
Opening width = 0.75 mm
Torque = 0 N·m
Displacement = 0 mm

101

Four helical openings
Opening width = 0.75 mm
Torque = 0.1 N·m
Displacement = 3.894 mm

101

Six helical openings
Opening width = 0.5 mm
Torque = 0 N·m
Displacement = 0 mm

101

Six helical openings
Opening width = 0.5 mm
Torque = 0.1 N·m
Displacement = 3.964 mm

101

Twelve helical openings
Opening width = 0.25 mm
Torque = 0 N·m
Displacement = 0 mm

101

Twelve helical openings
Opening width = 0.25 mm
Torque = 0.1 N·m
Displacement = 4.065 mm Two helical openings
Opening width = 1.5 mm
Torque = 5 N·m
Displacement = 5.092 mm Twelve helical openings
Opening width = 0.25 mm
Torque = 5 N·m
Displacement = 5.348 mm

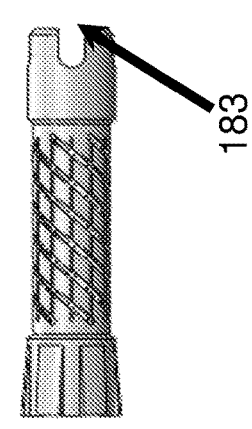
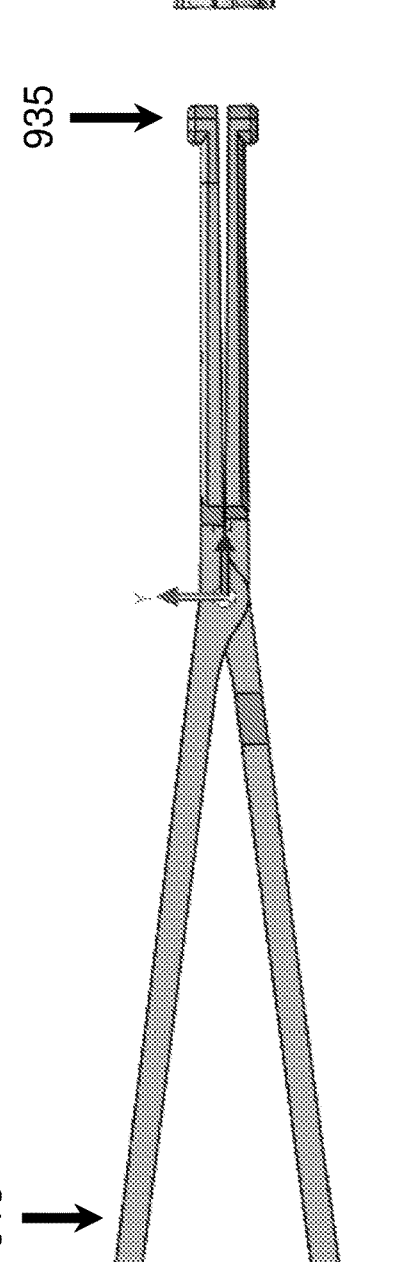
FIG. 32

Cross-sectional view

Cross-sectional view

FIG. 56

Cross-sectional view

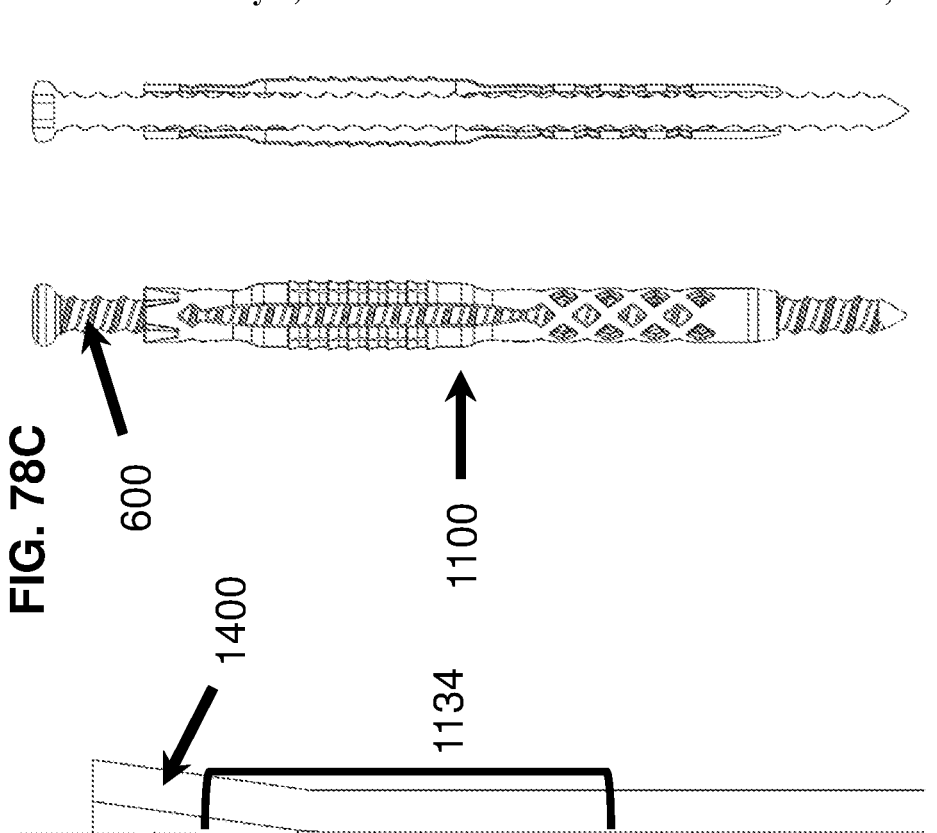
FIG. 78C
600
1100
1400
1134
1100
FIG. 78B
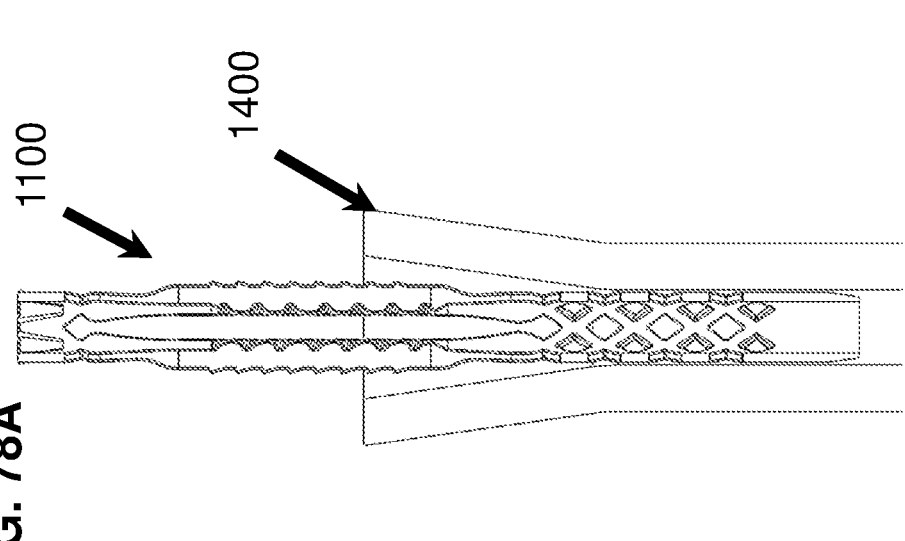
1100
1400
FIG. 78A

DEVICES, SYSTEMS, AND METHODS FOR BONE REPAIR OR IMPLANT FIXATION

BACKGROUND OF THE INVENTION

Fixation and repair of damaged bone is frequently compromised due to bone fractures that result in bone loss, compaction, or fragility from injury or disease. Metal, ceramics, and other biostable materials have been used for over a century to treat bone injuries and diseases. Although new biomaterials, with bone substituting and regeneration capabilities, have been developed for use in combination with biostable implants to expedite bone fracture repair, the interface between injectable fluidic biomaterials and the biostable implants cannot be adequately controlled with most devices on the market. Oftentimes implant failure results along with fracture collapse and nonunion with prolonged and disruptive disability for the patient.

Thus, there exists a need for devices and methods for effective biomaterial injection, placement, and fixation with robust adherence to surgical implants and bone.

SUMMARY OF THE DISCLOSURE

The devices, systems, and methods of the disclosure provide implants and uses thereof for repairing bone defects (e.g., bone fractures), stabilizing bone, or providing or improving implant fixation. The implants disclosed herein can be used to achieve uniform distribution and delivery of a biomaterial to the bone to be repaired or to a site of implant fixation.

In a first aspect, the disclosure features a device including a unitary body having from a proximal end to a distal end: a proximal region, a central region, and a distal region, in which the central region joins the proximal region to the distal region, and in which: a) the device includes an internal channel extending longitudinally through the proximal, central, and distal regions; b) the proximal region includes an opening to the internal channel and a plurality of circumferentially disposed and compressible wings; c) the central region includes an expandable body configured to radially expand; and d) the distal region includes an opening to the internal channel and internal threads.

In some embodiments, the proximal region of the device has an inner diameter of from about 3 mm to about 20 mm and an outer diameter of from about 4 mm to about 25 mm; the central region has an inner diameter of from about 1 mm to about 20 mm and an outer diameter of from about 1.25 mm to about 25 mm; or c) the distal region has an inner diameter of from about 1 mm to about 20 mm and an outer diameter of from about 4 mm to about 25 mm.

In some embodiments, a) the proximal region of the device has an inner diameter of from about 3 mm to about 20 mm (e.g., about 4 mm to about 10 mm, about 5 mm to about 15 mm, or about 10 mm to about 20 mm) and an outer diameter of from about 4 mm to about 25 mm (e.g., about 4 mm to about 10 mm, about 5 mm to about 15 mm, or about 10 mm to about 25 mm); b) the central region has an inner diameter of from 1 mm to about 20 mm and an outer diameter of from about 1.25 mm to about 25 mm (e.g., about 2 mm to about 5 mm, about 5 mm to about 15 mm, or about 10 mm to about 25 mm); c) the distal region has an inner diameter of from 1 mm to about 20 mm (e.g., about 1 mm to about 5 mm, about 5 mm to about 15 mm, or about 10 mm to about 20 mm) and an outer diameter of from about 4 mm to about 25 mm (e.g., about 4 mm to about 10 mm, about 5 mm to about 15 mm, or about 10 mm to about 25 mm); or d) in which the proximal region, the central region, and the distal region include an inner diameter of from 1 mm to about 20 mm (e.g., about 1 mm to about 5 mm, about 5 mm to about 15 mm, or about 10 mm to about 20 mm) and an outer diameter of from about 1.25 mm to about 25 mm (e.g., about 2 mm to about 5 mm, about 5 mm to about 15 mm, or about 10 mm to about 25 mm).

In some embodiments, the outer diameter of the proximal and distal regions is larger than the outer diameter of the central region. In some embodiments, the outer diameter of the proximal and/or distal regions is smaller than the outer diameter of the central region. In some embodiments, the outer diameter of the proximal and/or distal regions is equal to the outer diameter of the central region.

In some embodiments, the inner diameter of the proximal and distal regions is larger than the inner diameter of the central region. In some embodiments, the inner diameter of the proximal and/or distal regions is smaller than the inner diameter of the central region. In some embodiments, the inner diameter of the proximal and/or distal regions is equal to the outer diameter of the central region. In some embodiments, the outer diameter from the proximal end to the distal end of the device is the same. In some embodiments, the inner diameter from the proximal end to the distal end of the device is the same.

In some embodiments, the device has a length of from about 9 mm to about 110 mm, such as about 9 mm, 10 mm, 20 mm, 30 mm, 40 mm, 50 mm, 60 mm, 70 mm, 80 mm, 90 mm, 100 mm, or 110 mm. In some embodiments, proximal region has a length of from about 2 mm to about 30 mm. In some embodiments, the central region has a length of from about 5 mm to about 50 mm. In some embodiments, the distal region has a length of from about 2 mm to about 30 mm.

In some embodiments, the proximal region has a wall thickness of from about 0.6 mm to about 2.5 mm (e.g., about 0.6 mm to about 1 mm, about 1 mm to about 2 mm, about 1.25 mm to about 1.75 mm, or about 1.5 mm to about 2.5 mm), in which, optionally, the wall thickness of the proximal region is about 1.5 mm. In some embodiments, the central region has a wall thickness of from about 0.15 mm to about 2 mm (e.g., about 0.15 mm to about 0.5 mm, about 0.15 mm to about 1 mm, about 1 mm to about 2 mm, or about 1.5 mm to about 2 mm), in which, optionally, the wall thickness of the proximal region is about 0.25 mm. In some embodiments, the proximal region has a wall thickness of from about 0.6 mm to about 2.5 mm, in which, optionally, the wall thickness of the proximal region is about 1.5 mm (e.g., about 0.6 mm to about 1 mm, about 1 mm to about 2 mm, about 1.25 mm to about 1.75 mm, or about 1.5 mm to about 2.5 mm).

In some embodiments, each of the wings of the device includes a) a rectangular shape, having a length and a width; b) a proximal end disconnected from the proximal region and configured to protrude outwardly from the proximal region; and c) a distal end connected to the proximal region and configured to pivot the proximal end of the wing away from the proximal region.

In some embodiments, the proximal end of each of the wings of the device: a) protrudes outwardly from the proximal region at an angle of from about 2° to 10°; and b) is configured to reversibly deflect towards the proximal region to substantially eliminate the outward protrusion of the proximal end upon compression.

In some embodiments, the wings of the device have a length of from about 5 mm to about 20 mm (e.g., about 5 mm to about 10 mm, about 5 mm to about 15 mm, about 10 mm to about 15 mm, about 10 mm to about 20 mm, about 15 mm to about 20 mm, such as about 5 mm, 6 mm, 7 mm, 8 mm, 9 mm, 10 mm, 11 mm, 12 mm, 13 mm, 14 mm, 15 mm, 16 mm, 17 mm, 18 mm, 19 mm and 20 mm) and/or a width of from 1 mm to 15 mm (e.g., about 1 mm, 2 mm, 3 mm, 4 mm, 5 mm, 6 mm, 7 mm, 8 mm, 9 mm, 10 mm, 11 mm, 12 mm, 13 mm, 14 mm, and 15 mm).

In some embodiments, the device includes 3 to 20 wings, such as, e.g., 4 to 8 wings, such as 6 wings.

In some embodiments, the expandable body of the device includes a plurality of openings (e.g., about 2 to 20 openings), in which, optionally, the plurality of openings includes helical slits, segmented slits, longitudinal slits, or perforations. In some embodiments, the expandable body of the device includes a plurality of openings (e.g., about 2 to 5000 openings), in which, optionally, the plurality of openings includes slits or perforations, in which optionally the plurality of openings includes helical slits, segmented slits, longitudinal slits, circumferential slits, circular perforations, elliptical perforations, triangular perforations, polygonal perforations, or amorphous perforations. In some embodiments, the expandable body includes 2 to about 5000 openings (e.g., from about 2 to about 100, from about 2 to about 200, from about 2 to about 300, from about 2 to about 400, from about 2 to about 500, from about 2 to about 750, from about 2 to about 1000, from about 2 to about 1500, from about 2 to about 2000, from about 2 to about 3000, from about 2 to about 4000, from about 10 to about 50, from about 10 to about 100, from about 50 to about 100, from about 50 to about 250, from about 50 to about 500, from about 100 to about 250, from about 250 to about 500, from about 500 to about 1000, from about 1000 to about 2000, from about 2000 to about 3000, from about 3000 to about 4000, from about 4000 to about 5000, or from about 2500 to about 5000).

In some embodiments, the openings extend into the proximal region and/or the distal region.

In some embodiments, the openings have a width of from about 0.1 mm to about 2 mm and a length of from about 1 mm to about 20 mm.

In some embodiments, the perforations of the device have a circular or elliptical shape with a diameter of from about 1 mm to about 5 mm. In some embodiments, the openings include perforations that have, e.g., a circular, elliptical, triangular, polygonal, or amorphous shape and, optionally, a diameter of from about 0.1 mm to about 5 mm.

In some embodiments, the openings include perforations, in which a plurality of the perforations are connected by at least one slit, optionally in which the slit is a helical slit, a segmented slit, a longitudinal slit, or a circumferential slit. In some embodiments, the slit connects 2 to 100 (e.g., 2 to 10, 2 to 20, 10 to 20, 10 to 30, 10 to 50, 20 to 40, 20 to 60, 40 to 80, 50 to 100, 60 to 80, or 80 to 100) perforations.

In some embodiments, the openings include perforations, in which the perforations form a mesh or mesh-life structure. In some embodiments, the mesh or mesh-like structure is woven, perforated, crimped, welded, molded, sintered, or 3D-printed. In some embodiments, the mesh or mesh-like structure includes a percent porosity from about 5% to about 90% (e.g., from about 5% to about 10%, from about 5% to about 20%, from about 10% to about 25%, from about 20% to about 40%, from about 20% to about 70%, from about 30% to about 60%, from about 40% to about 60%, from about 50% to about 70%, from about 50% to about 90%, or from about 70% to about 90%). In some embodiments, the mesh or mesh-like structure includes a wire gauge from 5 to 50 (e.g., from 5 to 10, from 10 to 20, from 10 to 30, from 20 to 40, or from 30 to 40).

In some embodiments, the expandable body includes 1 to 70 (e.g., from 1 to 2, from 1 to 3, from 1 to 4, from 2 to 4, from 2 to 5, from 2 to 6, from 4 to 8, from 5 to 10, from 6 to 12, from 5 to 15, from 10 to 20, from 20 to 40, from 30 to 60, or from 50 to 70) longitudinal grooves. In some embodiments, the expandable body of the device includes from 1 to 70 longitudinal grooves (e.g., from 1 to 2, from 1 to 3, from 1 to 4, from 2 to 4, from 2 to 5, from 2 to 6, from 4 to 8, from 5 to 10, from 6 to 12, from 5 to 15, from 10 to 20, from 20 to 40, from 30 to 60, or from 50 to 70). In some embodiments, the longitudinal grooves include a depth of from about 0.15 mm to about 2.5 mm (e.g., from about 0.15 mm to about 0.5 mm, from about 0.15 mm to about 1 mm, from about 0.15 mm to about 1.5 mm, from about 0.5 mm to about 1 mm, from about 0.5 mm to about 1.5 mm, from about 1 mm, to about 2 mm, from about 1 mm to about 3 mm, from about 2 mm to about 3 mm, about 0.15 mm, about 0.2 mm, about 0.3 mm, about 0.4 mm, about 0.5 mm about 0.6 mm, about 0.7 mm, about 0.8 mm, about 0.9 mm, about 1 mm, about 1.1 mm, about 1.2 mm, about 1.3 mm, about 1.4 mm, about 1.5 mm, about 1.6 mm, about 1.7 mm, about 1.8 mm, about 1.9 mm, about 2 mm, about 2.1 mm, about 2.2 mm, about 2.3 mm, about 2.4 mm, or about 2.5). In some embodiments, the longitudinal grooves extend from a proximal end of the central region to a distal end of the central region.

In some embodiments, the internal threads of the distal region of the device have a thread pitch of from about 0.25 mm to about 2.5 mm (e.g., from about 0.25 mm to about 0.5 mm, from about 0.5 mm to about 1 mm, from about 0.5 mm to about 1.5 mm, from about 1 mm to about 2 mm, from about 1 mm to about 2.5 mm, or from about 1.5 mm to about 2.5 mm).

In some embodiments, the distal end of the distal region of the device includes a blunt edge. In some embodiments, the distal end of the distal region has a tapered edge. In some embodiments, the distal end of the distal region includes from 2 to 5 milling flutes, in which, optionally, the distal region includes 3 milling flutes. In some embodiments, the distal region includes from 2 to 4 notches and/or elongated slits, in which optionally the slits include a helical slit, a segmented slit, a longitudinal slit, or a circumferential slit. In some embodiments, the distal region includes from 1 to 6 openings, in which, optionally, the diameter of each opening is from about 2 mm to about 5 mm. In some embodiments, the distal region includes from 1 to 5000 openings, in which optionally the diameter of each opening is from about 0.01 mm to about 5 mm.

In some embodiments, the distal region includes external threads. In some embodiments, the external threads have a thread pitch of from about 0.25 mm to about 2.5 mm (e.g., from about 0.25 mm to about 0.5 mm, from about 0.5 mm to about 1 mm, from about 0.5 mm to about 1.5 mm, from about 1 mm to about 2 mm, from about 1 mm to about 2.5 mm, or from about 1.5 mm to about 2.5 mm). In some embodiments, the internal or external threads include a thread pitch of from about 0.25 mm to about 2.5 mm (e.g., from about 0.25 mm to about 0.5 mm, from about 0.5 mm to about 1 mm, from about 0.5 mm to about 1.5 mm, from about 1 mm to about 2 mm, from about 1 mm to about 2.5 mm, or from about 1.5 mm to about 2.5 mm). In some embodiments, the external thread is formed from protrusions, grooves, waves, or a mesh. In some embodiments, the protrusions, grooves, or waves are at from about 1 to about 365 points per 360°. In some embodiments, the external thread includes a continuous thread or non-continuous thread. In some embodiments, the external thread is broken by a slit, optionally in which the slit is a helical slit, a segmented slit, a longitudinal slit, or a circumferential slit. In some embodiments, the non-continuous thread includes a gap, in which the gap has a length from about 0.5 mm to about 30 mm. In some embodiments, the distal region includes a plurality of bendable tips disposed at the proximal end and/or the distal end.

In some embodiments, the distal region of the device includes a plurality of bendable tips disposed at the distal end. In some embodiments, the proximal region of the device includes internal threads. In some embodiments, the internal threads of proximal region have a thread pitch of from about 0.25 mm to about 2.5 mm (e.g., from about 0.25 mm to about 0.5 mm, from about 0.5 mm to about 1 mm, from about 0.5 mm to about 1.5 mm, from about 1 mm to about 2 mm, from about 1 mm to about 2.5 mm, or from about 1.5 mm to about 2.5 mm).

In some embodiments, the proximal region includes an internal or external protrusion. In some embodiments, the internal or external protrusion of the proximal region includes a bump, a spike, a tab, a fin, a ridge, or a raised surface. In some embodiments, the internal or external protrusion extends from a proximal end to a distal end of the proximal region. In some embodiments, a plurality of internal or external protrusions extends from a proximal end to a distal end of the proximal region. In some embodiments, the device includes from 1 to 5000 internal or external protrusions. In some embodiments, the proximal region includes an internal or external thread. In some embodiments, the internal or external thread of the proximal region includes a thread pitch of from about 0.25 mm to about 2.5 mm (e.g., from about 0.25 mm to about 0.5 mm, from about 0.5 mm to about 1 mm, from about 0.5 mm to about 1.5 mm, from about 1 mm to about 2 mm, from about 1 mm to about 2.5 mm, or from about 1.5 mm to about 2.5 mm). In some embodiments, the internal or external thread is formed from protrusions, grooves, waves, or a mesh. In some embodiments, the protrusions, grooves, or waves are at from about 1 to about 365 points per 360°. In some embodiments, the internal or external thread includes a continuous thread or non-continuous thread. In some embodiments, the non-continuous thread includes a gap, in which the gap has a length from about 0.5 mm to about 30 mm. In some embodiments, the internal or external thread is broken by a slit, optionally in which the slit is a helical slit, a segmented slit, a longitudinal slit, or a circumferential slit.

In some embodiments, the central region includes an internal or external protrusion. In some embodiments, the internal or external protrusion of the central region includes a bump, a spike, a tab, a fin, a ridge, or a raised surface. In some embodiments, the internal or external protrusion extends from a proximal end to a distal end of the central region. In some embodiments, a plurality of internal or external protrusions extends from a proximal end to a distal end of the central region. In some embodiments, the device includes from 1 to 5000 internal or external protrusions. In some embodiments, the central region includes an internal or external thread. In some embodiments, the internal or external thread of the central region includes a thread pitch of from about 0.25 mm to about 2.5 mm (e.g., from about 0.25 mm to about 0.5 mm, from about 0.5 mm to about 1 mm, from about 0.5 mm to about 1.5 mm, from about 1 mm to about 2 mm, from about 1 mm to about 2.5 mm, or from about 1.5 mm to about 2.5 mm). In some embodiments, the internal or external thread is formed from protrusions, grooves, waves, or a mesh. In some embodiments, the protrusions, grooves, or waves are at from about 1 to about 365 points per 360°. In some embodiments, the internal or external thread includes a continuous thread or non-continuous thread. In some embodiments, the non-continuous thread includes a gap, in which the gap has a length from about 0.5 mm to about 30 mm. In some embodiments, the internal or external thread is broken by a slit, optionally in which the slit is a helical slit, a segmented slit, a longitudinal slit, or a circumferential slit.

In some embodiments, the unitary body includes a plurality of longitudinal segments connected by a plurality of expandable arms. In some embodiments, the proximal region, central region, and/or distal region includes a plurality of segments. In some embodiments, the segments include longitudinal segments. In some embodiments, the plurality of segments extends from the proximal end, through the central region, to the distal end. In some embodiments, the plurality of segments includes a polygonal, circular, triangular, elliptical, cylindrical, or amorphous shape; in which, optionally the plurality of segments includes a rectangular shape. In some embodiments, the unitary body includes from 2 to 10 segments, in which the expandable body includes from 1 to 100 expandable arms. In some embodiments, the unitary body includes from 1 to 50 expandable arms per each segment. In some embodiments, each of the segments are the same size. In some embodiments, each of the segments is separated by at least one opening, in which the opening has a maximum width of about 0.1 mm to about 50 mm. In some embodiments, each of the segments includes a length of about 9 mm to about 110 mm. In some embodiments, each of the segments includes a width of about 0.1 mm to about 50 mm. In some embodiments, the expandable arms are separated by at least one opening, in which the opening includes a maximum width of about 1 mm to about 50 mm. In some embodiments, the unitary body includes about 1 to 50 pairs of expandable arms. In some embodiments, the pairs of expandable arms are separated by at least one opening, in which the opening includes a maximum width of about 0.1 mm to about 50 mm. In some embodiments, the expandable arms are c-shaped, s-shaped, u-shaped, or z-shaped. In some embodiments, the proximal region, central region, and/or distal region includes at least one expandable arm.

In some embodiments, the central region includes i) a first section including the expandable body, and (ii) a second section including a plurality of openings. In some embodiments, the central region includes from a proximal end to a distal end: i) the first section, and ii) the second section. In some embodiments, the first section includes a length of from about 5 mm to about 100 mm. In some embodiments, the second section includes a length of from about 5 mm to about 100 mm.

In some embodiments, the device is made from or includes a material selected from the group consisting of stainless steel or an alloy thereof, titanium or an alloy thereof, magnesium or an alloy thereof, polyetheretherke-tone (PEEK), hydroxyapatite, tricalcium phosphate, tetra-calcium phosphate, dicalcium phosphate, BIOGLASS® 45S5, ceramic composites, copper-based materials or composites, cobalt chrome, xenograft biomaterials, and combinations thereof.

In some embodiments, the proximal region, the central region, and the distal region of the device are optionally fabricated separately and combined to form the unitary body.

In a second aspect, the disclosure features a system including the device as described in the first aspect of the disclosure, in which the device is connected to a connector, a pusher, and/or the insertion tool.

In some embodiments, the system includes the insertion tool, in which the insertion tool includes from a proximal end to a distal end: a proximal region, a central region, and a distal region, in which the central region connects the proximal region to the distal region, and in which: a) the proximal region includes a handle; b) the central region includes an unthreaded shaft with a diameter that ends with a lip; and c) the distal region includes a shaft with a reduced diameter relative to the diameter of the shaft of the central region, in which the distal region further includes at least a first set of threads along the shaft and an unthreaded region.

In some embodiments, the first set of threads of the distal region of the insertion tool engage the internal threads of the proximal and distal regions of the device. In some embodiments, the first set of threads of the distal region of the insertion tool have a thread pitch of from about 0.25 mm to about 2.5 mm (e.g., from about 0.25 mm to about 0.5 mm, from about 0.5 mm to about 1 mm, from about 0.5 mm to about 1.5 mm, from about 1 mm to about 2 mm, from about 1 mm to about 2.5 mm, or from about 1.5 mm to about 2.5 mm). In some embodiments, the distal region of the insertion tool further includes a second set of threads disposed proximal to the first set of threads. In some embodiments, the second set of threads of the distal region include a thread pitch of from about 0.25 mm to about 2.5 mm (e.g., from about 0.25 mm to about 0.5 mm, from about 0.5 mm to about 1 mm, from about 0.5 mm to about 1.5 mm, from about 1 mm to about 2 mm, from about 1 mm to about 2.5 mm, or from about 1.5 mm to about 2.5 mm). In some embodiments, the first set of threads and the second set of threads of the distal region of the insertion tool are separated by the unthreaded region. In some embodiments, the unthreaded region has a length of from about 10 mm to about 100 mm. In some embodiments, the insertion tool includes an internal channel longitudinally extending through the proximal, central, and distal regions. In some embodiments, the internal channel of the insertion tool is sized to allow a guide wire to pass through the proximal, central, and distal regions of the insertion tool.

In some embodiments, the system includes or further includes the connector, in which the connector has a frustoconical shape having a proximal region, a distal region, and an internal channel extending from the proximal region to the distal region, in which: a) the proximal region includes Luer-lock threads; b) the distal region of the connector includes a plurality of circumferentially disposed, radially extended wedges; and c) the internal channel of the connector is sized to fit over the unthreaded region of the distal region of the insertion tool.

In some embodiments, the proximal region of the connector includes an outer diameter of from about 7 mm to about 12 mm and an inner diameter of from about 4 mm to about 5 mm.

In some embodiments, the Luer-lock threads includes a thread pitch of from about 1 mm to about 3 mm (e.g., 2.5 mm). For example, the Luer-lack fitting can be compliant with ISO standard (e.g., 80369-7, such as 80369-7-20219).

In some embodiments, the distal region of the connector includes a proximal end and a distal end. In some embodiments, the proximal end of the distal region of the connector includes an outer diameter of from about 7 mm to about 26 mm and an inner diameter of from about 4 mm to about 24.8 mm. In some embodiments, the distal end of the distal region of the connector includes an outer diameter of from about 1.8 mm to about 18.8 mm and an inner diameter of from about 0.6 mm to about 17.6 mm. In some embodiments, the connector includes a length from the proximal region to the distal region of from about 38 mm to about 120 mm.

In some embodiments, the connector includes a plurality of wedges, in which the number of wedges is equal to the number of wings at the proximal region of the device. In some embodiments, the wedges extend from the proximal end to the distal end of the distal region of the connector. In some embodiments, the proximal region of the connector further includes an alignment marker. In some embodiments, the alignment marker includes a colored marker, a textured marker, or a patterned marker. In some embodiments, the connector includes a circumferential groove centrally situated within the distal region of the connector. In some embodiments, the circumferential groove is configured to secure the connector to a bone plate. In some embodiments, the wedges of the connector are configured to fasten the distal region of the connector to the internal channel at the proximal region of the device. In some embodiments, the proximal region of the device includes an alignment marker. In some embodiments, the distal region of the connector is configured to be inserted into the internal channel of the device at the proximal region thereof by aligning the alignment marker of the connector with the alignment marker of the device.

In some embodiments, the system includes or further includes the pusher, in which the pusher has a proximal region and a distal region, in which: a) the proximal region of the pusher includes a handle; b) the distal region of the pusher includes a cylindrical shape; and c) the pusher further includes an internal channel extending longitudinally through the proximal and distal regions, in which the insertion tool includes a shaft at a distal region thereof that extends through the internal channel of the pusher.

In some embodiments, the internal channel of the pusher includes internal threads and in which the pusher is rotatable relative to the insertion tool. In some embodiments, the internal threads of the pusher include a thread pitch of from about 0.25 mm to about 2.5 mm (e.g., from about 0.25 mm to about 0.5 mm, from about 0.5 mm to about 1 mm, from about 0.5 mm to about 1.5 mm, from about 1 mm to about 2 mm, from about 1 mm to about 2.5 mm, or from about 1.5 mm to about 2.5 mm).

In some embodiments, the system includes a) the insertion tool including from a proximal end to a distal end: a proximal region, a central region, and a distal region, in which the central region connects the proximal region to the distal region, the proximal region including a handle, the central region including an unthreaded shaft with a diameter that ends with a lip, the distal region including a shaft with a reduced diameter relative to the diameter of the shaft of the central region, and the distal region further including a first set of threads distally disposed from a second set of threads and an unthreaded region separating the first and second sets of threads; b) the pusher including a proximal region and a distal region, the proximal region including a handle, the distal region including a cylindrical shape, and the pusher further including an internal channel extending longitudinally through the proximal and distal regions, the internal channel including a set of threads and in which the pusher is rotatable relative to the insertion tool; and c) the connector including a frustoconical shape having a proximal region, a distal region, and an internal channel extending from the proximal region to the distal region, the proximal region including Luer-lock threads, and the distal region including a plurality of circumferentially disposed, radially extended wedges; in which: a) the wedges of the connector fasten the distal region of the connector to the internal channel at the proximal region of the device; b) the shaft of the distal region of the insertion tool traverses the internal channel of the pusher from the proximal region to the distal region thereof and the second set of threads of the distal region of the insertion tool engage with the set of threads of the internal channel of the pusher; c) the first set of threads of the distal region of the insertion tool longitudinally traverse the internal channel of the connector and engage with the internal threads of the distal region of the device; d) the internal channel of the connector fits over the unthreaded region of the distal region of the insertion tool; and e) the proximal region of the connector contacts the distal region of the pusher.

In a third aspect, the disclosure features a method of bone repair or implant fixation, in which the method involves inserting a device of the first aspect of the disclosure into a bone.

In some embodiments, prior to inserting the device into the bone, the method includes drilling a hole into the bone, in which the inserting includes placing the device in the hole (e.g., screwing the device into the bone at the site of the hole).

In some embodiments, the method further includes compressing the device prior to inserting the device into the bone.

In some embodiments, compression of the device is maintained by a deployment device.

In some embodiments, the method includes inserting the device into the bone until the proximal end contacts the bone. The method further includes securing the proximal region of the device in the bone, such as by friction fitting the wings of the proximal region of the device against the bone. In some embodiments, the method further includes expanding the expandable body. In some embodiments, the method further includes expanding the expandable body by releasing the device from a compressed state. In some embodiments, the method includes expanding the expandable body by rotating the distal region of the device relative to the proximal region (e.g., the distal region rotates while the proximal region remains fixed). In other embodiments, the method includes expanding the expandable body using a balloon. The balloon (e.g., in a deflated or partially inflated state) may be inserted into the internal channel of the device following insertion into the hole in the bone. Following insertion, the balloon may be inflated to expand the expandable body of the device.

In some embodiments, the method further includes introducing a biomaterial to the internal channel of the device after expansion of the expandable body.

In some embodiments, the method includes uniformly distributing the biomaterial throughout the device and into the bone surrounding the device (e.g., by inserting a screw or other hardware into the internal channel of the device so as to displace the biomaterial from the internal channel and into the bone through, e.g., the slits of the helical body or other holes, perforations, or slots of the device).

In some embodiments, upon expansion of the expandable body, an opening in the expandable body expands. In some embodiments, delivery of a volume of the biomaterial is proportional to the expansion of the opening in the expandable body.

In some embodiments, the biomaterial hardens thereby securing the device to the bone.

In some embodiments, the method includes inserting a screw having a length through the internal channel of the device, thereby promoting the uniform distribution of the biomaterial throughout the device and into the bone surrounding the device. The screw can remain in the device to provide additional stability and fixation support. Alternatively, the screw can be inserted into the internal channel of the device after the biomaterial has hardened.

In some embodiments, the method further includes including aligning the screw with an internal protrusion or thread in the proximal region, central region, and/or distal region.

In some embodiments, the length of the screw traverses a length of the internal channel of the device, and in which the method further includes fastening a distal end of the screw to a distal cortex of the bone, in which, optionally, tightening the screw in the distal cortex causes bone compression (e.g., when used in combination with a bone plate or a washer to apply pressure to the bone cortex opposite of the screw tip).

In some embodiments, the screw includes a diameter or from about 1 mm to about 20 mm, threads having a thread pitch of from about 0.25 mm to about 2.5 mm (e.g., from about 0.25 mm to about 0.5 mm, from about 0.5 mm to about 1 mm, from about 0.5 mm to about 1.5 mm, from about 1 mm to about 2 mm, from about 1 mm to about 2.5 mm, or from about 1.5 mm to about 2.5 mm), a threadless body, or a material selected from the group consisting of stainless steel or an alloy thereof, titanium or an alloy thereof, magnesium or an alloy thereof, polyetheretherketone (PEEK), hydroxyapatite, tricalcium phosphate, tetracalcium phosphate, dicalcium phosphate, BIOGLASS® 45S5, ceramic composites, copper-based materials or composites, cobalt chrome, and combinations thereof. In some embodiments, the screw includes a length of from about 5 mm to about 300 mm (e.g., about 5 mm to about 125 mm) and can include any length within this range.

In some embodiments, the method further includes using the device to secure a bone plate to the bone, in which, optionally, the bone plate includes at least one hole providing access to the internal channel of the device.

In some embodiments, the method further includes securing a bone plate to the bone by inserting the screw through the bone plate hole and the internal channel of the device and fastening the distal end of the screw to the distal cortex of the bone.

In some embodiments, the bone plate includes two or more bone plate holes (e.g., three, four, five, six, or more holes) and the method can include securing the bone plate to the bone using more than one device of the first aspect of the disclosure, which is placed in the bone through the bone plate holes.

In some embodiments, the method further includes placing a washer into the internal channel at the proximal region of the device, in which, optionally, the washer includes a proximal region, a distal region, and an internal channel extending longitudinally through the proximal region and the distal region of the washer.

In some embodiments, prior to insertion of the screw through the internal channel of the device, the method further includes placing a washer into the internal channel at the proximal region of the device, in which the washer includes a proximal region, a distal region, and an internal channel extending longitudinally through the proximal region and the distal region of the washer, and inserting the screw through the internal channel of the washer and through the internal channel of the device. The washer can be used to narrow the channel at the proximal region of the device in order to promote compression and to minimize the risk of unintentional intrusion of the screw head through cortical bone during screw insertion.

In some embodiments, the proximal region of the washer has an outer diameter of from about 5 mm to about 30 mm and/or an inner diameter of from about 2 mm to about 20 mm, and/or the distal region of the washer has an outer diameter of from about 2.8 mm to about 19.8 mm and/or an inner diameter of from about 2 mm to about 18 mm, and/or the outer diameter of the washer proximal region is larger than the outer diameter of the washer distal region.

In some embodiments, prior to or after insertion of the device in the bone, the method further includes inserting a connector into the internal channel at the proximal region of the device, in which the connector has a frustoconical shape having a proximal region, a distal region, and an internal channel extending from the proximal region to the distal region, and in which: a) the proximal region includes Luer-lock threads, and b) the distal region of the connector includes a plurality of circumferentially disposed, radially extended wedges.

In some embodiments, the method includes fastening the connector to the internal channel at the proximal region of the device after the device is inserted into the bone and after the proximal region of the device is secured in the bone. In some embodiments, the connector further includes an alignment marker.

In some embodiments, the method includes coupling a biomaterial dispenser having a biomaterial to the connector using the Luer-lock threads.

In some embodiments, the biomaterial dispenser includes a syringe, a vial, or a reservoir that is sized to hold a suitable volume of the biomaterial (e.g., a volume of from about 1 ml to about 20 ml). The syringe, vial, or reservoir may include a tube. In some embodiments, the method includes introducing a volume of the biomaterial (e.g., from the biomaterial dispenser) of from about 1 ml to about 20 ml to the internal channel of the device. In some embodiments, the volume of the biomaterial introduced into the device is about 2.5 ml, about 5 ml, or about 10 ml.

In some embodiments, the biomaterial includes a polymeric adhesive, a bone void filler material, a cement, a phosphoserine-based bioadhesive, a cohesiveness agent, an osteogenic agent, a medicinal agent, or a pharmaceutical agent.

In some embodiments, the biomaterial includes a calcium phosphate-based bone cement, a non-self-hardening calcium phosphate based bone void filler, a flowable xenograft bone void filler, polymethacrylate (PMMA), polymethylmethacrylate (PMMA), calcium sulfate, a metal alloy, a polysaccharide, a nucleic acid, a carbohydrate, a protein, a polypeptide, a poly($\alpha$-hydroxy acid), a poly(lactone), a poly (amino acid), a poly(anhydride), a poly(orthoester), a poly (anhydride-co-imide), a poly(orthocarbonate), a poly($\alpha$-hydroxy alkanoate), a poly(dioxanone), a poly (phosphoester), poly(L-lactide) (PLLA), poly(D,L-lactide) (PDLLA), polyglycolide (PGA), poly(lactide-co-glycolide (PLGA), poly(L-lactide-co-D, L-lactide), poly(D,L-lactide-co-trimethylene carbonate), polyhydroxybutyrate (PHB), poly($\epsilon$-caprolactone), poly($\delta$-valerolactone), poly($\gamma$-butyro-lactone), poly(caprolactone), polyacrylic acid, polycarboxylic acid, poly(allylamine hydrochloride), poly(diallyldimethylammonium chloride), poly(ethyleneimine), polypropylene fumarate, polyvinyl alcohol, polyvinylpyrrolidone, polyethylene, carbon fibers, poly(ethylene glycol), poly(ethylene oxide), poly(vinyl alcohol), poly(vinylpyrrolidone), poly(ethyloxazoline), poly(ethylene oxide)-copoly(propylene oxide), a block copolymer, poly(ethylene terephthalate)polyamide, a homo-polymer or a co-polymer including one or more monomers selected from the group consisting of acrolein potassium, (meth)acrylamide, (meth) acrylic acid and salts thereof, (meth)acrylate, acrylonitrile, ethylene, ethylene glycol, ethyleneimine, ethyleneoxide, styrene sulfonate, vinyl acetate, vinyl alcohol, vinyl chloride, vinylpyrrolidone, a polyphenolic complexing agent selected from a gallotannin, an ellagitannin, a taragallotannin, a caffetannin, a proanthocyanidin, catechin, epicatechin, chlorogenic acid, and arbutin, alginic acid, arabic gum, guar gum, xantham gum, gelatin, chitin, chitosan, chitosan acetate, chitosan lactate, chondroitin sulfate, N,O-carboxymethyl chitosan, a dextran, fibrin glue, glycerol, hyaluronic acid, sodium hyaluronate, a cellulose, a glucosamine, a proteoglycan, a starch, lactic acid, a pluronic, sodium glycerophosphate, collagen, glycogen, a keratin, silk, transforming growth factors-beta (TGF-$\beta$), an activin, an inhibin, a bone morphogenetic proteins (BMP), an antibiotic, an enzyme inhibitor, an antihistamine, an anti-inflammatory agent, a muscle relaxant, an anti-spasmodics, an analgesic, a prostaglandin, an anti-depressant, a trophic factor, or a hormone.

In some embodiments, the method includes uncoupling the biomaterial dispenser and/or the connector from the proximal region of the device after the biomaterial is introduced to the internal channel of the device.

In some embodiments, the device is inserted into the bone using the insertion tool. The insertion tool can include, from a proximal end to a distal end: a proximal region, a central region, and a distal region, in which the central region connects the proximal region to the distal region, the proximal region includes a handle, the central region includes an unthreaded shaft with a diameter that ends with a lip, the distal region includes a shaft with a reduced diameter relative to the diameter of the shaft of the central region, and the distal region further includes a first set of threads distally disposed from a second set of threads and an unthreaded region separating the first and second sets of threads; and in which the distal region threads of the insertion tool are configured to engage with the internal threads of the distal region of the device. When using the insertion tool to place the device of the first aspect into bone, the method further includes engaging the device with the insertion tool (at the distal region of the insertion tool) and twisting the insertion tool until the device is placed (e.g., screwed) into the bone.

In some embodiments, during insertion of the device into the bone, the wings of the proximal region of the device compress, e.g., when they come into contact with the bone (e.g., when the device is inserted fully into the bone, the proximal region contacts the bone, which causes the wings of the device to compress). The method further includes rotating the device once inserted in the bone until the wings are able to expand (fully or partially back to their natural, expanded state). Expansion of the wings applies pressure (e.g., by friction fit) against the bone, thereby securing the proximal region of the device in the bone (e.g., fixing the device in the bone, such that the proximal region of the device can resist rotation, e.g., so that the distal end can be rotated independent of the proximal end.

In some embodiments, the method further includes, prior to engaging the insertion tool with the device, assembling a system including the device, the insertion tool, a pusher, and a connector. The pusher includes a proximal region (e.g., including a handle) and a distal region with a cylindrical shape. The pusher further includes a threaded internal channel longitudinally extending through the proximal and/or distal regions. The system can also include the connector, which has a frustoconical shape with a proximal region, a distal region, and an internal channel extending from the proximal region to the distal region. The proximal region of the connector includes Luer-lock threads and the distal region of the connector includes a plurality of circumferentially disposed, radially extended wedges (the wedges are configured to mate with the inside of the wings of the device in order to lock the connector into the device). The assembling includes a) threading the threaded internal channel of the pusher along the shaft of the distal region of the insertion tool until the threaded internal channel engages the second set of threads of the distal region of the insertion tool and the proximal region of the pusher is adjacent to the central region of the insertion tool; b) sliding the internal channel of the connector along the shaft of the distal region of the insertion tool until the connector overlaps with the unthreaded region of the distal region of the insertion tool, such that the connector is located distal to the pusher; and c) inserting the shaft of the distal region of the insertion tool through the internal channel of the device until the first set of threads of the insertion tool engage the internal threads of the distal region of the device.

In some embodiments, the method further includes a) inserting the device into the bone by twisting the handle of the insertion device until the device is fully inserted into the bone and b) inserting the connector into the internal channel of the proximal region of the device by twisting the handle of the pusher until the distal region of the pusher engages the proximal region of the connector, whereby the twisting translates the connector along the shaft of the insertion tool until the distal region of the connector engages the internal channel of the proximal region of the device. Insertion of the connector into the proximal region of the device causes the expansion of the wings of the device (e.g., from a compressed state that resulted from insertion of the device into the bone) as the wedges of the connector mate with the interior side of the proximal region of the device corresponding to the wings. Expansion of the wings of the device upon insertion of the connector secures (e.g., fixes or immobilizes) the proximal region of the device in the bone.

In some embodiments, the method further includes radially expanding the expandable body of the device by a) immobilizing the proximal region of the device using the pusher and connector and b) twisting the handle of the insertion tool in a first direction, whereby the distal region of the device twists independently of (or in relation to) the immobilized the proximal region of the device, thereby compressing the device and radially expanding the expandable body.

In some embodiments, the method further includes, after expanding the expandable body of the device, decoupling the pusher from the connector and unthreading the insertion tool from the device by twisting the handle of the insertion tool in a second direction that is opposite from the first direction. In some embodiments, the expandable body maintains an expanded form after removing the pusher and the insertion tool from the device. In some embodiments, the first direction is clockwise and the second direction is counterclockwise. In some embodiments, the first direction is counterclockwise, and the second direction is clockwise.

In some embodiments, the method includes using the system of the second aspect of the disclosure to insert the device into the bone.

In some embodiments, the method includes coupling the connector to a biomaterial dispenser after decoupling the pusher and the insertion tool from the device.

In fourth aspect, the disclosure features an extraction tool that can be used to remove the device from bone after insertion of the device into the bone. The extraction tool includes from a proximal end to a distal end: a proximal region, a central region, and a distal region in which the proximal region includes a grip handle, the central region includes a pivot joint, the distal region includes a pair of nubs, and two members pivotally coupled by the pivot joint. In some embodiments, the two members each include a nub to form the pair of nubs. In some embodiments, the pair of nubs are sized to fit into notches, elongated slits, or openings present in the distal region of a device of the disclosure (e.g., a device of the first aspect of the disclosure). In some embodiments, the distal region of the extraction tool is sized to traverse the internal channel of the device from the proximal end to the distal end.

In a fifth aspect, the disclosure features a method of extracting the device from a bone. The method includes inserting the distal region of the extraction tool into the internal channel of the device, engaging (e.g., fixedly engaging) the pair of nubs of the extraction tool with notches, elongated slits, or openings present at the distal region of the device, and twisting the extraction tool once engaged with the device to remove the device from the bone. In some embodiments, the method includes twisting the extraction tool clockwise to remove the device from the bone or twisting the extraction tool counterclockwise to remove the device from the bone. In some embodiments, prior to extracting the device, the method includes removing a screw (e.g., a bone screw) from the device.

In a sixth aspect, the disclosure features a kit that contains a device as described herein (e.g., a device of the first aspect). The kit can be used for treating a bone defect, repairing or stabilizing bone, or securing an implant to bone. The kit may include instructions for using the kit to treat a bone defect, repair or stabilize bone, or secure an implant to bone. In some embodiments, the kit further includes one or more of the following, the insertion tool, an extraction tool, a pusher, a connector, a screw, a washer, a container including a biomaterial, a biomaterial dispenser, and a bone plate.

The insertion tool of the kit includes, from a proximal end to a distal end: a the proximal region, a central region, and a distal region, in which the central region connects the proximal region to the distal region, the proximal region includes a handle, the central region includes an unthreaded shaft with a diameter that ends with a lip, the distal region includes a shaft with a reduced diameter relative to the diameter of the shaft of the central region, and the distal region further includes a first set of threads distally disposed from a second set of threads and an unthreaded region separating the first and second sets of threads.

The extraction tool of the kit includes, from a proximal end to a distal end, a proximal region, a central region, and a distal region, in which the proximal region includes a grip handle, the central region includes a pivot joint, the distal region includes a pair of nubs, and two members pivotally coupled by the pivot joint.

The pusher of the kit includes a proximal region and a distal region, in which the proximal region of the pusher includes a handle, the distal region of the pusher includes a cylindrical shape, and the pusher further includes a threaded internal channel longitudinally extending through the proximal and distal regions. The pusher is configured for engagement with the insertion tool, such that the second set of threads of the distal region of the insertion tool is configured to be engaged with the threaded internal channel of the pusher.

The connector of the kit includes a frustoconical shape with a proximal region, a distal region, and an internal channel extending from the proximal region to the distal region, in which the proximal region includes Luer-lock threads, the distal region of the connector includes a plurality of circumferentially disposed, radially extended wedges, and the internal channel of the connector is sized to fit over the unthreaded region of the distal region of the insertion tool.

In some embodiments, the kit further includes the screw (e.g., a bone screw), in which the screw includes a length sufficient to traverse a length of the device. The screw includes, e.g., a screw head, a diameter or from about 1 mm to about 20 mm, a length of from about 5 mm to about 300 mm (e.g., about 5 mm to about 50 mm), threads having a thread pitch of from about 0.25 mm to about 2.5 mm (e.g., from about 0.25 mm to about 0.5 mm, from about 0.5 mm to about 1 mm, from about 0.5 mm to about 1.5 mm, from about 1 mm to about 2 mm, from about 1 mm to about 2.5 mm, or from about 1.5 mm to about 2.5 mm), a threadless body, and/or a material selected from the group consisting of stainless steel or an alloy thereof, titanium or an alloy thereof, magnesium or an alloy thereof, polyetheretherketone (PEEK), hydroxyapatite, tricalcium phosphate, tetracalcium phosphate, dicalcium phosphate, BIOGLASS® 45S5, ceramic composites, copper-based materials or composites, cobalt chrome, and combinations thereof.

The washer of the kit includes a proximal region, a distal region, and an internal channel extending longitudinally through the proximal region and the distal region of the washer, in which the washer is sized to fit within the internal channel of the proximal region of the device. The proximal region of the washer may have an outer diameter of from about 5 mm to about 30 mm and an inner diameter of from about 1 mm to about 20 mm. The distal region of the washer may have an outer diameter of from about 2.8 mm to about 19.8 mm and an inner diameter of from about 1 to about 20 mm. The outer diameter of the proximal region of the washer preferably larger than the outer diameter of the distal region of the washer.

In some embodiments, the kit further includes the biomaterial, which may include a polymeric adhesive, a bone void filler material, a cement, a phosphoserine-based bioadhesive, a cohesiveness agent, an osteogenic agent, a medicinal agent, or a pharmaceutical agent. In other embodiments, the biomaterial includes a calcium phosphate-based bone cement, polymethacrylate (PMMA), polymethylmethacrylate (PMMA), calcium sulfate, a metal alloy, a polysaccharide, a nucleic acid, a carbohydrate, a protein, a polypeptide, a poly($\alpha$-hydroxy acid), a poly(lactone), a poly(amino acid), a poly(anhydride), a poly(orthoester), a poly(anhydride-co-imide), a poly(orthocarbonate), a poly($\alpha$-hydroxy alkanoate), a poly(dioxanone), a poly(phosphoester), poly(L-lactide) (PLLA), poly(D,L-lactide) (PDLLA), polyglycolide (PGA), poly(lactide-co-glycolide (PLGA), poly(L-lactide-co-D, L-lactide), poly(D,L-lactide-co-trimethylene carbonate), polyhydroxybutyrate (PHB), poly($\varepsilon$-caprolactone), poly($\delta$-valerolactone), poly($\gamma$-butyrolactone), poly(caprolactone), polyacrylic acid, polycarboxylic acid, poly(allylamine hydrochloride), poly(diallyldimethylammonium chloride), poly(ethyleneimine), polypropylene fumarate, polyvinyl alcohol, polyvinylpyrrolidone, polyethylene, carbon fibers, poly(ethylene glycol), poly(ethylene oxide), poly(vinyl alcohol), poly(vinylpyrrolidone), poly(ethyloxazoline), poly(ethylene oxide)-co-poly(propylene oxide), a block copolymer, poly(ethylene terephthalate)polyamide, a homo-polymer or a co-polymer including one or more monomers selected from the group consisting of acrolein potassium, (meth)acrylamide, (meth) acrylic acid and salts thereof, (meth)acrylate, acrylonitrile, ethylene, ethylene glycol, ethyleneimine, ethyleneoxide, styrene sulfonate, vinyl acetate, vinyl alcohol, vinyl chloride, vinylpyrrolidone, a polyphenolic complexing agent selected from a gallotannin, an ellagitannin, a taragallotannin, a caffetannin, a proanthocyanidin, catechin, epicatechin, chlorogenic acid, and arbutin, alginic acid, arabic gum, guar gum, xantham gum, gelatin, chitin, chitosan, chitosan acetate, chitosan lactate, chondroitin sulfate, N,O-carboxymethyl chitosan, a dextran, fibrin glue, glycerol, hyaluronic acid, sodium hyaluronate, a cellulose, a glucosamine, a proteoglycan, a starch, lactic acid, a pluronic, sodium glycerophosphate, collagen, glycogen, a keratin, silk, transforming growth factors-beta (TGF-$\beta$), an activin, an inhibin, a bone morphogenetic proteins (BMP), an antibiotic, an enzyme inhibitor, an antihistamine, an anti-inflammatory agent, a muscle relaxant, an anti-spasmodics, an analgesic, a prostaglandin, an anti-depressant, a trophic factor, or a hormone.

In some embodiments, the kit further includes the biomaterial dispenser, which can include a tube connected to a syringe, a vial, or a reservoir, e.g., that is sized to hold a volume of the biomaterial. In some embodiments, the biomaterial dispenser contains the biomaterial (i.e., the biomaterial is preloaded into the biomaterial dispenser).

In some embodiments, the kit further includes the bone plate, which may have one hole or multiple holes (e.g., two or more bone plate holes).

In a seventh aspect, the disclosure features a device including a unitary body including from a proximal end to a distal end: a proximal region, a central region, and a distal region, in which the central region joins the proximal region to the distal region, and in which: a) the device includes an internal channel extending longitudinally through the proximal, central, and distal regions; b) the proximal region includes a compressible body and an opening to the internal channel; c) the central region includes i) a plurality of openings and ii) an expandable and/or compressible body configured to radially expand or compress, in which the expandible and/or compressible body includes a plurality of longitudinal segments; and d) the distal region includes an opening to the internal channel.

In some embodiments, a) the proximal region includes an inner diameter of from about 3 mm to about 20 mm and an outer diameter of from about 4 mm to about 25 mm; b) the central region includes an inner diameter of from 1 mm to about 20 mm and an outer diameter of from about 1.25 mm to about 25 mm; c) the distal region includes an inner diameter of from 1 mm to about 20 mm and an outer diameter of from about 4 mm to about 25 mm; or d) in which the proximal region, the central region, and the distal region include an inner diameter of from 1 mm to about 20 mm and an outer diameter of from about 1.25 mm to about 25 mm.

In some embodiments, the outer diameter of the proximal and distal regions is larger than the outer diameter of the central region.

In some embodiments, the device further has a length of from about 9 mm to about 110 mm. In some embodiments, the proximal region includes a length of from about 2 mm to about 30 mm (e.g., from about 2 mm to about 5 mm, from about 2 mm to about 10 mm, from about 5 mm to about 10 mm, from about 5 mm to about 15 mm, from about 10 mm to about 15 mm, from about 10 mm to about 20 mm, from about 15 mm to about 25 mm, or from about 20 mm to about 30 mm). In some embodiments, the central region includes a length of from about 5 mm to about 100 mm. In some embodiments, the distal region includes a length of from about 2 mm to about 30 mm (e.g., from about 2 mm to about 5 mm, from about 2 mm to about 10 mm, from about 5 mm to about 10 mm, from about 5 mm to about 15 mm, from about 10 mm to about 15 mm, from about 10 mm to about 20 mm, from about 15 mm to about 25 mm, or from about 20 mm to about 30 mm).

In some embodiments, the proximal region includes a wall thickness of from about 0.6 mm to about 2.5 mm, in which optionally the wall thickness of the proximal region is about 1.5 mm. In some embodiments, the central region includes a wall thickness of from about 0.15 mm to about 2 mm, in which optionally the wall thickness of the central region is about 0.25 mm.

In some embodiments, the distal region includes a wall thickness of from about 0.6 mm to about 2.5 mm, in which optionally the wall thickness of the distal region is about 1.5 mm.

In some embodiments, the outer diameter from the proximal end to the distal end is the same. In some embodiments, the proximal region, the central region, and the distal region include an inner diameter of from 1 mm to about 20 mm and an outer diameter of from about 1.25 mm to about 25 mm.

In some embodiments, the proximal region, or the compressible body of the proximal region, includes a mesh or a mesh-like structure. In some embodiments, the mesh or mesh-like structure includes a diamond, square, circular, weave, or oval opening pattern. In some embodiments, the mesh or mesh-like structure is woven, perforated, crimped, welded, molded, sintered, or 3D-printed. In some embodiments, the mesh or mesh-like structure includes a percent porosity from about 5% to about 90% (e.g., from about 5% to about 10%, from about 5% to about 20%, from about 10% to about 25%, from about 20% to about 40%, from about 20% to about 70%, from about 30% to about 60%, from about 40% to about 60%, from about 50% to about 70%, from about 50% to about 90%, or from about 70% to about 90%). In some embodiments, the mesh or mesh-like structure includes a wire gauge from 5 to 50 (e.g., from 5 to 10, from 10 to 20, from 10 to 30, from 20 to 40, or from 30 to 40).

In some embodiments, the compressible body of the proximal region includes a flared shape.

In some embodiments, the compressible body of the proximal region includes a plurality of circumferentially disposed compressible wings. In some embodiments, each of the wings includes: a) a rectangular, round, elliptical, triangular, jagged, or parabolic shape, including a length and a width; b) a proximal end disconnected from the proximal region and configured to protrude outwardly from the proximal region; and c) a distal end connected to the proximal region and configured to pivot the proximal end of the wing away from the proximal region. In some embodiments, the proximal end of each of the wings: a) protrudes outwardly from the proximal region at an angle of from about 2° to 10°; and b) is configured to reversibly deflect towards the proximal region to substantially eliminate the outward protrusion of the proximal end upon compression. In some embodiments, the wings include a length of from about 5 mm to about 20 mm and/or a width of from 1 mm to 15 mm. In some embodiments, the device includes 3 to 20 wings, preferably in which the device includes 4 to 8 wings, such as 6 wings.

In some embodiments, the plurality of openings includes slits or perforations, in which optionally the plurality of openings includes helical slits, segmented slits, longitudinal slits, circumferential slits, circular perforations, elliptical perforations, triangular perforations, polygonal perforations, or amorphous perforations. In some embodiments, the openings extend into the proximal region and/or the distal region.

In some embodiments, the expandable and/or compressible body of the central region includes 2 to about 5000 openings (e.g., from about 2 to about 100, from about 2 to about 200, from about 2 to about 300, from about 2 to about 400, from about 2 to about 500, from about 2 to about 750, from about 2 to about 1000, from about 2 to about 1500, from about 2 to about 2000, from about 2 to about 3000, from about 2 to about 4000, from about 10 to about 50, from about 10 to about 100, from about 50 to about 100, from about 50 to about 250, from about 50 to about 500, from about 100 to about 250, from about 250 to about 500, from about 500 to about 1000, from about 1000 to about 2000, from about 2000 to about 3000, from about 3000 to about 4000, from about 4000 to about 5000, or from about 2500 to about 5000).

In some embodiments, the openings include a width of from about 0.01 mm to about 2 mm (e.g., from about 0.01 mm to about 0.1 mm, from about 0.01 mm to about 0.3 mm, from about 0.01 mm to about 0.5 mm, from about 0.1 mm to about 0.5 mm, from about 0.1 mm to about 1 mm, from about 0.5 mm to about 1 mm, from about 1 mm to about 1.5 mm, or from about 1.5 mm to about 2 mm) and a length of from about 0.01 mm to about 20 mm. In some embodiments, the plurality of openings includes perforations, in which the perforations include a circular, elliptical, triangular, polygonal, or amorphous shape including a diameter of from about 0.01 mm to about 5 mm (e.g., from about 0.01 mm to about 0.1 mm, from about 0.01 mm to about 0.3 mm, from about 0.01 mm to about 0.5 mm, from about 0.1 mm to about 0.5 mm, from about 0.1 mm to about 1 mm, from about 0.5 mm to about 1 mm, from about 1 mm to about 1.5 mm, from about 1 mm to about 5 mm, from about 1.5 mm to about 2 mm, from about 2 mm to about 5 mm, from about 2 mm to about 8 mm, from about 5 mm to about 10 mm, from about 5 mm to about 15 mm, from about 10 mm to about 15 mm, or from about 10 mm to about 20 mm).

In some embodiments, the openings include staggered or straight openings.

In some embodiments, the plurality of openings includes perforations, in which the perforations are connected by slits, in which optionally the slits include a helical slit, a segmented slit, a longitudinal slit, or a circumferential slit. In some embodiments, the slit connects 2 to 100 perforations (e.g., 2 to 10, 2 to 20, 10 to 20, 10 to 30, 10 to 50, 20 to 40, 20 to 60, 40 to 80, 50 to 100, 60 to 80, or 80 to 100).

In some embodiments, the openings include perforations, in which the perforations form a mesh or mesh-life structure. In some embodiments, the mesh or mesh-like structure is woven, perforated, crimped, welded, molded, sintered, or 3D-printed. In some embodiments, the mesh or mesh-like structure includes a percent porosity from about 5% to about 90% (e.g., from about 5% to about 10%, from about 5% to about 20%, from about 10% to about 25%, from about 20% to about 40%, from about 20% to about 70%, from about 30% to about 60%, from about 40% to about 60%, from about 50% to about 70%, from about 50% to about 90%, or from about 70% to about 90%). In some embodiments, the mesh or mesh-like structure includes a wire gauge from 5 to 50 (e.g., from 5 to 10, from 10 to 20, from 10 to 30, from 20 to 40, or from 30 to 40).

In some embodiments, the expandable and/or compressible body of the central region includes 1 to 70 longitudinal grooves (e.g., from 1 to 2, from 1 to 3, from 1 to 4, from 2 to 4, from 2 to 5, from 2 to 6, from 4 to 8, from 5 to 10, from 6 to 12, from 5 to 15, from 10 to 20, from 20 to 40, from 30 to 60, or from 50 to 70). In some embodiments, the longitudinal grooves include a depth of from about 0.15 mm to about 2.5 mm (e.g., from about 0.15 mm to about 0.5 mm, from about 0.15 mm to about 1 mm, from about 0.15 mm to about 1.5 mm, from about 0.5 mm to about 1 mm, from about 0.5 mm to about 1.5 mm, from about 1 mm, to about 2 mm, from about 1 mm to about 3 mm, from about 2 mm to about 3 mm, about 0.15 mm, about 0.2 mm, about 0.3 mm, about 0.4 mm, about 0.5 mm about 0.6 mm, about 0.7 mm, about 0.8 mm, about 0.9 mm, about 1 mm, about 1.1 mm, about 1.2 mm, about 1.3 mm, about 1.4 mm, about 1.5 mm, about 1.6 mm, about 1.7 mm, about 1.8 mm, about 1.9 mm, about 2 mm, about 2.1 mm, about 2.2 mm, about 2.3 mm, about 2.4 mm, or about 2.5). In some embodiments, the longitudinal grooves extend from a proximal end of the central region to a distal end of the central region.

In some embodiments, the distal end of the distal region includes a blunt and/or tapered edge. In some embodiments, the distal end of the distal region includes from 2 to 5 milling flutes, in which optionally the distal region includes 3 milling flutes. In some embodiments, the distal region includes from 2 to 4 notches and/or elongated slits, in which optionally the slits include a helical slit, a segmented slit, a longitudinal slit, or a circumferential slit.

In some embodiments, the distal region includes from 1 to 5000 openings, in which optionally the diameter of each opening is from about 0.01 mm to about 5 mm.

In some embodiments, the proximal region, the central region, and/or the distal region include an internal or external protrusion. In some embodiments, the internal or external protrusion includes one or more of a bump, a spike, a tab, a fin, a ridge, or a raised surface. In some embodiments, the internal or external protrusion extends from a proximal end to a distal end of the device, the proximal region, the central region, or the distal region. In some embodiments, a plurality of internal or external protrusions extends from a proximal end to a distal end of the device, the proximal region, the central region, or the distal region. In some embodiments, the device includes from 1 to 5000 internal or external protrusions. The internal or external protrusions, which can be shaped in a thread-like pattern, can be configured to replicate the function of a thread.

In some embodiments, the proximal region, the central region, and/or the distal region include an internal or external thread. In some embodiments, the internal or external thread has a thread pitch of from about 0.25 mm to about 2.5 mm (e.g., from about 0.25 mm to about 0.5 mm, from about 0.5 mm to about 1 mm, from about 0.5 mm to about 1.5 mm, from about 1 mm to about 2 mm, from about 1 mm to about 2.5 mm, or from about 1.5 mm to about 2.5 mm). In some embodiments, the internal or external thread is formed from protrusions, grooves, waves, or a mesh. In some embodiments, the protrusions, grooves, or waves are at from about 1 to about 365 points per 360° (e.g., at 4-20 equidistant points along the circumference of the proximal, central, and/or distal region). In some embodiments, the internal or external thread includes a continuous thread or non-continuous thread. In some embodiments, the non-continuous thread includes a gap, in which optionally the gap has a length from about 0.5 mm to about 30 mm. In some embodiments, the internal or external thread is broken by a slit, in which optionally the slit is a helical slit, a segmented slit, a longitudinal slit, or a circumferential slit.

In some embodiments, the plurality of longitudinal segments is connected by a plurality of expandable arms. In some embodiments, the proximal region and/or distal region include a plurality of segments. In some embodiments, the segments include longitudinal segments. In some embodiments, the plurality of segments of the central region extends into the proximal region and/or distal region. In some embodiments, the plurality of segments extends from the proximal end, through the central region, to the distal end. In some embodiments, the plurality of segments is polygonal, circular, triangular, elliptical, cylindrical, or amorphous; in which, optionally the plurality of segments is rectangular. In some embodiments, the device includes from 2 to 20 (e.g., from 2 to 4, from 2 to 6, from 2 to 8, from 2 to 10, from 4 to 8, from 4 to 10, from 4 to 12, from 10 to 16, or from 10 to 20) segments, in which the expandable body includes from 1 to 100 expandable arms. In some embodiments, the unitary body includes from 1 to 50 expandable arms per each segment. In some embodiments, each of the segments is the same size. In some embodiments, each of the segments is separated by at least one opening, in which the opening has a maximum width of about 0.1 mm to about 50 mm. In some embodiments, each of the segments includes a length of about 9 mm to about 110 mm. In some embodiments, each of the segments includes a width of about 0.1 mm to about 50 mm. In some embodiments, the expandable arms are separated by at least one opening, in which the opening has a maximum width of about 0.1 mm to about 50 mm. In some embodiments, the unitary body includes from 1 to 50 pairs of expandable arms. In some embodiments, the pairs are separated by at least one opening, in which the opening has a maximum width of about 0.1 mm to about 20 mm. In some embodiments, the expandable arms are c-shaped, s-shaped, u-shaped, or z-shaped. In some embodiments, the proximal region, central region, and/or distal region includes at least one expandable arm.

In some embodiments, the central region includes i) a first section including the expandable and/or compressible body, and (ii) a second section including the plurality of openings. In some embodiments, the central region includes from a proximal end to a distal end: i) the first section, and ii) the second section. In some embodiments, the first section includes a length of from about 5 mm to about 100 mm. In some embodiments, the second section includes a length of from about 5 mm to about 100 mm.

In an eight aspect, the disclosure features a device including a unitary body including a proximal end and a distal end, in which: a) the unitary body includes an expandable and/or compressible body configured to radially expand or compress, in which the unitary body includes a rolled surface having an internal channel extending longitudinally from the proximal end to the distal end; b) the unitary body includes a plurality of openings; c) the internal channel includes an internal protrusion and/or internal thread; d) the proximal end includes an opening to the internal channel; and e) the distal end includes an opening to the internal channel.

In some embodiments, the unitary body includes from the proximal end to the distal end: a proximal region, a central region, and a distal region, in which the central region joins the proximal region to the distal region. In some embodiments, the proximal region includes a length of from about 0.5 mm to about 30 mm. In some embodiments, the central region includes a length of from about 5 mm to about 50 mm. In some embodiments, the distal region includes a length of from about 0.5 mm to about 30 mm. In some embodiments, the proximal region and/or the distal region do not include openings.

In some embodiments, a) the unitary body includes an internal diameter from about 1.25 mm to about 25 mm; b)

the proximal region includes an inner diameter of from about 3 mm to about 20 mm and an outer diameter of from about 4 mm to about 25 mm; c) the central region includes an inner diameter of from 1 mm to about 20 mm and an outer diameter of from about 1.25 mm to about 25 mm; d) the distal region includes an inner diameter of from 1 mm to about 20 mm and an outer diameter of from about 4 mm to about 25 mm; or e) the proximal region, the central region, and the distal region include an inner diameter of from 1 mm to about 20 mm and an outer diameter of from about 1.25 mm to about 25 mm.

In some embodiments, the outer diameter from the proximal end to the distal end is constant.

In some embodiments, the device includes a length of from about 9 mm to about 110 mm.

In some embodiments, the unitary body includes a wall thickness of from about 0.6 mm to about 2.5 mm. In some embodiments, the proximal region includes a wall thickness of from about 0.6 mm to about 2.5 mm; in which optionally the wall thickness of the proximal region is about 1.5 mm. In some embodiments, the central region includes a wall thickness of from about 0.15 mm to about 2 mm; in which optionally the wall thickness of the central region is about 0.25 mm. In some embodiments, the distal region includes a wall thickness of from about 0.6 mm to about 2.5 mm; in which optionally the wall thickness of the distal region is about 1.5 mm.

In some embodiments, the plurality of openings includes slits or perforations; optionally in which the openings include helical slits, segmented slits, longitudinal slits, circumferential slits, circular perforations, oval perforations, or polygonal perforations. In some embodiments, the openings include staggered openings or straight openings.

In some embodiments, the plurality of openings includes perforations, in which the perforations are connected by the slits. In some embodiments, from 2 to 100 2 to 10, 2 to 20, 10 to 20, 10 to 30, 10 to 50, 20 to 40, 20 to 60, 40 to 80, 50 to 100, 60 to 80, or 80 to 100) perforations are connected by a slit, optionally in which the slit includes a helical slit, a segmented slit, a longitudinal slit, or a circumferential slit.

In some embodiments, the openings in the unitary body form a mesh or mesh-like structure. In some embodiments, the mesh or mesh-like structure is woven, perforated, crimped, welded, molded, sintered, or 3D-printed. In some embodiments, the mesh or mesh-like structure includes a percent porosity from about 5% to about 90% (e.g., from about 5% to about 10%, from about 5% to about 20%, from about 10% to about 25%, from about 20% to about 40%, from about 20% to about 70%, from about 30% to about 60%, from about 40% to about 60%, from about 50% to about 70%, from about 50% to about 90%, or from about 70% to about 90%). In some embodiments, the mesh or mesh-like structure includes a wire gauge from 5 to 50 (e.g., from 5 to 10, from 10 to 20, from 10 to 30, from 20 to 40, or from 30 to 40).

In some embodiments, the unitary body includes 2 to 5000 openings (e.g., from about 2 to about 100, from about 2 to about 200, from about 2 to about 300, from about 2 to about 400, from about 2 to about 500, from about 2 to about 750, from about 2 to about 1000, from about 2 to about 1500, from about 2 to about 2000, from about 2 to about 3000, from about 2 to about 4000, from about 10 to about 50, from about 10 to about 100, from about 50 to about 100, from about 50 to about 250, from about 50 to about 500, from about 100 to about 250, from about 250 to about 500, from about 500 to about 1000, from about 1000 to about 2000, from about 2000 to about 3000, from about 3000 to about 4000, from about 4000 to about 5000, or from about 2500 to about 5000). In some embodiments, the central region includes 2 to 5000 openings (e.g., from about 2 to about 100, from about 2 to about 200, from about 2 to about 300, from about 2 to about 400, from about 2 to about 500, from about 2 to about 750, from about 2 to about 1000, from about 2 to about 1500, from about 2 to about 2000, from about 2 to about 3000, from about 2 to about 4000, from about 10 to about 50, from about 10 to about 100, from about 50 to about 100, from about 50 to about 250, from about 50 to about 500, from about 100 to about 250, from about 250 to about 500, from about 500 to about 1000, from about 1000 to about 2000, from about 2000 to about 3000, from about 3000 to about 4000, from about 4000 to about 5000, or from about 2500 to about 5000).

In some embodiments, the openings include a width of from about 0.1 mm to about 2 mm and a length of from about 0.1 mm to about 20 mm. In some embodiments, the plurality of openings includes perforations, in which the perforations include a circular or elliptical shape including a diameter of from about 0.1 mm to about 5 mm.

In some embodiments, the expandable and/or compressible body includes 2 to 70 (e.g., from 1 to 2, from 1 to 3, from 1 to 4, from 2 to 4, from 2 to 5, from 2 to 6, from 4 to 8, from 5 to 10, from 6 to 12, from 5 to 15, from 10 to 20, from 20 to 40, from 30 to 60, from 50 to 70) longitudinal grooves. In some embodiments, the longitudinal grooves include a depth of from about 0.15 mm to about 2.5 mm (e.g., from about 0.15 mm to about 0.5 mm, from about 0.15 mm to about 1 mm, from about 0.15 mm to about 1.5 mm, from about 0.5 mm to about 1 mm, from about 0.5 mm to about 1.5 mm, from about 1 mm, to about 2 mm, from about 1 mm to about 3 mm, from about 2 mm to about 3 mm, about 0.15 mm, about 0.2 mm, about 0.3 mm, about 0.4 mm, about 0.5 mm about 0.6 mm, about 0.7 mm, about 0.8 mm, about 0.9 mm, about 1 mm, about 1.1 mm, about 1.2 mm, about 1.3 mm, about 1.4 mm, about 1.5 mm, about 1.6 mm, about 1.7 mm, about 1.8 mm, about 1.9 mm, about 2 mm, about 2.1 mm, about 2.2 mm, about 2.3 mm, about 2.4 mm, or about 2.5). In some embodiments, the longitudinal grooves extend from a proximal end of the central region to a distal end of the central region.

In some embodiments, the proximal region, the central region, and/or distal region include the internal protrusion. In some embodiments, the unitary body includes an external protrusion, in which optionally the proximal region, the central region, and/or the distal region includes an external protrusion or in which optionally the external protrusion is a bump, a spike, a tab, a fin, a ridge, or a raised surface. In some embodiments, the internal protrusion is a bump, a spike, a tab, a fin, a ridge, or a raised surface. In some embodiments, the internal protrusion or the external protrusion extends from a proximal end to a distal end of the device, the proximal region, the central region, or the distal region. In some embodiments, a plurality of internal or external protrusions extends from a proximal end to a distal end of the device, the proximal region, the central region, or the distal region. In some embodiments, the device includes from 1 to 5000 internal or external protrusions. The internal or external protrusions, which can be shaped in a thread-like pattern, can be configured to replicate the function of a thread.

In some embodiments, the proximal region, the central region, and/or distal region include the internal thread. In some embodiments, the unitary body includes an external thread; in which optionally the proximal region, the central region, and/or distal region include an external thread. In some embodiments, the internal or external thread has a thread pitch of from about 0.25 mm to about 2.5 mm (e.g., from about 0.25 mm to about 0.5 mm, from about 0.5 mm to about 1 mm, from about 0.5 mm to about 1.5 mm, from about 1 mm to about 2 mm, from about 1 mm to about 2.5 mm, or from about 1.5 mm to about 2.5 mm). In some embodiments, the internal or external thread is formed from protrusions, grooves, waves, or a mesh. In some embodiments, the protrusions, grooves, or waves are at from about 1 to about 365 points per 360° (e.g., at 4-20 equidistant points along the circumference of the proximal, central, and/or distal region). In some embodiments, the internal or external thread includes a continuous thread or non-continuous thread. In some embodiments, the internal or external thread is broken by a slit. In some embodiments, the non-continuous thread includes a gap, in which the gap has a length from about 0.5 mm to about 30 mm.

In some embodiments, the proximal end includes a blunt and/or tapered edge. In some embodiments, the distal end includes a blunt and/or tapered edge. In some embodiments, the distal end includes a milling flute. In some embodiments, the distal end includes from 2 to 5 milling flutes; in which optionally the distal region includes 3 milling flutes. In some embodiments, the distal region includes from 2 to 4 notches and/or elongated slits. In some embodiments, the distal region includes a plurality of bendable tips disposed at the proximal end and/or the distal end.

In some embodiments, the rolled surface has a left side and ride side, in which upon radially expanding, the left side and right-side overlap by from about 0.1 mm to about 20 mm. In some embodiments, upon radially expanding, the rolled surface does not overlap. In some embodiments, the right side sits on top of the left side. In other embodiments, the left side sits on top of the right side.

In some embodiments, the device is made from or includes a material selected from the group consisting of stainless steel or an alloy thereof, titanium or an alloy thereof, magnesium or an alloy thereof, polyetheretherketone (PEEK), hydroxyapatite, tricalcium phosphate, tetracalcium phosphate, dicalcium phosphate, BIOGLASS® 45S5, ceramic composites, copper-based materials or composites, cobalt chrome, xenograft biomaterials, and combinations thereof.

In a ninth aspect, the disclosure features a device of the seventh aspect or the eighth aspect preloaded in a funnel.

In a tenth aspect, the disclosure features a system including the device of the seventh aspect or the eighth aspect connected to a connector. In some embodiments, the device is pre-loaded into a funnel.

In an eleventh aspect, the disclosure features a method of bone repair including inserting the device of the seventh aspect or the eighth aspect into a bone.

In some embodiments, prior to inserting the device into the bone, the method includes drilling a hole into the bone, in which the inserting includes placing the device in the hole.

In some embodiments, the method further includes expanding or compressing the device.

In some embodiments, the method further includes inserting the device into a funnel.

In some embodiments, the method further includes compressing the device by inserting the device into a funnel.

In some embodiments, prior to or after insertion of the device into the funnel, the method further includes aligning the funnel with the hole in the bone.

In some embodiments, prior to or after insertion of the device into the funnel, the method further includes reversibly connecting the funnel to the proximal end of the device.

In some embodiments, the method further includes inserting the device through the funnel into the hole in the bone, in which the device expands as it exits or upon exiting the funnel.

In some embodiments, the method further includes introducing a biomaterial to the internal channel of the device after expansion of the expandable body.

In some embodiments, prior to or after insertion of the device in the bone, the method further includes inserting a connector into the internal channel at the proximal region of the device, in which the connector includes a frustoconical shape having a proximal region, a distal region, and an internal channel extending from the proximal region to the distal region, and in which: a) the proximal region includes Luer-lock threads; and b) the distal region of the connector includes a plurality of circumferentially disposed, radially extended wedges.

In some embodiments, the method includes fastening the connector to the internal channel at the proximal region of the device after the device is inserted into the bone and after the proximal region of the device is secured in the bone.

In some embodiments, the connector further includes an alignment marker.

In some embodiments, the method further includes coupling a biomaterial dispenser including a biomaterial to the connector using the Luer-lock threads.

In some embodiments, the biomaterial dispenser includes a syringe, a vial, or a reservoir; in which optionally the syringe, the vial, or the reservoir include a tube.

In some embodiments, the method includes introducing a volume of the biomaterial of from about 1 ml to about 20 ml (e.g., from about 1 ml to about 2 ml, from about 1 ml to about 3 ml, from about 1 ml to about 4 ml, from about 1 ml to about 5 ml, from about 1 ml to about 10 ml, from about 5 ml to about 10 ml, from about 5 ml to about 15 ml, from about 10 ml to about 15 ml, from about 15 ml to about 20 ml, or from about 15 ml to about 20 ml) to the internal channel of the device.

In some embodiments, the volume of the biomaterial is about 2.5 ml, about 5 ml, or about 10 ml.

In some embodiments, the biomaterial includes a polymeric adhesive, a bone void filler material, a cement, a phosphoserine-based bioadhesive, a cohesiveness agent, an osteogenic agent, a medicinal agent, or a pharmaceutical agent.

In some embodiments, the biomaterial includes a calcium phosphate-based bone cement, a non-self-hardening calcium phosphate based bone void filler, a flowable xenograft bone void filler, polymethacrylate (PMMA), polymethylmethacrylate (PMMA), calcium sulfate, a metal alloy, a polysaccharide, a nucleic acid, a carbohydrate, a protein, a polypeptide, a poly(α-hydroxy acid), a poly(lactone), a poly (amino acid), a poly(anhydride), a poly(orthoester), a poly (anhydride-co-imide), a poly(orthocarbonate), a poly(α-hydroxy alkanoate), a poly(dioxanone), a poly (phosphoester), poly(L-lactide) (PLLA), poly(D,L-lactide) (PDLLA), polyglycolide (PGA), poly(lactide-co-glycolide (PLGA), poly(L-lactide-co-D, L-lactide), poly(D,L-lactide-co-trimethylene carbonate), polyhydroxybutyrate (PHB), poly(ε-caprolactone), poly(δ-valerolactone), poly(γ-butyrolactone), poly(caprolactone), polyacrylic acid, polycarboxylic acid, poly(allylamine hydrochloride), poly(diallyldimethylammonium chloride), poly(ethyleneimine), polypropylene fumarate, polyvinyl alcohol, polyvinylpyrrolidone, polyethylene, carbon fibers, poly(ethylene glycol), poly(ethylene oxide), poly(vinyl alcohol), poly(vinylpyrrolidone), poly(ethyloxazoline), poly(ethylene oxide)-co-poly(propylene oxide), a block copolymer, poly(ethylene terephthalate)polyamide, a homo-polymer or a co-polymer including one or more monomers selected from the group consisting of acrolein potassium, (meth)acrylamide, (meth) acrylic acid and salts thereof, (meth)acrylate, acrylonitrile, ethylene, ethylene glycol, ethyleneimine, ethyleneoxide, styrene sulfonate, vinyl acetate, vinyl alcohol, vinyl chloride, vinylpyrrolidone, a polyphenolic complexing agent selected from a gallotannin, an ellagitannin, a taragallotannin, a caffetannin, a proanthocyanidin, catechin, epicatechin, chlorogenic acid, and arbutin, alginic acid, arabic gum, guar gum, xantham gum, gelatin, chitin, chitosan, chitosan acetate, chitosan lactate, chondroitin sulfate, N,O-carboxymethyl chitosan, a dextran, fibrin glue, glycerol, hyaluronic acid, sodium hyaluronate, a cellulose, a glucosamine, a proteoglycan, a starch, lactic acid, a pluronic, sodium glycerophosphate, collagen, glycogen, a keratin, silk, transforming growth factors-beta (TGF-β), an activin, an inhibin, a bone morphogenetic proteins (BMP), an antibiotic, an enzyme inhibitor, an antihistamine, an anti-inflammatory agent, a muscle relaxant, an anti-spasmodics, an analgesic, a prostaglandin, an anti-depressant, a trophic factor, or a hormone.

In some embodiments, the method further includes uncoupling the biomaterial dispenser and/or the connector from the proximal region of the device after the biomaterial is introduced to the internal channel of the device.

In some embodiments, the method further includes uniformly distributing the biomaterial throughout the device and into the bone surrounding the device.

In some embodiments, the method further includes uncoupling the biomaterial dispenser and/or the connector from the proximal region of the device after the biomaterial is introduced to the internal channel of the device.

In some embodiments, the biomaterial hardens thereby securing the device to the bone.

In some embodiments, the method further includes inserting a screw including a length through the internal channel of the device (e.g., before or after hardening of the biomaterial).

In some embodiments, the method further includes aligning the screw with an internal protrusion or thread.

In some embodiments, the length of the screw traverses a length of the internal channel of the device, and in which the method further includes fastening a distal end of the screw to a distal cortex of the bone; in which, optionally, tightening the screw in the distal cortex causes bone compression.

In some embodiments, tightening the screw in the distal cortex does not cause rotation of the device.

In a twelfth aspect, the disclosure features a method of extracting the device of the seventh aspect or the eighth aspect from a bone, including: a) inserting a distal region of an extraction tool into the internal channel of the device; and c) twisting the extraction tool to remove the device from the bone.

In some embodiments, twisting the extraction tool does causes rotation of the device.

In some embodiments, the method further includes a) twisting the extraction tool clockwise to remove the device from the bone; or b) twisting the extraction tool counter-clockwise to remove the device from the bone.

In some embodiments, prior to extracting the device, the method includes removing a screw from the device.

In a thirteenth aspect, the disclosure features a kit for treating a bone defect including the device of the seventh aspect or the eighth aspect.

In some embodiments, the kit further includes one or more of the following: a) an insertion tool; b) an extraction tool; c) a funnel; d) a connector; e) a screw or suture anchor; f) a washer; g) a container including a biomaterial; h) a biomaterial dispenser; and i) a bone plate.

In some embodiments, the kit further includes the connector, in which the connector includes a frustoconical shape with a proximal region, a distal region, and an internal channel extending from the proximal region to the distal region, in which: a) the proximal region includes Luer-lock threads; and b) the distal region of the connector includes a plurality of circumferentially disposed, radially extended wedges.

In some embodiments, the kit further includes the screw, in which the screw includes a length sufficient to traverse a length of the device.

In some embodiments, the screw includes: a) a screw head; b) a diameter or from about 1 mm to about 20 mm; c) a length of from about 5 mm to about 300 mm; d) threads having a thread pitch of from about 0.25 mm to about 2.5 mm; e) a threadless body; or f) a material selected from the group consisting of stainless steel or an alloy thereof, titanium or an alloy thereof, magnesium or an alloy thereof, polyetheretherketone (PEEK), hydroxyapatite, tricalcium phosphate, tetracalcium phosphate, dicalcium phosphate, BIOGLASS® 45S5, ceramic composites, copper-based materials or composites, cobalt chrome, and combinations thereof.

In some embodiments, the kit further includes the washer, in which the washer includes a proximal region, a distal region, and an internal channel extending longitudinally through the proximal region and the distal region of the washer, in which the washer is sized to fit within the internal channel of the proximal region of the device.

In some embodiments, a) the proximal region of the washer includes an outer diameter of from about 5 mm to about 30 mm; b) the proximal region of the washer includes an inner diameter of from about 2 mm to about 20 mm; c) the distal region of the washer includes an outer diameter of from about 2.8 mm to about 19.8 mm; d) the distal region of the washer includes an inner diameter of from about 2 to about 20 mm; and/or e) the outer diameter of the washer proximal region is larger than the outer diameter of the washer distal region.

In some embodiments, the kit further includes the biomaterial.

In some embodiments, the biomaterial includes a polymeric adhesive, a bone void filler material, a cement, a phosphoserine-based bioadhesive, a cohesiveness agent, an osteogenic agent, a medicinal agent, or a pharmaceutical agent.

In some embodiments, the biomaterial includes a calcium phosphate-based bone cement, a non-self-hardening calcium phosphate based bone void filler, a flowable xenograft bone void filler, polymethacrylate (PMMA), polymethylmethacrylate (PMMA), calcium sulfate, a metal alloy, a polysaccharide, a nucleic acid, a carbohydrate, a protein, a polypeptide, a poly(α-hydroxy acid), a poly(lactone), a poly (amino acid), a poly(anhydride), a poly(orthoester), a poly (anhydride-co-imide), a poly(orthocarbonate), a poly(α-hydroxy alkanoate), a poly(dioxanone), a poly (phosphoester), poly(L-lactide) (PLLA), poly(D,L-lactide) (PDLLA), polyglycolide (PGA), poly(lactide-co-glycolide (PLGA), poly(L-lactide-co-D, L-lactide), poly(D,L-lactideco-trimethylene carbonate), polyhydroxybutyrate (PHB), poly(ε-caprolactone), poly(δ-valerolactone), poly(γ-butyrolactone), poly(caprolactone), polyacrylic acid, polycarboxylic acid, poly(allylamine hydrochloride), poly(diallyldimethylammonium chloride), poly(ethyleneimine), polypropylene fumarate, polyvinyl alcohol, polyvinylpyrrolidone, polyethylene, carbon fibers, poly(ethylene glycol), poly(ethylene oxide), poly(vinyl alcohol), poly(vinylpyrrolidone), poly(ethyloxazoline), poly(ethylene oxide)-co-poly(propylene oxide), a block copolymer, poly(ethylene terephthalate)polyamide, a homo-polymer or a co-polymer including one or more monomers selected from the group consisting of acrolein potassium, (meth)acrylamide, (meth)acrylic acid and salts thereof, (meth)acrylate, acrylonitrile, ethylene, ethylene glycol, ethyleneimine, ethyleneoxide, styrene sulfonate, vinyl acetate, vinyl alcohol, vinyl chloride, vinylpyrrolidone, a polyphenolic complexing agent selected from a gallotannin, an ellagitannin, a taragallotannin, a caffetannin, a proanthocyanidin, catechin, epicatechin, chlorogenic acid, and arbutin, alginic acid, arabic gum, guar gum, xantham gum, gelatin, chitin, chitosan, chitosan acetate, chitosan lactate, chondroitin sulfate, N,O-carboxymethyl chitosan, a dextran, fibrin glue, glycerol, hyaluronic acid, sodium hyaluronate, a cellulose, a glucosamine, a proteoglycan, a starch, lactic acid, a pluronic, sodium glycerophosphate, collagen, glycogen, a keratin, silk, transforming growth factors-beta (TGF-β), an activin, an inhibin, a bone morphogenetic proteins (BMP), an antibiotic, an enzyme inhibitor, an antihistamine, an anti-inflammatory agent, a muscle relaxant, an anti-spasmodics, an analgesic, a prostaglandin, an anti-depressant, a trophic factor, or a hormone.

In some embodiments, the kit further includes the biomaterial dispenser.

In some embodiments, the biomaterial dispenser includes a tube connected to a syringe, a vial, or a reservoir, in which optionally, the tube further includes the biomaterial.

In some embodiments, the kit further includes the bone plate.

In some embodiments, the bone plate includes from two or more bone plate holes.

In some embodiments, the kit further includes a suture anchor, optionally, in which the suture anchor is a soft tissue suture anchor. In some embodiments, the kit further includes an intramedullary pin. In some embodiments, the kit further includes a nail device. In some embodiments, the kit further includes a spinal attachment device. The suture anchor, intramedullary pin, nail device, and/or spinal attachment device can be made from a material selected from stainless steel or an alloy thereof, titanium or an alloy thereof, magnesium or an alloy thereof, polyetheretherketone (PEEK), hydroxyapatite, tricalcium phosphate, tetracalcium phosphate, dicalcium phosphate, BIOGLASS® 45S5, ceramic composites, copper-based materials or composites, cobalt chrome, xenograft biomaterials, and combinations thereof. The suture anchor, intramedullary pin, nail device, and/or spinal attachment device can also be 3D printed using these materials or others.

Definitions

To facilitate the understanding of this disclosure, a number of terms are defined below. Terms defined herein have meanings as commonly understood by a person of ordinary skill in the areas relevant to the disclosure. Terms such as "a", "an," and "the" are not intended to refer to only a singular entity, but include the general class of which a specific example may be used for illustration. The terminology herein is used to describe specific embodiments of the disclosure, but their usage does not limit the disclosure, except as outlined in the claims.

As used herein, the term "about" refers to a value that is within 10% above or below the value being described.

As used herein, any values provided in a range of values include both the upper and lower bounds, and any values contained within the upper and lower bounds.

The term "biomaterial," as used herein, refers to any adhesive biocompatible substance, of natural or synthetic origin, suitable for introduction into living tissue for a medical purpose (e.g., therapeutic, diagnostic, or preventative use) and used to fill a void, affix, join, treat, heal or regenerate bone.

The term "bone defect," as used herein, refers to any bone deficient region, such as a void, gap, recess, or other discontinuity in a bone. A bone defect can be artificially or naturally established, and can occur, for example, due to disease or trauma. Thus, a bone defect can occur as a consequence of pathologic or inflammatory diseases, formation and/or removal of a bone tumor, a surgical intervention, a congenital defect, or a bone fracture, and the like. For example, in the case of certain diseases, such as bone tumors, the bone defect may be artificially established due to removal of the tumor tissue. The screws of the disclosure can be applied, for example, in the repair of periodontal defects, in craniofacial or maxillofacial surgery or reconstruction, in hand surgery, in joint reconstruction, in fracture repair, in orthopedic surgical procedures, and in spinal fusion. The term "bony defect" is also intended to include anatomical sites where augmentation to a bony feature is desired by the patient in the absence of disease or trauma, such as in elective cosmetic surgery. Thus, the "defect" can be one that is subjectively perceived by the patient, and where augmentation of the bone deficient region is desired.

The term "elongated slit," as used herein, refers to an aperture having a substantially greater size in one dimension (e.g., length, height, or width) relative to the size of the aperture in another dimension (e.g., length, height, or width).

As used herein, the term "milling flute" refers to one or more cutting edges that cut a piece of a material (e.g., bone tissue) as the milling flute rotates. A milling flute may be a cutting projection that is integral to the device of the disclosure.

The term "mesh," as used herein, refers to a structure characterized by having one or more openings arranged parallel, diagonally, vertically, spirally, helically, relative to the longitudinal direction of the device.

The term "opening," as used herein, refers to any orifice, aperture, void, gap, or hole characterized by the absence of a particular material or structure that defines the region of the of the device in which the opening is disposed. The "opening" may be round or take any overall shape or geometry outlined by edges that bound the opening.

By "treating" or "treatment" is meant the medical management of a patient with the intent that an amelioration, repair, or prevention of an injury or disease, pathological condition, or disorder will result. This term includes active treatment, that is, treatment directed specifically toward improvement of the injury or disease, pathological condition, or disorder, and also includes causal treatment, that is, treatment directed toward removal of the cause of the injury or disease, pathological condition, or disorder. In addition, this term includes palliative treatment, that is, treatment designed for the relief of symptoms rather than the curing of the injury or disease, pathological condition, or disorder; preventive treatment, that is, treatment directed to prevention of the injury or disease, pathological condition, or disorder; and supportive treatment, that is, treatment employed to supplement another specific therapy directed toward the improvement of the injury or disease, pathological condition, or disorder.

As used herein, the term "unitary" refers to an undivided body which is of a one-piece construction (e.g., a unitary body that can be 3D printed in its entirety).

BRIEF DESCRIPTION OF THE DRAWINGS

FIG. 2 is a schematic drawing showing a side view of an embodiment of device 100. Proximal region 101 is shown including wings 105. Distal region 151 is shown including milling flutes 175. Expandable body 130 having a plurality of slits 140 is also shown.

FIG. 10 is a schematic drawing showing a side view of screw 600, bone plate 800, and device 100.

FIG. 13A is a schematic drawing showing a side view of an embodiment of device 100 in contact with bone plate 800.

FIG. 13B is a schematic drawing showing a cross-sectional view of an embodiment of device 100 in contact with bone plate 800. Bone plate 800 hole is shown having a conical shape.

FIG. 13C is a schematic drawing showing a side view of an embodiment of device 100, screw 600, and bone plate 800. Screw 600 is inserted through bone plate 800 and traverses the length of internal channel 190 of device 100.

FIG. 13D is a schematic drawing showing a cross-sectional view of an embodiment of device 100, screw 600, and bone plate 800. Screw 600 is inserted through bone plate 800 and traverses the length of internal channel 190 of device 100. Screw head 675 is shown in contact with bone plate 800.

FIG. 14A is a schematic drawing showing an enlarged side view showing distal and central regions of an embodiment of device 100 engaged with screw 600.

FIG. 14B is a schematic drawing showing a cross-sectional view of device 100 and screw 600 shown in FIG. 14A.

FIG. 14C is a schematic drawing showing an enlarged side view of showing distal and proximal regions of an embodiment of device 100 and screw 600. Screw 600 traverses the length of internal channel 190 of device 100 and exits through distal opening 155 of device 100. The dashed arrow points toward the direction of the bone.

FIG. 14D is a schematic drawing showing a cross-sectional view of device 100 and screw 600 shown in FIG. 14C.

FIG. 15 is a schematic drawing showing a side view of an embodiment of device 100, washer 700, and screw 600. Proximal region 101, expandable body, and distal region 151 of device 100 are shown.

FIG. 18A is a schematic drawing showing a side view of system 1000 of the disclosure, including insertion tool 200, pusher 300, connector 400, and device 100. The threads at distal region 240 of insertion tool 200 are engaged to internal threads 160 at distal region 151 of device 100. Pusher 300 is shown connected to insertion tool 200 and contacting connector 400.

FIG. 18B is a schematic drawing showing an enlarged cross-sectional view of system 1000 shown in FIG. 18A. The threads at distal region 240 of insertion tool 200 are engaged to internal threads 160 at distal region 151 of device 100. Pusher 300 is shown connected to insertion tool 200 and contacting connector 400.

FIG. 19A is a schematic drawing showing a side view of distal region 151, central region 126, and proximal region 101 of device 100. Washer 700 is shown inserted into internal channel 190 of device 100 at proximal region 101.

FIG. 19B is a schematic drawing showing a cross-sectional view of distal region 151, central region 126, and proximal region 101 of device 100 shown in FIG. 19A. Washer 700 is shown inserted into internal channel 190 of device 100 at proximal region 101.

FIG. 19C is a schematic drawing showing a side view of device 100 with screw 600 inserted through internal channel 190 of device 100 and washer 700 present in] internal channel 190 of device 100 at proximal region 101. Screw head 675 contacts washer 700.

FIG. 19D is a schematic drawing showing a cross-sectional view of device 100 with screw 600 inserted through internal channel 190 of device 100 and washer 700 inserted in proximal region 101 of device 100, as shown in FIG. 19C. Screw head 675 is shown in contact with washer 700.

No torque has been applied to device 100 and expandable body 130 is unexpanded. The displacement of expandable body 130 is 0 mm.

Figures 25A, 25B:
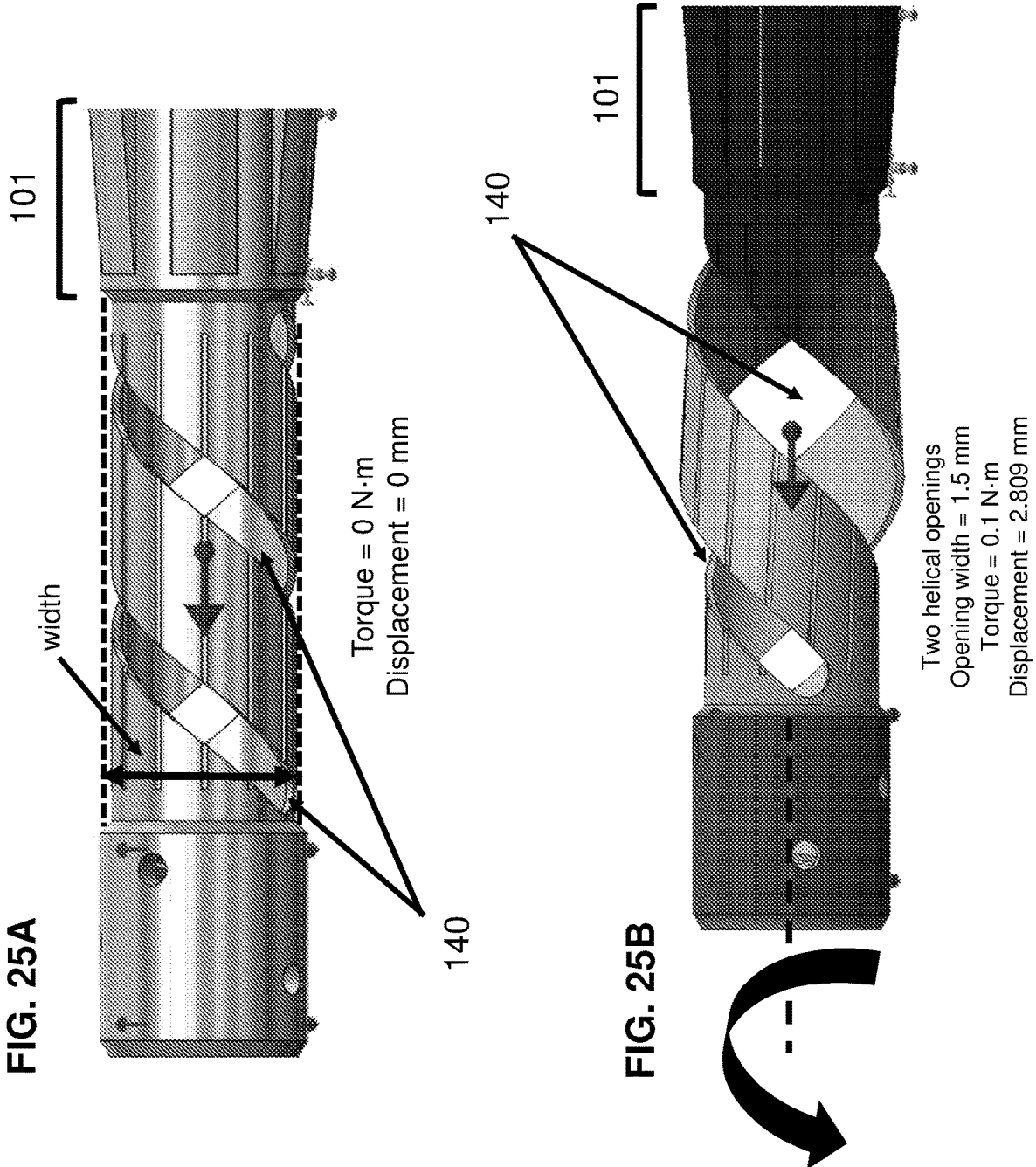
FIG. 25A is a schematic drawing showing an embodiment of device 100 showing an unexpanded expandable body 130. Expandable body 130 is shown with two helical openings 140 of width of 1.5 mm and longitudinal grooves 150.

FIG. 25B is a schematic drawing showing device 100 of FIG. 25A after radial expansion of expandable body 130 after application of torque of 0.1 N·m. Expandable body 130 is shown with two helical openings 140 of width of 1.5 mm. Expansion of expandable body 130 occurs when proximal region 101 of device 100 is secured to the bone, rendering proximal region 101 unable to rotate, while distal region 151 is rotatable independently of proximal region 101. By applying torque to distal region 151, distal region 151 of device 100 compresses towards proximal region 101, and expandable body 130 radially expands. Expandable body 130 is shown having a displacement of 2.809 mm, in response to the applied torque.

Figures 26A, 26B:
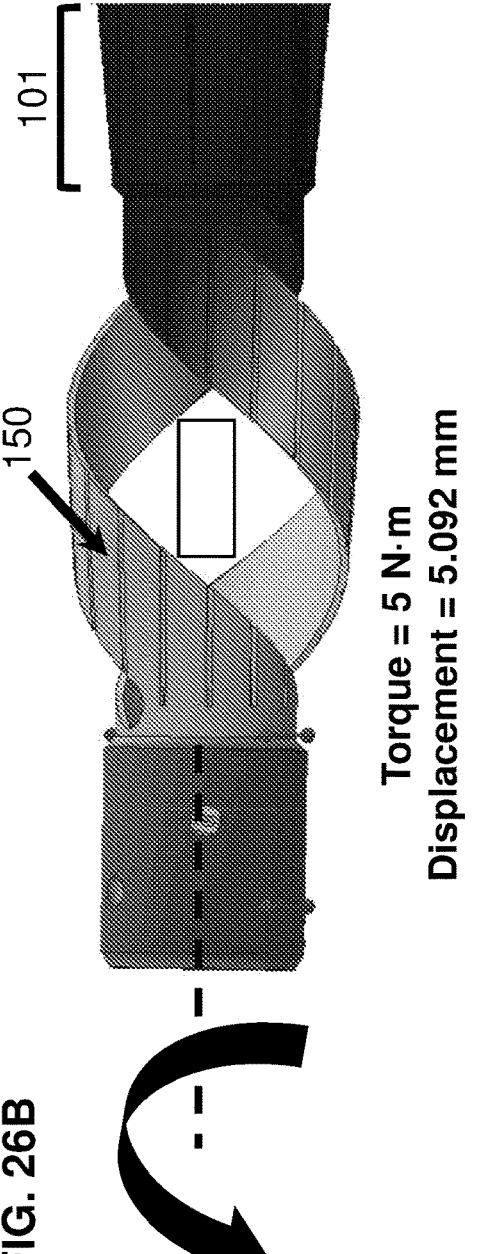

FIG. 26A is a schematic drawing showing an embodiment of device 100 with a radially expanded expandable body 130. Expandable body 130 is shown without longitudinal grooves 150. Expansion of expandable body 130 occurs after a torque of 5 N·m is applied to device 100 when proximal region 101 of device 100 is secured to the bone, rendering proximal region 101 unable to rotate, while distal region 151 is rotatable independently of proximal region 101. By applying torque to distal region 151, distal region 151 of device 100 compresses towards proximal region 101, and expandable body 130 radially expands. Expandable body 130 is shown having a displacement of 5.048 mm, in response to the applied torque.

FIG. 26B is a schematic drawing showing device 100 with a radially expanded expandable body 130. Expandable body 130 is shown with longitudinal grooves 150. Expansion of expandable body 130 occurs after a torque of 5 N·m is applied to device 100 when proximal region 101 of device 100 is secured to the bone, rendering proximal region 101 unable to rotate, while distal region 151 is rotatable independently of proximal region 101. By applying torque to distal region 151, distal region 151 of device 100 compresses towards proximal region 101, and expandable body 130 radially expands. Expandable body 130 is shown having a displacement of 5.092 mm, in response to the applied torque.

Figures 27A, 27B:
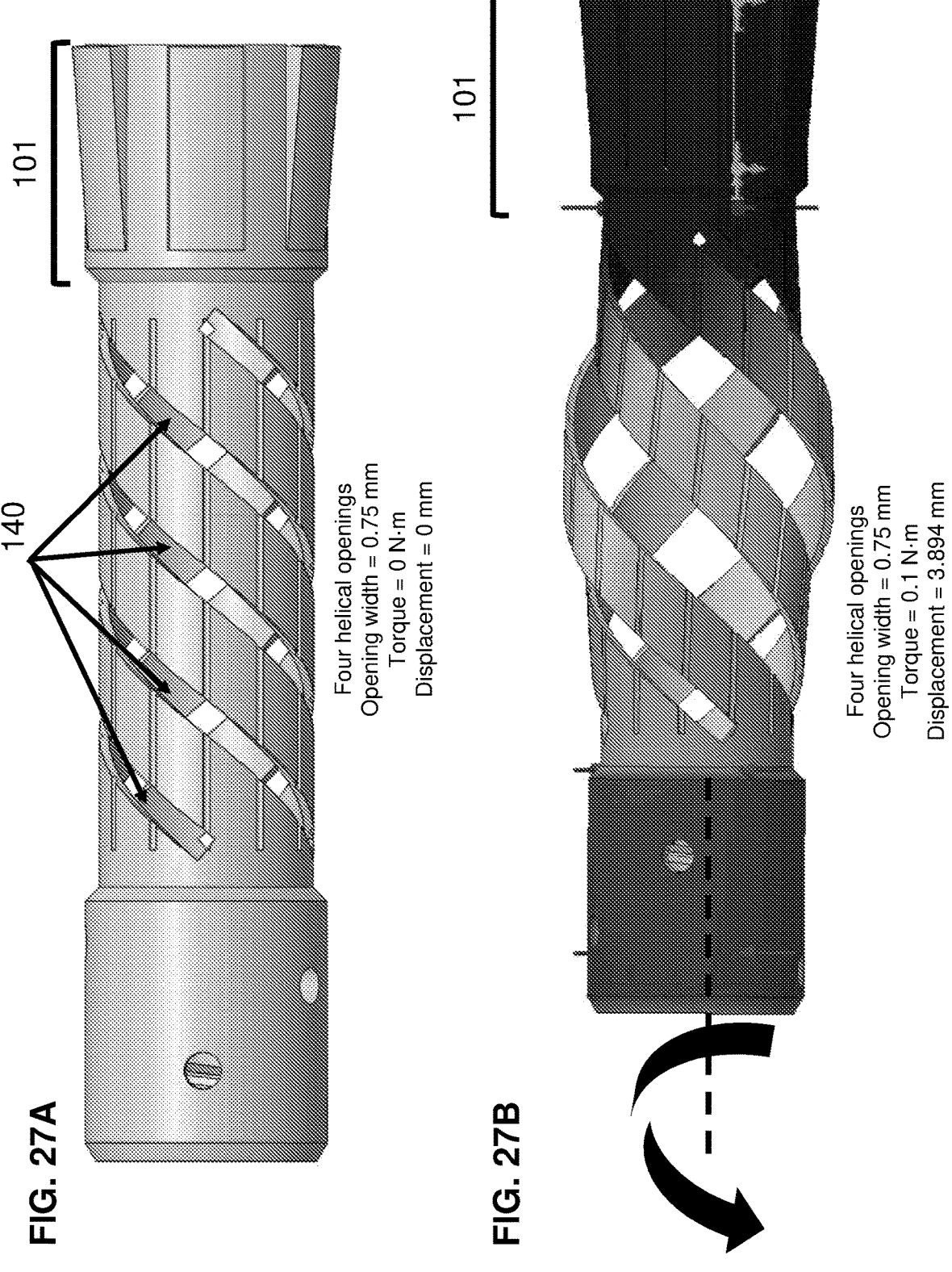

FIG. 27A is a schematic drawing showing an embodiment of device 100 with expandable body 130. No torque has been applied to device 100 and expandable body 130 is unexpanded. The displacement of expandable body 130 is 0 mm. Four helical openings 140 of expandable body 130 are present in central region 126 of device 100. Each of helical openings 140 have a width of 0.75 mm.

FIG. 27B is a schematic drawing showing device 100 of FIG. 27A with radially expanded expandable body 130 after application of a torque of 0.1 N·m to device 100. Securing proximal region 101 of device 100 to bone renders proximal region 101 unable to rotate, while distal region 151 is able to rotate independently of proximal region 101. By applying torque to distal region 151, distal region 151 of device 100 compresses towards proximal region 101, and expandable body 130 radially expands. Expandable body 130 is shown having a displacement of 3.894 mm, in response to the applied torque. Each of four helical openings 140 of expandable body 130 have a width of 0.75 mm.

Figures 28A, 28B:
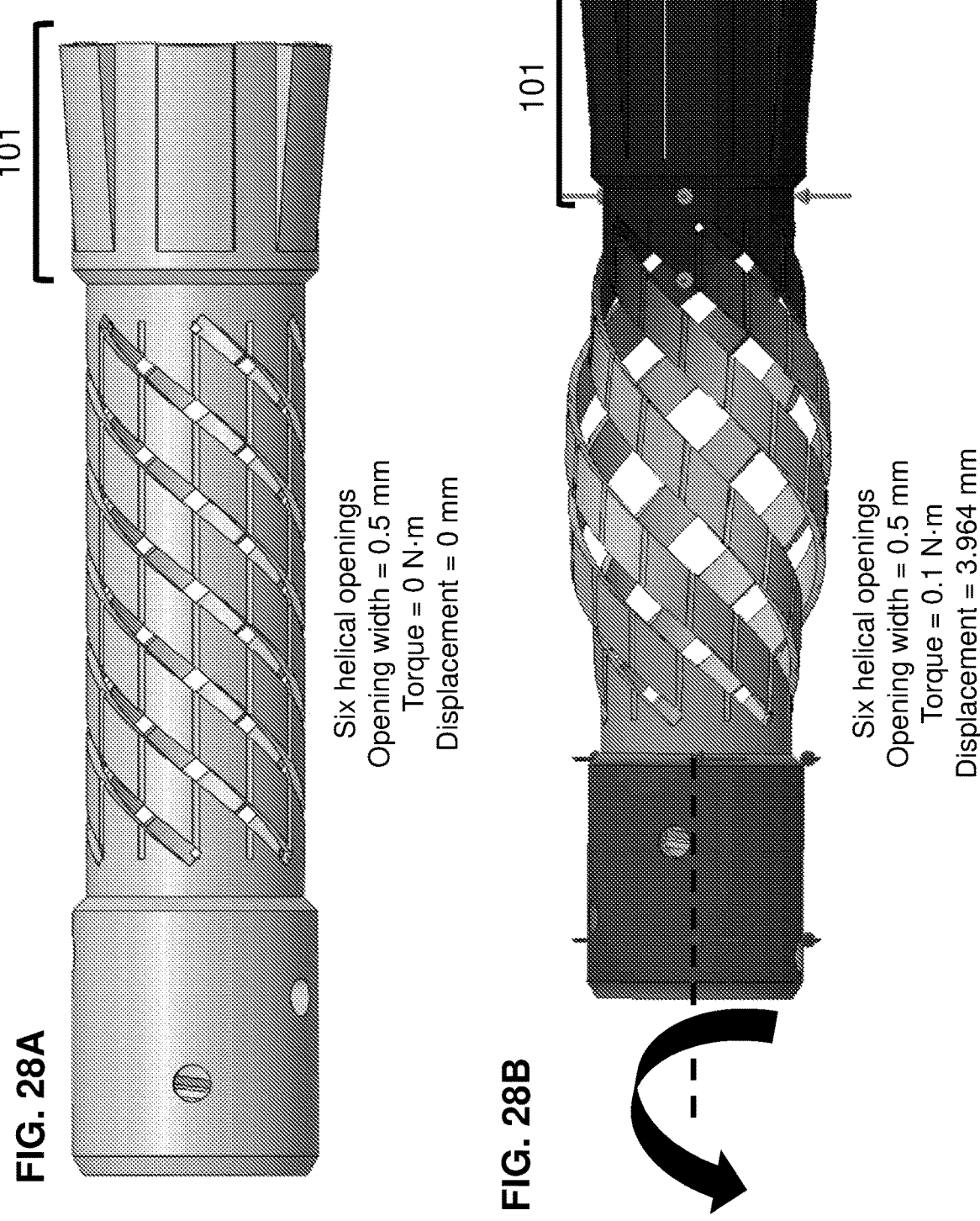

FIG. 28A is a schematic drawing showing an embodiment of device 100 with expandable body 130. No torque has been applied to device 100 and expandable body 130 is unexpanded. The displacement of expandable body 130 is 0 mm. Six helical openings 140 of expandable body 130 are present in central region 126 of device 100. Each of helical openings 140 have a width of 0.5 mm.

FIG. 28B is a schematic drawing showing device 100 of FIG. 28A with radially expanded expandable body 130 after application of a torque of 0.1 N·m to device 100. Securing proximal region 101 of device 100 to bone renders proximal region 101 unable to rotate, while distal region 151 is able to rotate independently of proximal region 101. By applying torque to distal region 151, distal region 151 of device 100 compresses towards proximal region 101, and expandable body 130 radially expands. Expandable body 130 is shown having a displacement of 3.964 mm, in response to the applied torque. Each of six helical openings 140 of expandable body 130 have a width of 0.5 mm.

Figures 29A, 29B:
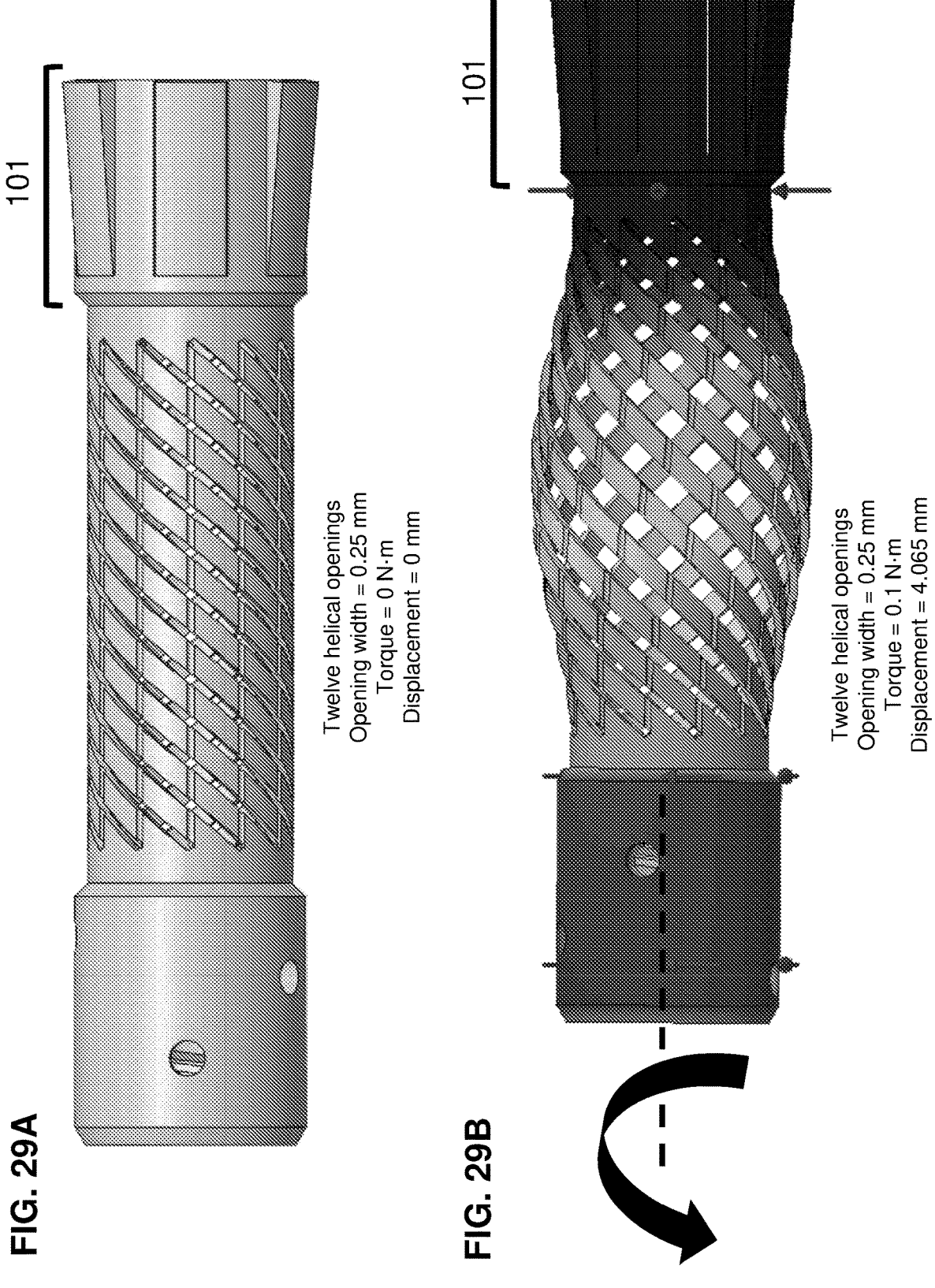

FIG. 29A is a schematic drawing showing an embodiment of device 100 with expandable body 130. No torque has been applied to device 100 and expandable body 130 is unexpanded. The displacement of expandable body 130 is 0 mm. Twelve helical openings 140 of expandable body 130 are present in central region 126 of device 100. Each of helical openings 140 have a width of 0.25 mm.

FIG. 29B is a schematic drawing showing device 100 of FIG. 29A with radially expanded expandable body 130 after application of a torque of 0.1 N·m to device 100. Securing proximal region 101 of device 100 to bone renders proximal region 101 unable to rotate, while distal region 151 is able to rotate independently of proximal region 101. By applying torque to distal region 151, distal region 151 of device 100 compresses towards proximal region 101, and expandable body 130 radially expands. Expandable body 130 is shown having a displacement of 4.065 mm, in response to the applied torque. Each of twelve helical openings 140 of expandable body 130 have a width of 0.25 mm.

Figure 30A:
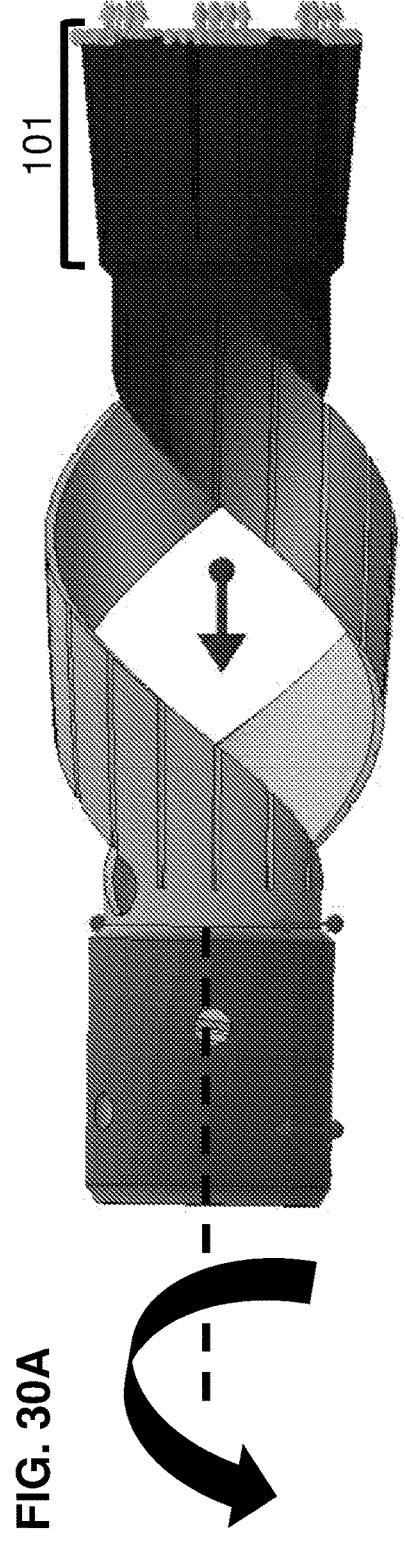

FIG. 30A is a schematic drawing showing a side view of an embodiment of device 100 with radially expanded expandable body 130, which occurs after application of 5 N·m of torque to distal region 151 of device 100. Two helical openings 140 of expandable body 130 have a width of 1.5 mm and expandable body 130 is radially displaced by 5.092 mm.

Figure 30B:
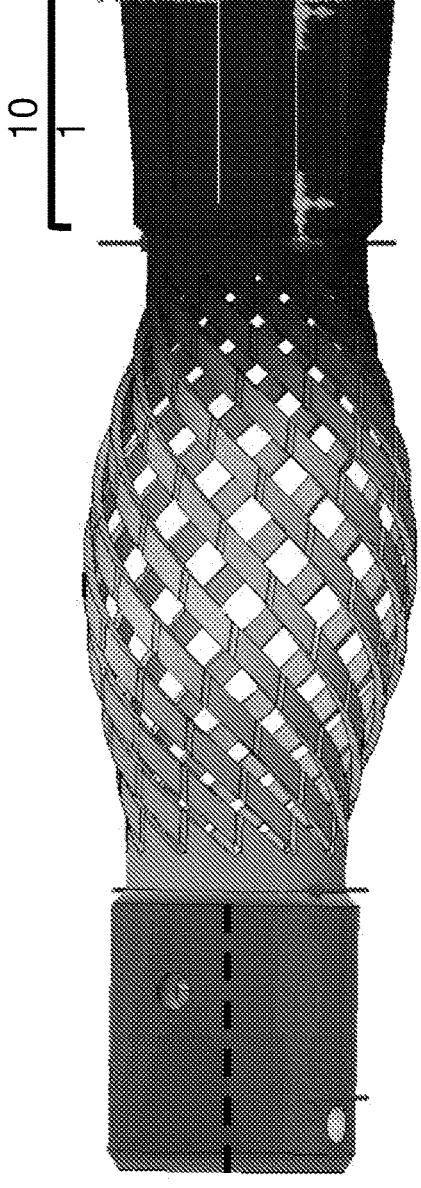

FIG. 30B is a schematic drawing showing a side view of an embodiment of device 100 with radially expanded expandable body 130, which occurs in response to application of 5 N·m of torque to distal region 151 of device 100. Twelve helical openings 140 of expandable body 130 have a width of 0.25 mm and expandable body 130 is radially displaced by 5.348 mm.

Figures 31A, 31B:
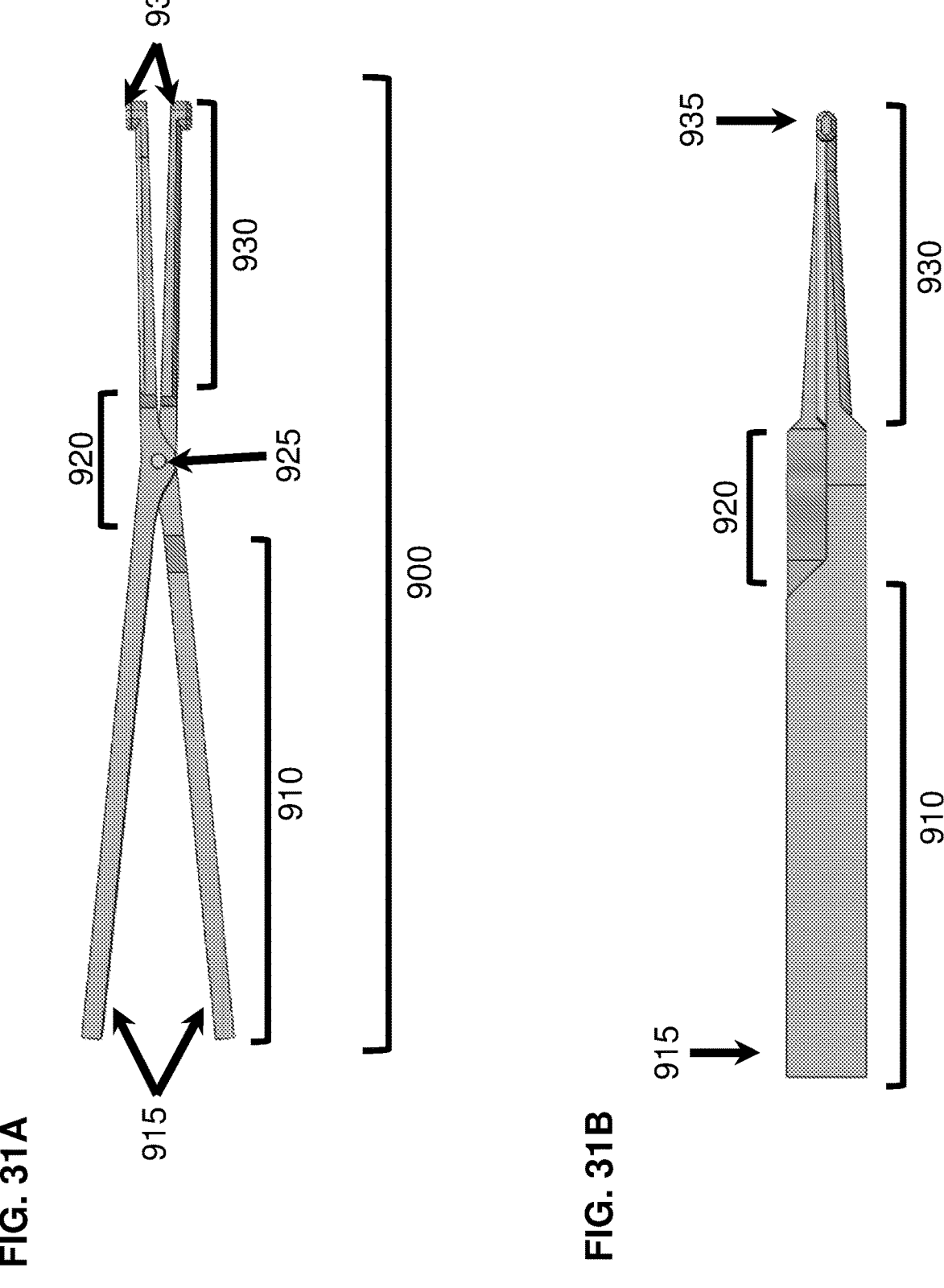

FIG. 31A is a schematic drawing showing extraction tool 900 having proximal region 910, central region 920, and distal region 930. Proximal region 910 has grip handle 915, central region 920 includes pivot joint 925, distal region 930 includes a pair of nubs 935, and extraction tool 900 is composed of two members pivotally coupled by pivot joint 925. Proximal region 910 of the two members composes grip handle 915. Distal region 930 of each member includes a nub.

FIG. 31B is a schematic drawing showing a top view of extraction tool 900 of FIG. 31A showing proximal region 910, central region 920, and distal region 930. Grip handle 915 and nubs 935 are shown.

FIG. 32 is a schematic drawing showing a side view of extraction tool 900 and device 100. Device 100 is shown with notches 183 at distal region 151. Grip handle 915 and nubs 935 of extraction tool 900 are shown.

Figures 33A, 33B:
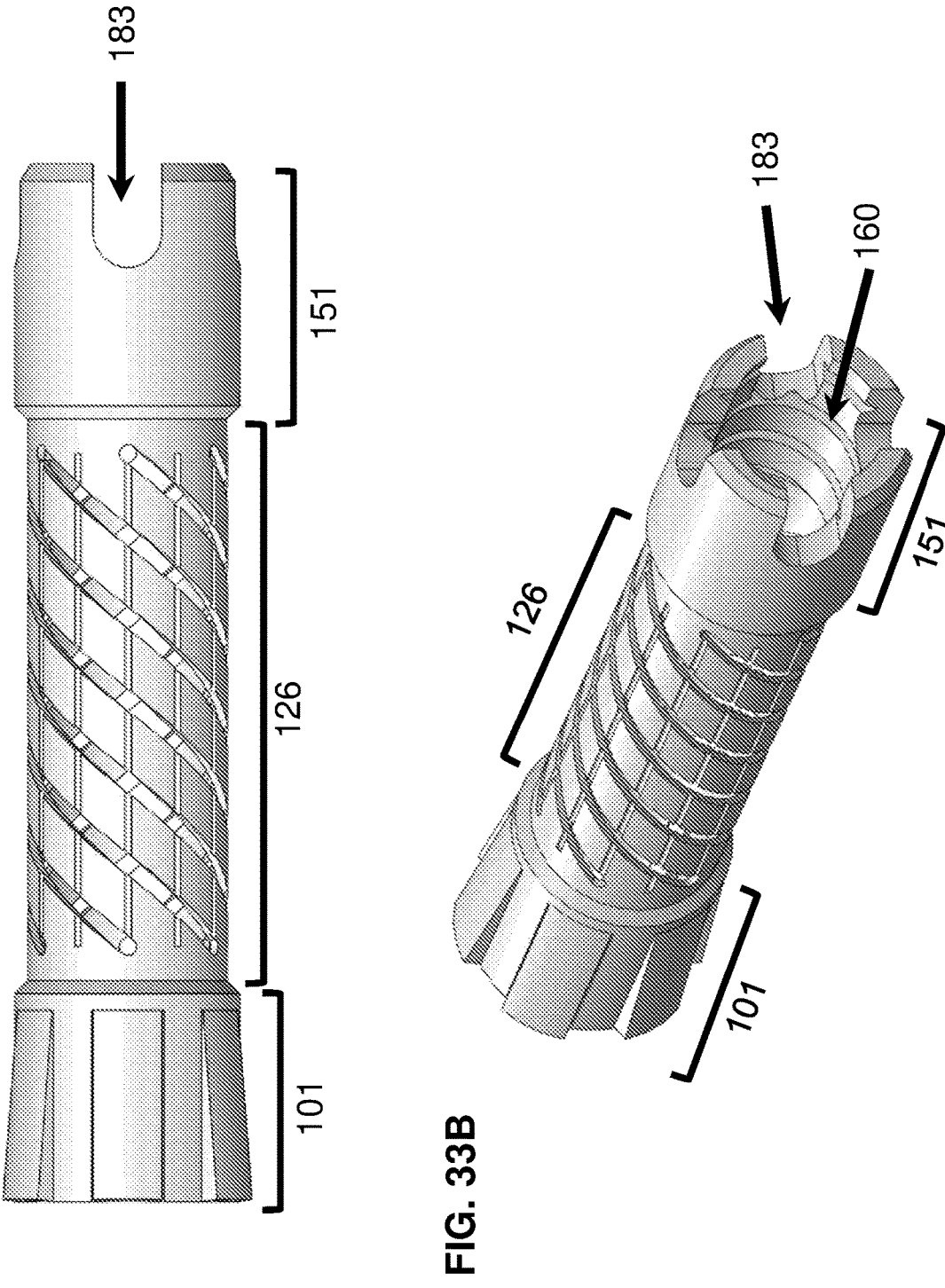

FIG. 33A is a schematic drawing showing an embodiment of device 100 showing proximal region 101, central region 126, and distal region 151, which includes notch 183.

FIG. 33B is a schematic drawing showing a perspective view of device 100 of FIG. 33A showing proximal region 101, central region 126, and distal region 151. Four notches 183 and internal threads 160 are shown in distal region 151.

Figures 34A, 34B:
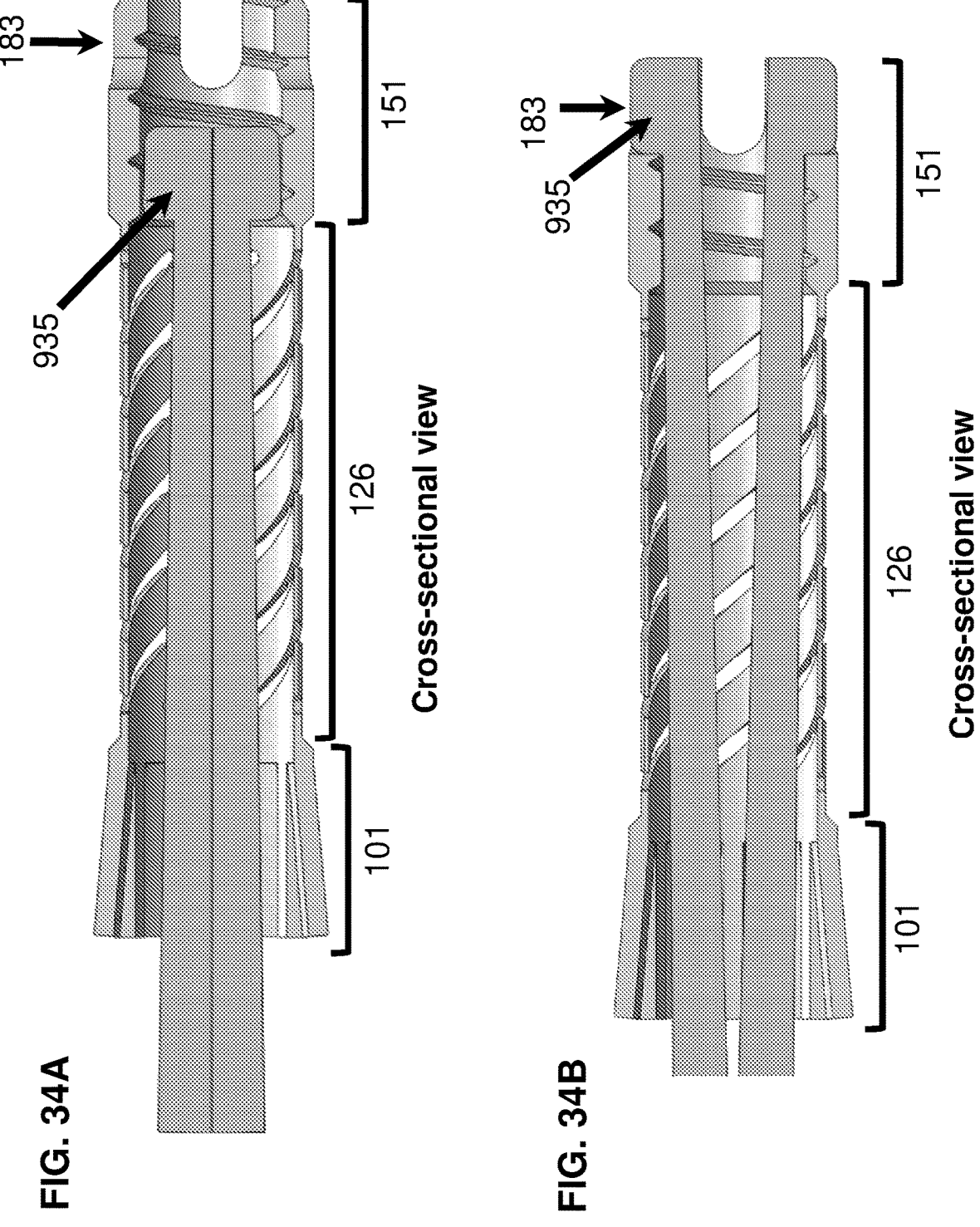

FIG. 34A is a schematic drawing showing a cross-sectional view of device 100 with extraction tool 900 partially inserted into internal channel 190 of device 100.

FIG. 34B is a schematic drawing showing a cross-sectional view of device 100 with extraction tool 900 inserted into internal channel 190, such that nubs 935 are engaged with notches 183 at distal region 151 of device 100.

Figure 35:
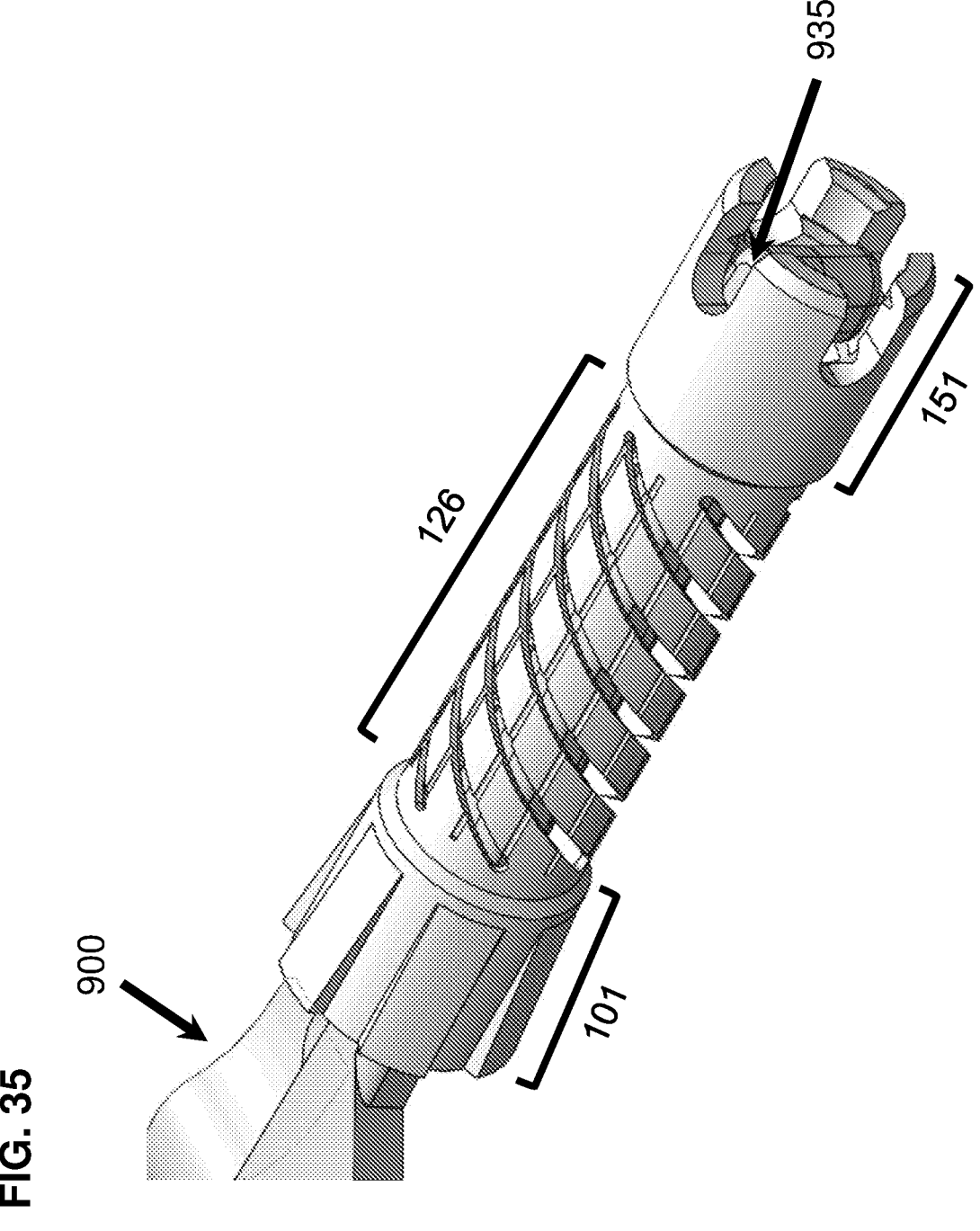

FIG. 35 is a schematic drawing showing a perspective view of an embodiment of device 100 showing proximal region 101, central region 126, and distal region 151; distal region 151 is shown with four notches 183. Extraction tool 900 is shown partially inserted into internal channel 190 of device 100.

Figure 36:
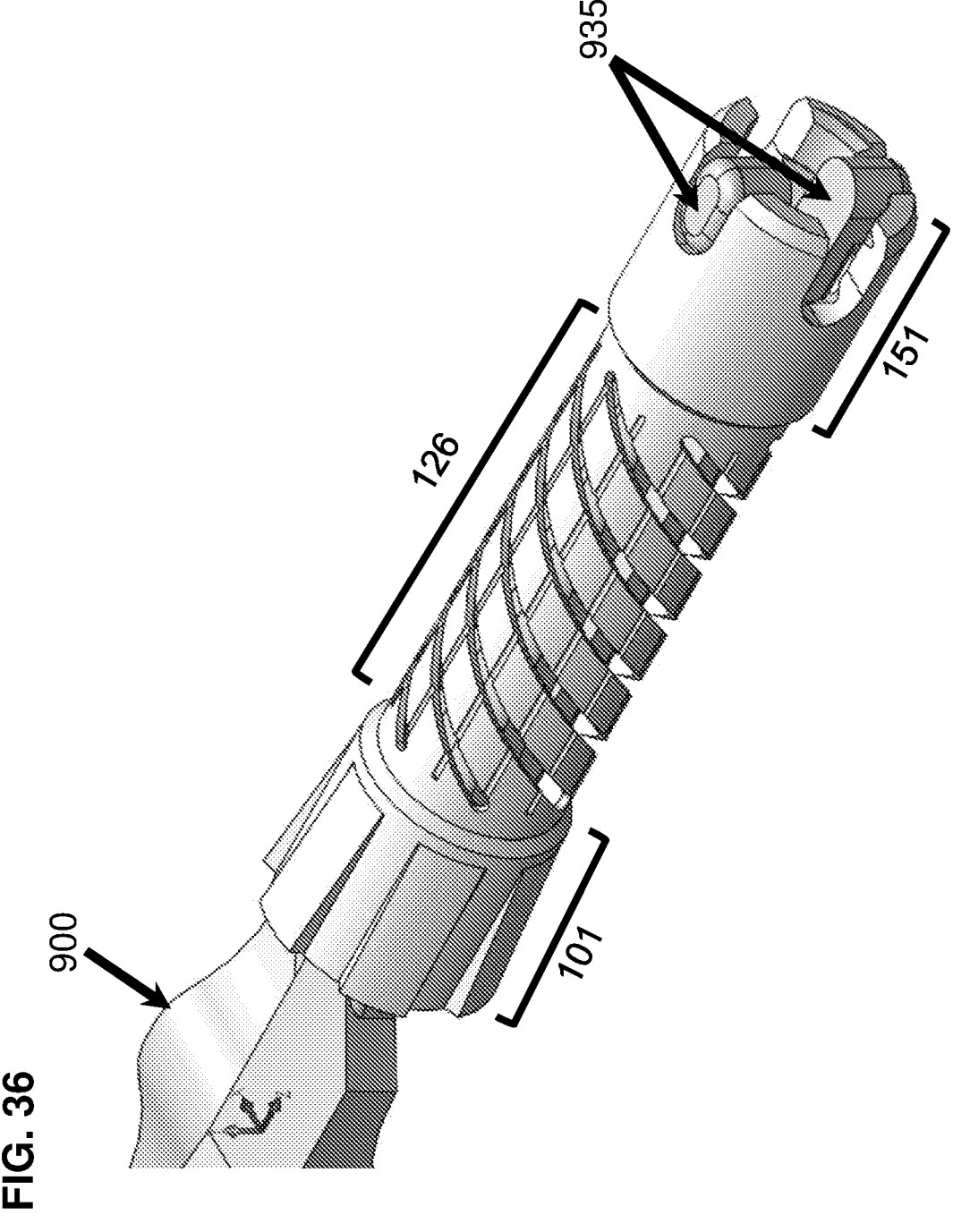

FIG. 36 is a schematic drawing showing a perspective view of device 100 of FIG. 35. Extraction tool 900 is shown fully inserted into internal channel 190 of device 100 and nubs 935 are engaged with notches 183 at distal region 151 of device 100.

Figure 37:
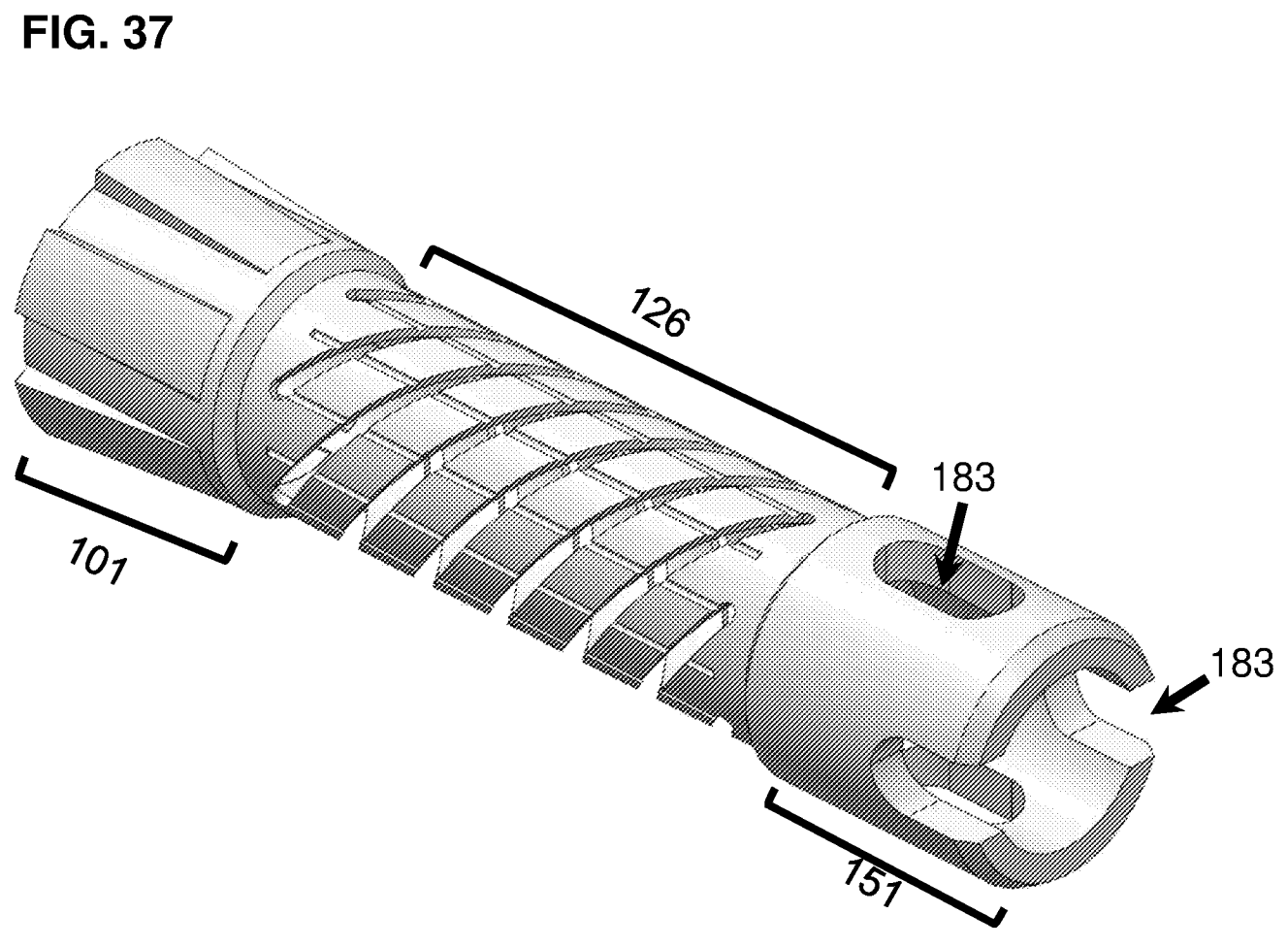

FIG. 37 is a schematic drawing showing an embodiment of device 100 showing proximal region 101, central region 126, and distal region 151. Distal region with two notches 183 at the end of distal region 151 and two internal notches 183 at distal region 151. Distal region 151 is shown with two notches 183 disposed at the distal end of distal region 151 and two notches 183 centrally disposed within distal region 151.

Figure 38:
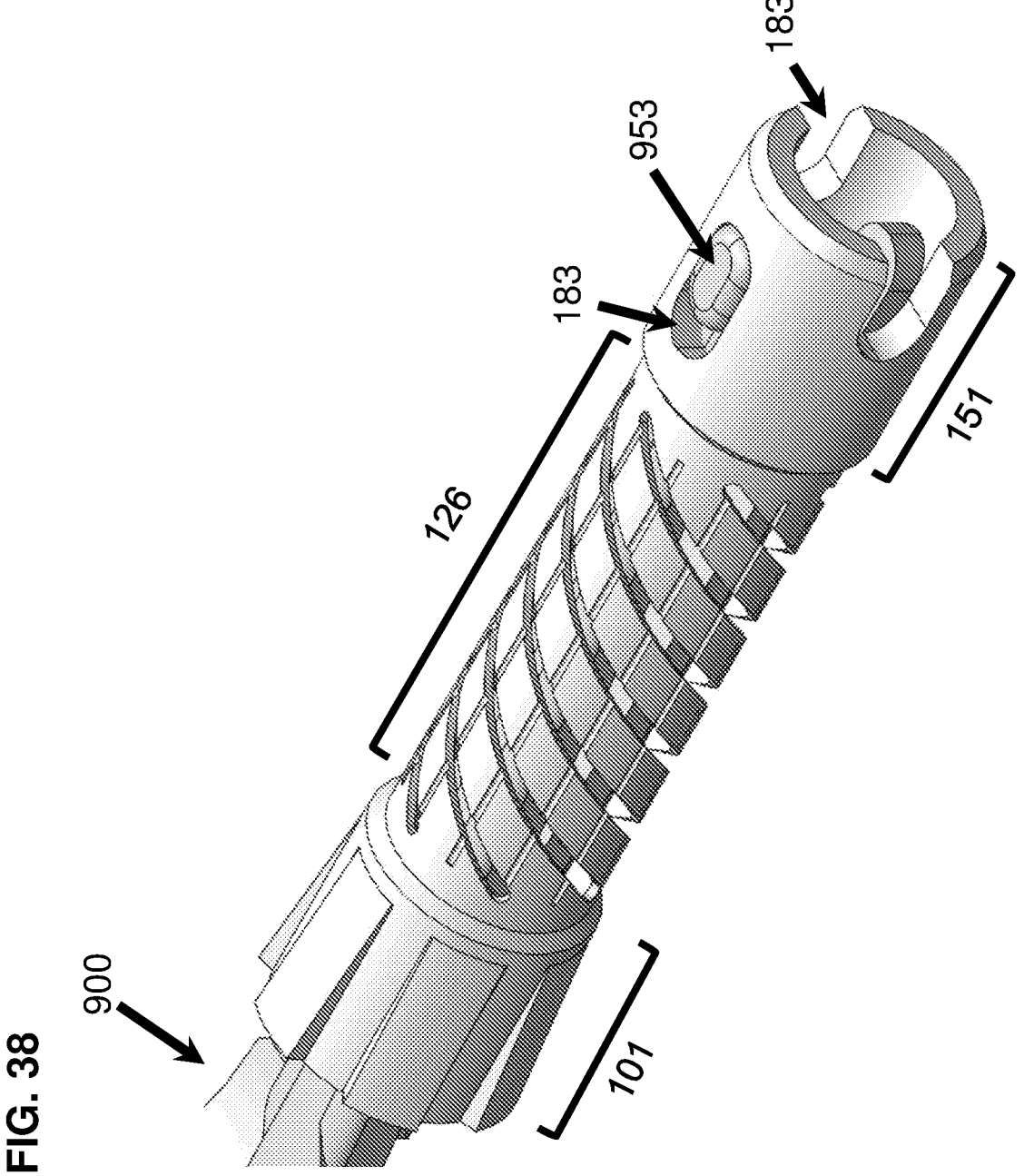

FIG. 38 is a schematic drawing showing a perspective view of device 100 of FIG. 37 showing insertion of extraction tool 900 into internal channel 190. As shown, nubs 935 of extraction tool are engaged with centrally disposed internal notches 183 at distal region of device 100.

Figure 39:
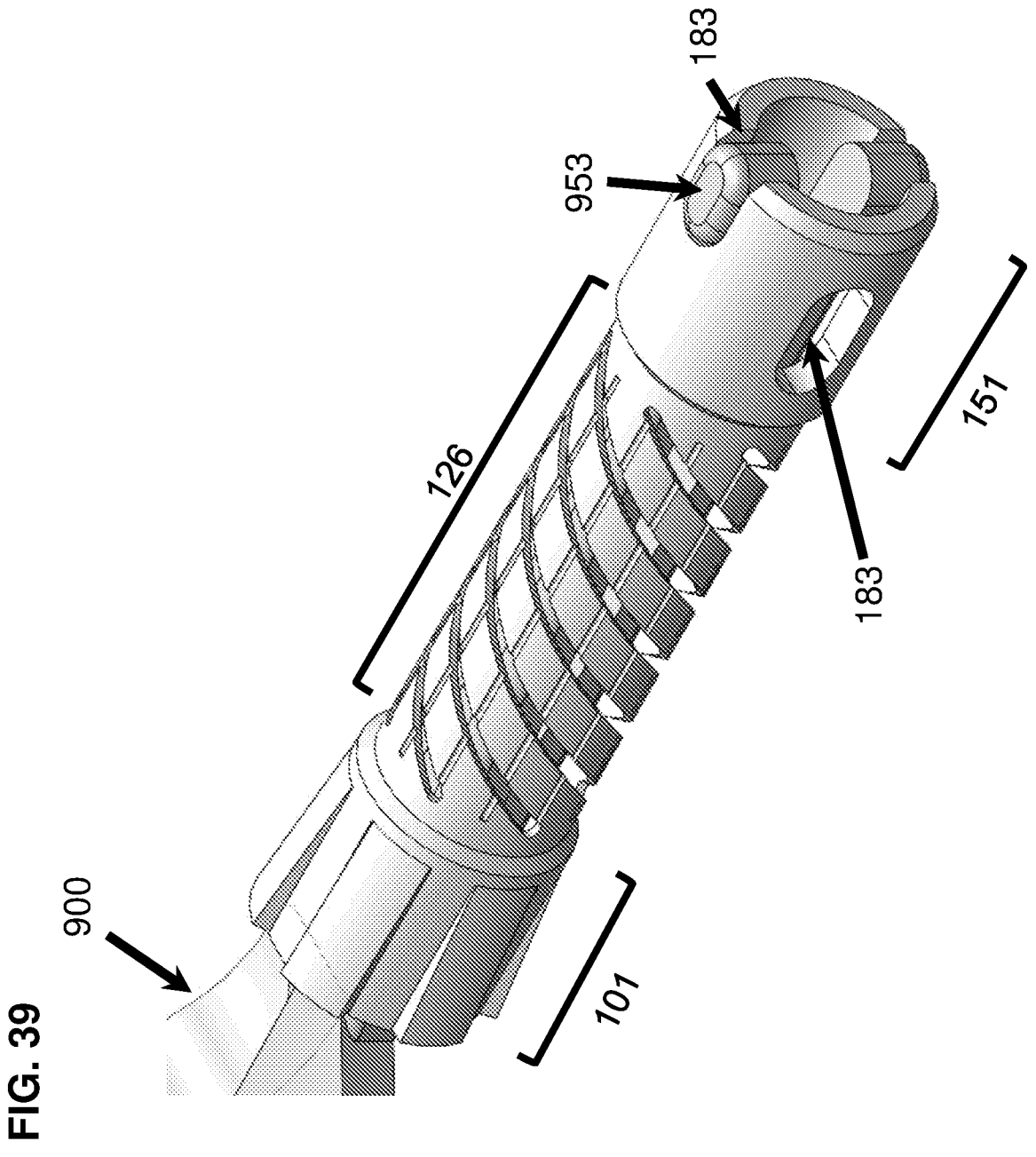

FIG. 39 is schematic drawing showing a perspective view of device 100 of FIG. 37 showing insertion of extraction tool 900 into internal channel 190. As shown, nubs 935 of extraction tool are engaged with distal end disposed notches 183 at distal region of device 100.

Figure 40:
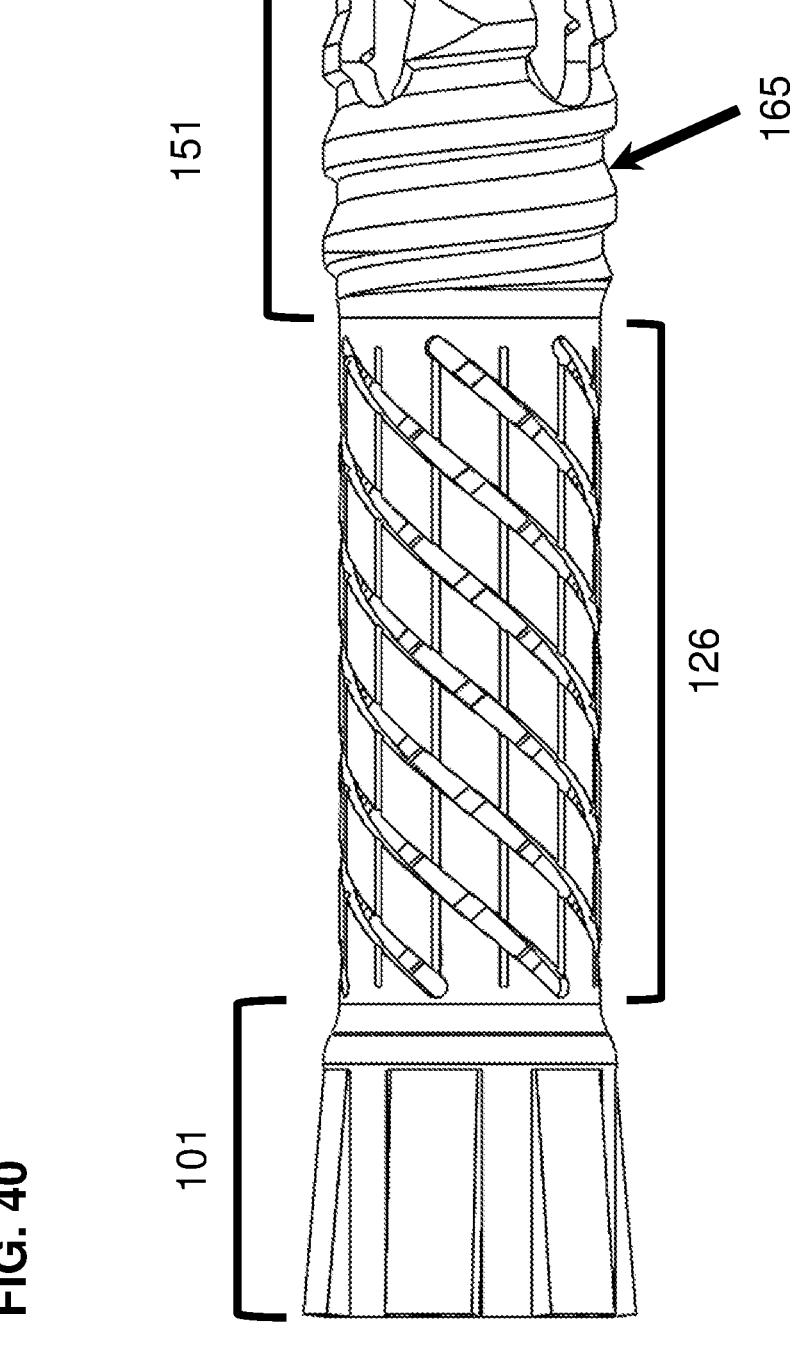

FIG. 40 is a schematic drawing showing a side view of an embodiment of device 100 having proximal region 101, central region 126, and distal region 151 with external threads 165.

Figure 41:
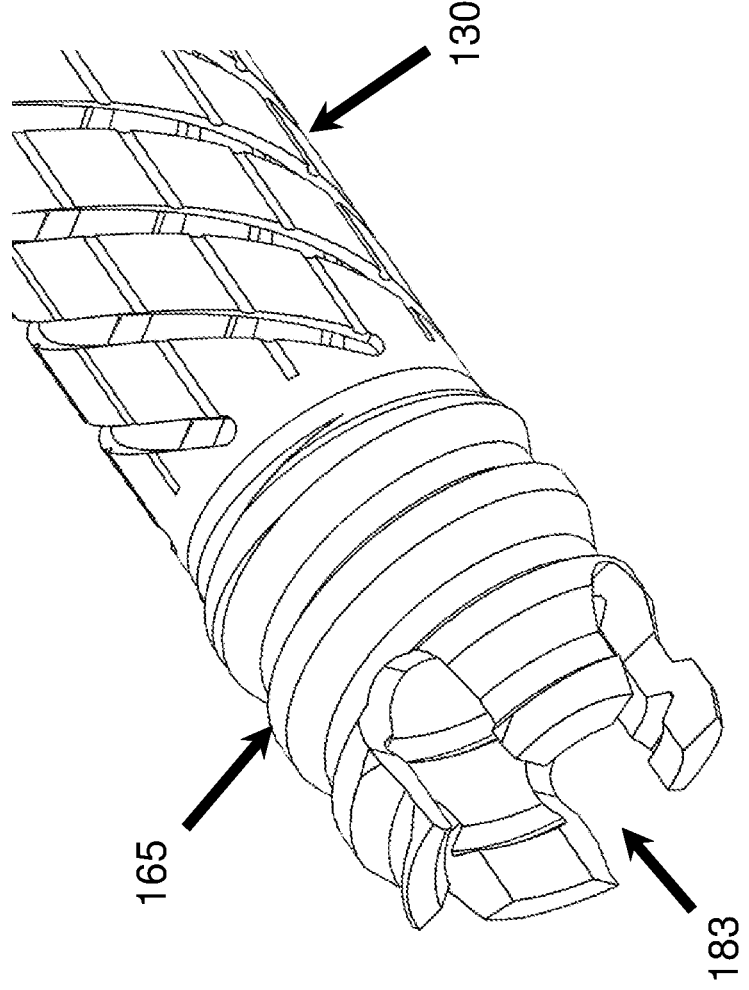

FIG. 41 is a schematic drawing showing an enlarged perspective view of distal region and a portion of central region of device 100 of FIG. 40. Distal region 151 includes external threads 165.

Figures 42A, 42B:
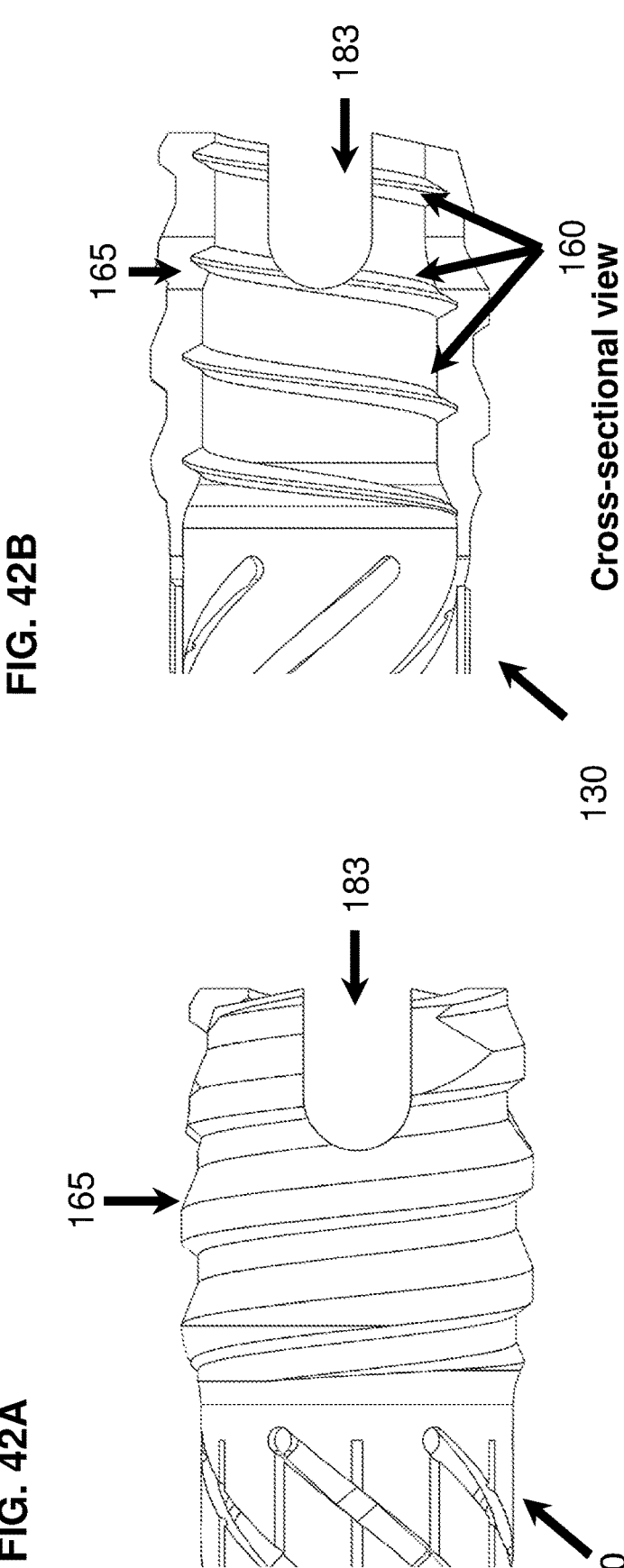

FIG. 42A is a schematic drawing showing an enlarged side view of distal region and a portion of central region of device 100 of FIG. 40 showing external threads 165 and notch 183 at distal region 151.

FIG. 42B is a schematic drawing showing a cross-sectional view of device 100 of FIG. 42A. Internal threads 160 of device 100 at distal region 151 are shown.

Figure 43:
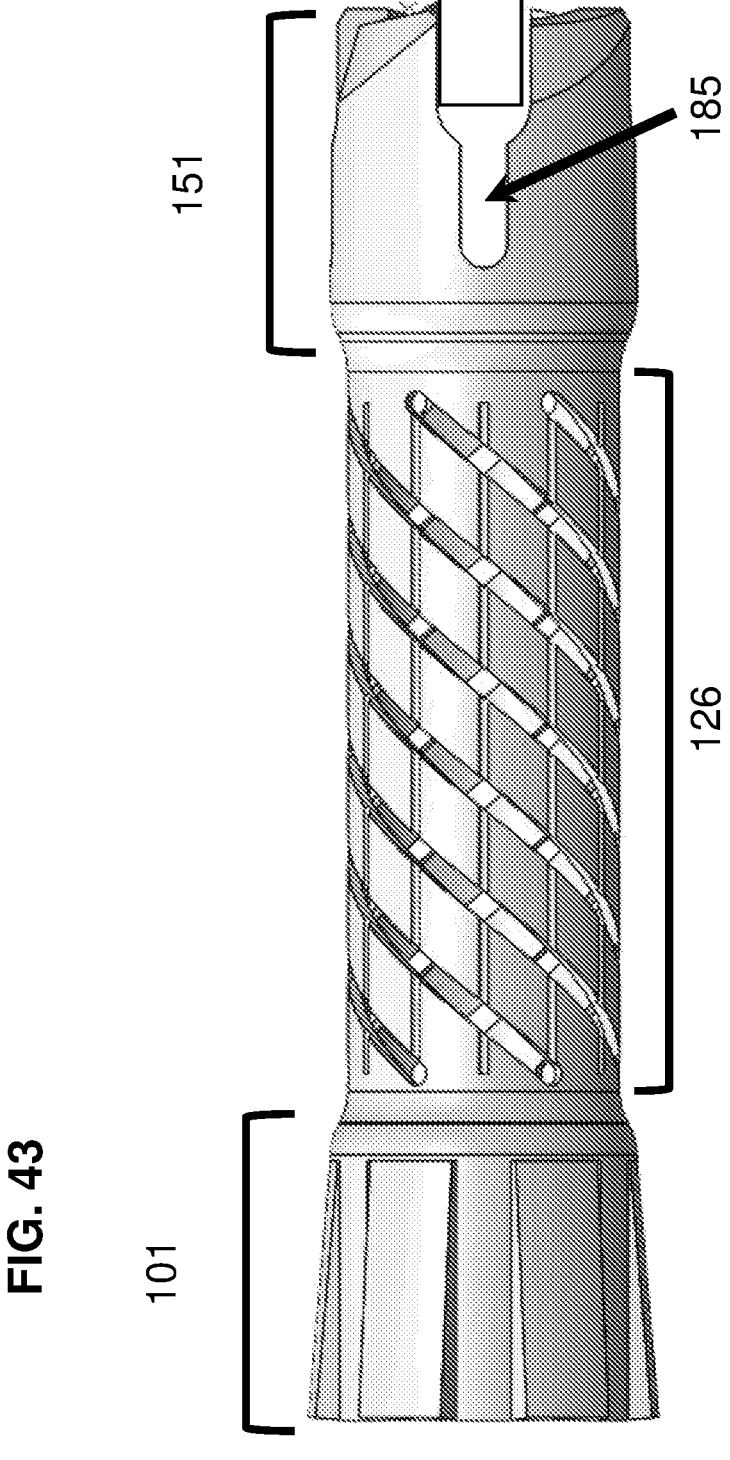

FIG. 43 is a schematic drawing showing a side view of an embodiment of device 100 having proximal region 101, central region 126 and distal region 151 with notches 183 having elongated slit 185.

Figure 44:
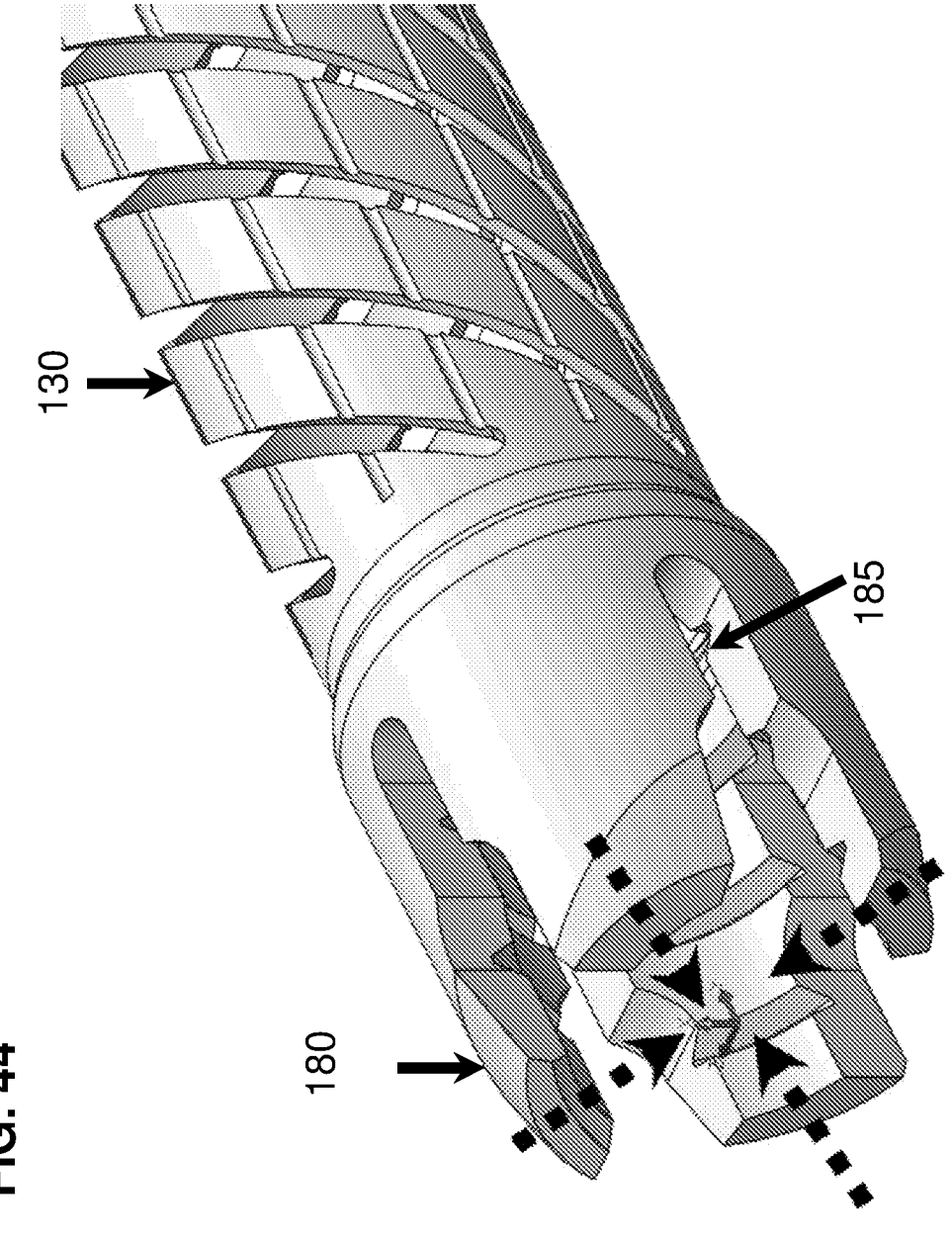

FIG. 44 is a schematic drawing showing an enlarged perspective view of device 100 of FIG. 43 with a portion of central region 126 and distal region 151. Distal region 151 is shown with notches 183 and elongated slit 185. Also shown are bendable tips 180 of distal region 151.

Figure 45:
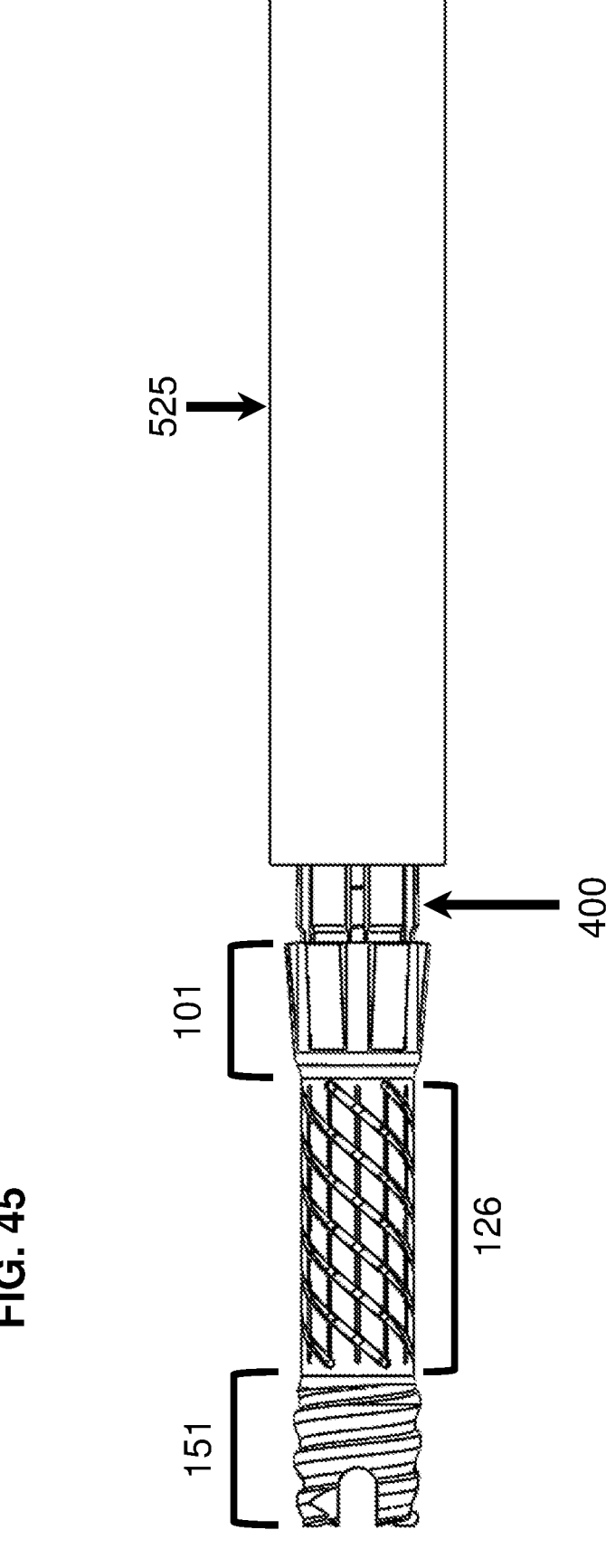

FIG. 45 is a schematic drawing showing a side view of an embodiment of device 100 with proximal region 101, central region 126, and distal region 151. Connector 400 is fastened to internal channel 190 at proximal opening 103 of device 100. Connector 400 is also connected to tube 525, which is configured to deliver biomaterial 550 to internal channel 190 of device 100.

Figure 46:
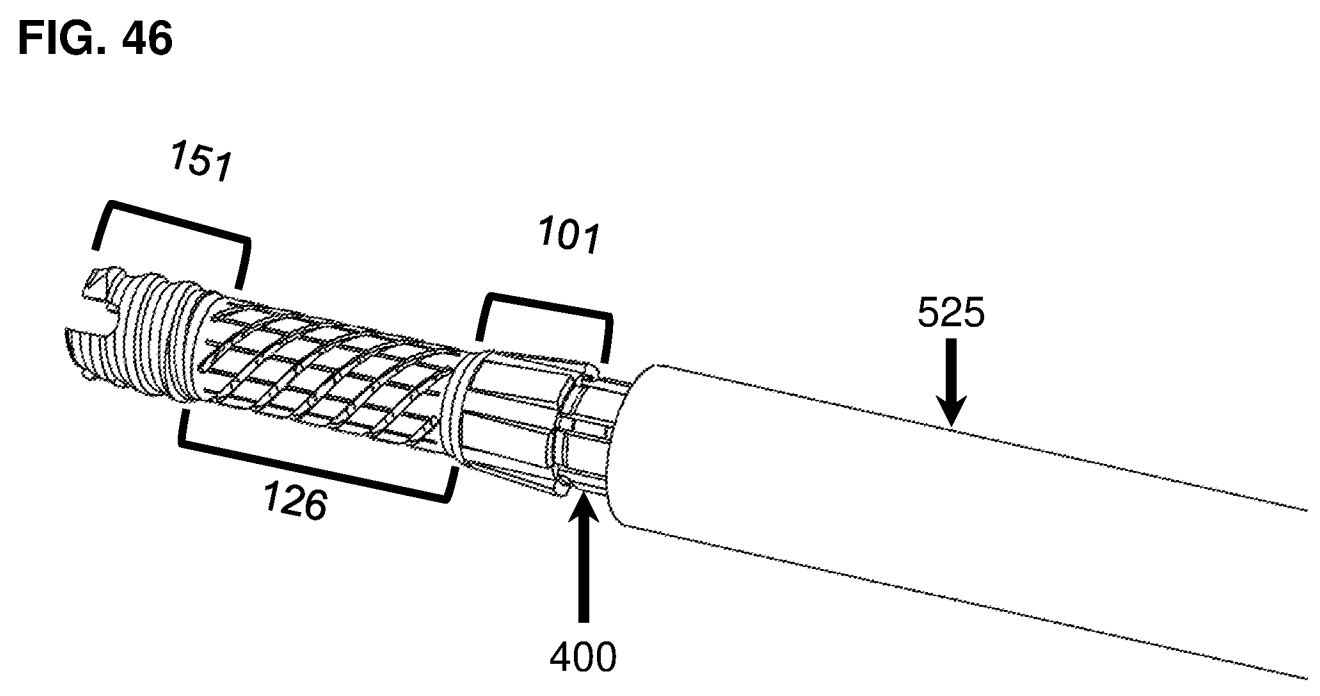

FIG. 46 is a schematic drawing showing a perspective view of device 100 of FIG. 45.

Figure 47:
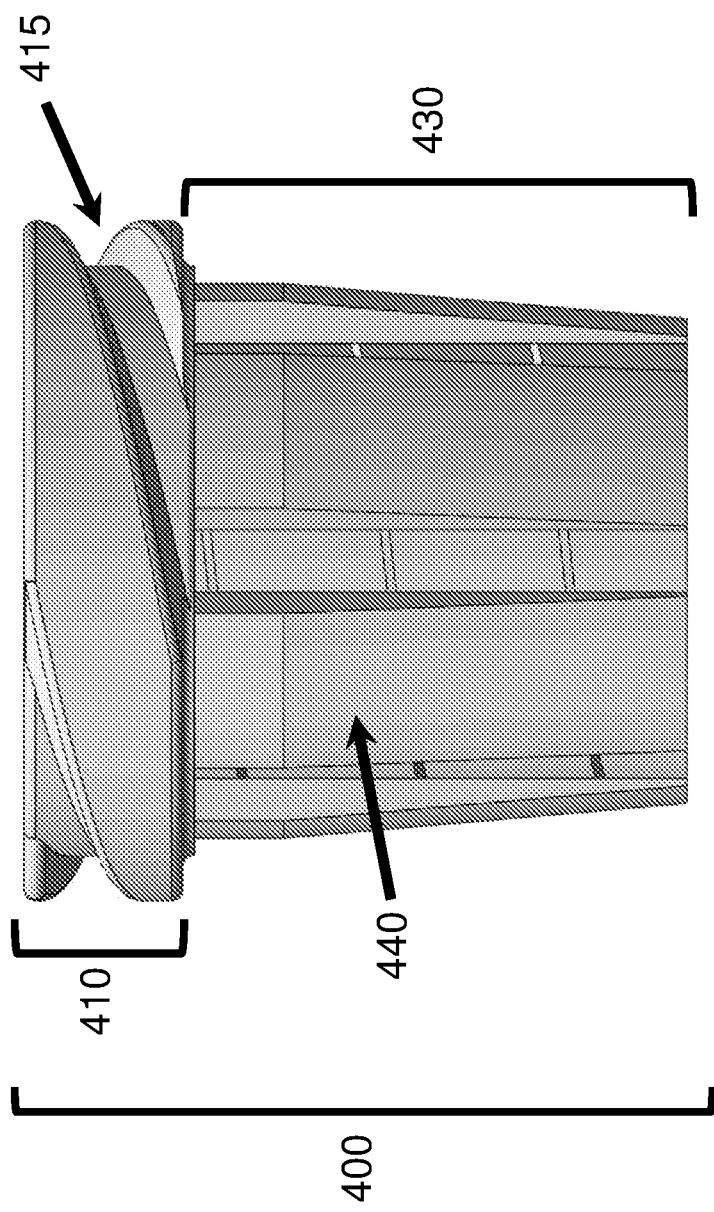

FIG. 47 is a schematic drawing showing a side view of an embodiment of connector 400. Connector 400 includes proximal region 410, distal region 430, a plurality of wedges 440, and female Luer-lock threading disposed at proximal region 410.

Figure 48:
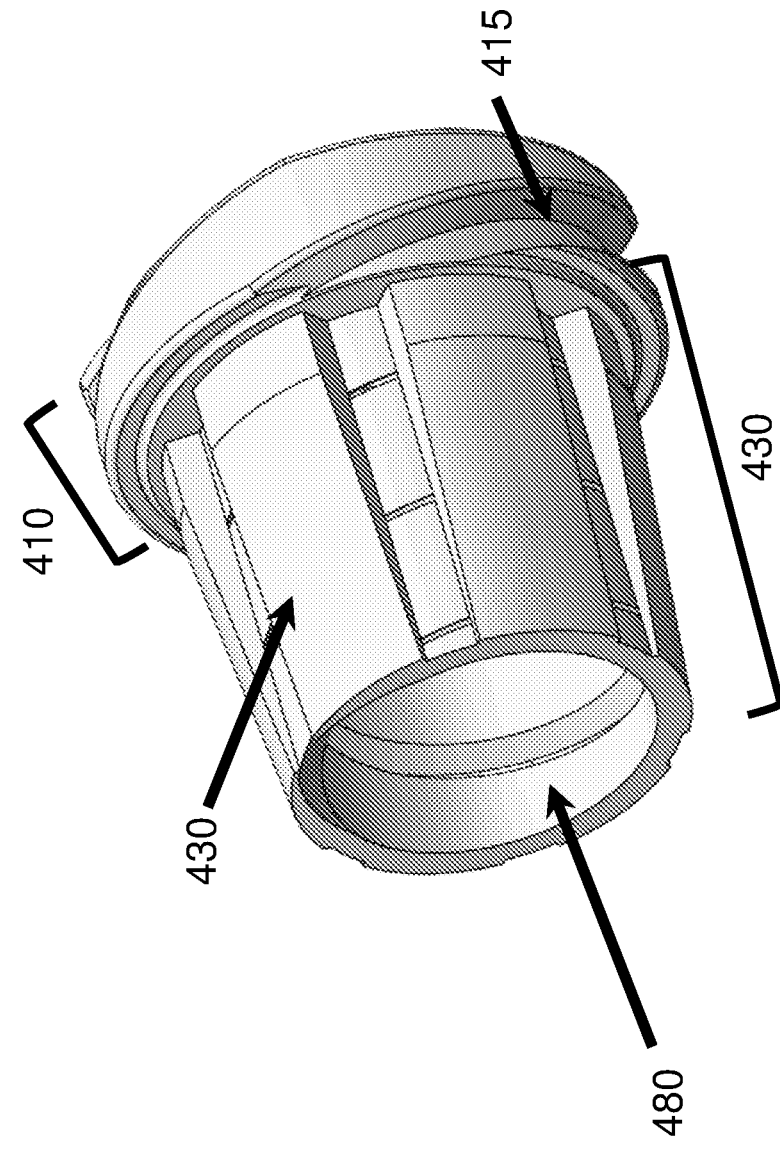

FIG. 48 is a schematic drawing showing a perspective view of connector 400 of FIG. 47.

Figure 49:
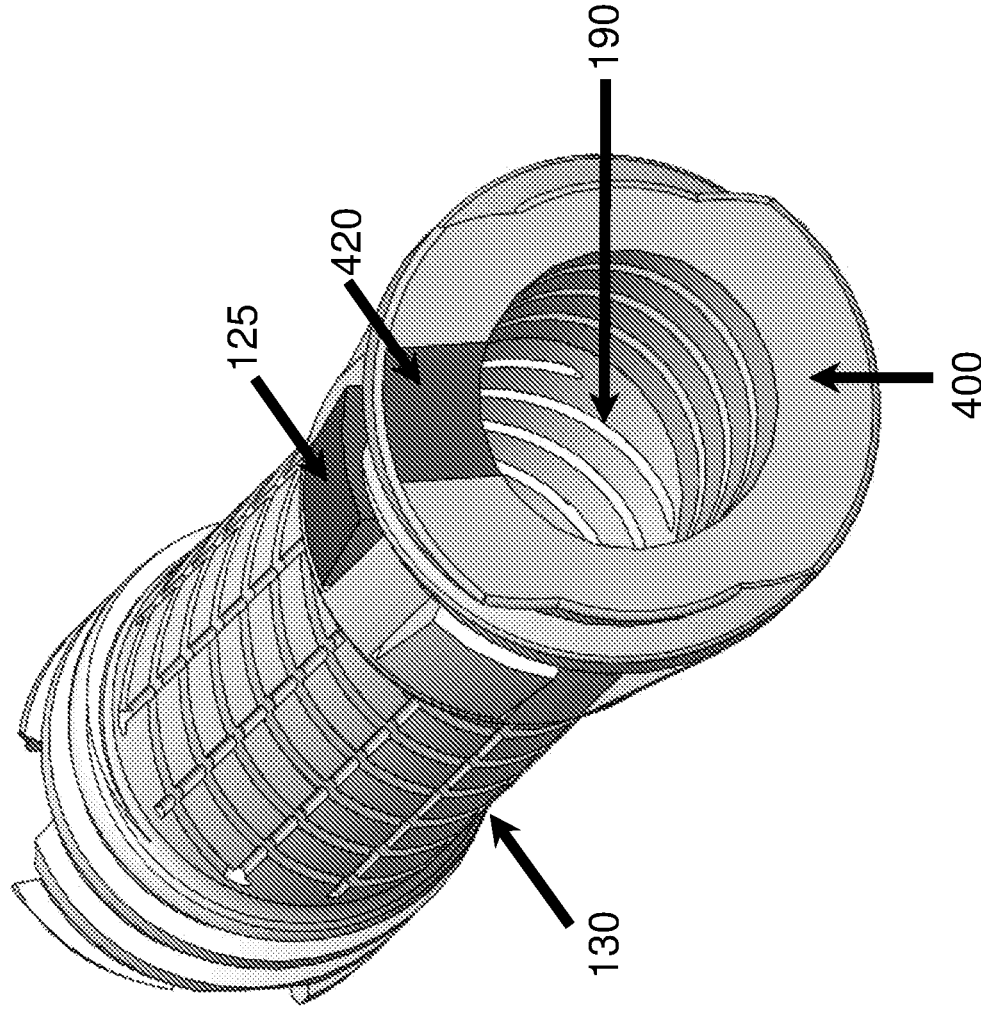

FIG. 49 is a schematic drawing showing a perspective view of connector 400 of FIG. 47 inserted into proximal opening 103 of device 100. As shown, connector 400 and proximal region 101 are aligned using alignment marker 125 of device 100 and alignment marker 420 of connector 400.

Figure 50:
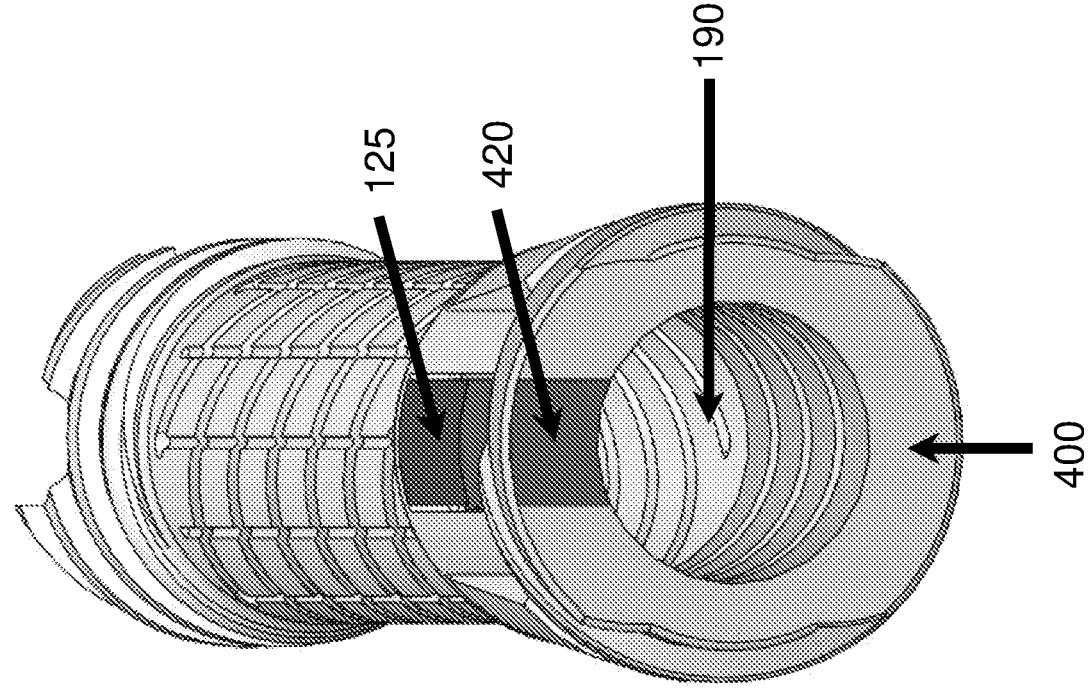

FIG. 50 is a schematic drawing showing a proximal to distal view of connector 400 and device 100 of FIG. 49.

Figures 51A, 51B:
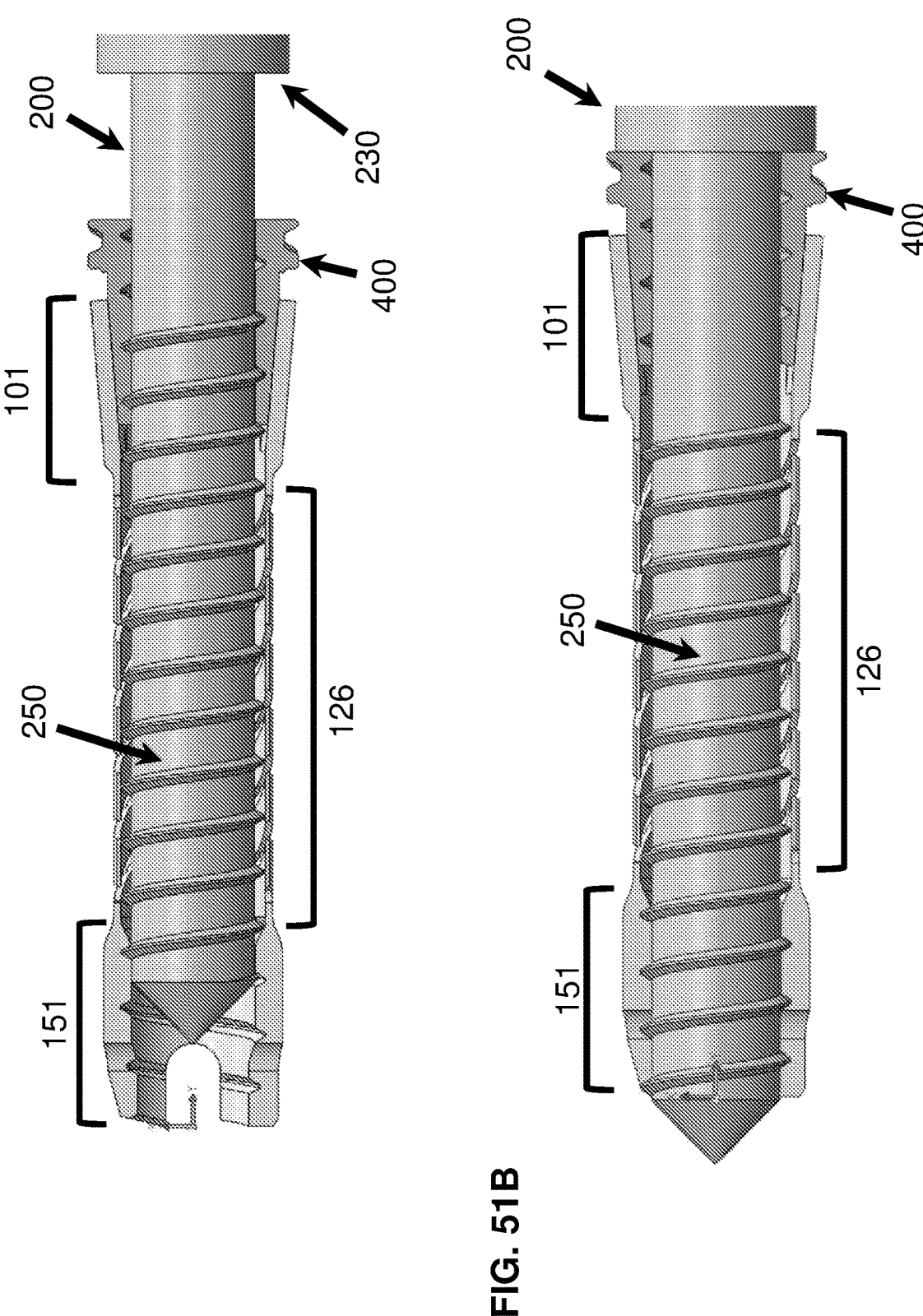

FIG. 51A is a schematic drawing showing a cross-sectional view of an embodiment of device 100 engaged by connector 400 and distal region 240 of insertion tool 200. Insertion tool 200 has external threads 250 at distal region 240 that engage with internal threads 160 of device 100.

FIG. 51B is a schematic drawing showing a cross-sectional view of an embodiment of device 100 engaged by connector 400 and insertion tool 200. Insertion tool 200 has external threads 240 at distal region 240 that engage with internal threads 160 of device 100. Lip 230 of central region 220 of insertion tool 200 lip is shown pressed against proximal region 410 of connector 400 to secure connector 400 into proximal opening 103 of device 100.

Figure 52:
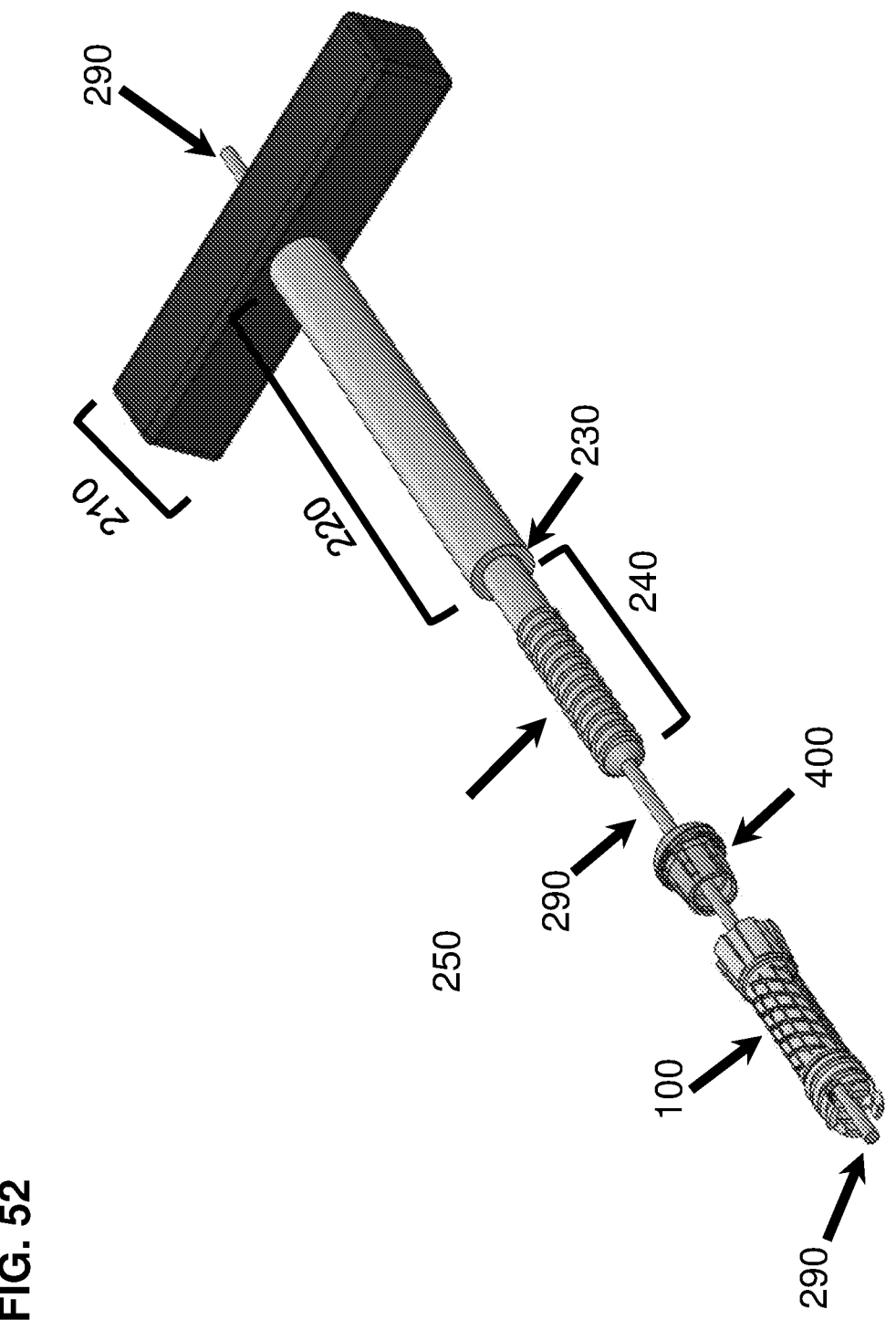

FIG. 52 is a schematic drawing showing an embodiment of device 100, connector 400, insertion tool 200, and guide wire 290. Insertion tool 200 has internal channel 280 longitudinally traversing therethrough configured to lead guide wire 290 from proximal region 210 of insertion tool 200 to the bone distal to distal region 151 of device 100.

Figure 53B:
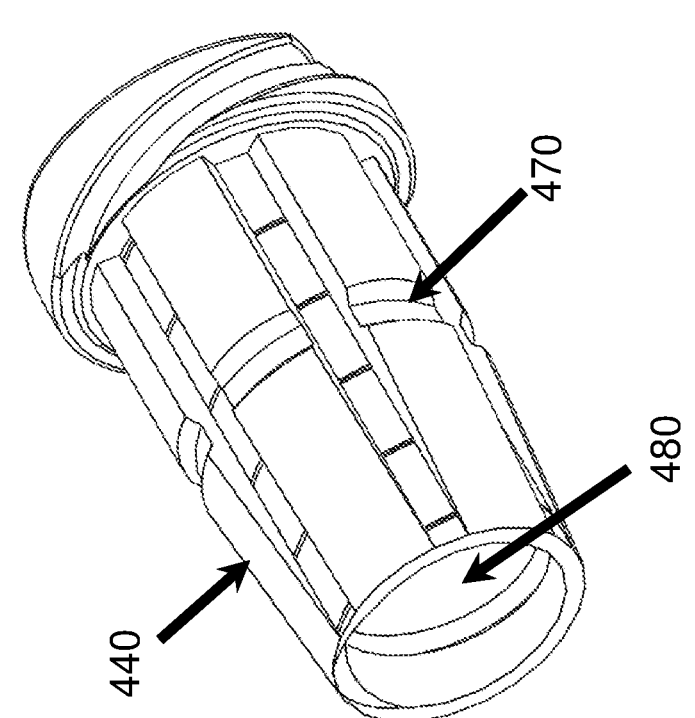
Figure 53A:
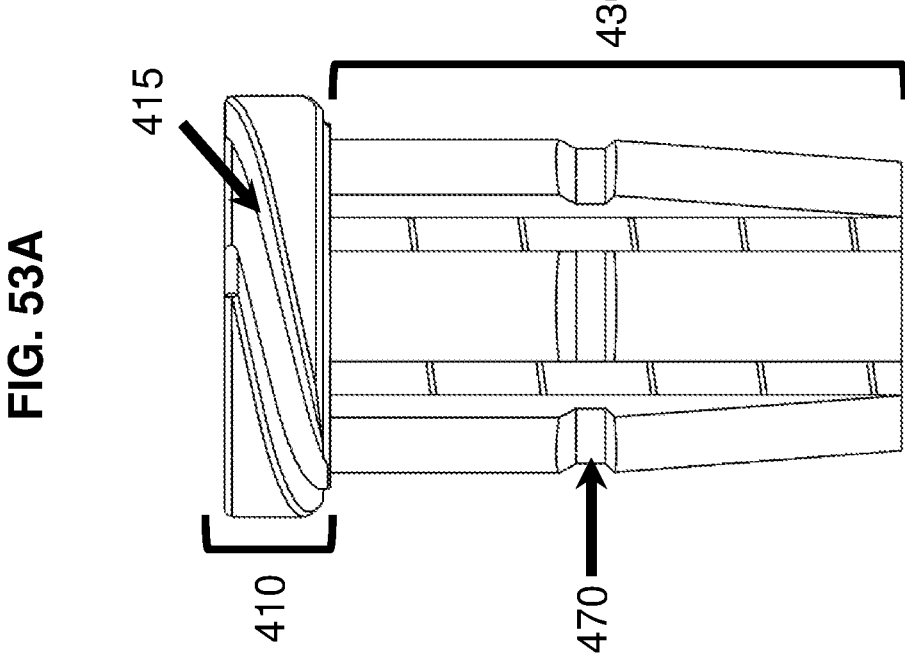

FIG. 53A is a schematic drawing showing a side view of an embodiment of connector 400 with proximal region 410 and distal region 430. Connector 400 includes circumferential groove 470 disposed in distal region 430.

FIG. 53B is a schematic drawing showing a perspective view of connector 400 of FIG. 53A.

Figure 54:

FIG. 54 is a schematic drawing showing a cross-sectional view of an embodiment of device 100, insertion tool 200, connector 400, bone plate 800, and pusher 300. External threads 250 of insertion tool 200 are shown engaging with internal threads 160 of device 100 at distal region 151. Distal region 320 of pusher 300 is shown in contact with proximal region of connector 400. Connector 400 has circumferential groove 470 that fastens connector 400 to bone plate 800. Furthermore, connector 400 also includes a plurality of wedges 440 securing distal region 430 of connector 400 to internal channel 190 of device 100 at proximal region 101.

Figure 55:
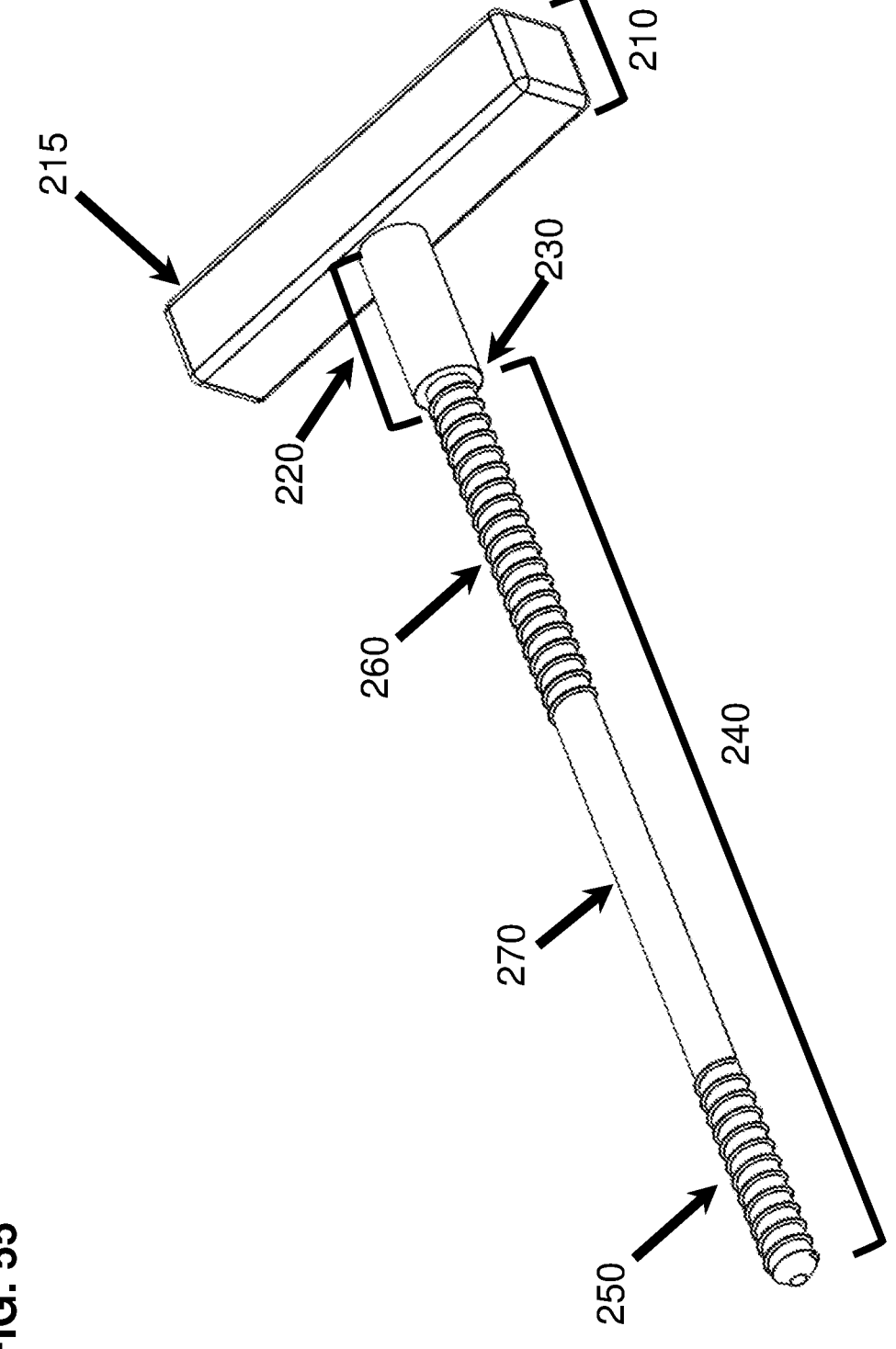

FIG. 55 is a schematic drawing showing an embodiment of insertion tool 200. Insertion tool 200 is shown with proximal region 210, central region 220, and distal region 240. Distal region 240 includes a first set of external threads 250 and a second set of external threads 260. External threads 250 and external threads 260 of distal region 240 are separated by unthreaded region 270 disposed therebetween. Handle 215 makes up proximal region 210 of insertion tool 200. Central region 220 is an unthreaded shaft 225 with a diameter that is larger than the diameter of distal region 240.

The difference in diameter between central region 220 and distal region 240 produces lip 230 of insertion tool 200.

Figure 56:
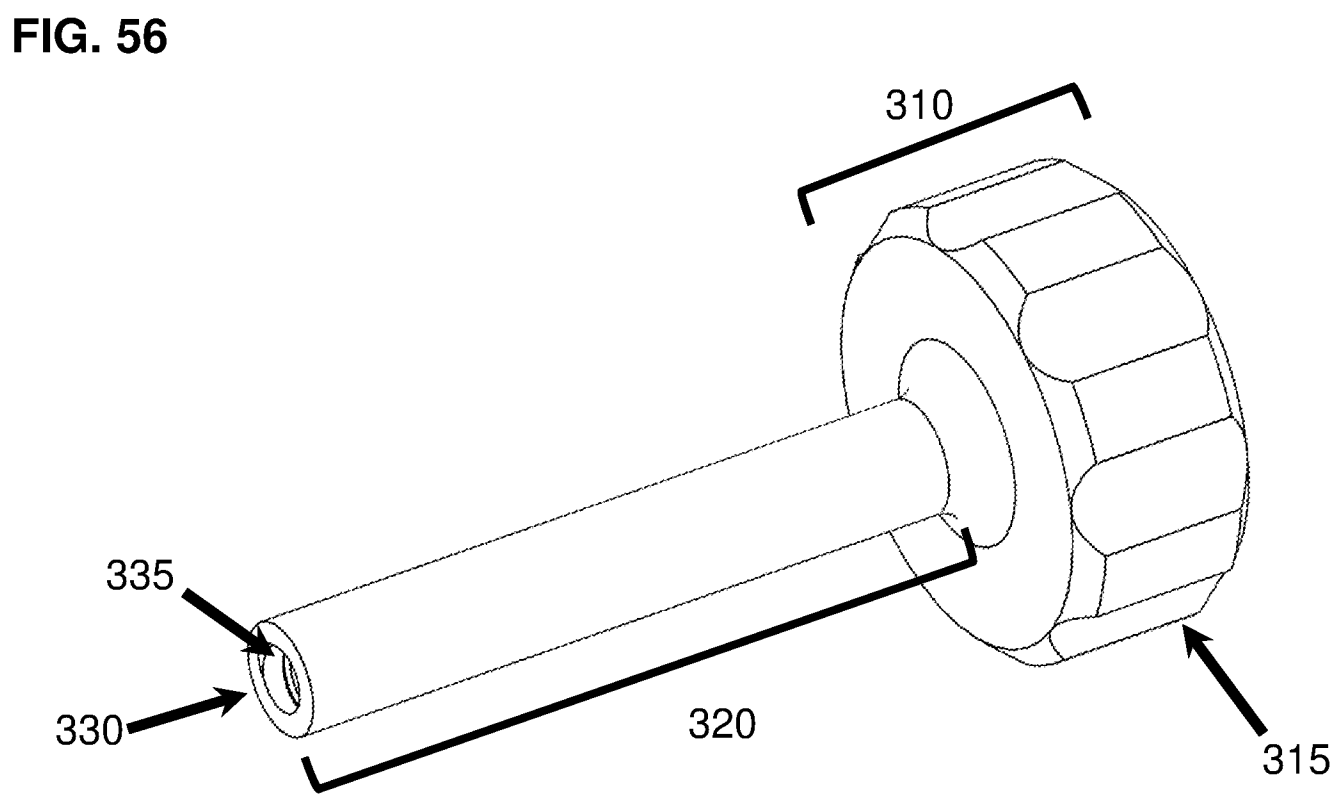

FIG. 56 is a schematic drawing showing an embodiment of pusher 300 with proximal region 310 and distal region 320. Proximal region of pusher 300 includes handle 315. Distal region 320 of pusher 300 is a shaft with a blunt end. Pusher 300 also has internal channel 330 with internal threads 335.

Figure 57:
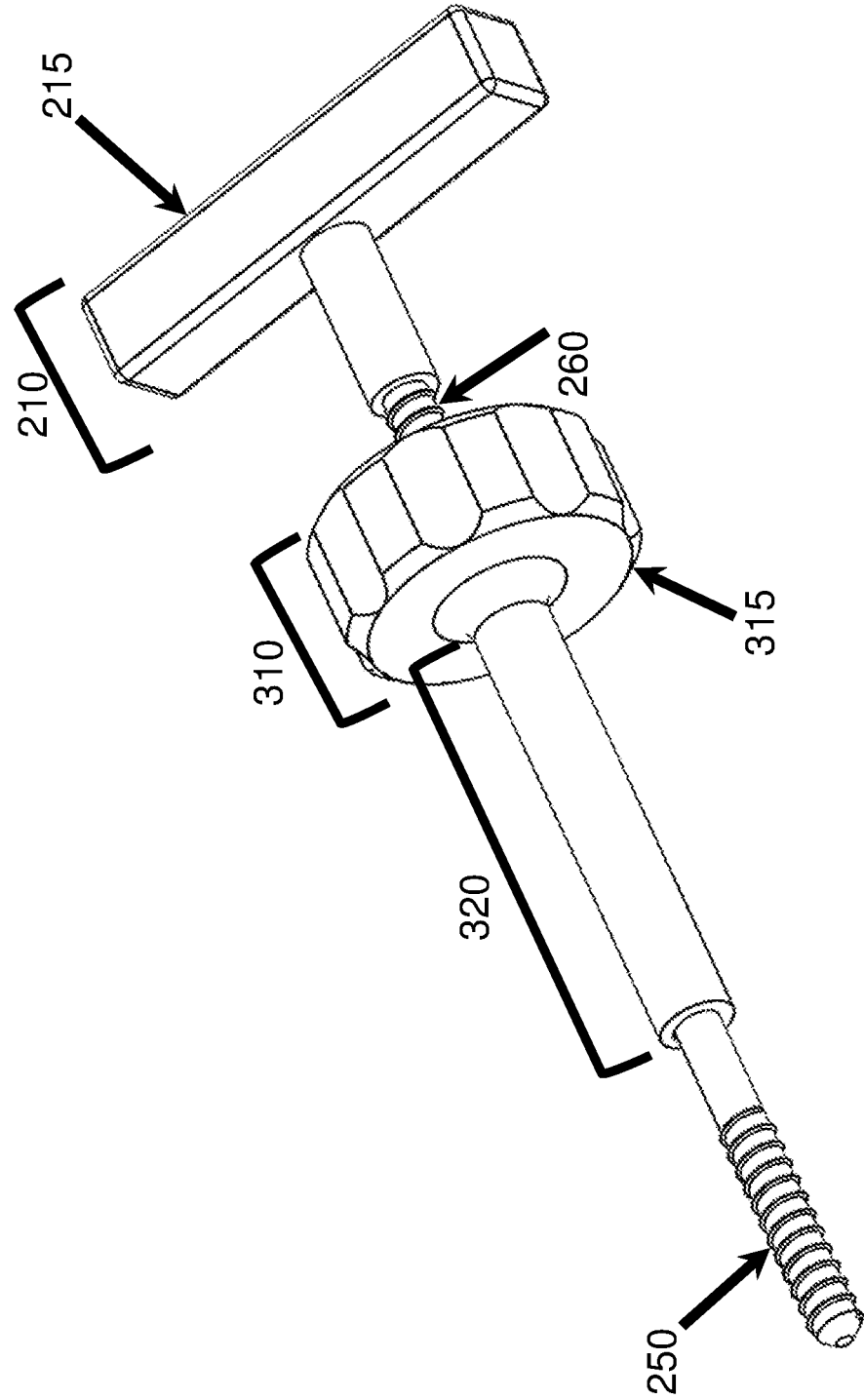

FIG. 57 is a schematic drawing showing insertion tool 200 of FIG. 55 engaged with pusher 300 of FIG. 56. Distal region 240 of insertion tool 200 is shown traversing internal channel 330 of pusher 300. The second set of external threads 260 of insertion tool 200 are engaged with internal threads 335 of pusher 300.

Figure 58:
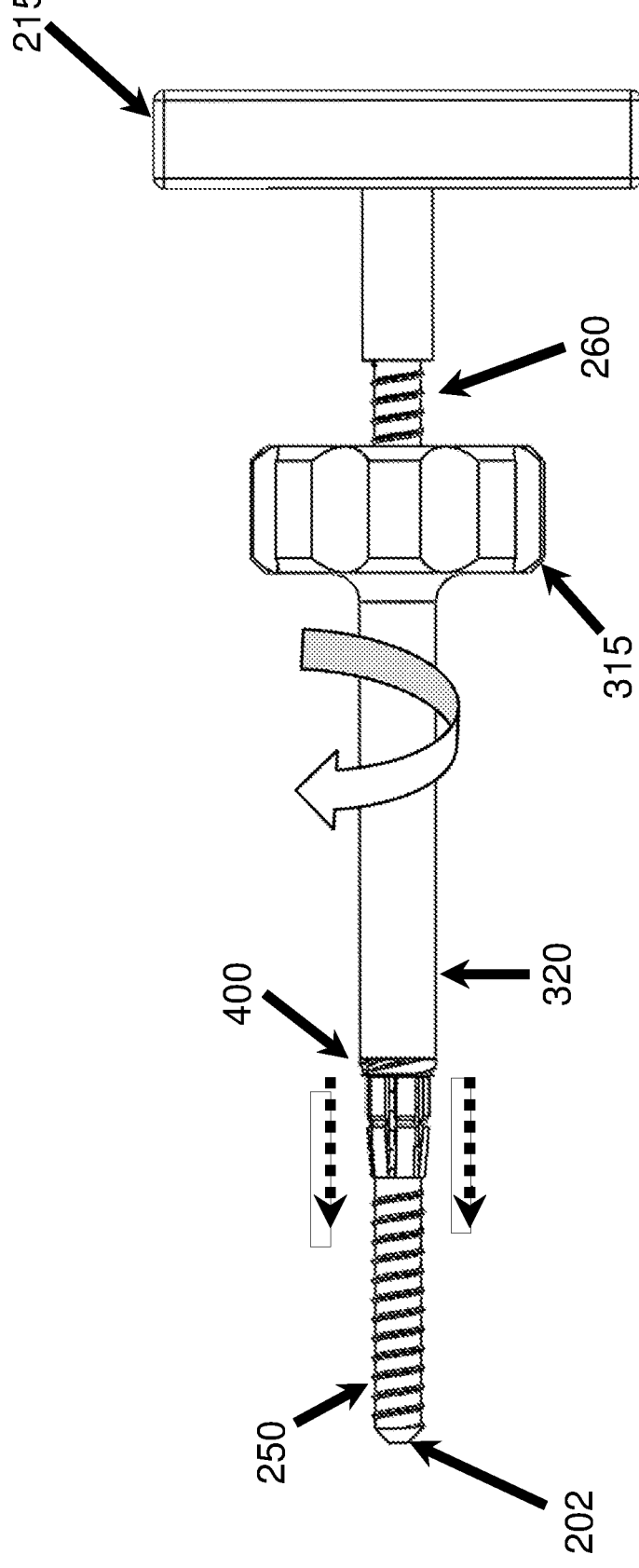

FIG. 58 is a schematic drawing showing insertion tool 200 of FIG. 55 engaged with pusher 300 of FIG. 56 and connector 400 of FIGS. 53A and 53B. Connector 400 is shown inserted onto distal region 240 of insertion tool 200 and in contact with distal region 320 of pusher 300. Pusher 300 is connected to insertion tool 200 via the engagement of internal threads 335 of pusher 300 with the second set of external threads 260 of insertion tool 200. Twisting handle 315 of pusher 300 allows pusher 300 to rotate independently of insertion tool 200, thereby translating pusher 300 longitudinally towards connector 400, which allows distal region 320 of pusher 300 to contact proximal region 410 of connector 400. Continuing to twist handle 315 of pusher 300 pushes connector 400 towards distal end 202 of insertion tool 200.

Figure 59:
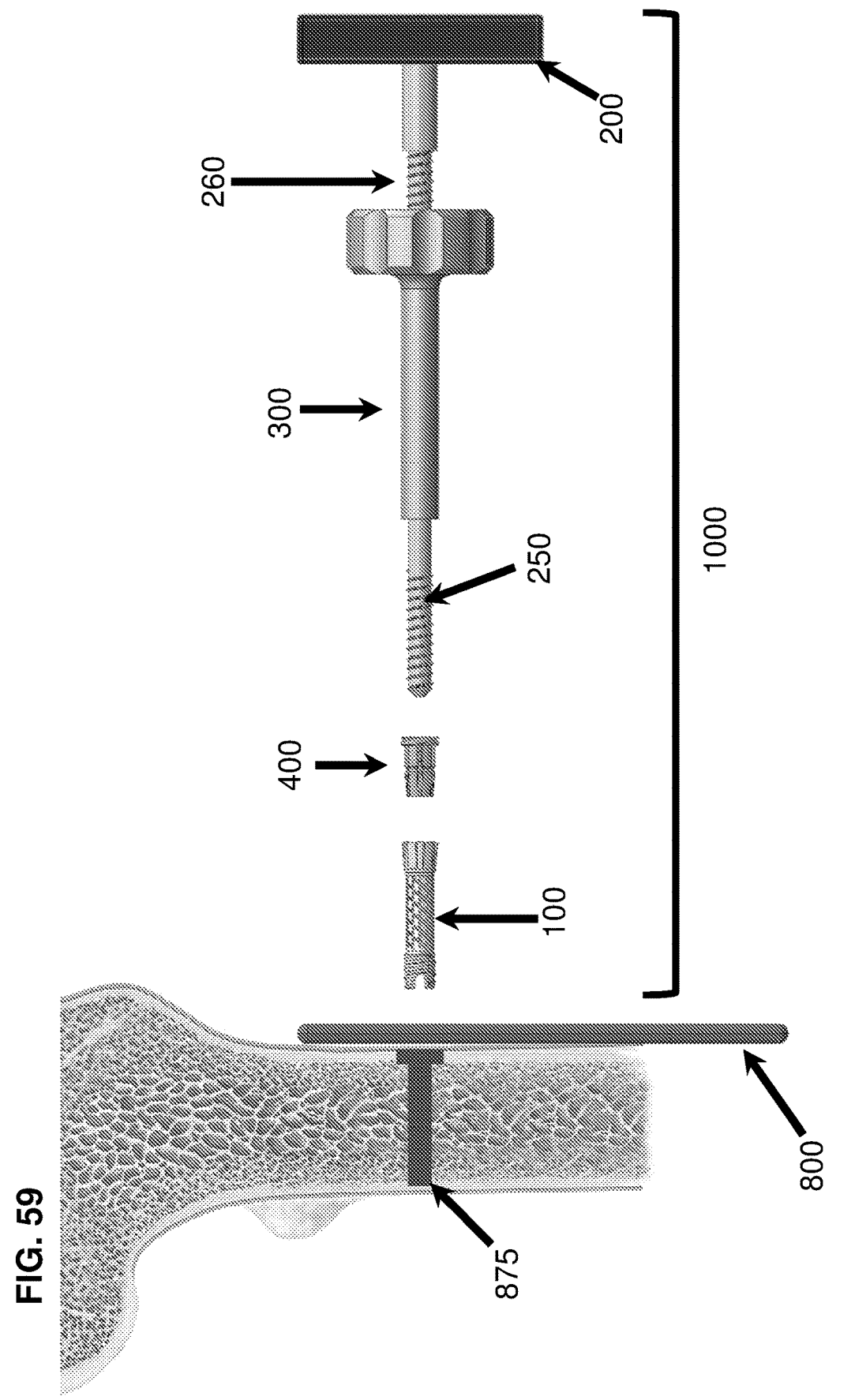

FIG. 59 is a schematic drawing showing an embodiment of system 1000 including insertion tool 200, pusher 300, connector 400, and device 100. Only insertion tool 200 and pusher 300 of system 1000 are shown engaged. Also shown is bone plate 800 and a bone with a predrilled bone hole.

Figure 60:
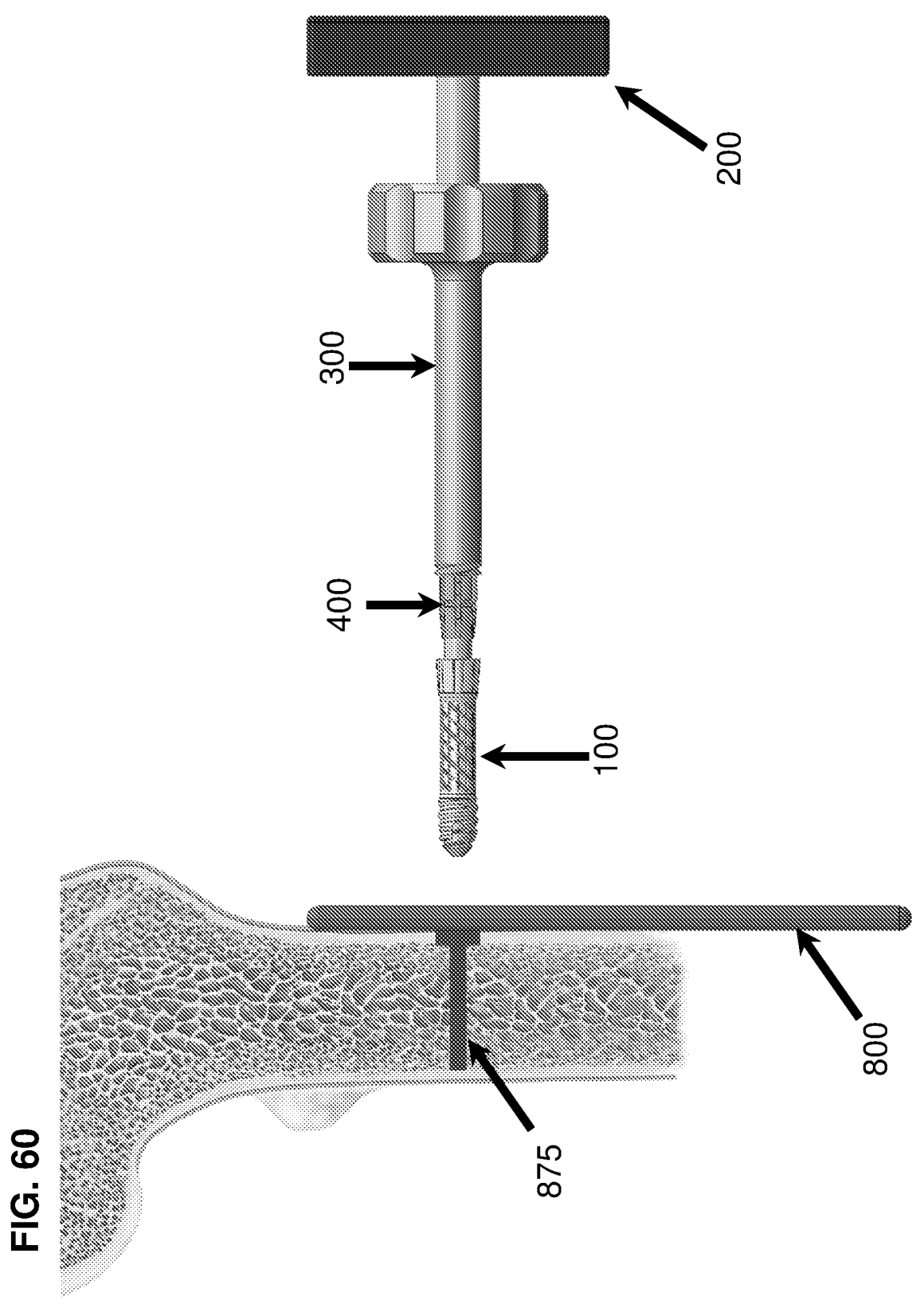

FIG. 60 is a schematic drawing showing system 1000 of FIG. 59, in which insertion tool 200, pusher 300, connector 400, and device 100 are shown assembled.

Figure 61:
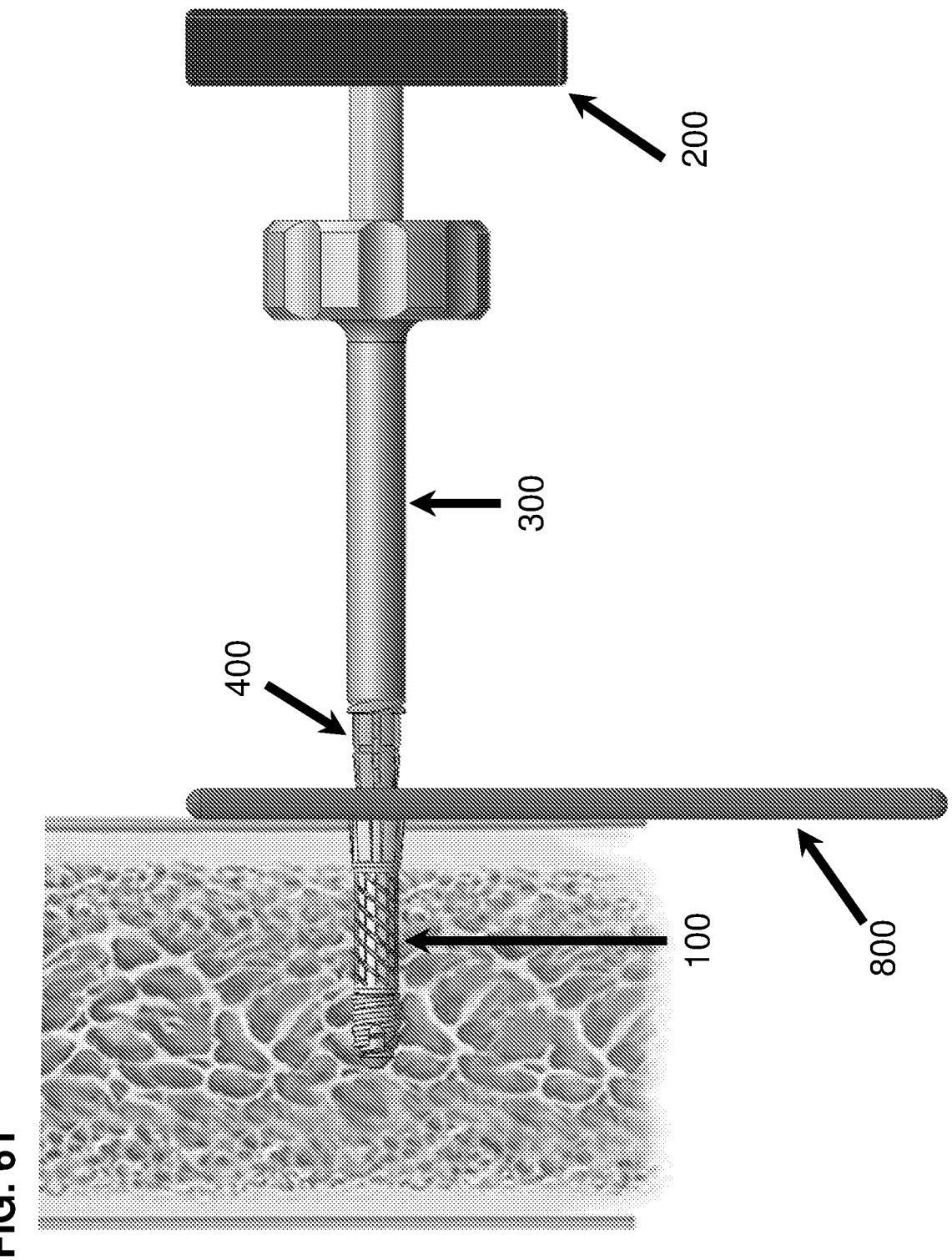

FIG. 61 is a schematic drawing showing use of system 1000 of FIG. 60 to insert device 100 through a hole in bone plate 800 and into the bone.

Figure 62:
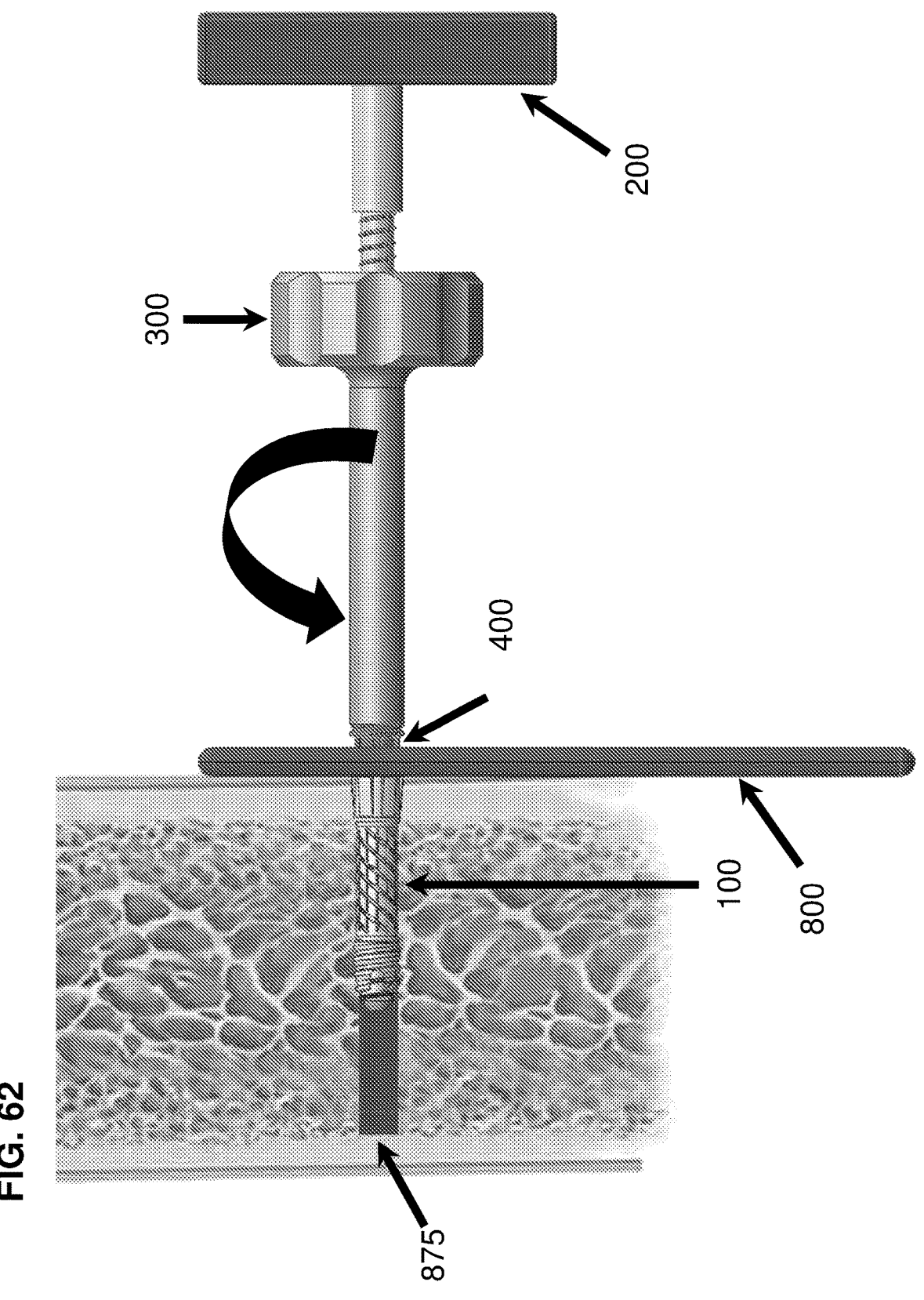

FIG. 62 is a schematic drawing showing use of system 1000 following insertion of device 100 into bone, as shown in FIG. 61, in which twisting of pusher 300 pushes connector 400 through the hole in bone plate 800 so that distal region 430 of connector 400 enters internal channel 190 at proximal region 101 of device 100 and fixedly engages connector 400 to device 100 by allowing wedges 440 of connector 400 to engage with an interior side of wings 105 of device 100, which causes wings 105 to expand into bone. Expansion of wings 105 locks proximal region 101 of device in the bone. In addition, circumferential groove 470 of connector 400 engages with bone plate 800, thereby securing connector 400 to bone plate 800.

Figure 63:
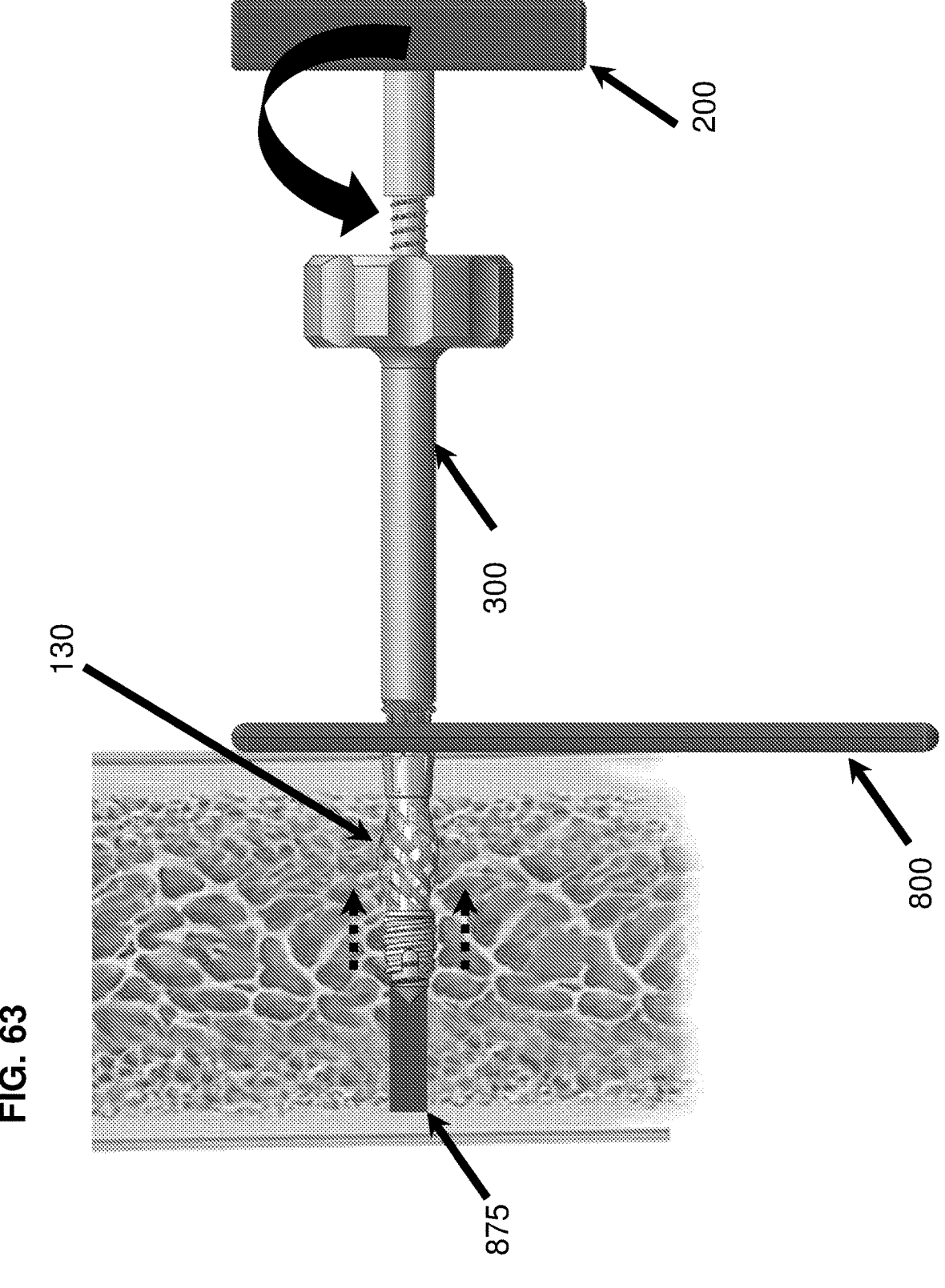

FIG. 63 is a schematic drawing showing use of system 1000 following the step shown in FIG. 62, in which twisting of handle 215 of insertion tool 200 while holding pusher 300 in contact with connector 400 causes compression of distal region 151 of device 100, which causes expandable body 130 of central region 126 of device 100 to radially expand due to torque applied to distal region 151 of device 100 by insertion tool 200.

Figure 64:
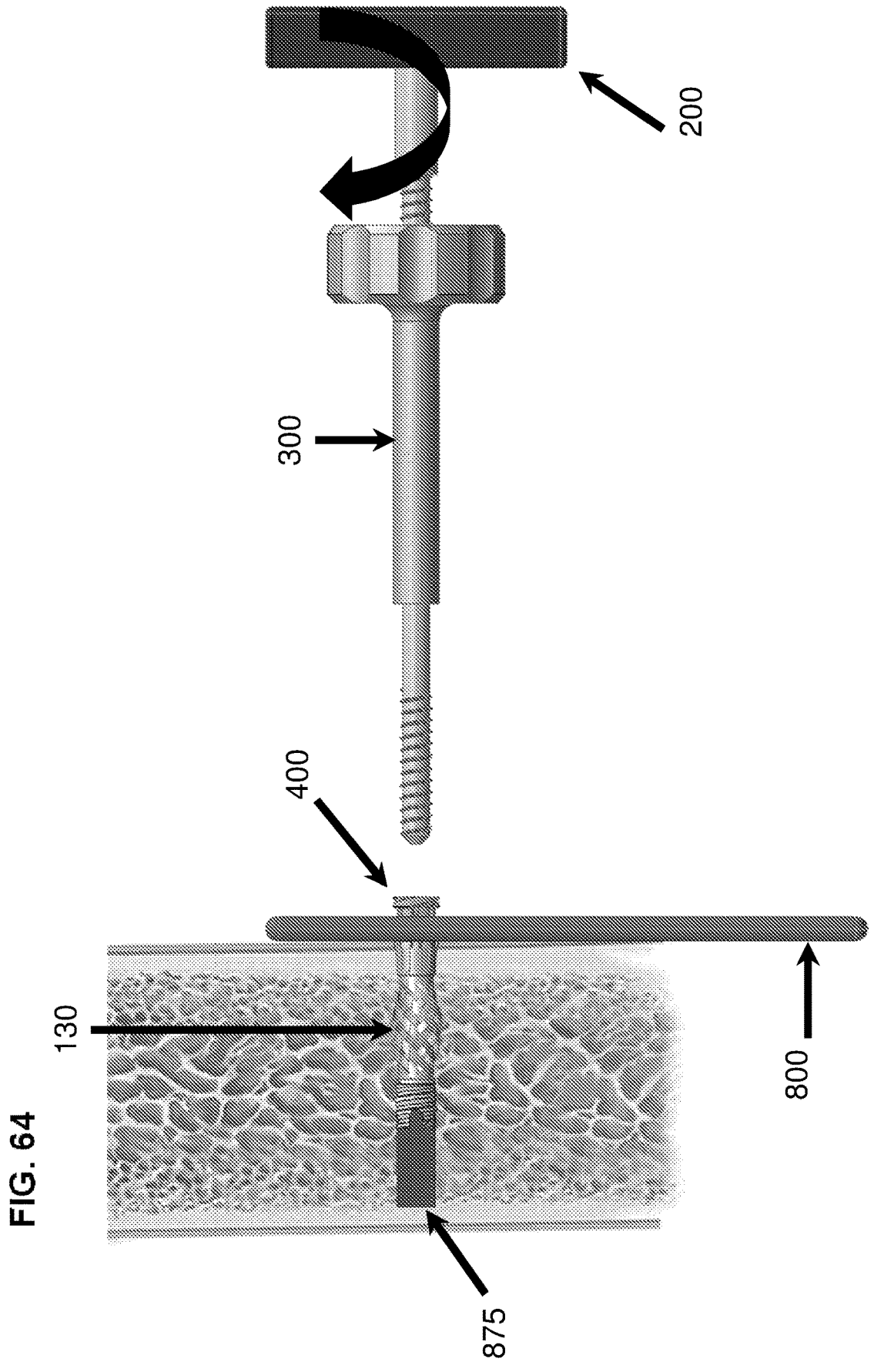

FIG. 64 is a schematic drawing showing use of system 1000 following the step shown in FIG. 63. Twisting of handle 215 of insertion tool 200 in a direction opposite to the twisting shown in FIG. 63 causes insertion tool 200 and pusher 300 to disengage from device 100, while leaving connector 300 engaged with device 100. Expandable body 130 of device 100 remains in a radially expanded state.

Figure 65:
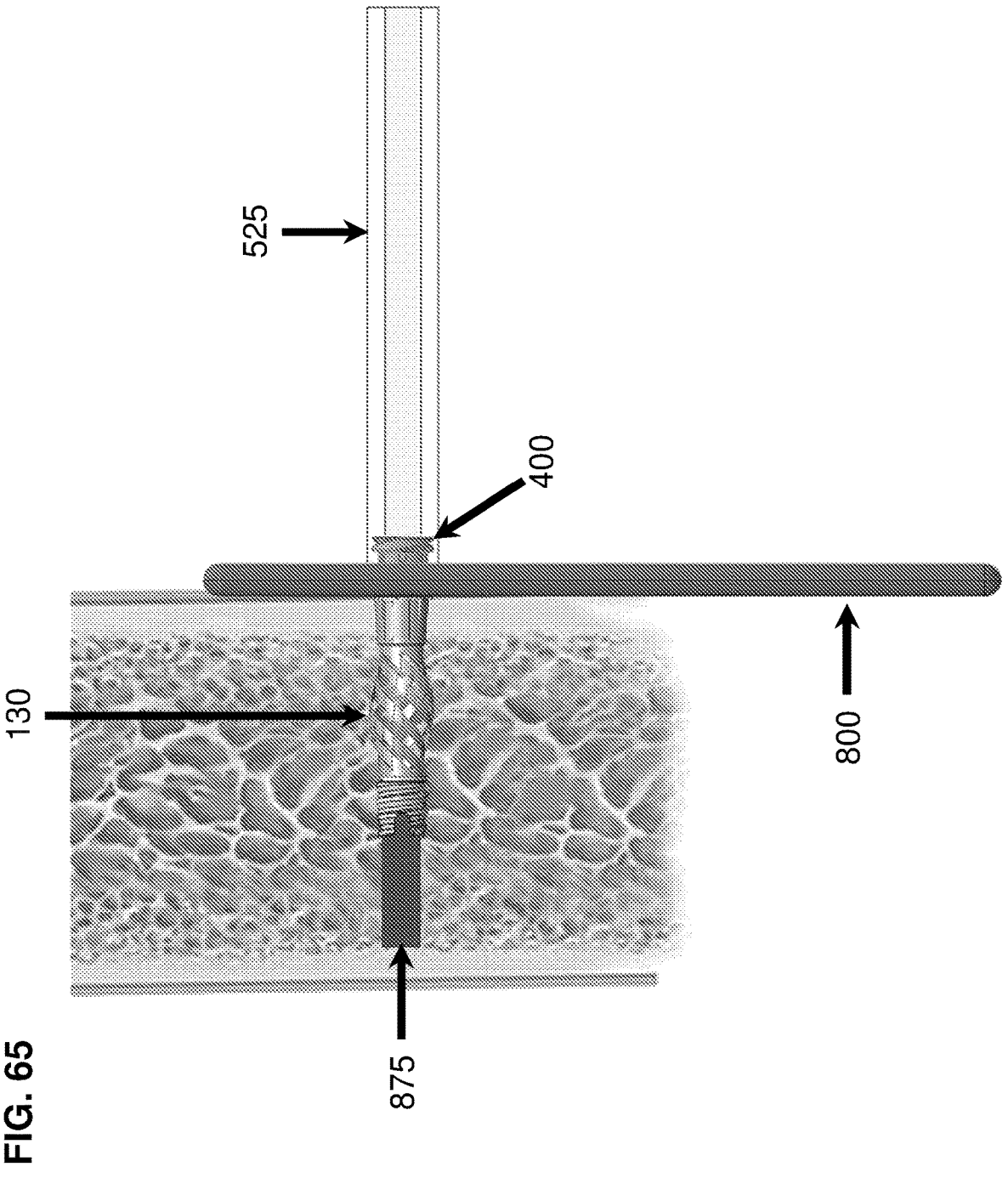

FIG. 65 is a schematic drawing showing attachment of tube 525 of biomaterial dispenser 500 to connector 400 via Luer-lock threads 415 following the step shown in FIG. 64 so that biomaterial dispenser 500 is fluidically connected to connector 400.

Figure 66:
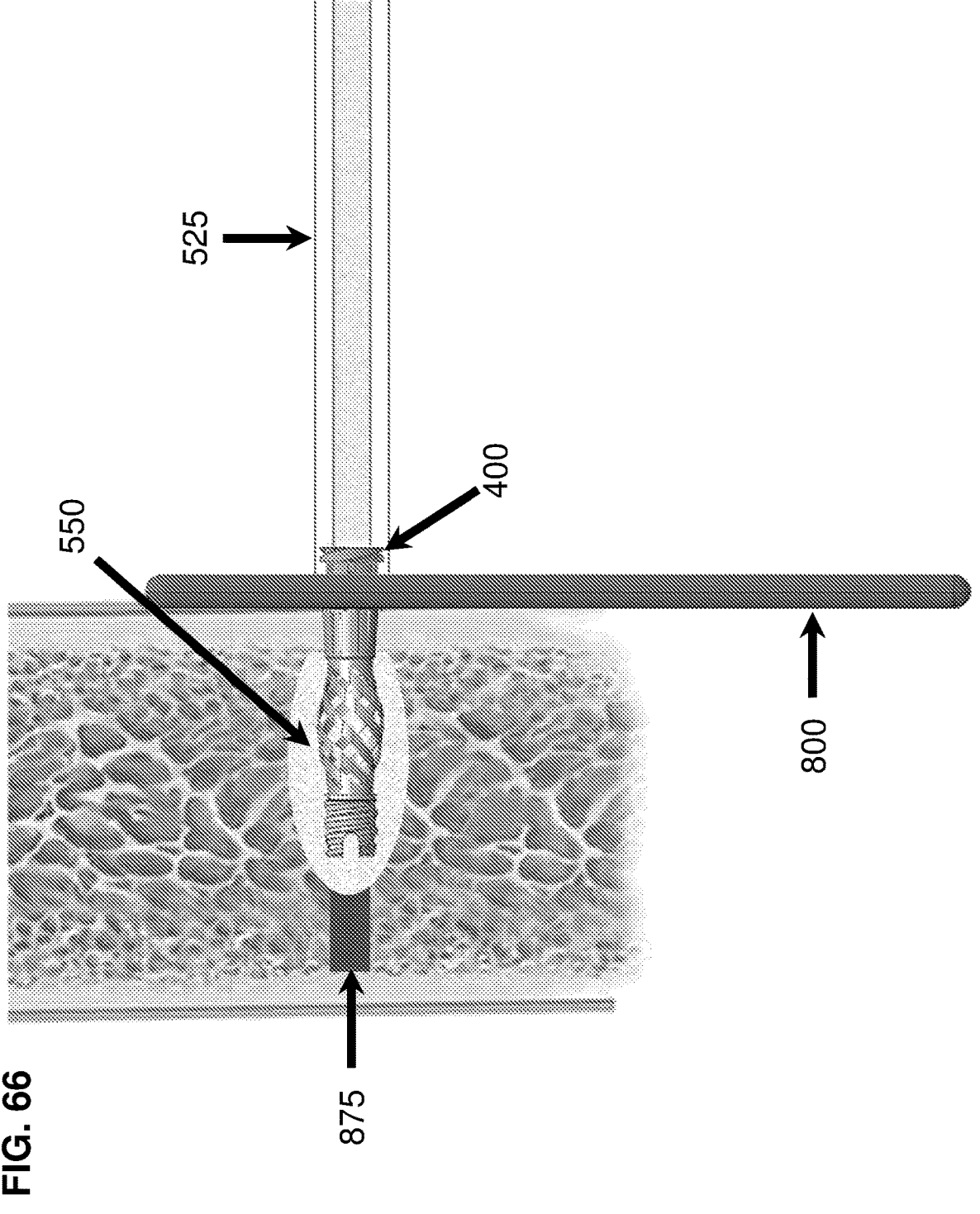

FIG. 66 is a schematic drawing showing a step following the step shown in FIG. 65, in which biomaterial 550 is introduced from biomaterial dispenser 500 into internal channel 190 of device 100. Biomaterial 550 is uniformly delivered to the bone due to the radially expanded state of expandable body 130.

Figure 67:
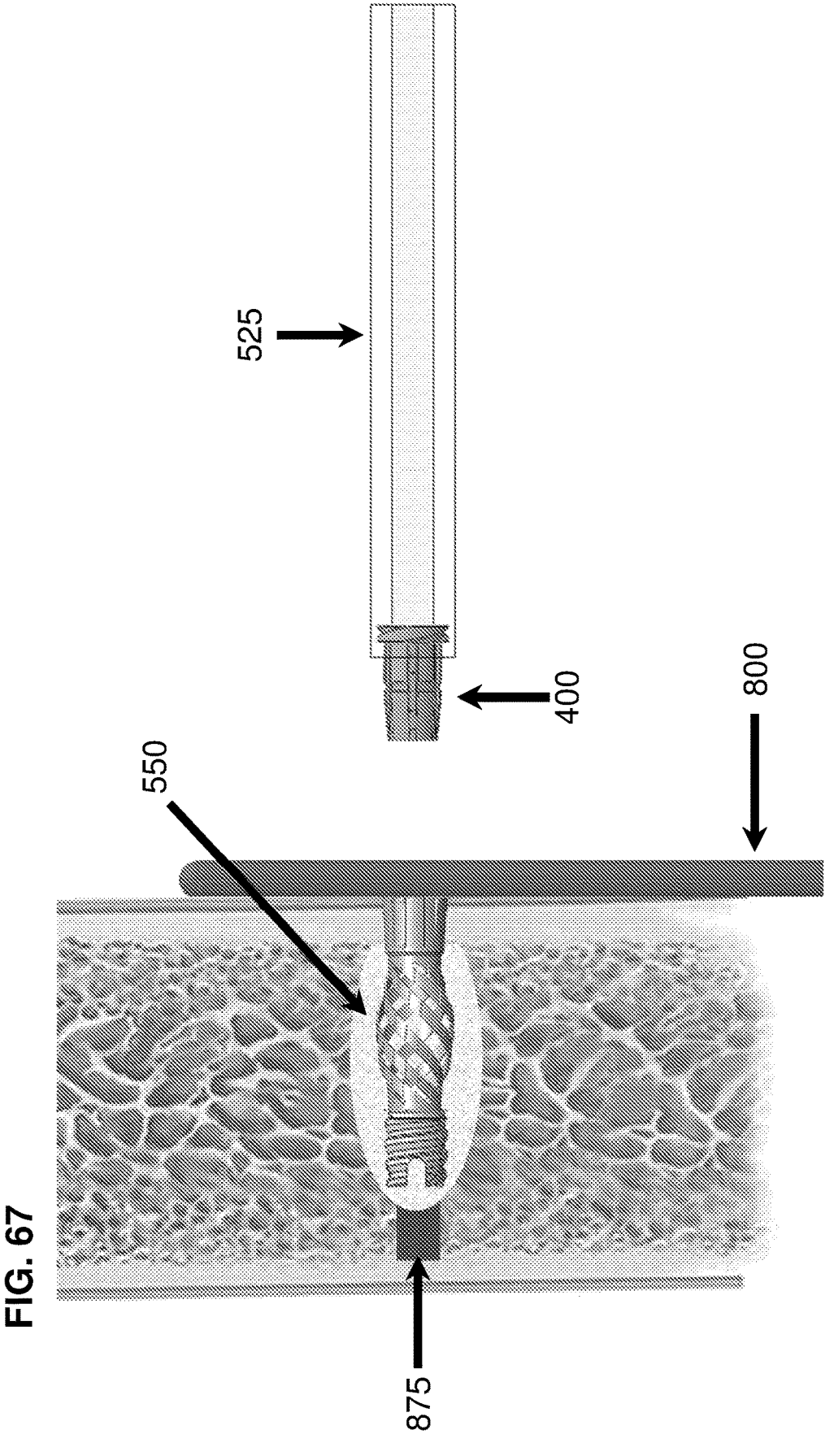

FIG. 67 is a schematic drawing showing a step following the step shown in FIG. 66, in which connector 400 and tube 525 of biomaterial dispenser 500 are disconnected from device 100.

Figure 68:
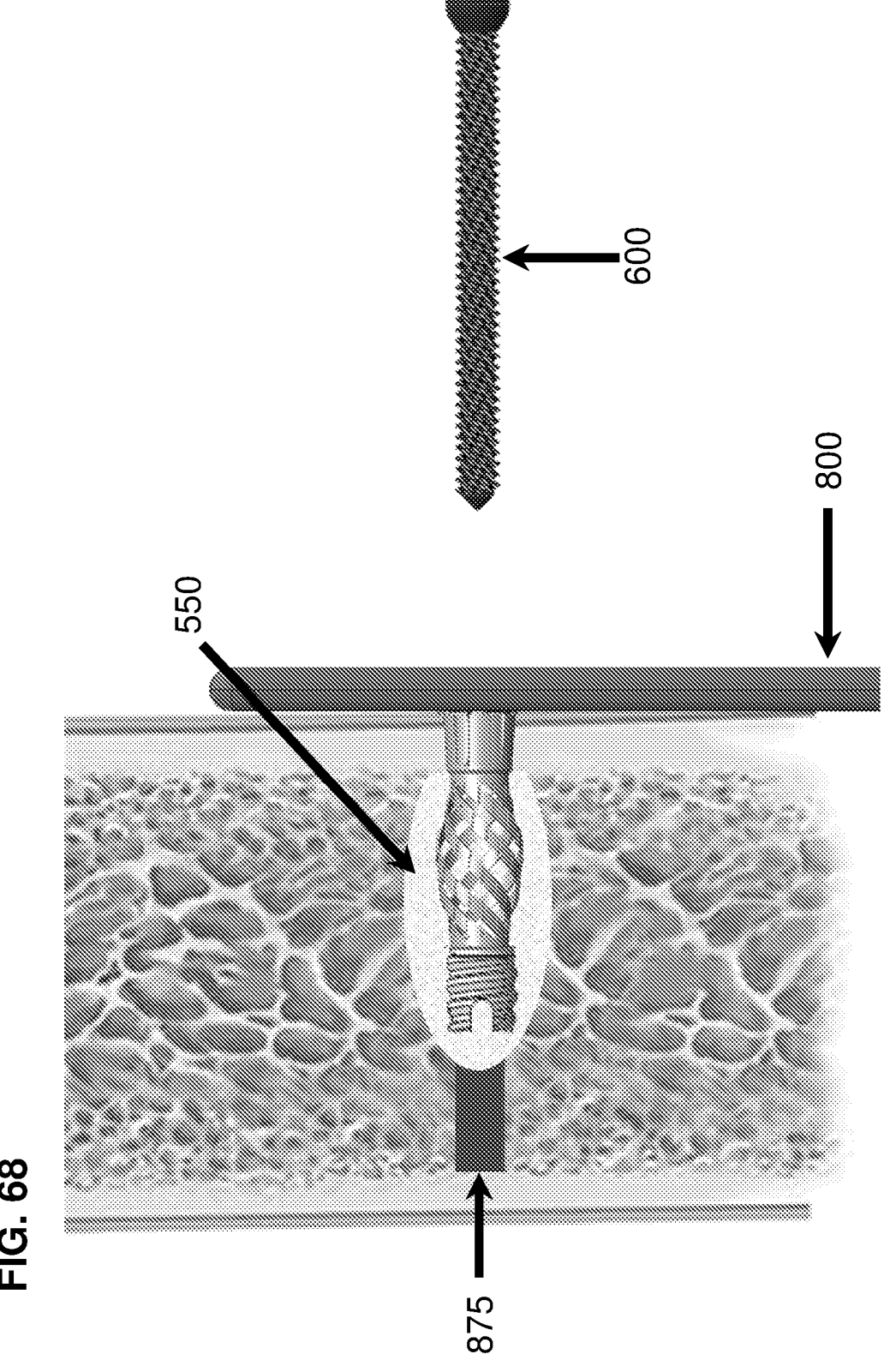

FIG. 68 is a schematic drawing showing a step following the step shown in FIG. 67 showing introduction of screw 600 through the hole in bone plate 800 and into internal channel 190 of device 100.

Figure 69:
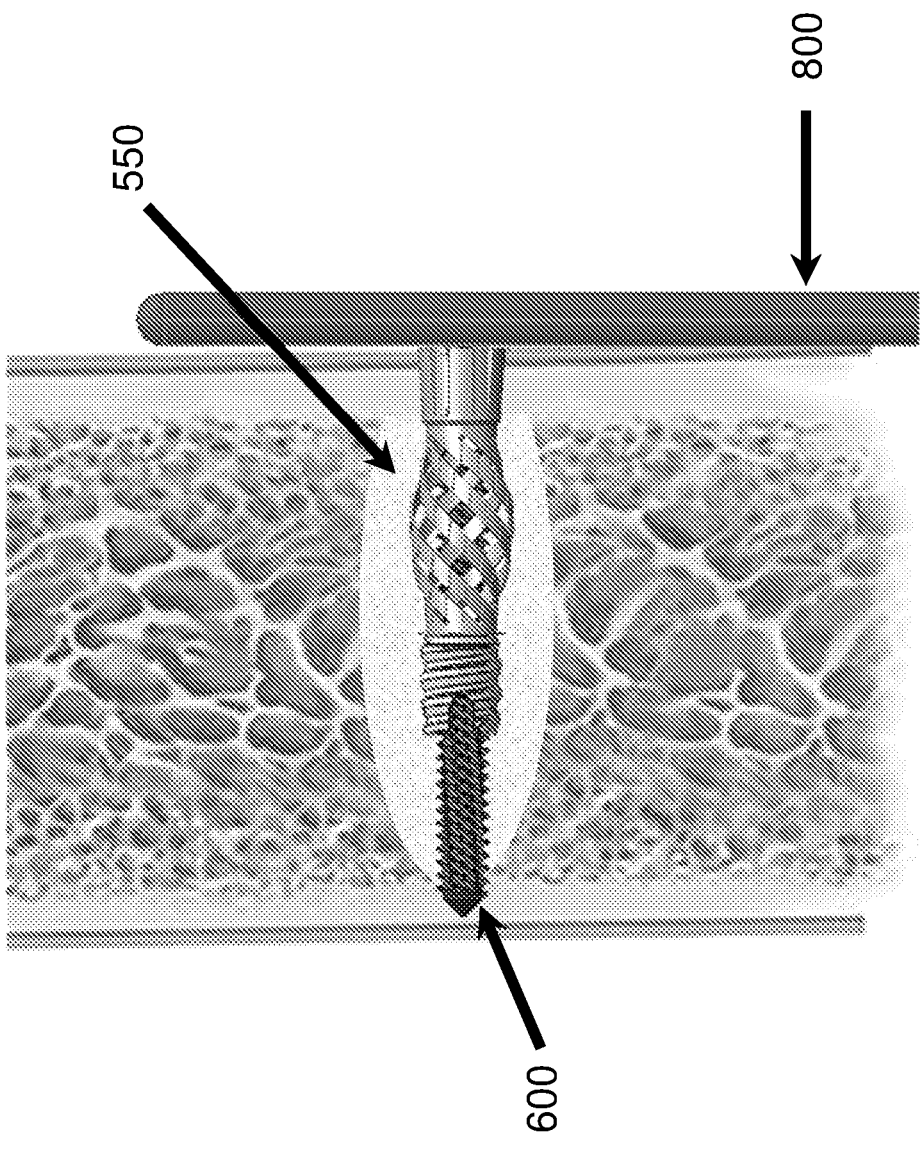

FIG. 69 is a schematic drawing showing a step following the step shown in FIG. 68, in which screw 600 has been inserted into device 100 and in which screw 600 is secured to the bone by at its distal tip. Insertion of screw 600 into device 100 distributes biomaterial 550 out of expandable body 130 and into bone surrounding device 100.

Figure 70B:
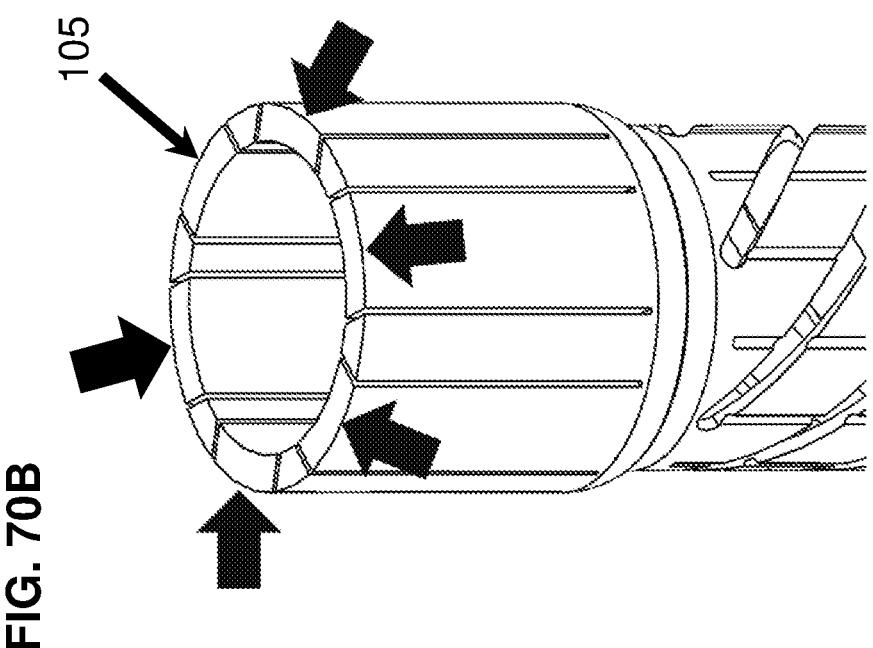
Figure 70A:
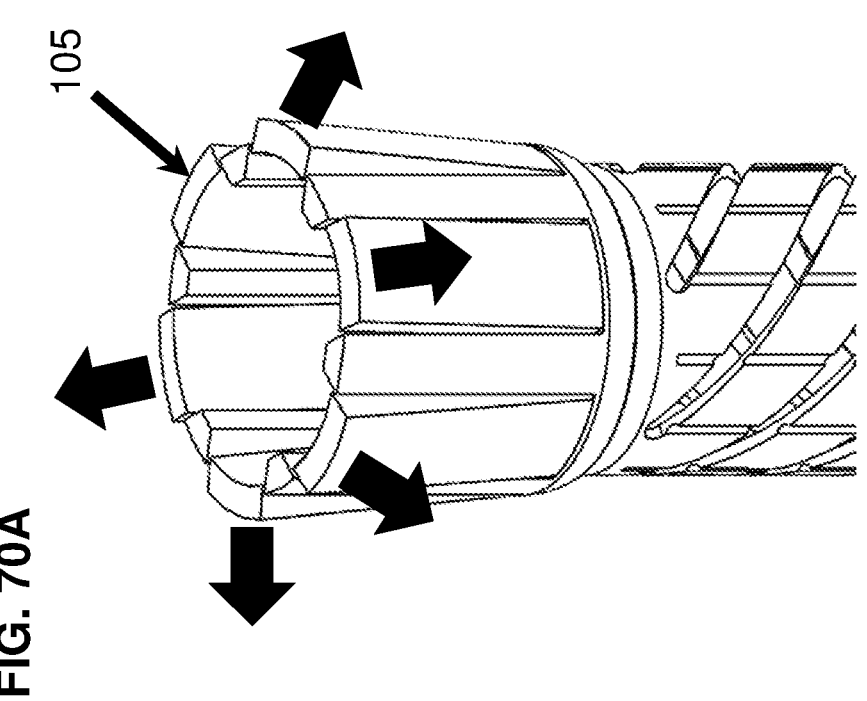

FIG. 70A is a schematic drawing showing proximal region 101 of device 100 in an uncompressed state. Arrows show proximal end 106 of wings 105 protruding outwardly from proximal region 101 of device 100.

FIG. 70B is a schematic drawing showing proximal region 101 of device 100 in a compressed state. Arrows show proximal end 106 of wings 105 deflected inwardly toward proximal region 101 of device 100.

Figure 71:
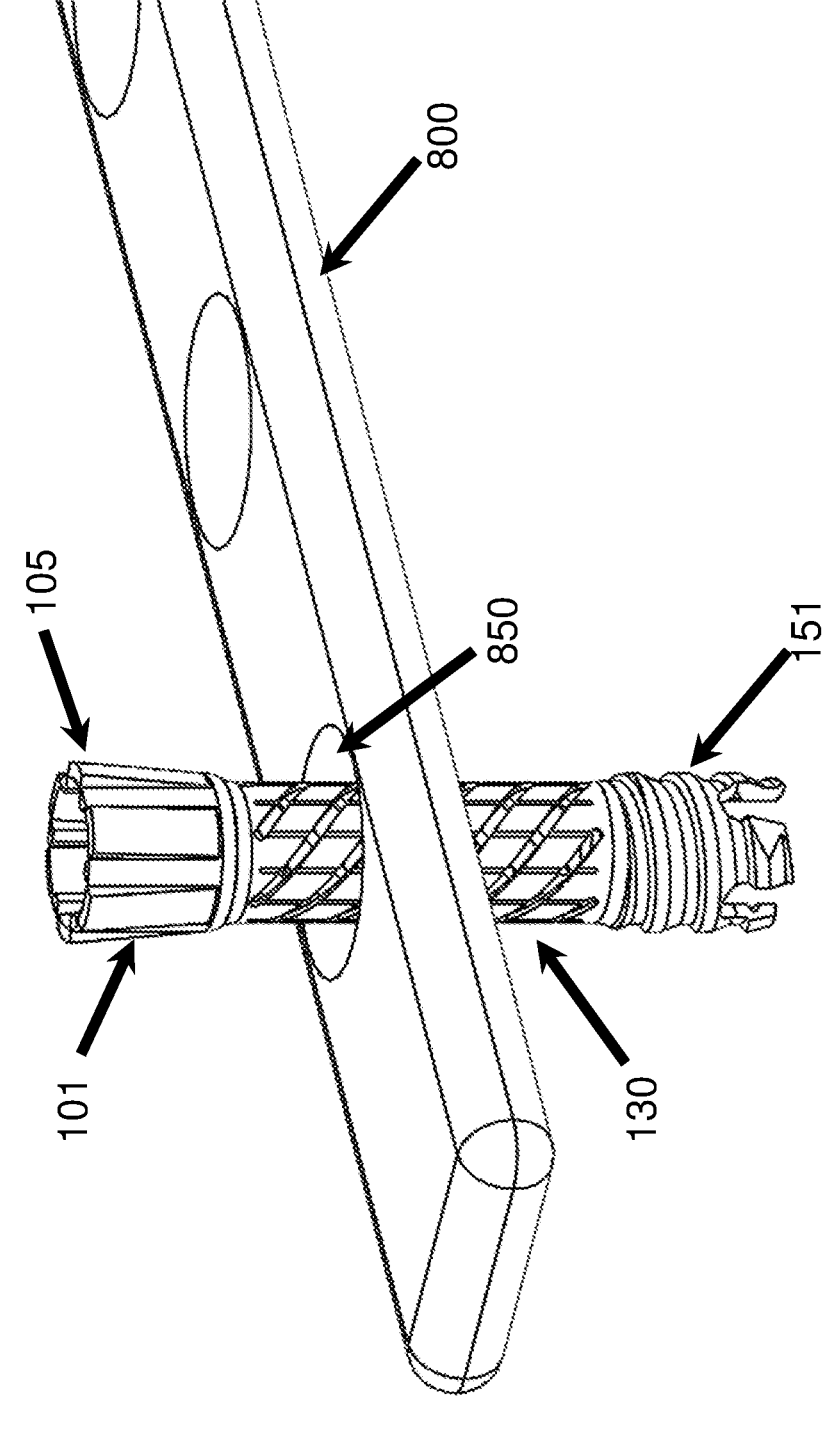

FIG. 71 is a schematic drawing showing device 100 in the process of being inserted through hole 850 of bone plate 800.

Figures 72A, 72B:
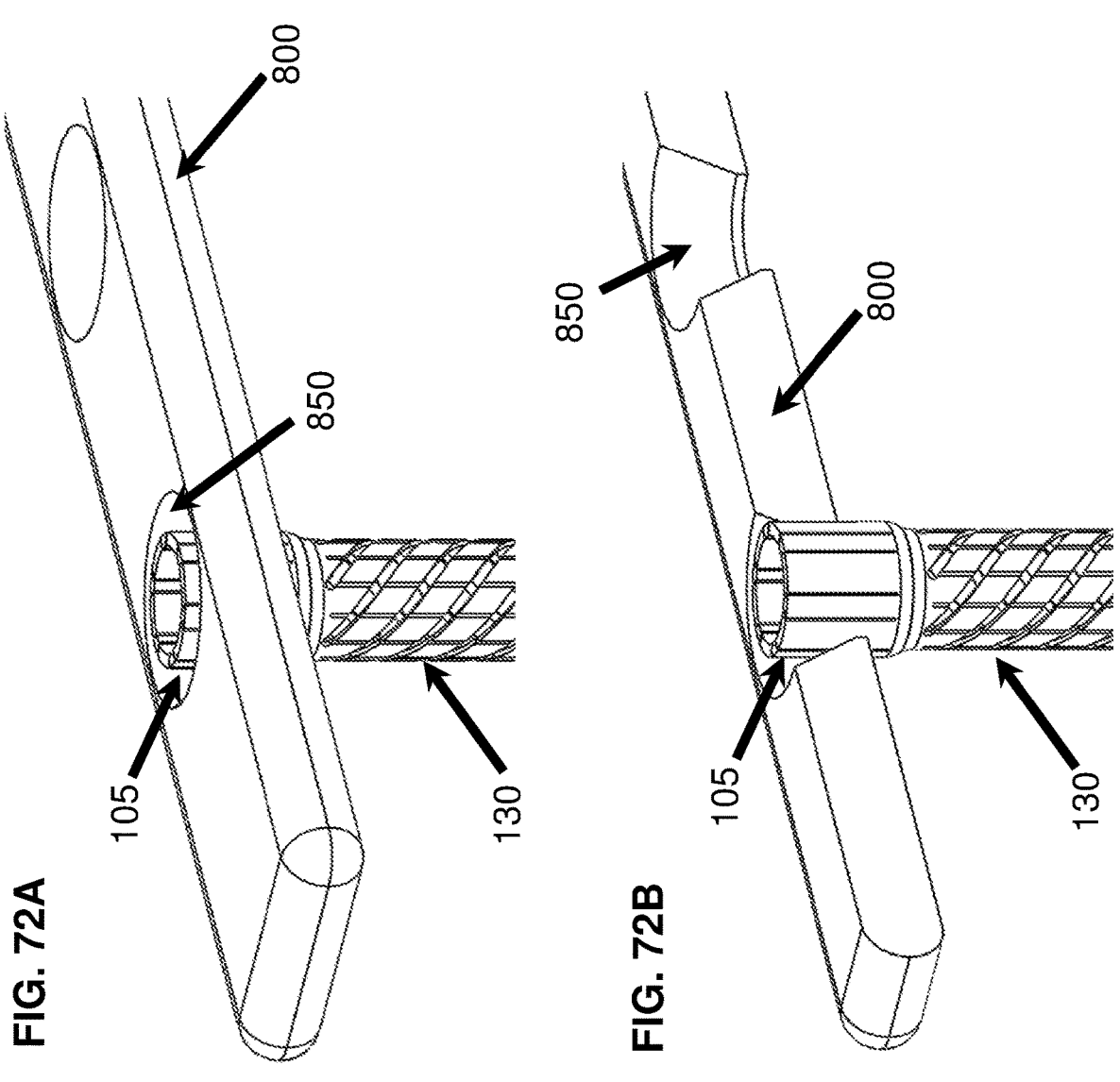

FIG. 72A is a schematic drawing showing device 100 in the process of being inserted through hole 850 of bone plate 800, which causes inward deflection (compression) of wings 105 at proximal end 106 of device 100.

FIG. 72B is a schematic drawing showing a cross-sectional view of bone plate 800 of FIG. 72A.

Figure 73B:
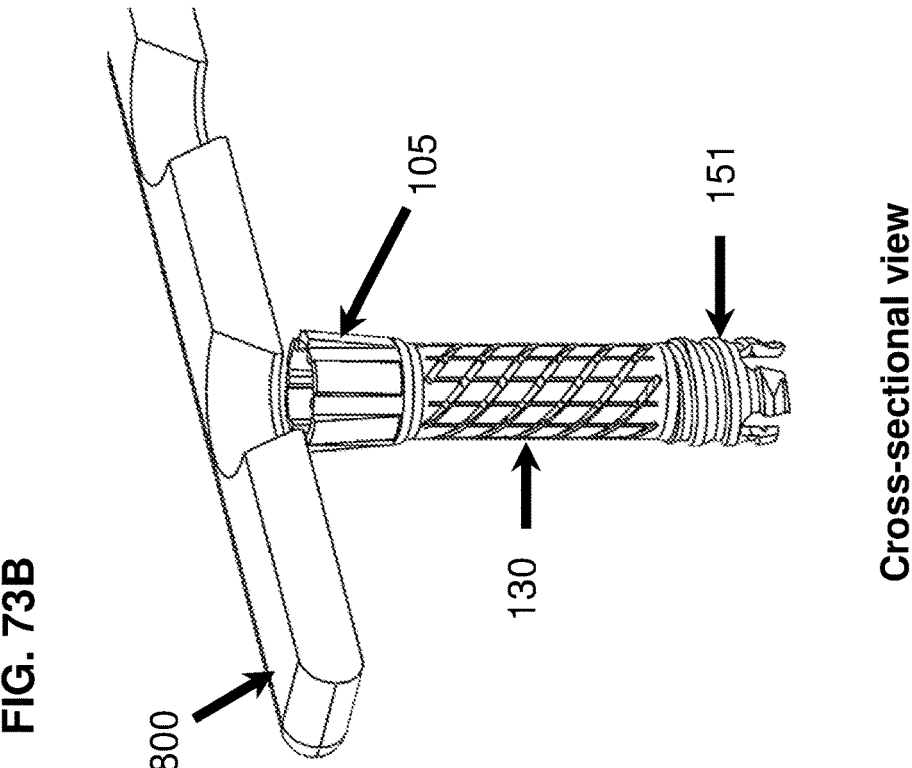
Figure 73A:
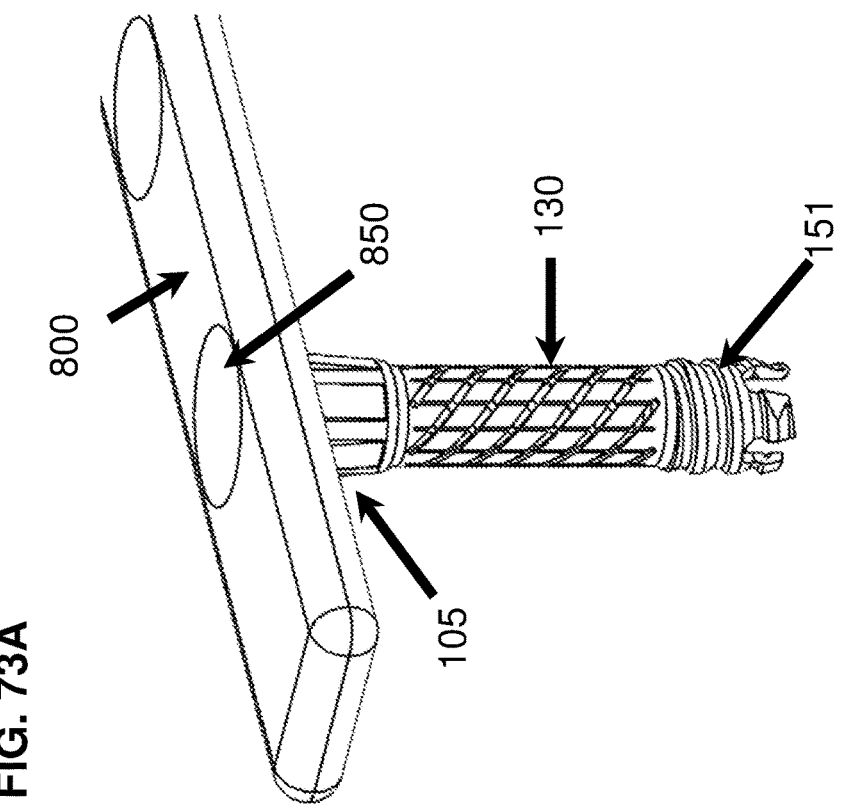

FIG. 73A is a schematic drawing showing device 100 following its complete insertion through bone plate 800. Once device 100 passes through bone plate 800, wings 105 may return to an uncompressed/expanded (outwardly protruding) state. Engagement of connector with proximal region 101 of device 100 can also be used to force wings 105 to return to an uncompressed/expanded state.

FIG. 73B is a schematic drawing showing a cross-sectional view of bone plate 800 of FIG. 73A.

Figures 74A, 74B:
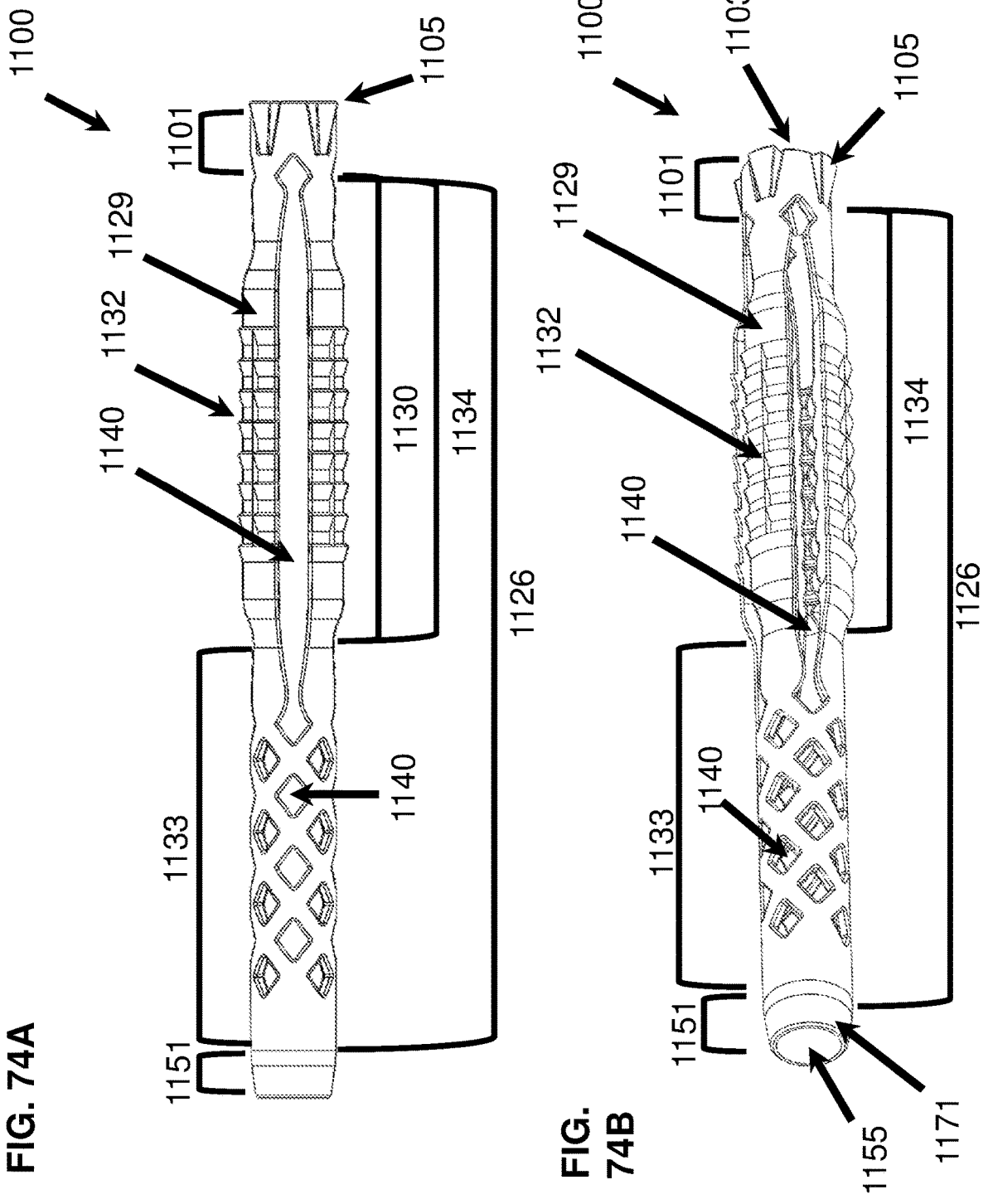

FIG. 74A is a schematic drawing showing a side view of an embodiment of device 1100 having proximal region 1101, central region 1126, and distal region 1151.

FIG. 74B is a schematic drawing showing an isometric view of an embodiment of device 1100 having proximal region 1101, central region 1126, and distal region 1151.

Figure 75:
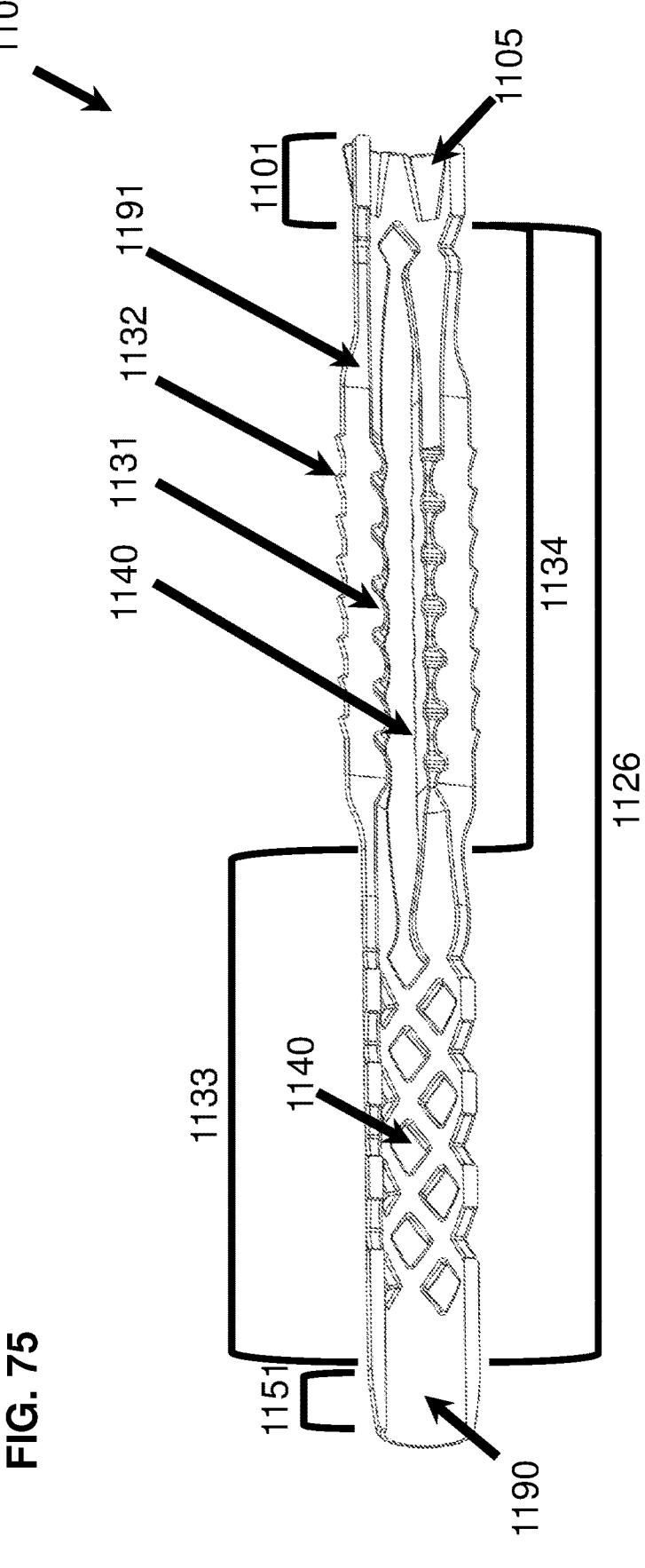

FIG. 75 is a schematic drawing showing a cross-sectional view of an embodiment of device 1100 having proximal region 1101, central region 1126, and distal region 1151. Internal protrusions 1131 and external protrusions 1132 are shown.

Figure 76:
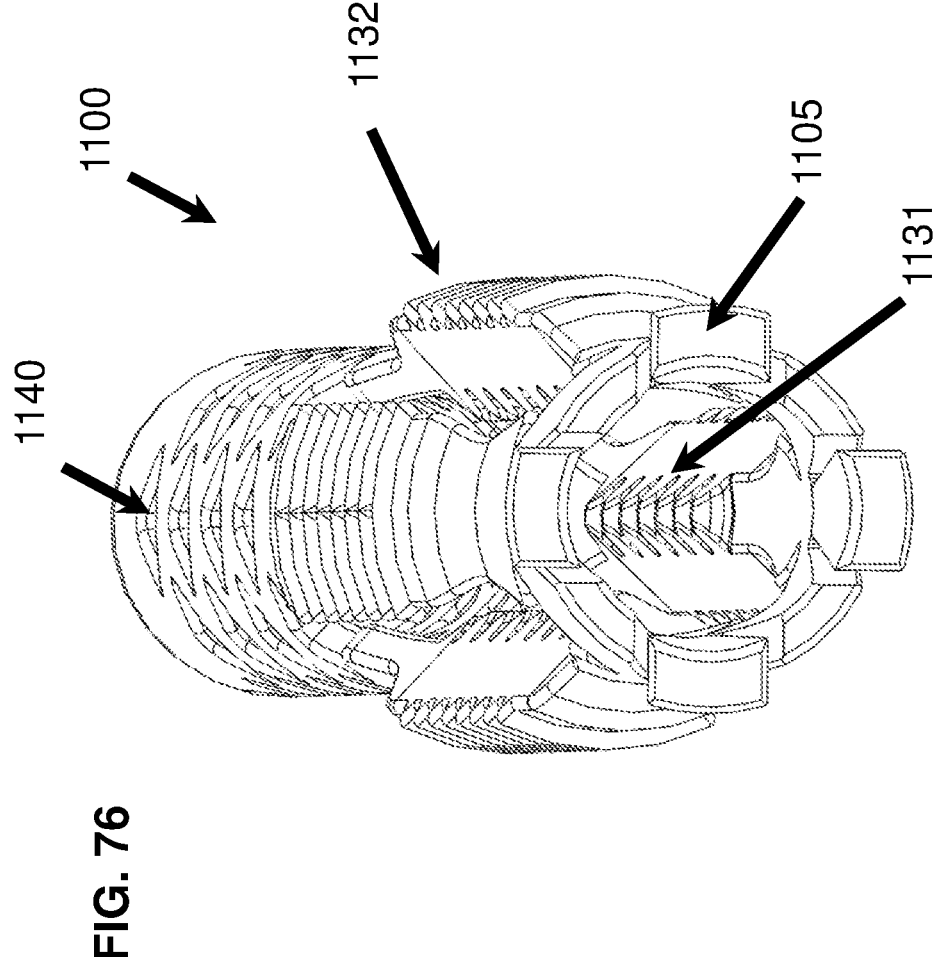

FIG. 76 is a schematic drawing showing an isometric view of an embodiment of device 1100 having internal protrusions 1131, external protrusions 1132, and wings 1105.

Figure 77:
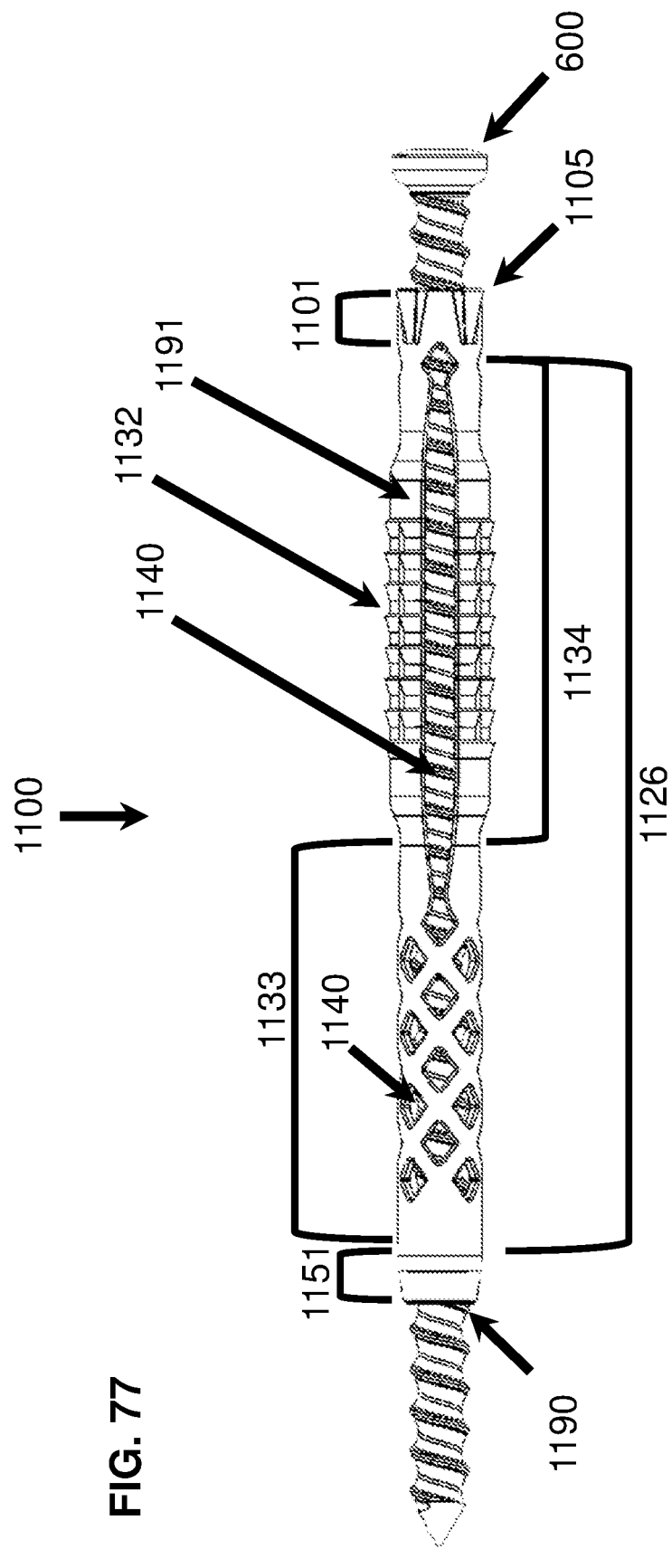

FIG. 77 is a schematic drawing showing a side view of an embodiment of device 1100 having proximal region 1101, central region 1126, and distal region 1151, in which device 1100 has a screw 600 inserted in internal channel 1190.

FIG. 78A is a schematic drawing showing a cross-sectional view of an embodiment of device 1100 being inserted into funnel 1400.

FIG. 78B is a schematic drawing showing a cross-sectional view of an embodiment of device 1100 inserted into funnel 1400. Compression of first section 1134 is shown, in which first section 1134 is the expandable and/or compressible body of device 1100.

FIG. 78C is a schematic drawing showing a side view of an embodiment of device 1100, in which device 1100 has a screw 600 inserted in internal channel 1190.

Figure 79:
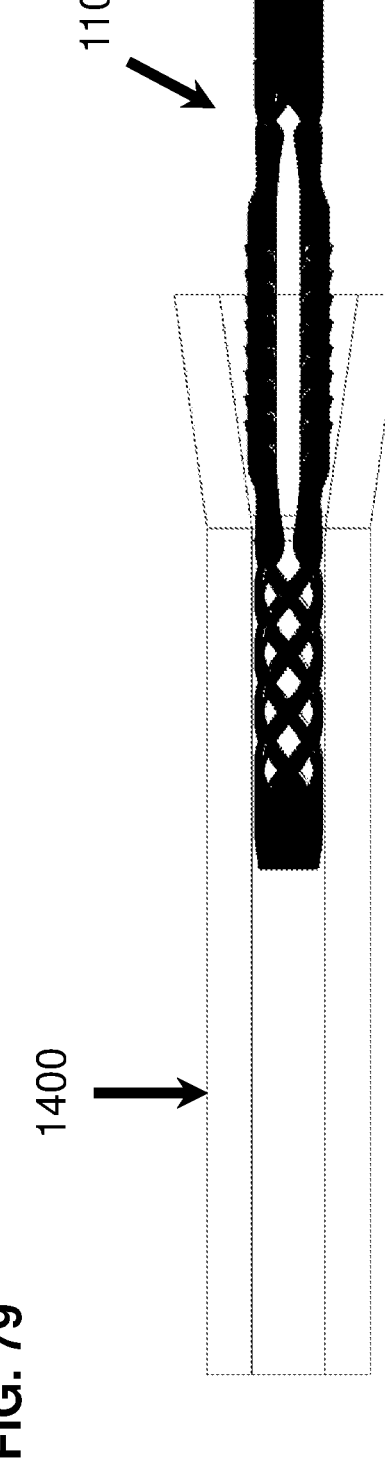

FIG. 79 is a schematic drawing showing a cross-sectional view of an embodiment of device 1100 being inserted into funnel 1400.

Figure 80:
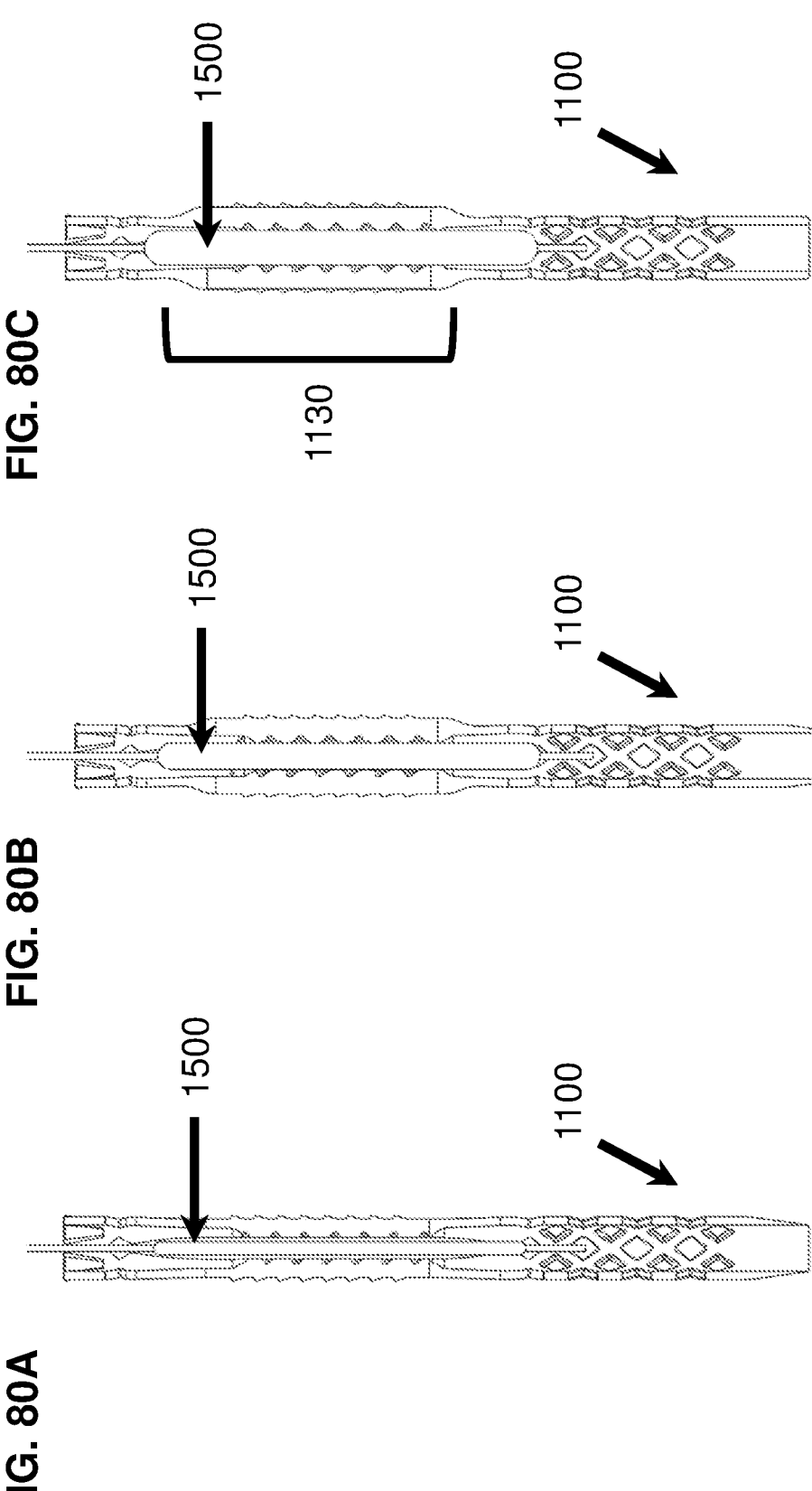

FIG. 80A is a schematic drawing showing a cross-sectional view of an embodiment of device 1100 with uninflated balloon 1500 inserted therein.

FIG. 80B is a schematic drawing showing a cross-sectional view of an embodiment of device 1100 with partially balloon 1500 inserted therein.

FIG. 80C is a schematic drawing showing a cross-sectional view of an embodiment of device 1100 with inflated balloon 1500 inserted therein, in which the expandable and/or compressible body of first section 1134 of device 1100 is expanded by inflated balloon 1500.

Figure 81:
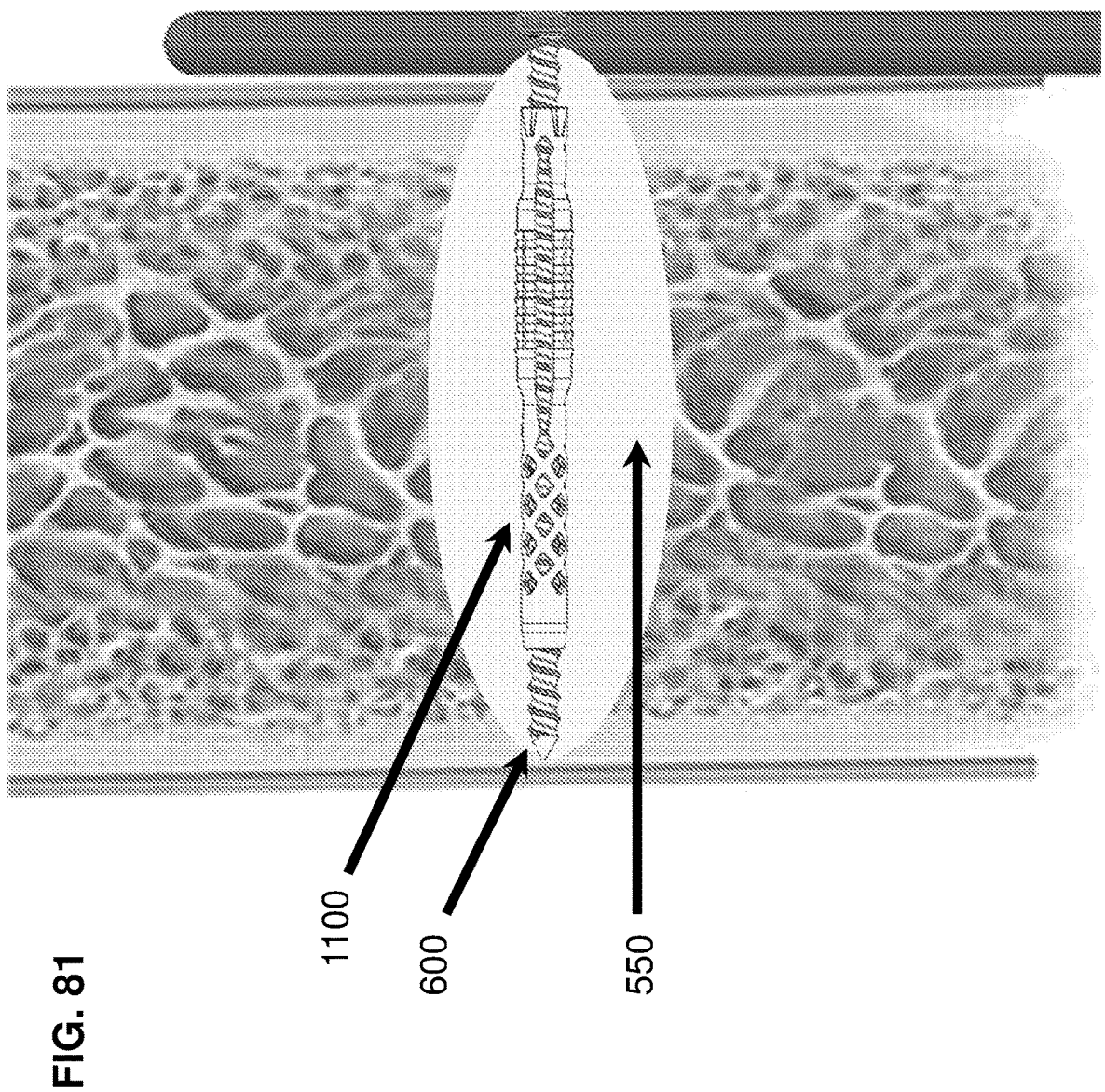

FIG. 81 is a schematic drawing showing a side view of an embodiment of device 1100 in which screw 600 has been inserted into device 1100 and in which screw 600 is secured to the bone at its distal tip. Insertion of screw 600 into device 1100 distributes biomaterial 550 out of device 1100 and into bone surrounding device 1100.

Figures 82A, 82B:
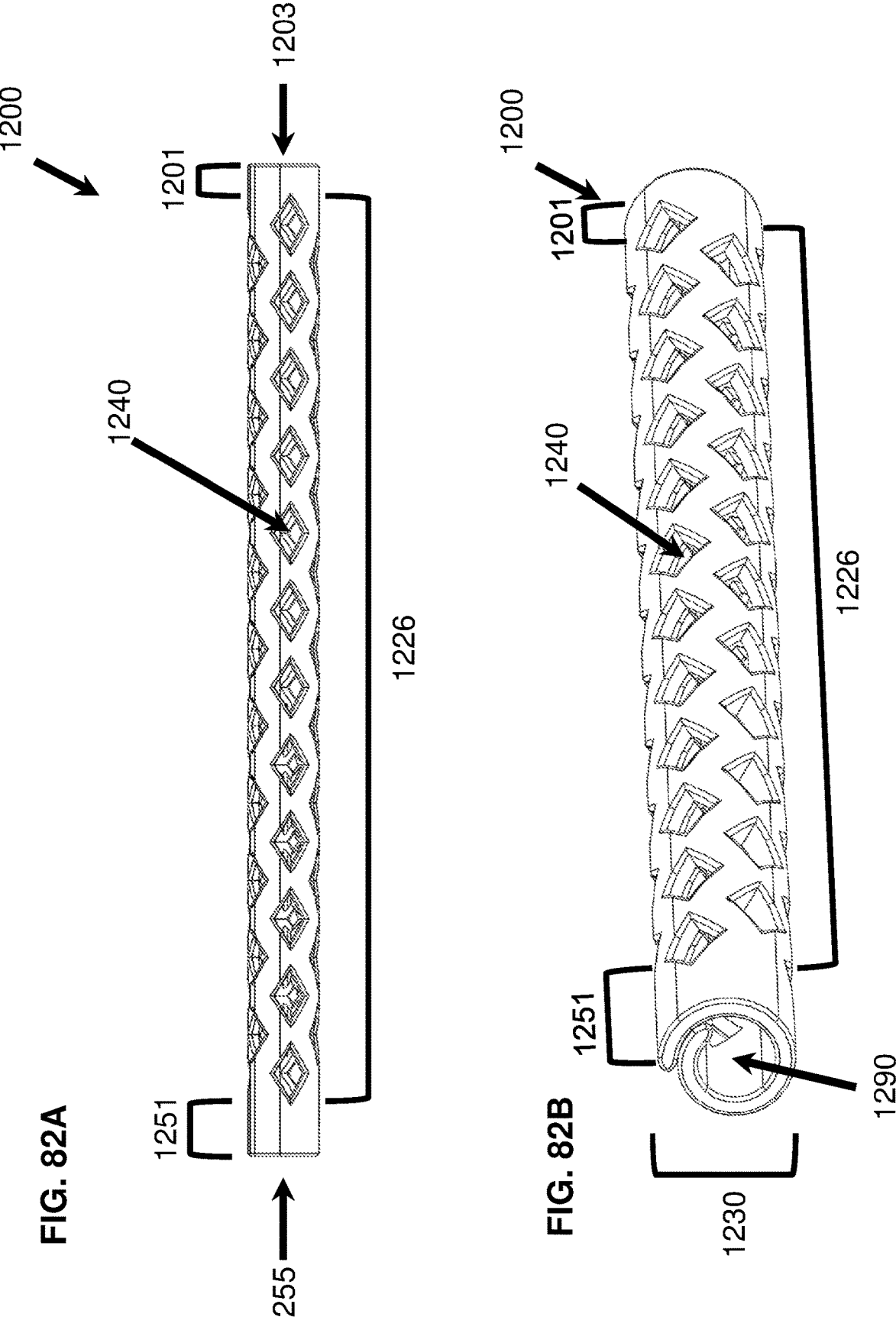

FIG. 82A is a schematic drawing showing a side view of an embodiment of device 1200 with proximal region 1201, central region 1226, and distal region 1251.

FIG. 82B is a schematic drawing showing an isometric view of an embodiment of device 1200 with proximal region 1201, central region 1226, and distal region 1251.

Figures 83A, 83B:
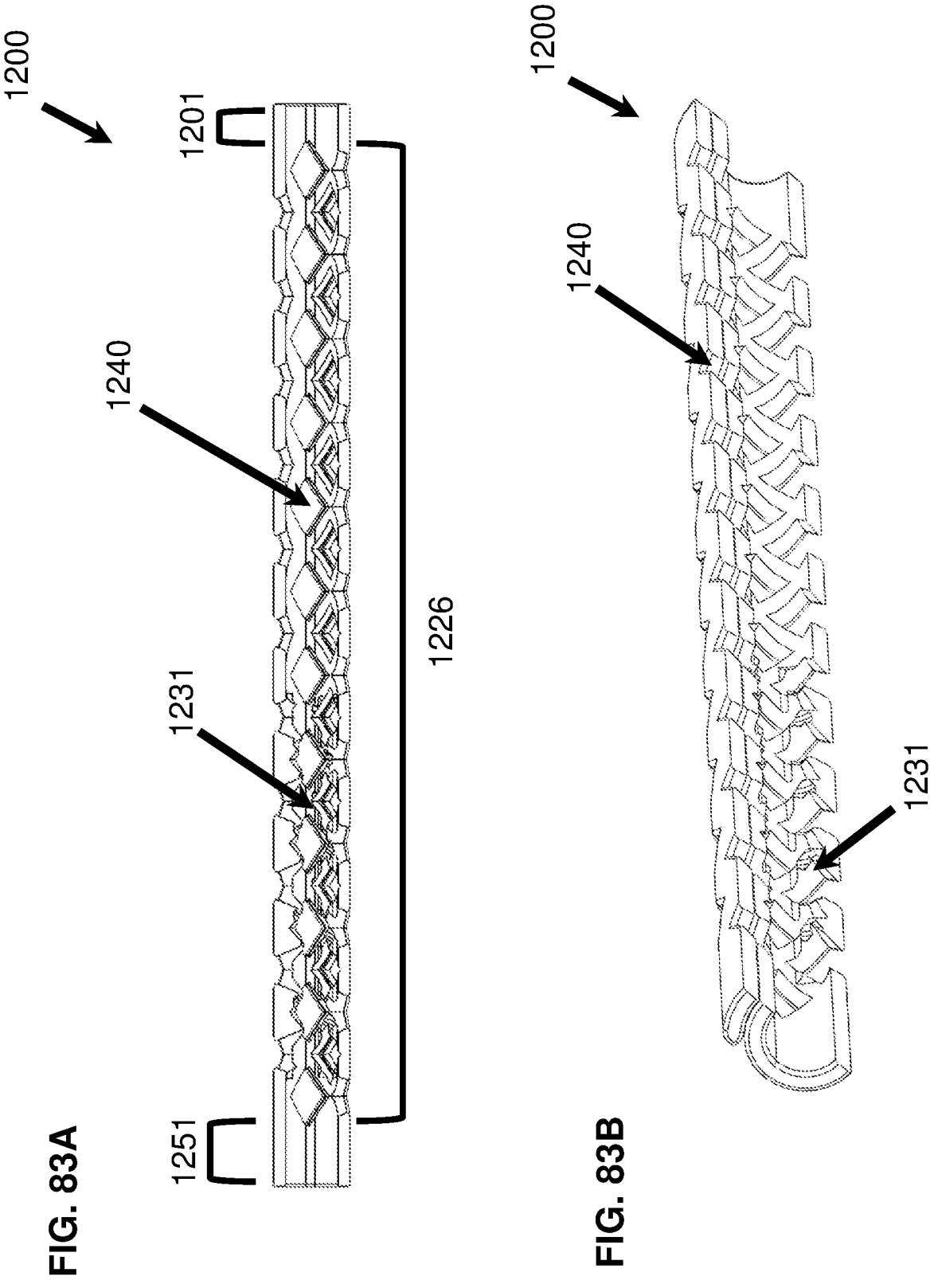

FIG. 83A is a schematic drawing showing a cross-sectional view of an embodiment of device 1200 with proximal region 1201, central region 1226, and distal region 1251.

FIG. 83B is a schematic drawing showing a cross-sectional view of an embodiment of device 1200 of FIG. 82A.

Figure 84:
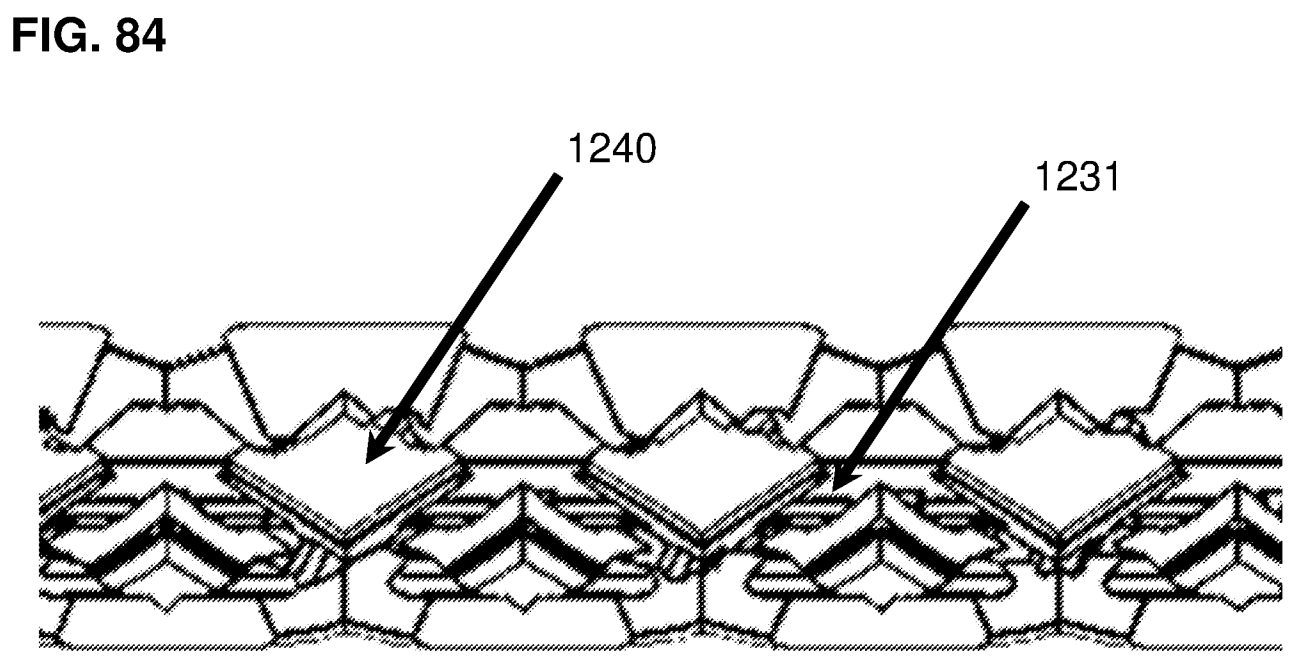

FIG. 84 is a schematic drawing showing an enlarged view of central region 1226 of device 1200 of FIG. 82A. Openings 1240 and internal protrusions 1231 are shown.

Figures 85A, 85B, 85C:
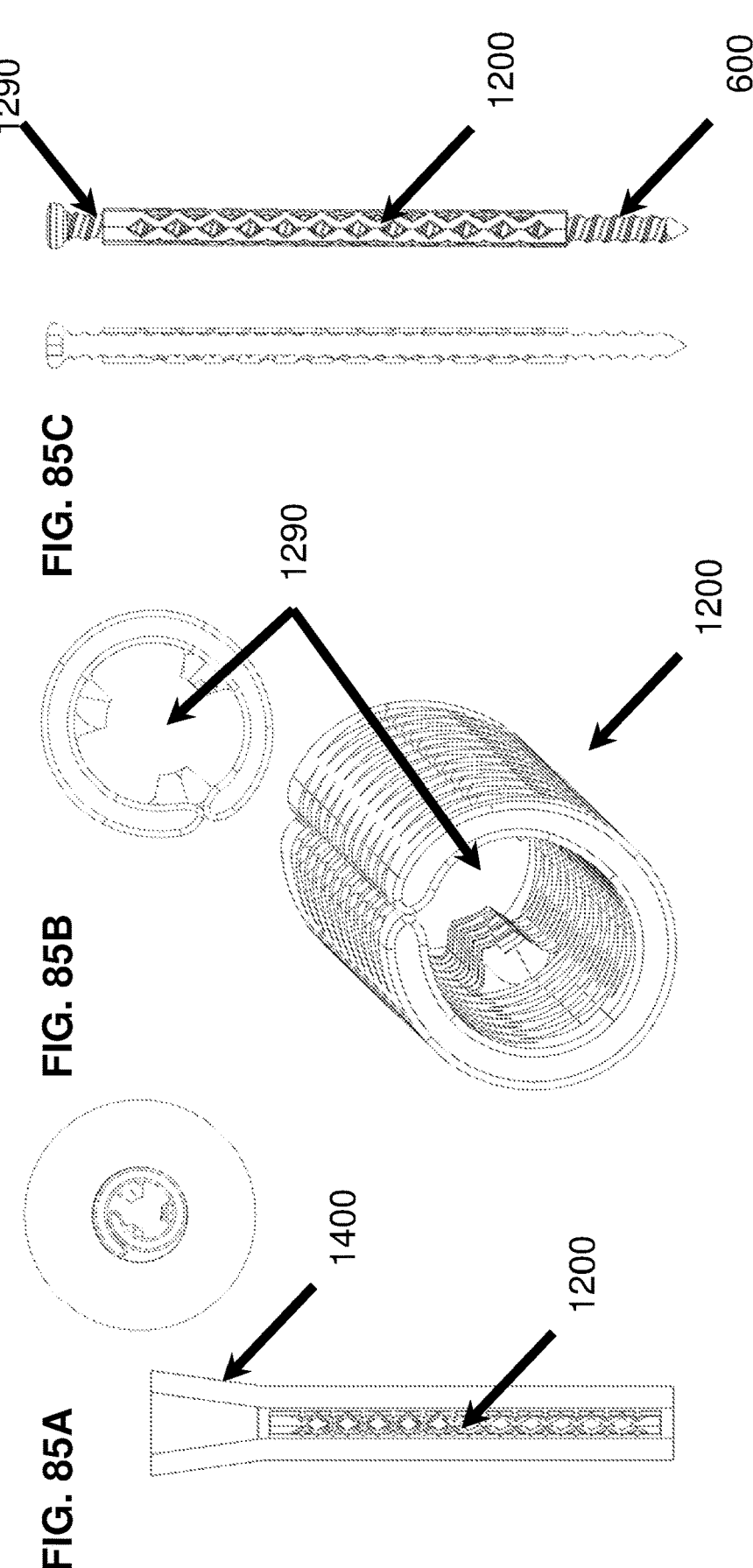

FIG. 85A is a schematic drawing showing two cross-sectional views of an embodiment of device 1200 being inserted into funnel 1400 such that a right side and a left side of device 1200 overlap.

FIG. 85B is a schematic drawing showing an isometric view and a cross-sectional view of an embodiment of device 1200 expanded such that a right side and a left side of device 1200 do not overlap.

FIG. 85C is a schematic drawing showing a side view and a cross-sectional view of an embodiment of device 1200 with screw 600 inserted into internal channel 1290.

Figures 86A, 86B:
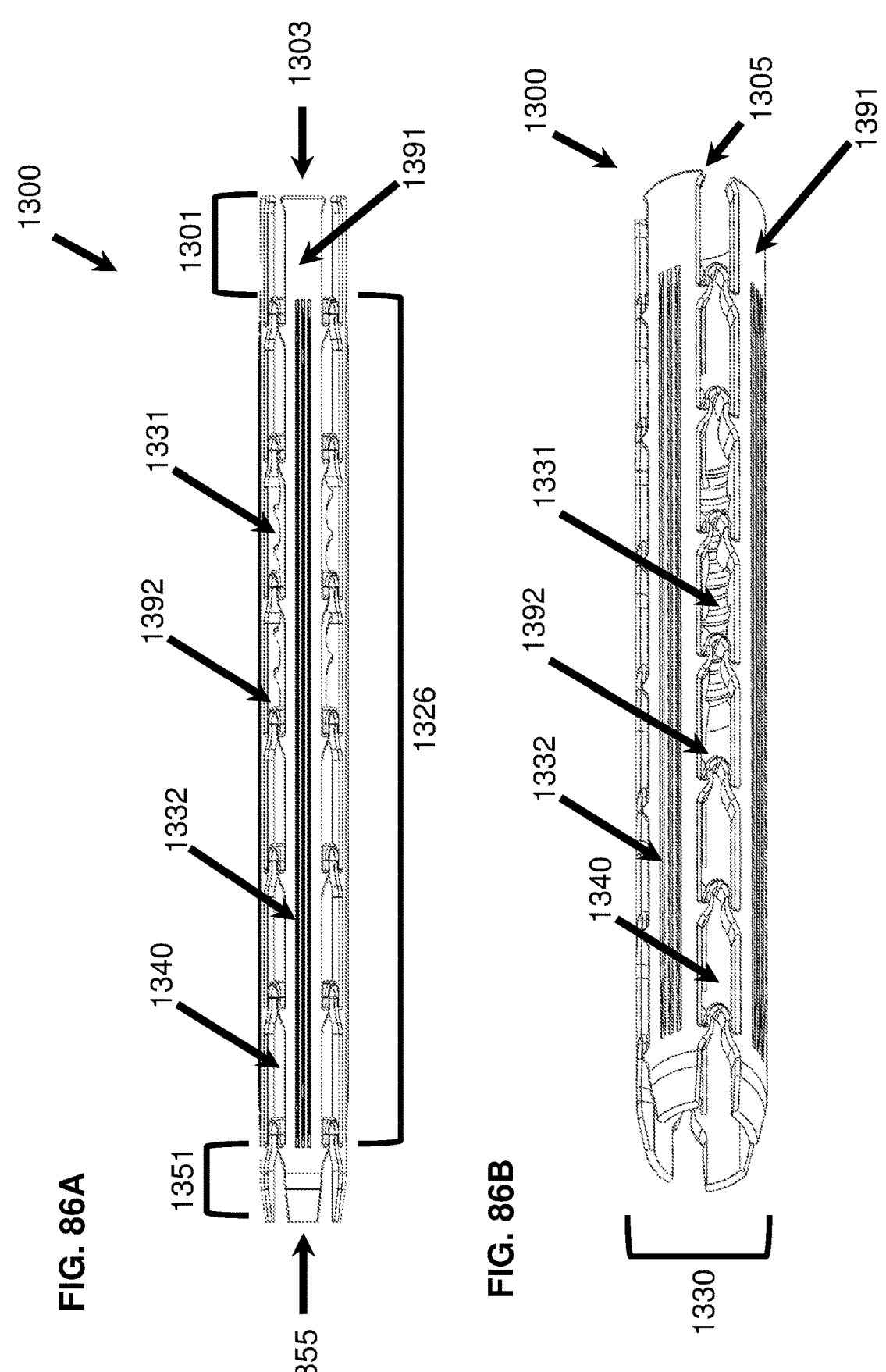

FIG. 86A is a schematic drawing showing a side view of an embodiment of device 1300 with proximal region 1301, central region 1326, and distal region 1351.

FIG. 86B is a schematic drawing showing an isometric view of an embodiment of device 1300. External protrusions 1332 are shown.

Figures 87A, 87B:
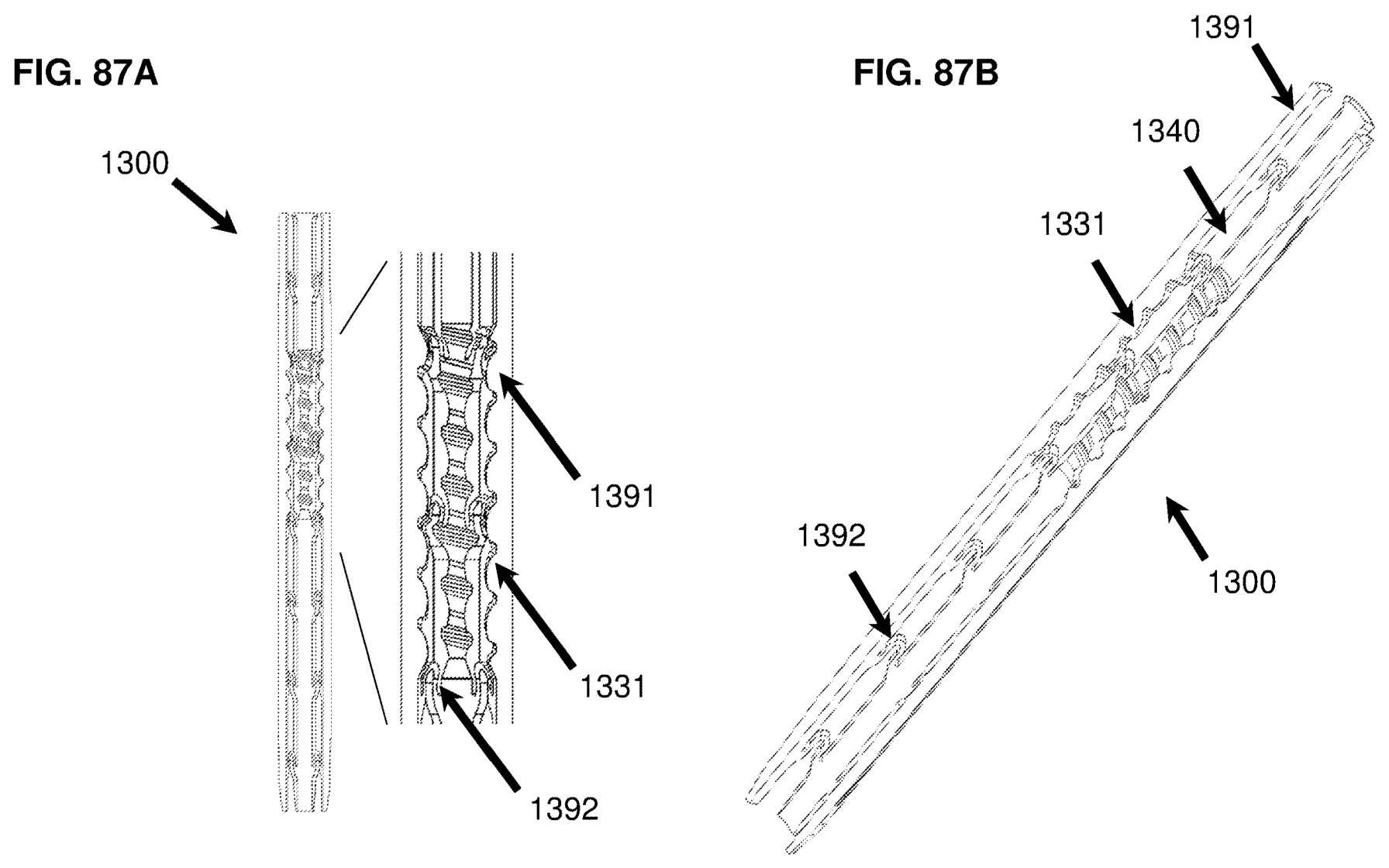

FIG. 87A is a schematic drawing showing a cross-sectional view and an enlarged view of an embodiment of device 1300. Internal protrusions 1331 are shown.

FIG. 87B is a schematic drawing showing a cross-sectional view of an embodiment of device 1300. Internal protrusions 1331 are shown.

Figure 88:
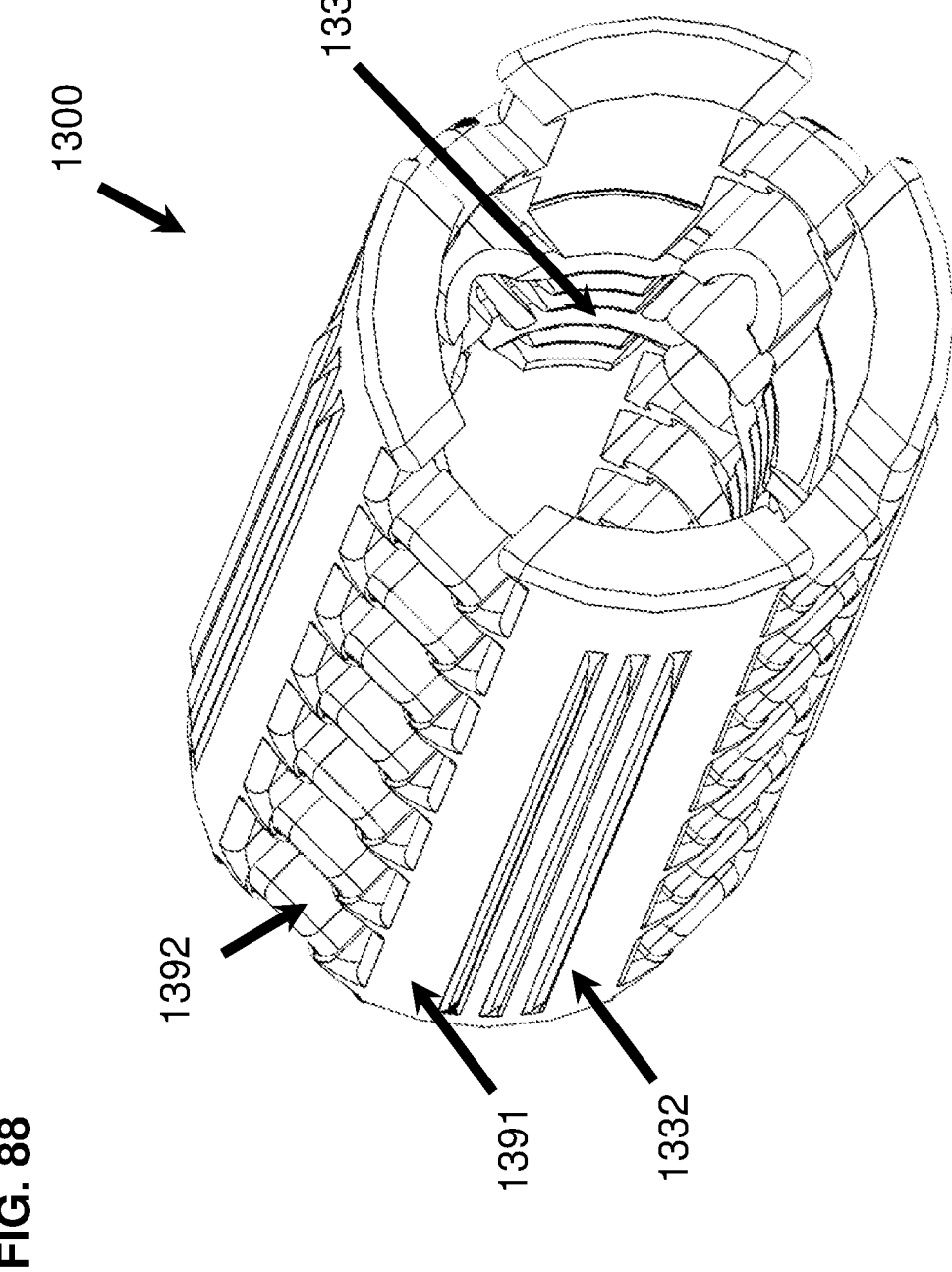

FIG. 88 is a schematic drawing showing an isometric view of an embodiment of device 1300. Internal protrusions 1331 and external protrusions 1332 are shown.

Figure 89:
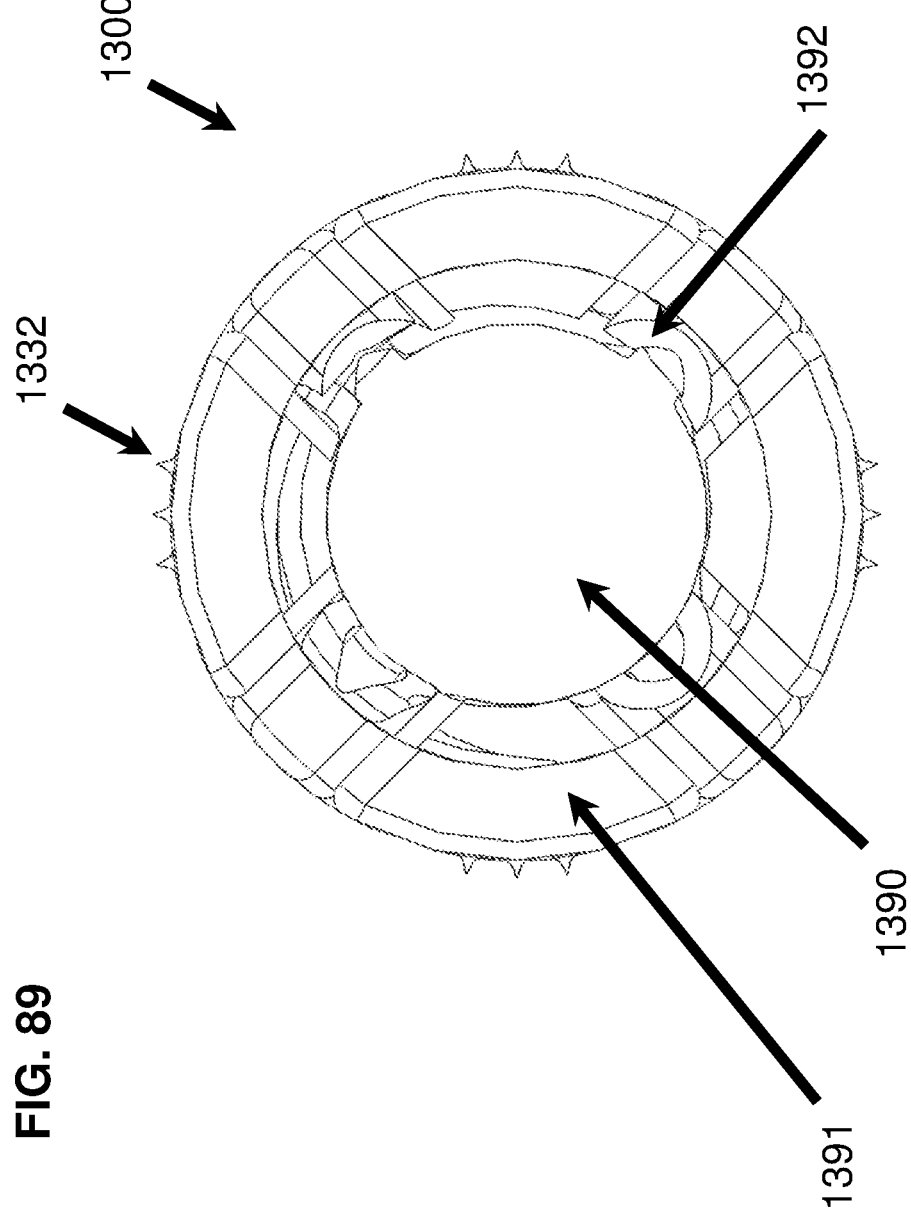

FIG. 89 is a schematic drawing showing a cross-sectional view of an embodiment of device 1300. External protrusions 1332 are shown.

Figure 90B:
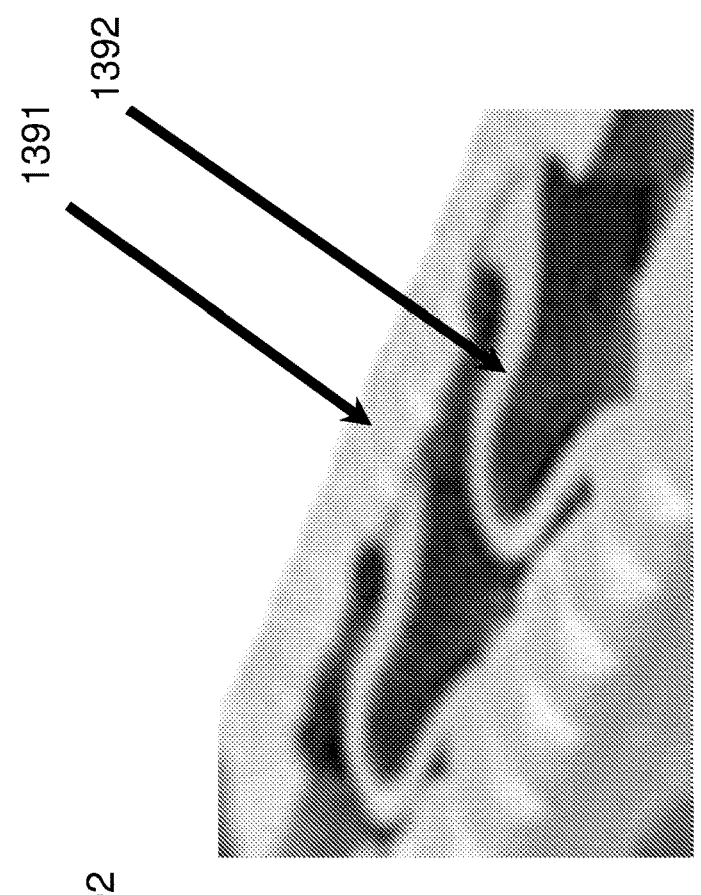
Figure 90A:
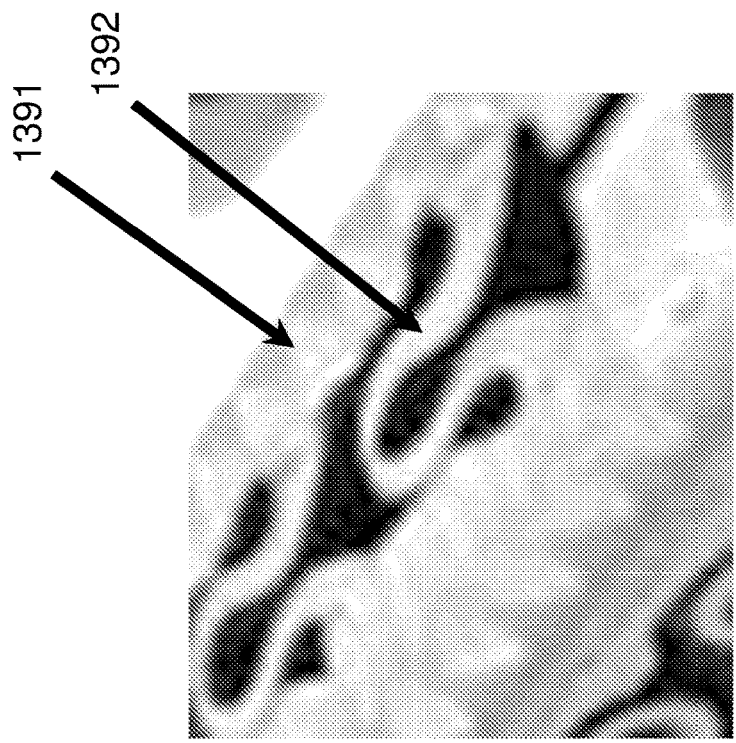

FIG. 90A is a schematic drawing showing an enlarged view of the central region an embodiment of device 1300. Expandable arms 1392 are shown compressed.

FIG. 90B is a schematic drawing showing an enlarged view of the central region an embodiment of device 1300. Expandable arms 1392 are shown expanded.

Figure 91:
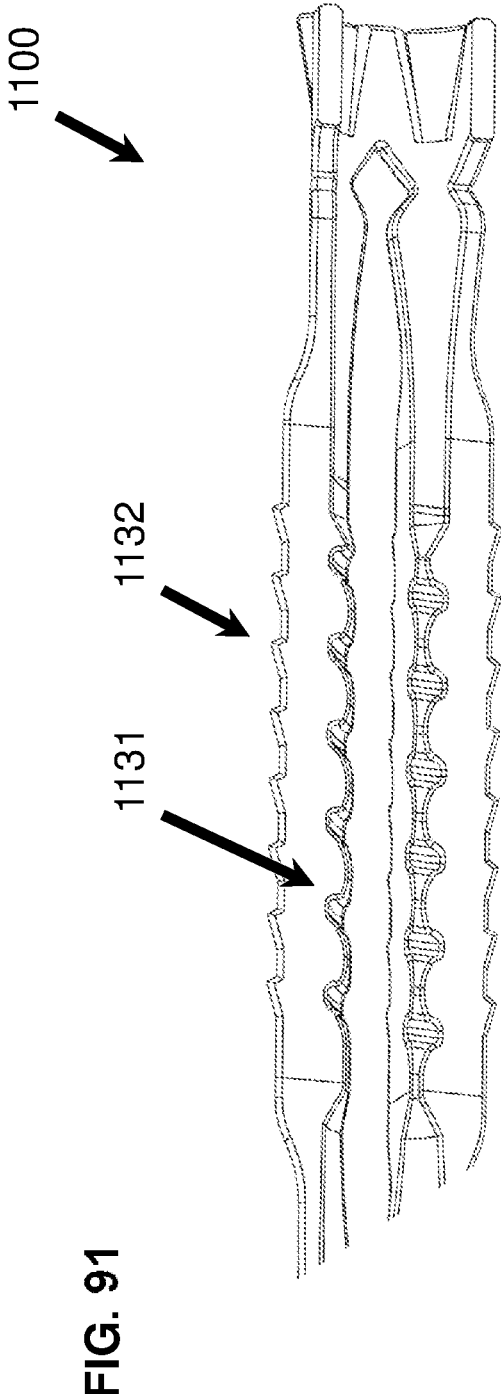

FIG. 91 is a schematic drawing showing a cross-sectional view of device 1100 with internal protrusions 1131 and external protrusions 1132.

Figure 92B:
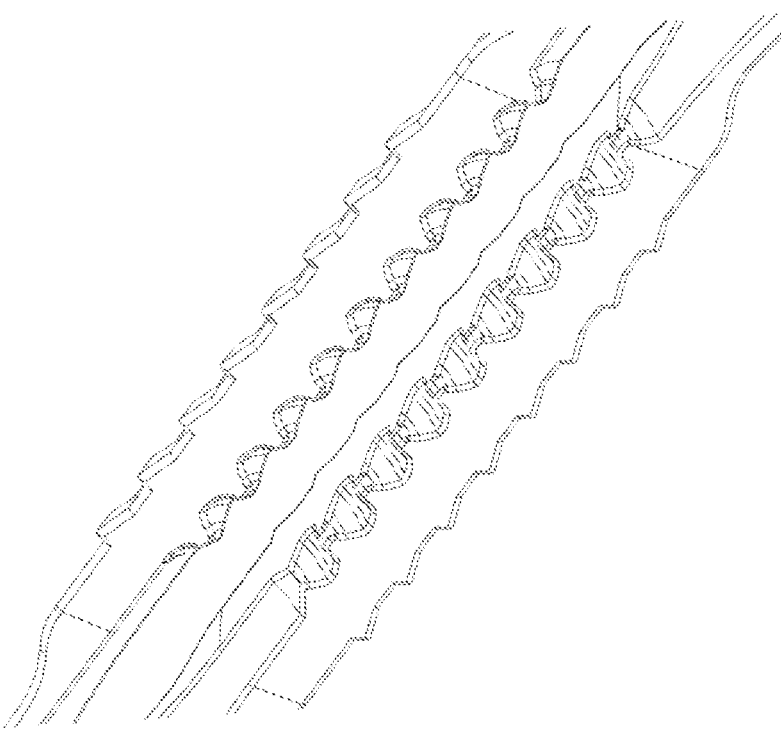
Figure 92A:
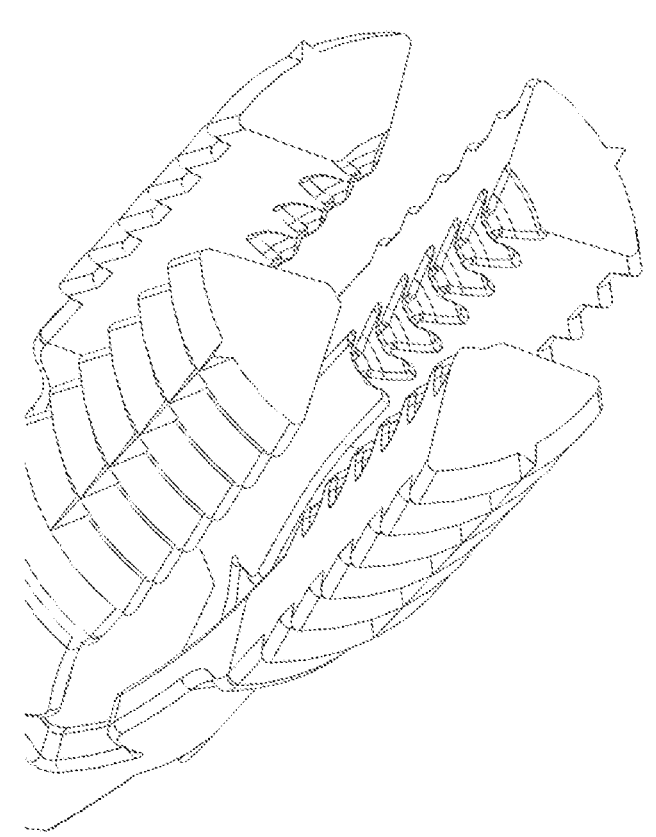

FIG. 92A is a schematic drawing showing an embodiment of threads or protrusions formed from protrusions at 4 points per 360°.

FIG. 92B is a schematic drawing showing a cross-sectional view of the device of FIG. 92A showing an embodiment of threads formed from protrusions at 4 points per 360°.

Figure 93:
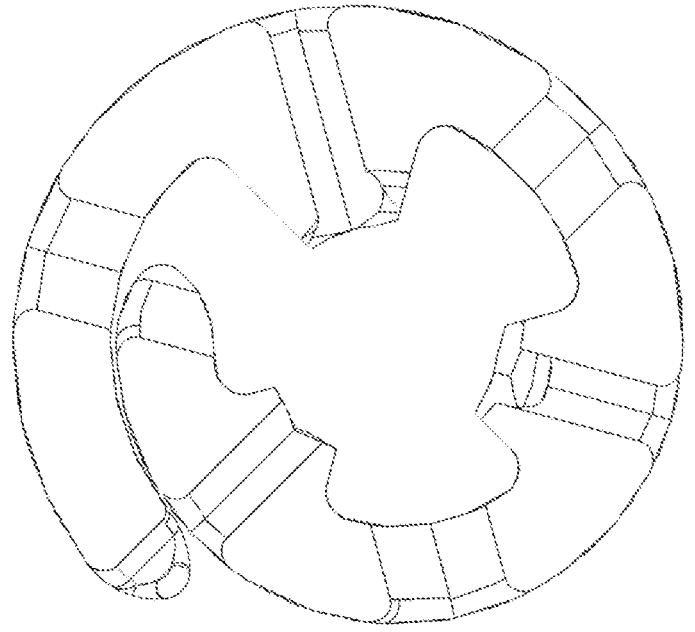

FIG. 93 is a schematic drawing showing an embodiment of threads formed from grooves at 3 points per 360°.

Figure 94:
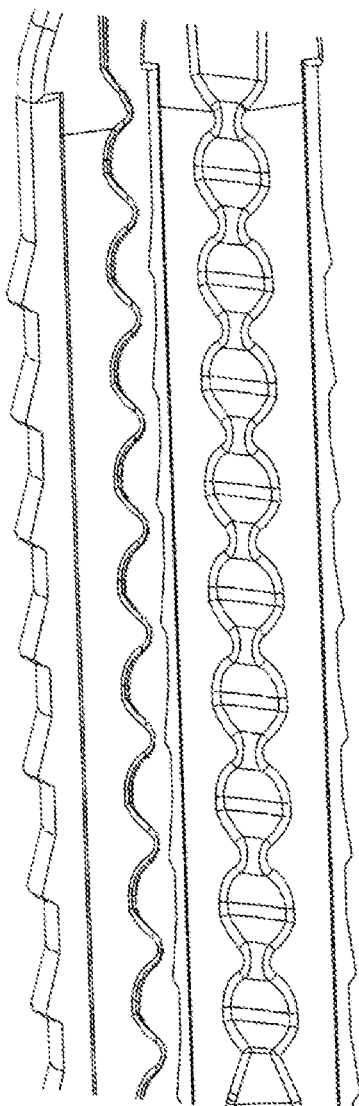

FIG. 94 is a schematic drawing showing an embodiment of threads formed from waves at 4 points per 360°.

Figure 95:
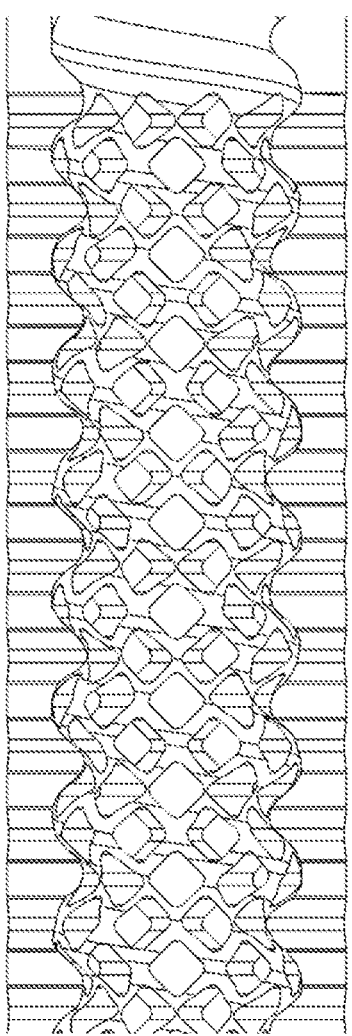

FIG. 95 is a schematic drawing showing an embodiment of threads formed from mesh.

DETAILED DESCRIPTION

Featured herein are devices, systems, kits, and methods of use thereof for bone repair, bone stabilization, and/or implant fixation. In some embodiments, the devices, systems, and methods herein described are useful for treating a bone defect (e.g., a bone fracture) or for implant fixation by installing at least one of the devices described herein, e.g., using the systems, kits, and/or methods described herein. In some embodiments, the devices, systems, kits, and methods can be used to deliver a biomaterial to bone. A biomaterial can be used to repair a bone defect, to stabilize weak or insufficient bone, or to stabilize implanted hardware. The devices and methods herein described can be used to provide uniform biomaterial delivery to produce robust adhesion between an implant (e.g., an implantable screw) and a bone tissue. Furthermore, the devices and methods overcome challenges associated with the repair of weak or deficient bone and bone augmentation using injected biomaterials (e.g., biomaterials with non-Newtonian fluid dynamic characteristics).

Devices for Bone Repair

Devices of the disclosure are implants that can be used for multiple purposes, including in the repair of bone defects. The devices are configured for insertion into bone (e.g., into bone hole 875 that is predrilled in the bone prior to insertion of a device). Once inserted, the device can be used to uniformly deliver a biomaterial to the bone, secure the bone structure, and promote bone repair and/or healing. The devices can be used in combination with, or to secure, other hardware, such as, e.g., a bone plate, a soft tissue suture anchor, an intramedullary pin, a nail, screw, or other similar hardware, and a spinal attachment device.

Device Body

The device has a unitary cylindrical body. The device includes an internal channel that extends longitudinally through the proximal, central, and distal regions. In some embodiments, the device includes a proximal region, a distal region, and a central region disposed therebetween.

The internal channel includes an internal surface. The internal surface may be smooth or rough, e.g., including at least one internal protrusion. The internal channel may be straight, curved, radial, or helical, depending on the implantable device to be used with the present device.

In some embodiments, the device has a length of from about 9 mm to about 110 mm (e.g., from about 10 mm to about 110 mm, from about 20 mm to about 110 mm, from about 25 mm to about 110 mm, from about 30 mm to about 110 mm, from about 35 mm to about 110 mm, from about 40 mm to about 110 m, from about 45 mm to about 110 mm, from about 50 mm to about 110 mm, from about 55 mm to about 110 mm, from about 60 mm to about 110 mm, from about 65 mm to about 110 mm, from about 70 mm to about 110 mm, from about 75 mm to about 110 mm, from about 80 mm to about 110 mm, from about 85 mm to about 110 mm, from about 90 mm to about 110 mm, from about 95 mm to about 110 mm, from about 100 mm to about 110 mm, from about 105 mm to about 110 mm, about 9 mm, about 10 mm, about 11 mm, about 12 mm, about 13 mm, about 14 mm, about 15 mm, about 16 mm, about 17 mm, about 18 mm, about 19 mm, about 20 mm, about 21 mm, about 22 mm, about 23 mm, about 24 mm, about 25 mm, about 26 mm, about 27 mm, about 28 mm, about 29 mm, about 30 mm, about 31 mm, about 32 mm, about 33 mm, about 34 mm, about 35 mm, about 36 mm, about 37 mm, about 38 mm, about 39 mm, about 40 mm, about 41 mm, about 42 mm, about 43 mm, about 44 mm, about 45 mm, about 46 mm, about 47 mm, about 48 mm, about 49 mm, about 50 mm, about 51 mm, about 52 mm, about 53 mm, about 54 mm, about 55 mm, about 56 mm, about 57 mm, about 58 mm, about 59 mm, about 60 mm, about 61 mm, about 62 mm, about 63 mm, about 64 mm, about 65 mm, about 66 mm, about 67 mm, about 68 mm, about 69 mm, about 70 mm, about 71 mm, about 72 mm, about 73 mm, about 74 mm, about 75 mm, about 76 mm, about 77 mm, about 78 mm, about 79 mm, about 80 mm, about 81 mm, about 82 mm, about 83 mm, about 84 mm, about 85 mm, about 86 mm, about 87 mm, about 88 mm, about 89 mm, about 90 mm, about 91 mm, about 92 mm, about 93 mm, about 94 mm, about 95 mm, about 96 mm, about 97 mm, about 98 mm, about 99 mm, about 100 mm, about 101 mm, about 102 mm, about 103 mm, about 104 mm, about 105 mm, about 106 mm, about 107 mm, about 108 mm, about 109 mm, or about 110 mm). In some embodiments, the device has a length greater than 9 mm (e.g., greater than 10 mm, greater than 15 mm, greater than 20 mm, greater than 25 mm, greater than 30 mm, greater than 40 mm, greater than 50 mm, greater than 60 mm, greater than 70 mm, greater than 80 mm, greater than 90, greater than 100 mm, or greater than 110 mm). In some embodiments, the device has a length less than 110 mm (e.g., less than 100 mm, less than 90 mm, less than 80 mm, less than 70 mm, less than 60 mm, less than 50 mm, less than 40 mm, less than 30 mm, less than 20 mm, or less than 10 mm).

In some embodiments, the device is made from or includes a material selected from stainless steel or an alloy thereof, titanium or an alloy thereof, magnesium or an alloy thereof, polyetheretherketone (PEEK), hydroxyapatite, tricalcium phosphate, tetracalcium phosphate, dicalcium phosphate, BIOGLASS® 45S5, ceramic composites, copper-based materials or composites, cobalt chrome, xenograft biomaterials, and combinations thereof. The device can also be 3D printed using these materials or others.

Proximal Region

In some embodiments, the device includes a proximal region that has a proximal end, a distal end, and a proximal opening to the internal channel.

In some embodiments, the proximal region has an outer diameter of from about 4 mm to about 25 mm (e.g., from about 4 mm to about 8 mm, from about 4 mm to about 10 mm, from about 4 mm to about 15 mm, from about 5 mm to about 10 mm, from about 10 mm to about 15 mm, from about 10 mm to about 20 mm, from about 15 mm to about 25 mm, from about 20 mm to about 25 mm, about 4 mm, about 5 mm, about 6 mm, about 7 mm, about 8 mm, about 9 mm, about 10 mm, about 11 mm, about 12 mm, about 13 mm, about 14 mm, about 15 mm, about 16 mm, about 17 mm, about 18 mm, about 19 mm, about 20 mm, about 21 mm, about 22 mm, about 23 mm, about 24 mm, or about 25 mm). In certain embodiments, the outer diameter of proximal region is smaller than, larger than, or equal to the outer diameter of central region.

In some embodiments, the proximal region has an inner diameter of from about 1 mm to about 20 mm (e.g., from about 1 mm to about 2 mm, from about 1 mm to about 3 mm, from about 1 mm to about 4 mm, from about 1 mm to about 5 mm, from about 1 mm to about 10 mm, from about 5 mm to about 10 mm, from about 5 mm to about 15 mm, from about 10 mm to about 15 mm, from about 15 mm to about 20 mm, from about 15 mm to about 20 mm, about 3 mm, about 4 mm, about 5 mm, about 6 mm, about 7 mm, about 8 mm, about 9 mm, about 10 mm, about 11 mm, about 12 mm, about 13 mm, about 14 mm, about 15 mm, about 16 mm, about 17 mm, about 18 mm, about 19 mm, or about 20 mm). In certain embodiments, the inner diameter of the proximal region is smaller than, larger than, or equal to the inner diameter of the central region.

In some embodiments, the proximal region has a length of from about 0.1 mm to about 30 mm (e.g., from about 0.1 mm to about 1 mm, from about 0.1 mm to about 5 mm, from about 0.1 mm to about 10 mm, from about 5 mm to about 10 mm, from about 5 mm to about 15 mm, from about 5 mm to about 20 mm, from about 10 mm to about 20 mm, from about 10 mm to about 30 mm, from about 15 mm to about 25 mm, from about 20 mm to about 30 mm, about 0.1 mm, about 0.5 mm, about 1 mm, about 2 mm, about 3 mm, about 4 mm, about 5 mm, about 6 mm, about 7 mm, about 8 mm, about 9 mm, about 10 mm, about 11 mm, about 12 mm, about 13 mm, about 14 mm, about 15 mm, about 16 mm, about 17 mm, about 18 mm, about 19 mm, about 20 mm, about 21 mm, about 22 mm, about 23 mm, about 24 mm, about 25 mm, about 26 mm, about 27 mm, about 28 mm, about 29 mm, or about 30 mm).

In some embodiments, the proximal region has a wall thickness of from about 0.15 mm to about 3 mm (e.g., from about 0.15 mm to about 0.5 mm, from about 0.15 mm to about 1 mm, from about 0.15 mm to about 1.5 mm, from about 0.5 mm to about 1 mm, from about 0.5 mm to about 1.5 mm, from about 1 mm, to about 2 mm, from about 1 mm to about 3 mm, from about 2 mm to about 3 mm, about 0.15 mm, about 0.2 mm, about 0.3 mm, about 0.4 mmm about 0.5 mm, about 0.6 mm, about 0.7 mm, about 0.8 mm, about 0.9 mm, about 1 mm, about 1.1 mm, about 1.2 mm, about 1.3 mm, about 1.4 mm, about 1.5 mm, about 1.6 mm, about 1.7 mm, about 1.8 mm, about 1.9 mm, about 2 mm, about 2.1 mm, about 2.2 mm, about 2.3 mm, about 2.4 mm, about 2.5 mm, about 2.6 mm, about 2.7 mm, about 2.8 mm, about 2.9 mm, or about 3 mm). In certain embodiments, the wall thickness of the proximal region is smaller than, larger than, or equal to the wall thickness of the central region.

In some embodiments, the proximal region 1301 includes from 3 to 20 (e.g., from 3 to 15, from 4 to 10, from 5 to 8, 3, 4, 5, 6, 7, 8, 9, 10, 11, 12, 13, 14, 15, 16, 17, 18, 19, or 20) wings that radially extend around the outer surface of the proximal region.

In some embodiments, the proximal end of proximal region has a blunt edge. In some embodiments, the proximal end of proximal region has a tapered edge. In some embodiments, the proximal end of the proximal region has at least one or a plurality of milling flutes, notches, bendable tips, and/or elongated tips.

In some embodiments, the proximal region has a plurality of openings (e.g., slits or perforations). In some embodiments, proximal region does not have openings other than the opening to the internal channel. In some embodiments, device does not have a proximal region.

Central Region

The device includes a central region that has a proximal end and a distal end. In some embodiments, the central region is disposed between a proximal region and a distal region. In some embodiments, the central region of device includes an expandable and/or compressible body.

In some embodiments, the central region has an outer diameter of from about 1.25 mm to about 25 mm (e.g., from about 1.25 mm to about 2 mm, from about 1.25 mm to about 3 mm, from about 1 mm to about 2 mm, from about 1 mm to about 3 mm, from about 1 mm to about 4 mm, from about 1 mm to about 5 mm, from about 4 mm to about 8 mm, from about 4 mm to about 10 mm, from about 4 mm to about 15 mm, from about 5 mm to about 10 mm, from about 10 mm to about 15 mm, from about 10 mm to about 20 mm, from about 15 mm to about 25 mm, from about 20 mm to about 25 mm, about 1.5 mm, about 1.75 mm, about 2 mm, about 3 mm, about 4 mm, about 5 mm, about 6 mm, about 7 mm, about 8 mm, about 9 mm, about 10 mm, about 11 mm, about 12 mm, about 13 mm, about 14 mm, about 15 mm, about 16 mm, about 17 mm, about 18 mm, about 19 mm, about 20 mm, about 21 mm, about 22 mm, about 23 mm, about 24 mm, or about 25 mm). The central region includes an outer diameter that is smaller than, larger than, or equal to the outer diameter of the proximal and distal regions.

In some embodiments, the central region has an inner diameter of from about 1 mm to about 20 mm (e.g., from about 1 mm to about 2 mm, from about 1 mm to about 3 mm, from about 1 mm to about 4 mm, from about 1 mm to about 5 mm, from about 1 mm to about 10 mm, from about 5 mm to about 10 mm, from about 5 mm to about 15 mm, from about 10 mm to about 15 mm, from about 15 mm to about 20 mm, from about 15 mm to about 20 mm, about 1 mm, about 2 mm, about 3 mm, about 4 mm, about 5 mm, about 6 mm, about 7 mm, about 8 mm, about 9 mm, about 10 mm, about 11 mm, about 12 mm, about 13 mm, about 14 mm, about 15 mm, about 16 mm, about 17 mm, about 18 mm, about 19 mm, or about 20 mm). The central region includes an inner diameter that is smaller than, larger than, or equal to the inner diameter of the proximal and distal regions.

In some embodiments, the central region has a length of from about 5 mm to about 110 mm (e.g., from about 10 mm to about 110 mm, from about 20 mm to about 110 mm, from about 25 mm to about 110 mm, from about 30 mm to about 110 mm, from about 35 mm to about 110 mm, from about 40 mm to about 110 m, from about 45 mm to about 110 mm, from about 50 mm to about 110 mm, from about 55 mm to about 110 mm, from about 60 mm to about 110 mm, from about 65 mm to about 110 mm, from about 70 mm to about 110 mm, from about 75 mm to about 110 mm, from about 80 mm to about 110 mm, from about 85 mm to about 110 mm, from about 90 mm to about 110 mm, from about 95 mm to about 110 mm, from about 100 mm to about 110 mm, from about 105 mm to about 110 mm, about 9 mm, about 10 mm, about 11 mm, about 12 mm, about 13 mm, about 14 mm, about 15 mm, about 16 mm, about 17 mm, about 18 mm, about 19 mm, about 20 mm, about 21 mm, about 22 mm, about 23 mm, about 24 mm, about 25 mm, about 26 mm, about 27 mm, about 28 mm, about 29 mm, about 30 mm, about 31 mm, about 32 mm, about 33 mm, about 34 mm, about 35 mm, about 36 mm, about 37 mm, about 38 mm, about 39 mm, about 40 mm, about 41 mm, about 42 mm, about 43 mm, about 44 mm, about 45 mm, about 46 mm, about 47 mm, about 48 mm, about 49 mm, about 50 mm, about 51 mm, about 52 mm, about 53 mm, about 54 mm, about 55 mm, about 56 mm, about 57 mm, about 58 mm, about 59 mm, about 60 mm, about 61 mm, about 62 mm, about 63 mm, about 64 mm, about 65 mm, about 66 mm, about 67 mm, about 68 mm, about 69 mm, about 70 mm, about 71 mm, about 72 mm, about 73 mm, about 74 mm, about 75 mm, about 76 mm, about 77 mm, about 78 mm, about 79 mm, about 80 mm, about 81 mm, about 82 mm, about 83 mm, about 84 mm, about 85 mm, about 86 mm, about 87 mm, about 88 mm, about 89 mm, about 90 mm, about 91 mm, about 92 mm, about 93 mm, about 94 mm, about 95 mm, about 96 mm, about 97 mm, about 98 mm, about 99 mm, about 100 mm, about 101 mm, about 102 mm, about 103 mm, about 104 mm, about 105 mm, about 106 mm, about 107 mm, about 108 mm, about 109 mm, or about 110 mm).

In some embodiments, the central region has a wall thickness of from about 0.15 mm to about 3 mm (e.g., from about 0.15 mm to about 0.5 mm, from about 0.15 mm to about 1 mm, from about 0.15 mm to about 1.5 mm, from about 0.5 mm to about 1 mm, from about 0.5 mm to about 1.5 mm, from about 1 mm, to about 2 mm, from about 1 mm to about 3 mm, from about 2 mm to about 3 mm, about 0.15 mm, about 0.2 mm, about 0.3 mm, about 0.4 mmm about 0.5 mm, about 0.6 mm, about 0.7 mm, about 0.8 mm, about 0.9 mm, about 1 mm, about 1.1 mm, about 1.2 mm, about 1.3 mm, about 1.4 mm, about 1.5 mm, about 1.6 mm, about 1.7 mm, about 1.8 mm, about 1.9 mm, about 2 mm, about 2.1 mm, about 2.2 mm, about 2.3 mm, about 2.4 mm, about 2.5 mm, about 2.6 mm, about 2.7 mm, about 2.8 mm, about 2.9 mm, or about 3 mm). In certain embodiments, the wall thickness of central region is smaller than, larger than, or equal to the wall thickness of the proximal and distal regions.

In some embodiments, the central region includes a plurality of openings (e.g., slits or perforations).

In some embodiments, the central region has from 2 to 20 (e.g., from 2 to 4, from 2 to 6, from 2 to 8, from 2 to 10, from 4 to 8, from 4 to 10, from 4 to 12, from 10 to 16, from 10 to 20, 2, 3, 4, 5, 6, 7, 8, 9, 10, 11, 12, 13, 14, 15, 16, 17, 18, 19, or 20) segments. In some embodiments, the segments of the central region are connected by a plurality of expandable arms. In some embodiments, the central region has from 2 to 100 (e.g., 2 to 10, 2 to 20, 10 to 20, 10 to 30, 10 to 50, 20 to 40, 20 to 60, 40 to 80, 50 to 100, 60 to 80, 80 to 100, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100) expandable arms.

In some embodiments, the central region includes i) a first section including an expandable and/or compressible body, and (ii) a second section including a plurality of openings. In some embodiments, the central region includes from a proximal end to a distal end: i) the first section, and ii) the second section. The first section has a length of from about 5 mm to about 110 mm (e.g., from about 10 mm to about 110 mm, from about 20 mm to about 110 mm, from about 25 mm to about 110 mm, from about 30 mm to about 110 mm, from about 35 mm to about 110 mm, from about 40 mm to about 110 m, from about 45 mm to about 110 mm, from about 50 mm to about 110 mm, from about 55 mm to about 110 mm, from about 60 mm to about 110 mm, from about 65 mm to about 110 mm, from about 70 mm to about 110 mm, from about 75 mm to about 110 mm, from about 80 mm to about 110 mm, from about 85 mm to about 110 mm, from about 90 mm to about 110 mm, from about 95 mm to about 110 mm, from about 100 mm to about 110 mm, from about 105 mm to about 110 mm, about 9 mm, about 10 mm, about 11 mm, about 12 mm, about 13 mm, about 14 mm, about 15 mm, about 16 mm, about 17 mm, about 18 mm, about 19 mm, about 20 mm, about 21 mm, about 22 mm, about 23 mm, about 24 mm, about 25 mm, about 26 mm, about 27 mm, about 28 mm, about 29 mm, about 30 mm, about 31 mm, about 32 mm, about 33 mm, about 34 mm, about 35 mm, about 36 mm, about 37 mm, about 38 mm, about 39 mm, about 40 mm, about 41 mm, about 42 mm, about 43 mm, about 44 mm, about 45 mm, about 46 mm, about 47 mm, about 48 mm, about 49 mm, about 50 mm, about 51 mm, about 52 mm, about 53 mm, about 54 mm, about 55 mm, about 56 mm, about 57 mm, about 58 mm, about 59 mm, about 60 mm, about 61 mm, about 62 mm, about 63 mm, about 64 mm, about 65 mm, about 66 mm, about 67 mm, about 68 mm, about 69 mm, about 70 mm, about 71 mm, about 72 mm, about 73 mm, about 74 mm, about 75 mm, about 76 mm, about 77 mm, about 78 mm, about 79 mm, about 80 mm, about 81 mm, about 82 mm, about 83 mm, about 84 mm, about 85 mm, about 86 mm, about 87 mm, about 88 mm, about 89 mm, about 90 mm, about 91 mm, about 92 mm, about 93 mm, about 94 mm, about 95 mm, about 96 mm, about 97 mm, about 98 mm, about 99 mm, about 100 mm, about 101 mm, about 102 mm, about 103 mm, about 104 mm, about 105 mm, about 106 mm, about 107 mm, about 108 mm, about 109 mm, or about 110 mm). The second section includes a length of from about 5 mm to about 110 mm (e.g., from about 10 mm to about 110 mm, from about 20 mm to about 110 mm, from about 25 mm to about 110 mm, from about 30 mm to about 110 mm, from about 35 mm to about 110 mm, from about 40 mm to about 110 m, from about 45 mm to about 110 mm, from about 50 mm to about 110 mm, from about 55 mm to about 110 mm, from about 60 mm to about 110 mm, from about 65 mm to about 110 mm, from about 70 mm to about 110 mm, from about 75 mm to about 110 mm, from about 80 mm to about 110 mm, from about 85 mm to about 110 mm, from about 90 mm to about 110 mm, from about 95 mm to about 110 mm, from about 100 mm to about 110 mm, from about 105 mm to about 110 mm, about 9 mm, about 10 mm, about 11 mm, about 12 mm, about 13 mm, about 14 mm, about 15 mm, about 16 mm, about 17 mm, about 18 mm, about 19 mm, about 20 mm, about 21 mm, about 22 mm, about 23 mm, about 24 mm, about 25 mm, about 26 mm, about 27 mm, about 28 mm, about 29 mm, about 30 mm, about 31 mm, about 32 mm, about 33 mm, about 34 mm, about 35 mm, about 36 mm, about 37 mm, about 38 mm, about 39 mm, about 40 mm, about 41 mm, about 42 mm, about 43 mm, about 44 mm, about 45 mm, about 46 mm, about 47 mm, about 48 mm, about 49 mm, about 50 mm, about 51 mm, about 52 mm, about 53 mm, about 54 mm, about 55 mm, about 56 mm, about 57 mm, about 58 mm, about 59 mm, about 60 mm, about 61 mm, about 62 mm, about 63 mm, about 64 mm, about 65 mm, about 66 mm, about 67 mm, about 68 mm, about 69 mm, about 70 mm, about 71 mm, about 72 mm, about 73 mm, about 74 mm, about 75 mm, about 76 mm, about 77 mm, about 78 mm, about 79 mm, about 80 mm, about 81 mm, about 82 mm, about 83 mm, about 84 mm, about 85 mm, about 86 mm, about 87 mm, about 88 mm, about 89 mm, about 90 mm, about 91 mm, about 92 mm, about 93 mm, about 94 mm, about 95 mm, about 96 mm, about 97 mm, about 98 mm, about 99 mm, about 100 mm, about 101 mm, about 102 mm, about 103 mm, about 104 mm, about 105 mm, about 106 mm, about 107 mm, about 108 mm, about 109 mm, or about 110 mm).

Distal Region

In some embodiments, the device includes a distal region that has a proximal end, a distal end, and a distal opening to the internal channel.

In some embodiments, distal region has an outer diameter of from about 4 mm to about 25 mm (e.g., about 4 mm to about 5 mm, about 5 mm to about 15 mm, about 10 mm to about 25 mm, about 4 mm, about 5 mm, about 6 mm, about 7 mm, about 8 mm, about 9 mm, about 10 mm, about 11 mm, about 12 mm, about 13 mm, about 14 mm, about 15 mm, about 16 mm, about 17 mm, about 18 mm, about 19 mm, about 20 mm, about 21 mm, about 22 mm, about 23 mm, about 24 mm, or about 25 mm). In certain embodiments, the outer diameter of distal region is smaller than, larger than, or equal to the outer diameter of central region.

In some embodiments, distal region has an inner diameter of from about 1 mm to about 20 mm (e.g., from about 1 mm to about 2 mm, from about 1 mm to about 3 mm, from about 1 mm to about 4 mm, from about 1 mm to about 5 mm, from about 2 mm to about 5 mm, from about 4 mm to about 8 mm, from about 5 mm to about 10 mm, from about 8 mm to about 12 mm, from about 10 mm to about 15 mm, from about 10 mm to about 20 mm, from about 15 mm to about 20 mm, about 1 mm, about 2 mm, about 3 mm, about 4 mm, about 5 mm, about 6 mm, about 7 mm, about 8 mm, about 9 mm, about 10 mm, about 11 mm, about 12 mm, about 13 mm, about 14 mm, about 15 mm, about 16 mm, about 17 mm, about 18 mm, about 19 mm, or about 20 mm). In certain embodiments, the inner diameter of distal region is smaller than, larger than, or equal to the inner diameter of central region 1126.

In some embodiments, distal region has a length of from about 0.1 mm to about 30 mm (e.g., from about 0.1 mm to about 1 mm, from about 0.1 mm to about 5 mm, from about 0.1 mm to about 10 mm, from about 5 mm to about 10 mm, from about 5 mm to about 15 mm, from about 5 mm to about 20 mm, from about 10 mm to about 20 mm, from about 10 mm to about 30 mm, from about 15 mm to about 25 mm, from about 20 mm to about 30 mm, about 0.1 mm, about 0.5 mm, about 1 mm, about 2 mm, about 3 mm, about 4 mm, about 5 mm, about 6 mm, about 7 mm, about 8 mm, about 9 mm, about 10 mm, about 11 mm, about 12 mm, about 13 mm, about 14 mm, about 15 mm, about 16 mm, about 17 mm, about 18 mm, about 19 mm, about 20 mm, about 21 mm, about 22 mm, about 23 mm, about 24 mm, about 25 mm, about 26 mm, about 27 mm, about 28 mm, about 29 mm, or about 30 mm).

In some embodiments, distal region 1251 has a wall thickness of from about 0.15 mm to about 3 mm (e.g., from about 0.15 mm to about 0.5 mm, from about 0.15 mm to about 1 mm, from about 0.15 mm to about 1.5 mm, from about 0.5 mm to about 1 mm, from about 0.5 mm to about 1.5 mm, from about 1 mm, to about 2 mm, from about 1 mm to about 3 mm, from about 2 mm to about 3 mm, about 0.15 mm, about 0.2 mm, about 0.3 mm, about 0.4 mmm about 0.5 mm, about 0.6 mm, about 0.7 mm, about 0.8 mm, about 0.9 mm, about 1 mm, about 1.1 mm, about 1.2 mm, about 1.3 mm, about 1.4 mm, about 1.5 mm, about 1.6 mm, about 1.7 mm, about 1.8 mm, about 1.9 mm, about 2 mm, about 2.1 mm, about 2.2 mm, about 2.3 mm, about 2.4 mm, about 2.5 mm, about 2.6 mm, about 2.7 mm, about 2.8 mm, about 2.9 mm, or about 3 mm). In certain embodiments, the wall thickness of distal region is smaller than, larger than, or equal to the wall thickness of central region 1126.

In some embodiments, the distal end of distal region has a blunt edge. In some embodiments, the distal end of distal region has a tapered edge. In some embodiments, the distal end of the distal region has at least one or a plurality of milling flutes, notches, bendable tips, and/or elongated tips.

In some embodiments, the distal region has a plurality of openings (e.g., slits or perforations). In some embodiments, distal region does not have openings other than the opening to the internal channel. In some embodiments, device does not have a distal region.

Expandable and/or Compressible Bodies

In some embodiments, the device has at least one expandable and/or compressible body configured to radially expand and/or compress, e.g., at least one body that is configured to both expand and compress, at least one expandable body configured to radially expand, and/or at least one compressible body configured to radially compress. The proximal region, central region, and/or distal region may include at least one expandable and/or compressible body. Alternatively, an expandable and/or compressible body may extend through at least two of the proximal region, central region, and distal region. For example, in some embodiments, one expandable and/or compressible body extends from the proximal end to the distal end of the device, i.e., the entire device is an expandable and/or compressible body.

In some embodiments, the expandable and/or compressible body includes a flared or a tapered shape. In some embodiments, the compressible body includes a plurality of circumferentially disposed compressible wings. In some embodiments, the expandable and/or compressible body includes a plurality of segments connected by a plurality of expandable arms.

In some embodiments, the expandable and/or compressible body includes a mesh or mesh-life structure. In some embodiments, the mesh or mesh-like structure includes a diamond, square, circular, weave, or oval opening pattern. In some embodiments, the mesh or mesh-like structure is woven, perforated, crimped, welded, molded, sintered, or 3D-printed. In some embodiments, the mesh or mesh-like structure includes a percent porosity from about 5% to about 90% (e.g., from about 5% to about 10%, from about 5% to about 20%, from about 10% to about 25%, from about 20% to about 40%, from about 20% to about 70%, from about 30% to about 60%, from about 40% to about 60%, from about 50% to about 70%, from about 50% to about 90%, or from about 70% to about 90%). In some embodiments, the mesh or mesh-like structure includes a wire gauge from 5 to 50 (e.g., from 5 to 10, from 10 to 20, from 10 to 30, from 20 to 40, or from 30 to 40).

In some embodiments, the expandable and/or compressible body is configured to expand and/or compress to allow for uniform distribution and delivery of biomaterial to bone surrounding the device. In some embodiments, the expandable and/or compressible body is configured to expand and/or compress thereby providing a volume for receiving biomaterial, which can be delivered through expandable body to the bone. In some embodiments, the expandable body may expand to a volume of from about 1 ml to about 20 ml (e.g., from about 1 ml to about 2 ml, from about 1 ml to about 3 ml, from about 1 ml to about 4 ml, from about 1 ml to about 5 ml, from about 1 ml to about 10 ml, from about 5 ml to about 10 ml, from about 5 ml to about 15 ml, from about 10 ml to about 15 ml, from about 15 ml to about 20 ml, from about 15 ml to about 20 ml, from about 1 ml to about 2 ml, from about 1 ml to about 3 ml, from about 1 ml to about 4 ml, from about 1 ml to about 5 ml, from about 1 ml to about 10 ml, from about 5 ml to about 10 ml, from about 5 ml to about 15 ml, from about 10 ml to about 15 ml, from about 15 ml to about 20 ml, from about 15 ml to about 20 ml, about 1 ml, about 1.1 ml, about 1.2 ml, about 1.3 ml, about 1.4 ml, about 1.5 ml, about 1.6 ml, about 1.7 ml, about 1.8 ml, about 1.9 ml, about 2 ml, about 2.1 ml, about 2.2 ml, about 2.3 ml, about 2.4 ml, about 2.5 ml, about 2.6 ml, about 2.7 ml, about 2.8 ml, about 2.9 ml, about 3 ml, about 3.1 ml, about 3.2 ml, about 3.3 ml, about 3.4 ml, about 3.5 ml, about 3.6 ml, about 3.7 ml, about 3.8 ml, about 3.9 ml, about 4 ml, about 4.1 ml, about 4.2 ml, about 4.3 ml, about 4.4 ml, about 4.5 ml, about 4.6 ml, about 4.7 ml, about 4.8 ml, about 4.9 ml, about 5 ml, about 5.1 ml, about 5.2 ml, about 5.3 ml, about 5.4 ml, about 5.5 ml, about 5.6 ml, about 5.7 ml, about 5.8 ml, about 5.9 ml, about 6 ml, about 6.1 ml, about 6.2 ml, about 6.3 ml, about 6.4 ml, about 6.5 ml, about 6.6 ml, about 6.7 ml, about 6.8 ml, about 6.9 ml, about 7 ml, about 7.1 ml, about 7.2 ml, about 7.3 ml, about 7.4 ml, about 7.5 ml, about 7.6 ml, about 7.7 ml, about 7.8 ml, about 7.9 ml, about 8 ml, about 8.1 ml, about 8.2 ml, about 8.3 ml, about 8.4 ml, about 8.5 ml, about 8.6 ml, about 8.7 ml, about 8.8 ml, about 8.9 ml, about 9 ml, about 9.1 ml, about 9.2 ml, about 9.3 ml, about 9.4 ml, about 9.5 ml, about 9.6 ml, about 9.7 ml, about 9.8 ml, about 9.9 ml, about 10 ml, about 11 ml, about 11.1 ml, about 11.2 ml, about 11.3 ml, about 11.4 ml, about 11.5 ml, about 11.6 ml, about 11.7 ml, about 11.8 ml, about 11.9 ml, about 12 ml, about 12.1 ml, about 12.2 ml, about 12.3 ml, about 12.4 ml, about 12.5 ml, about 12.6 ml, about 12.7 ml, about 12.8 ml, about 12.9 ml, about 13 ml, about 13.1 ml, about 13.2 ml, about 13.3 ml, about 13.4 ml, about 13.5 ml, about 13.6 ml, about 13.7 ml, about 13.8 ml, about 13.9 ml, about 14 ml, about 14.1 ml, about 14.2 ml, about 14.3 ml, about 14.4 ml, about 14.5 ml, about 14.6 ml, about 14.7 ml, about 14.8 ml, about 14.9 ml, about 15 ml, about 15.1 ml, about 15.2 ml, about 15.3 ml, about 15.4 ml, about 15.5 ml, about 15.6 ml, about 15.7 ml, about 15.8 ml, about 15.9 ml, about 16 ml, about 16.1 ml, about 16.2 ml, about 16.3 ml, about 16.4 ml, about 16.5 ml, about 16.6 ml, about 16.7 ml, about 16.8 ml, about 16.9 ml, about 17 ml, about 17.1 ml, about 17.2 ml, about 17.3 ml, about 17.4 ml, about 17.5 ml, about 17.6 ml, about 17.7 ml, about 17.8 ml, about 17.9 ml, about 18 ml, about 18.1 ml, about 18.2 ml, about 18.3 ml, about 18.4 ml, about 18.5 ml, about 18.6 ml, about 18.7 ml, about 18.8 ml, about 18.9 ml, about 19 ml, about 19.1 ml, about 19.2 ml, about 19.3 ml, about 19.4 ml, about 19.5 ml, about 19.6 ml, about 19.7 ml, about 19.8 ml, about 19.9 ml, or about 20 ml).

In some embodiments, the expandable and/or compressible body is configured to expand and/or compress to lock the device into a first position. For example, following deployment of the device into a hole in a bone, the device may expand against the bone, thereby locking the device into a first position. Compression of the device may facilitate insertion of the device into bone. For example, compression of the compressible body facilitates loading of the device into a delivery device, such as a funnel or equivalent device. The device in its compressed form can be delivered/pushed through the delivery device (e.g., by using a pusher or obturator) until the device is inserted fully into a hole in the bone. Once the device exits the delivery device and is fully or at least partially inserted in bone, the device can return to an uncompressed state. If desired, the device could then be expanded in situ, using, e.g., an expansion tool (e.g., a balloon).

Wings

In some embodiments, the device includes from 3 to 20 (e.g., from 3 to 15, from 4 to 10, from 5 to 8, 3, 4, 5, 6, 7, 8, 9, 10, 11, 12, 13, 14, 15, 16, 17, 18, 19, or 20) wings that radially extend around an outer surface of device.

In some embodiments, the wings have proximal end and distal end. In some embodiments, the proximal end of wings is positioned at the same position as proximal end of proximal region. In some embodiments, distal end of wings is positioned at a distance of from about 2 mm to about 30 mm (e.g., from about 2 mm to about 5 mm, from about 2 mm to about 10 mm, from about 5 mm to about 10 mm, from about 5 mm to about 15 mm, from about 10 mm to about 15 mm, from about 10 mm to about 20 mm, from about 15 mm to about 25 mm, from about 20 mm to about 30 mm, about 2 mm, about 3 mm, about 4 mm, about 5 mm, about 6 mm, about 7 mm, about 8 mm, about 9 mm, about 10 mm, about 11 mm, about 12 mm, about 13 mm, about 14 mm, about 15 mm, about 16 mm, about 17 mm, about 18 mm, about 19 mm, about 20 mm, about 21 mm, about 22 mm, about 23 mm, about 24 mm, about 25 mm, about 26 mm, about 27 mm, about 28 mm, about 29 mm, or about 30 mm) from the proximal opening of the internal channel (along the longitudinal axis of device 100).

In some embodiments, the wings have a rectangular shape having a length and a width. In some embodiments, all of the wings have substantially equal length and width. In some embodiments, the wings have different length and widths. In some embodiments, the length of each wing is from about 5 mm to about 20 mm (e.g., about 5 mm to about 10 mm, about 5 mm to about 15 mm, about 10 mm to about 15 mm, about 10 mm to about 20 mm, about 15 mm to about 20 mm, about 5 mm to about 10 mm, about 5 mm to about 15 mm, about 10 mm to about 15 mm, about 10 mm to about 20 mm, about 15 mm to about 20 mm, about 5 mm, about 6 mm, about 7 mm, about 8 mm, about 9 mm, about 10 mm, about 11 mm, about 12 mm, about 13 mm, about 14 mm, about 15 mm, about 16 mm, about 17 mm, about 18 mm, about 19 mm, or about 20 mm). In some embodiments, the width of each wing is from about 1 mm to about 15 mm (e.g., about 1 mm to about 5 mm, about 1 mm to about 10 mm, about 5 mm to about 10 mm, about 5 mm to about 15 mm, about 10 mm to about 15 mm, about 1 mm to about 5 mm, about 1 mm to about 10 mm, about 5 mm to about 10 mm, about 5 mm to about 15 mm, about 10 mm to about 15 mm, about 1 mm, about 2 mm, about 3 mm, about 4 mm, about 5 mm, about 6 mm, about 7 mm, about 8 mm, about 9 mm, about 10 mm, about 11 mm, about 12 mm, about 13 mm, about 14 mm, or about 15 mm).

In some embodiments, the proximal end of the wings is configured to radially protrude outwardly from the proximal region in an uncompressed (expanded) state and at an angle of from about 2° to about 10° (e.g., about 2°, about 3°, about 4°, about 5°, about 6°, about 7°, about 8°, about 9°, or about 10°). In some embodiments, the proximal end 106 of wings is disconnected from proximal region.

In some embodiments, the distal end of each wing is connected to the proximal region and is configured to pivot the proximal end of the wing away from the proximal region. In some embodiments, the wings are configured to reversibly deflect inwardly towards the internal channel of the proximal region thereby substantially eliminating the outward protrusion of the proximal end of the wings upon compression.

Segments and Expandable Arms

In some embodiments, the body of the device includes a plurality of longitudinal segments connected by a plurality of expandable arms. In some embodiments, the proximal region, central region, and/or distal region includes at least one expandable arm. In some embodiments, the proximal region, central region, and/or distal region include a plurality of segments.

In some embodiments, a plurality of segments of the central region extends into the proximal region and/or distal region. In certain embodiments, the plurality of segments extends from the proximal end, through the central region, to the distal end.

The segments may be a variety of shapes and sizes. In some embodiments, the segments include longitudinal segments.

In some embodiments, the segments are polygonal, circular, triangular, elliptical, cylindrical, or amorphous. In some embodiments, the longitudinal segments are rectangular, having a length from the proximal end to the distal end greater than a width.

The device, the proximal region, the central region, and/or the distal region may include from 2 to 20 segments (e.g., from 2 to 4, from 2 to 6, from 2 to 8, from 2 to 10, from 4 to 8, from 4 to 10, from 4 to 12, from 10 to 16, from 10 to 20, 2, 3, 4, 5, 6, 7, 8, 9, 10, 11, 12, 13, 14, 15, 16, 17, 18, 19 or 20). The device, the proximal region, the central region, and/or the distal region may include from 2 to 100 (e.g., 2 to 10, 2 to 20, 10 to 20, 10 to 30, 10 to 50, 20 to 40, 20 to 60, 40 to 80, 50 to 100, 60 to 80, or 80 to 100) expandable arms connecting the segments. In some embodiments, the device includes from 1 to 50 expandable arms per each segment (e.g., from 1 to 5, from 1 to 10, from 4 to 8, from 5 to 10, from 8 to 12, from 8 to 16, from 10 to 15, from 10 to 20, from 20 to 30, from 20 to 40, from 30 to 40, or from 40 to 50). In some embodiments, the device includes from 1 to 50 pairs of expandable arms.

In some embodiments, each of the segments are the same. In some embodiments, each of the segments are separated by at least one opening, in which the opening has a maximum width of about 0.1 mm to about 50 mm.

In some embodiments, each of the segments include a length of about 9 mm to about 110 mm.

In some embodiments, each of the segments include a width of about 0.1 mm to about 50 mm.

In some embodiments, the expandable arms are separated by at least one opening, in which the opening has a maximum width of about 0.1 mm to about 50 mm. In some embodiments, the pairs of expandable arms are separated by at least one opening, in which the opening has a maximum width of about 0.1 mm to about 20 mm.

The expandable arms may be in a variety of shapes. In some embodiments, the expandable arms are c-shaped, s-shaped, u-shaped, or z-shaped.

In some embodiments, the expandable arms may be non-releasably connected to the segments.

In some embodiments, the expandable arms are releasably connected to the segments.

Rolled Surfaces

In some embodiments, the device has a rolled surface having an internal channel extending longitudinally from the proximal end to the distal end. The rolled surface has proximal side, a distal side, a left side and a right side, in which upon radially expanding, the left side and right side may overlap or not overlap.

In some embodiments, the rolled surface has a length of from about 9 mm to about 110 mm (e.g., from about 10 mm to about 110 mm, from about 20 mm to about 110 mm, from about 25 mm to about 110 mm, from about 30 mm to about 110 mm, from about 35 mm to about 110 mm, from about 40 mm to about 110 m, from about 45 mm to about 110 mm, from about 50 mm to about 110 mm, from about 55 mm to about 110 mm, from about 60 mm to about 110 mm, from about 65 mm to about 110 mm, from about 70 mm to about 110 mm, from about 75 mm to about 110 mm, from about 80 mm to about 110 mm, from about 85 mm to about 110 mm, from about 90 mm to about 110 mm, from about 95 mm to about 110 mm, from about 100 mm to about 110 mm, from about 105 mm to about 110 mm, about 9 mm, about 10 mm, about 11 mm, about 12 mm, about 13 mm, about 14 mm, about 15 mm, about 16 mm, about 17 mm, about 18 mm, about 19 mm, about 20 mm, about 21 mm, about 22 mm, about 23 mm, about 24 mm, about 25 mm, about 26 mm, about 27 mm, about 28 mm, about 29 mm, about 30 mm, about 31 mm, about 32 mm, about 33 mm, about 34 mm, about 35 mm, about 36 mm, about 37 mm, about 38 mm, about 39 mm, about 40 mm, about 41 mm, about 42 mm, about 43 mm, about 44 mm, about 45 mm, about 46 mm, about 47 mm, about 48 mm, about 49 mm, about 50 mm, about 51 mm, about 52 mm, about 53 mm, about 54 mm, about 55 mm, about 56 mm, about 57 mm, about 58 mm, about 59 mm, about 60 mm, about 61 mm, about 62 mm, about 63 mm, about 64 mm, about 65 mm, about 66 mm, about 67 mm, about 68 mm, about 69 mm, about 70 mm, about 71 mm, about 72 mm, about 73 mm, about 74 mm, about 75 mm, about 76 mm, about 77 mm, about 78 mm, about 79 mm, about 80 mm, about 81 mm, about 82 mm, about 83 mm, about 84 mm, about 85 mm, about 86 mm, about 87 mm, about 88 mm, about 89 mm, about 90 mm, about 91 mm, about 92 mm, about 93 mm, about 94 mm, about 95 mm, about 96 mm, about 97 mm, about 98 mm, about 99 mm, about 100 mm, about 101 mm, about 102 mm, about 103 mm, about 104 mm, about 105 mm, about 106 mm, about 107 mm, about 108 mm, about 109 mm, or about 110 mm). In some embodiments, the rolled surface has a length greater than 9 mm (e.g., greater than 10 mm, greater than 15 mm, greater than 20 mm, greater than 25 mm, greater than 30 mm, greater than 40 mm, greater than 50 mm, greater than 60 mm, greater than 70 mm, greater than 80 mm, greater than 90, greater than 100 mm, or greater than 110 mm). In some embodiments, the rolled surface has a length less than 110 mm (e.g., less than 100 mm, less than 90 mm, less than 80 mm, less than 70 mm, less than 60 mm, less than 50 mm, less than 40 mm, less than 30 mm, less than 20 mm, or less than 10 mm).

In some embodiments, the rolled surface has a width, from the right side to the left side, of from about 9 mm to about 200 mm (e.g., from about 10 mm to about 100 mm, from about 20 mm to about 100 mm, from about 25 mm to about 100 mm, from about 30 mm to about 100 mm, from about 35 mm to about 100 mm, from about 40 mm to about 100 m, from about 45 mm to about 100 mm, from about 50 mm to about 100 mm, from about 50 mm to about 150 mm, from about 50 mm to about 200 mm, from about 55 mm to about 100 mm, from about 60 mm to about 100 mm, from about 65 mm to about 100 mm, from about 70 mm to about 100 mm, from about 75 mm to about 100 mm, from about 80 mm to about 100 mm, from about 85 mm to about 100 mm, from about 90 mm to about 100 mm, from about 95 mm to about 100 mm, from about 100 mm to about 125 mm, from about 100 mm to about 150 mm, from about 100 mm to about 200 mm, from about 105 mm to about 110 mm, from about 150 mm to about 200 mm, about 9 mm, about 10 mm, about 11 mm, about 12 mm, about 13 mm, about 14 mm, about 15 mm, about 16 mm, about 17 mm, about 18 mm, about 19 mm, about 20 mm, about 21 mm, about 22 mm, about 23 mm, about 24 mm, about 25 mm, about 26 mm, about 27 mm, about 28 mm, about 29 mm, about 30 mm, about 31 mm, about 32 mm, about 33 mm, about 34 mm, about 35 mm, about 36 mm, about 37 mm, about 38 mm, about 39 mm, about 40 mm, about 41 mm, about 42 mm, about 43 mm, about 44 mm, about 45 mm, about 46 mm, about 47 mm, about 48 mm, about 49 mm, about 50 mm, about 51 mm, about 52 mm, about 53 mm, about 54 mm, about 55 mm, about 56 mm, about 57 mm, about 58 mm, about 59 mm, about 60 mm, about 61 mm, about 62 mm, about 63 mm, about 64 mm, about 65 mm, about 66 mm, about 67 mm, about 68 mm, about 69 mm, about 70 mm, about 71 mm, about 72 mm, about 73 mm, about 74 mm, about 75 mm, about 76 mm, about 77 mm, about 78 mm, about 79 mm, about 80 mm, about 81 mm, about 82 mm, about 83 mm, about 84 mm, about 85 mm, about 86 mm, about 87 mm, about 88 mm, about 89 mm, about 90 mm, about 91 mm, about 92 mm, about 93 mm, about 94 mm, about 95 mm, about 96 mm, about 97 mm, about 98 mm, about 99 mm, about 100 mm, about 101 mm, about 102 mm, about 103 mm, about 104 mm, about 105 mm, about 106 mm, about 107 mm, about 108 mm, about 109 mm, about 110 mm, about 120 mm, about 130 mm, about 140 mm, about 150 mm, about 160 mm, about 170 mm, about 180 mm, about 190 mm, or about 200 mm).

In embodiments, the left side and right side overlap in a compressed (unexpanded) or uncompressed (expanded) state from about 0.1 mm to about 30 mm (e.g., from about 0.1 mm to about 1 mm, from about 0.1 mm to about 2 mm, from about 0.1 mm to about 20 mm, from about 0.5 mm to about 1 mm, from 0.5 mm to about 2 mm, from about 1 mm to about 2 mm, from about 2 mm to about 4 mm, from about 2 mm to about 8 mm, from about 5 mm to about 10 mm, from about 10 mm to about 15 mm, from about 15 mm to about 20 mm, or from about 20 mm to about 30 mm). The roll may result in the left side being on top of the right side, or vice versa.

In embodiments, the left side and right side do not overlap in an uncompressed (expanded) state, and there is a groove from the left side to the right side, wherein the groove has a width from about 0.1 mm to about 30 mm (e.g., from about 0.1 mm to about 1 mm, from about 0.1 mm to about 2 mm, from about 0.1 mm to about 20 mm, from about 0.5 mm to about 1 mm, from 0.5 mm to about 2 mm, from about 1 mm to about 2 mm, from about 2 mm to about 4 mm, from about 2 mm to about 8 mm, from about 5 mm to about 10 mm, from about 10 mm to about 15 mm, from about 15 mm to about 20 mm, or from about 20 mm to about 30 mm).

In embodiments in which the rolled surface overlaps upon expansion, the overlap forms a ridge. The formation of a ridge upon deployment in a bone may be advantageous in that the ridge may catch the internal surface of the hole in the bone, such that the device may rotate in one direction but not another. In some embodiments, a deployed device having a rolled surface may rotate left, but not right. In some embodiments, a deployed device having a rolled surface may rotate right, but not left. In some embodiments, the device may not rotate in the direction that a screw is twisted, but may rotate in the direction that a screw is extracted, such that the device and screw are extracted together.

In embodiments in which the rolled surface does not overlap upon expansion, the left side and the right side of the device form a groove. The formation of a groove upon deployment in a bone may be advantageous in that groove (e.g., the edge of the left side and/or right side of the device) may catch the internal surface of the hole in the bone, such that the device may not rotate.

Openings

The device has a plurality of openings, including proximal and distal openings to the internal channel, but also a plurality of openings in the outer surface of the device. The proximal region, central region, and/or distal region may include at least one opening.

In some embodiments, the openings extend from one region into at least one other, for example an opening in the central region may extend into the proximal region and/or the distal region. In some embodiments, an opening may extend from the proximal end of the device to the distal end of the device. In some embodiments in which at least one opening extends from the proximal end to the distal end, the unitary body of the device (e.g., a plurality of segments separated by a plurality of openings, e.g., slits) may be connected by at least one extendable arm.

In some embodiments, the openings are slits or perforations. In some embodiments, the openings include helical slits, segmented slits, longitudinal slits, or circumferential slits. In some embodiments, the openings include circular perforations, elliptical perforations, triangular perforations, polygonal perforations, or amorphous perforations.

In some embodiment, the device includes from about 2 to about 5000 (e.g., from about 2 to about 100, from about 2 to about 200, from about 2 to about 300, from about 2 to about 400, from about 2 to about 500, from about 2 to about 750, from about 2 to about 1000, from about 2 to about 1500, from about 2 to about 2000, from about 2 to about 3000, from about 2 to about 4000, from about 10 to about 50, from about 10 to about 100, from about 50 to about 100, from about 50 to about 250, from about 50 to about 500, from about 100 to about 250, from about 250 to about 500, from about 500 to about 1000, from about 1000 to about 2000, from about 2000 to about 3000, from about 3000 to about 4000, from about 4000 to about 5000, from about 2500 to about 5000, about 2, about 3, about 4, about 5, about 6, about 7, about 8, about 9, about 10, about 11, about 12, about 13, about 14, about 15, about 16, about 17, about 18, about 19, about 20, about 21, about 22, about 23, about 24, about 25, about 26, about 27, about 28, about 29, about 30, about 31, about 32, about 33, about 34, about 35, about 36, about 37, about 38, about 39, about 40, about 41, about 42, about 43, about 44, about 45, about 46, about 47, about 48, about 49, about 50, about 51, about 52, about 53, about 54, about 55, about 56, about 57, about 58, about 59, about 60, about 61, about 62, about 63, about 64, about 65, about 66, about 67, about 68, about 69, about 70, about 75, about 80, about 85, about 90, about 95, about 100, about 125, about 150, about 175, about 200, about 250, about 300, about 350, about 400, about 450, about 500, about 750, about 1000, about 2000, about 3000, about 4000, or about 5000) openings.

In some embodiments, the openings include a width of from about 0.01 mm to about 2 mm (e.g., from about 0.01 mm to about 0.1 mm, from about 0.01 mm to about 0.3 mm, from about 0.01 mm to about 0.5 mm, from about 0.1 mm to about 0.5 mm, from about 0.1 mm to about 1 mm, from about 0.5 mm to about 1 mm, from about 1 mm to about 1.5 mm, or from about 1.5 mm to about 2 mm) and a length of from about 0.01 mm to about 20 mm (e.g., from about 0.01 mm to about 0.1 mm, from about 0.01 mm to about 0.3 mm, from about 0.01 mm to about 0.5 mm, from about 0.1 mm to about 0.5 mm, from about 0.1 mm to about 1 mm, from about 0.5 mm to about 1 mm, from about 1 mm to about 1.5 mm, from about 1 mm to about 5 mm, from about 1.5 mm to about 2 mm, from about 2 mm to about 5 mm, from about 2 mm to about 8 mm, from about 5 mm to about 10 mm, from about 5 mm to about 15 mm, from about 10 mm to about 15 mm, or from about 10 mm to about 20 mm).

In some embodiments, the openings have a length of from about 1 mm to about 20 mm (e.g., about 1 mm, about 2 mm, about 3 mm, about 4 mm, about 5 mm, about 6 mm, about 7 mm, about 8 mm, about 9 mm, about 10 mm, about 11 mm, about 12 mm, about 13 mm, about 14 mm, about 15 mm, about 16 mm, about 17 mm, 18 mm, about 19 mm, or about 20 mm). In some embodiments, the slits have a width of from about 0.1 mm to about 2 mm (e.g., about 0.1 mm, about 0.2 mm, about 0.3 mm, about 0.4 mm, about 0.5 mm, about 0.6 mm, about 0.7 mm, about 0.8 mm, about 0.9 mm, about 1 mm, about 1.1 mm, about 1.2 mm, about 1.3 mm, about 1.4 mm, about 1.5 mm, about 1.6 mm, about 1.7 mm, about 1.8 mm, about 1.9 mm, or about 2 mm).

In some embodiments, the openings have a diameter of from about 0.01 mm to about 5 mm ((e.g., from about 0.01 mm to about 0.1 mm, from about 0.01 mm to about 0.3 mm, from about 0.01 mm to about 0.5 mm, from about 0.1 mm to about 0.5 mm, from about 0.1 mm to about 1 mm, from about 0.5 mm to about 1 mm, from about 1 mm to about 1.5 mm, from about 1 mm to about 5 mm, from about 1.5 mm to about 2 mm, from about 2 mm to about 5 mm, about 0.01 mm, about 0.05 mm, about 0.1 mm, about 0.15 mm, about 0.2 mm, about 0.25 mm, about 0.3 mm, about 0.35 mm, about 0.4 mm, about 0.45 mm, about 0.5 mm, about 0.55 mm, about 0.6 mm, about 0.65 mm, about 0.7 mm, about 0.75 mm, about 0.8 mm, about 0.85 mm, about 0.9 mm, about 0.95 mm, about 1 mm, about 2 mm, about 3 mm, about 4 mm, or about 5 mm).

In some embodiments, the openings include staggered or straight openings.

In some embodiments, a plurality of perforations is connected by at least one slit. In some embodiments, the slits include helical slits, segmented slits, longitudinal slits, or circumferential slits. In some embodiments, from about 2 to about 100 (e.g., from about 2 to about 4, from about 2 to about 10, from 4 to about 10, from 5 to about 10, from 6 to about 12, from 10 to about 20, from about 10 to about 50, from about 20 to about 60, from about 50 to about 100, or from about 75 to about 100) perforations are connected by at least one slit.

In some embodiments, the perforations form a mesh or mesh-life structure. In some embodiments, the mesh or mesh-like structure is woven, perforated, crimped, welded, molded, sintered, or 3D-printed. In some embodiments, the mesh or mesh-like structure includes a percent porosity from about 5% to about 90% (e.g., from about 5% to about 10%, from about 5% to about 20%, from about 10% to about 25%, from about 20% to about 40%, from about 20% to about 70%, from about 30% to about 60%, from about 40% to about 60%, from about 50% to about 70%, from about 50% to about 90%, or from about 70% to about 90%). In some embodiments, the mesh or mesh-like structure includes a wire gauge from 5 to 50 (e.g., from 5 to 10, from 10 to 20, from 10 to 30, from 20 to 40, or from 30 to 40).

The openings are configured for the distribution and delivery of biomaterial to the bone surrounding device. The openings may be configured for the uniform distribution and delivery of biomaterial, or configured to distribute and deliver biomaterial at different levels around the outside surface of the device. The porosity of the device, or at regions of the device, determines the distribution and delivery of the biomaterial.

Threads

In some embodiments, the device includes a thread or threads, such as internal and/or external threads. The thread may be present in the proximal region, the central region, and/or distal region.

The thread may aid in the placement of implantable devices (e.g., a screw or suture anchor) in the device and/or the use of the device with other components of a delivery system. For example, a component of a delivery system device may thread onto the device.

In some embodiments, the thread has a thread pitch of from about 0.25 mm to about 2.5 mm (e.g., from about 0.25 mm to about 0.5 mm, from about 0.5 mm to about 1 mm, from about 0.5 mm to about 1.5 mm, from about 1 mm to about 2 mm, from about 1 mm to about 2.5 mm, or from about 1.5 mm to about 2.5 mm, about 0.25 mm, about 0.3 mm, about 0.4 mm, about 0.5 mm, about 0.6 mm, about 0.7 mm, about 0.8 mm, about 0.9 mm, about 1 mm, about 1.1 mm, about 1.2 mm, about 1.3 mm, about 1.4 mm, about 1.5 mm, about 1.6 mm, about 1.7 mm, about 1.8 mm, about 1.9 mm, about 2 mm, about 2.1 mm, about 2.2 mm, about 2.3 mm, about 2.4 mm, or about 2.5 mm).

In some embodiments, the thread is formed from protrusions (see, e.g., FIG. 92B), grooves (see, e.g., FIG. 93), waves (see, e.g., FIG. 94), or a mesh (see, e.g., FIG. 95). In some embodiments, the internal channel is lined with a mesh so as to form internal threads.

In some embodiments, the protrusions, grooves, or waves are at from about 1 to about 360 points per 360° (e.g., from about 1 to about 4, from about 1 to about 6, from about 1 to about 8, from about 1 to about 10, from about 2 to about 4, from about 2 to about 6, from about 2 to about 10, from about 4 to about 10, from about 10 to about 20, from about 10 to about 50, from about 10 to about 100, from about 40 to about 60, from about 50 to about 100, from about 90 to about 180, from about 100 to about 200, from about 200 to about 300, or from about 300 to about 360), in which 360 points per 360° points defines a full thread.

In some embodiments, the thread is a continuous thread or non-continuous thread. In some embodiments, the thread is broken by at least one opening, e.g., at least one slit or at least one perforation. In some embodiments, the non-continuous thread includes a gap, in which the gap has a length from about 0.5 mm to about 30 mm (e.g., from about 0.5 mm to about 1 mm, from about 1 mm to about 2 mm, from about 2 mm to about 4 mm, from about 5 mm to about 10 mm, from about 10 mm to about 20 mm, or from about 20 mm to about 30 mm).

In some embodiments, the device includes a thread-like equivalent. A thread-like equivalent is a repeating pattern which allows a second device with threads or thread equivalents to be screwed on and secured. Examples of thread-like equivalents include protrusions that repeat, grooves, mesh, or waves.

Protrusions

In some embodiments, the device includes at least one protrusion, such as an internal protrusion or an external protrusion. In some embodiments the proximal region, the central region, and/or distal region include at least one internal or at least one external protrusion.

In some embodiments, at least one protrusion (e.g., a ridge) extends from a proximal end to a distal end of the device, the proximal region, the central region, and/or the distal region.

The protrusion may aid in the placement of implantable devices (e.g., a screw or suture anchor) in the device, and/or the use of the device with other components of a delivery system. For example, a component of a delivery system device may snap onto the device using interlocking or friction fitting protrusions.

In some embodiments, the protrusion is a bump, a spike, a tab, a fin, a ridge, or a raised surface.

In some embodiments, the protrusion includes mesh or a mesh-like structure. In some embodiments, the internal channel is lined with a mesh so as to form internal protrusions. In some embodiments, the mesh or mesh-like structure includes a diamond, square, circular, weave, or oval opening pattern. In some embodiments, the mesh or mesh-like structure is woven, perforated, crimped, welded, molded, sintered, or 3D-printed. In some embodiments, the mesh or mesh-like structure includes a percent porosity from about 5% to about 90% (e.g., from about 5% to about 10%, from about 5% to about 20%, from about 10% to about 25%, from about 20% to about 40%, from about 20% to about 70%, from about 30% to about 60%, from about 40% to about 60%, from about 50% to about 70%, from about 50% to about 90%, or from about 70% to about 90%). In some embodiments, the mesh or mesh-like structure includes a wire gauge from 5 to 50 (e.g., from 5 to 10, from 10 to 20, from 10 to 30, from 20 to 40, or from 30 to 40).

In some embodiments, the device, the proximal region, the central region, and/or the distal region has from about 1 to about 5000 (e.g., from about 1 to about 100, from about 1 to about 200, from about 1 to about 300, from about 1 to about 400, from about 1 to about 500, from about 1 to about 750, from about 1 to about 1000, from about 1 to about 1500, from about 1 to about 2000, from about 1 to about 3000, from about 1 to about 4000, from about 10 to about 50, from about 10 to about 100, from about 50 to about 100, from about 50 to about 250, from about 50 to about 500, from about 100 to about 250, from about 250 to about 500, from about 500 to about 1000, from about 1000 to about 2000, from about 2000 to about 3000, from about 3000 to about 4000, from about 4000 to about 5000, from about 2500 to about 5000, about 2, about 3, about 4, about 5, about 6, about 7, about 8, about 9, about 10, about 11, about 12, about 13, about 14, about 15, about 16, about 17, about 18, about 19, about 20, about 21, about 22, about 23, about 24, about 25, about 26, about 27, about 28, about 29, about 30, about 31, about 32, about 33, about 34, about 35, about 36, about 37, about 38, about 39, about 40, about 41, about 42, about 43, about 44, about 45, about 46, about 47, about 48, about 49, about 50, about 51, about 52, about 53, about 54, about 55, about 56, about 57, about 58, about 59, about 60, about 61, about 62, about 63, about 64, about 65, about 66, about 67, about 68, about 69, about 70, about 75, about 80, about 85, about 90, about 95, about 100, about 125, about 150, about 175, about 200, about 250, about 300, about 350, about 400, about 450, about 500, about 750, about 1000, about 2000, about 3000, about 4000, or about 5000) internal protrusions.

In some embodiments, the device, the proximal region, the central region, and/or the distal region has from about 1 to about 5000 (e.g., from about 1 to about 100, from about 1 to about 200, from about 1 to about 300, from about 1 to about 400, from about 1 to about 500, from about 1 to about 750, from about 1 to about 1000, from about 1 to about 1500, from about 1 to about 2000, from about 1 to about 3000, from about 1 to about 4000, from about 10 to about 50, from about 10 to about 100, from about 50 to about 100, from about 50 to about 250, from about 50 to about 500, from about 100 to about 250, from about 250 to about 500, from about 500 to about 1000, from about 1000 to about 2000, from about 2000 to about 3000, from about 3000 to about 4000, from about 4000 to about 5000, from about 2500 to about 5000, about 2, about 3, about 4, about 5, about 6, about 7, about 8, about 9, about 10, about 11, about 12, about 13, about 14, about 15, about 16, about 17, about 18, about 19, about 20, about 21, about 22, about 23, about 24, about 25, about 26, about 27, about 28, about 29, about 30, about 31, about 32, about 33, about 34, about 35, about 36, about 37, about 38, about 39, about 40, about 41, about 42, about 43, about 44, about 45, about 46, about 47, about 48, about 49, about 50, about 51, about 52, about 53, about 54, about 55, about 56, about 57, about 58, about 59, about 60, about 61, about 62, about 63, about 64, about 65, about 66, about 67, about 68, about 69, about 70, about 75, about 80, about 85, about 90, about 95, about 100, about 125, about 150, about 175, about 200, about 250, about 300, about 350, about 400, about 450, about 500, about 750, about 1000, about 2000, about 3000, about 4000, or about 5000) external protrusions.

Device Ends

The device includes a proximal end at the proximal end of the proximal region and a distal end at the distal end of the distal region.

In some embodiments, the proximal end and/or the distal end is blunt. In some embodiments, the proximal end and/or the distal end is tapered.

In some embodiments, the proximal end and/or the distal end includes at least one milling flute. In some embodiments, the milling flutes have sharpened edges. In some embodiments, the proximal end and/or the distal end has 2 to 5 (e.g., from 2 to 4, 2, 3, 4, or 5) milling flutes.

In some embodiments, the proximal end and/or the distal end includes at least one notch. In some embodiments, the proximal end and/or the distal end has from 2 to 4 (e.g., 2, 3, or 4) notches.

In some embodiments, the proximal end and/or the distal end includes at least one bendable tip. In some embodiments, the proximal end and/or the distal end has from 1 to 5 (e.g., 1, 2, 3, 4, or 5) bendable tips.

In some embodiments, the proximal end and/or the distal end includes at least one elongated slit. In some embodiments, the proximal end and/or the distal end has from 2 to 4 (e.g., 2, 3, or 4) elongated slits.

Grooves

In some embodiments, in which the device includes from 1 to 70 longitudinal grooves (e.g., from 1 to 2, from 1 to 3, from 1 to 4, from 2 to 4, from 2 to 5, from 2 to 6, from 4 to 8, from 5 to 10, from 6 to 12, from 5 to 15, from 10 to 20, from 20 to 40, from 30 to 60, or from 50 to 70). In some embodiments, the longitudinal grooves include a depth of from about 0.15 mm to about 2.5 mm (e.g., from about 0.15 mm to about 0.5 mm, from about 0.15 mm to about 1 mm, from about 0.15 mm to about 1.5 mm, from about 0.5 mm to about 1 mm, from about 0.5 mm to about 1.5 mm, from about 1 mm, to about 2 mm, from about 1 mm to about 3 mm, from about 2 mm to about 3 mm, about 0.15 mm, about 0.2 mm, about 0.3 mm, about 0.4 mm, about 0.5 mm about 0.6 mm, about 0.7 mm, about 0.8 mm, about 0.9 mm, about 1 mm, about 1.1 mm, about 1.2 mm, about 1.3 mm, about 1.4 mm, about 1.5 mm, about 1.6 mm, about 1.7 mm, about 1.8 mm, about 1.9 mm, about 2 mm, about 2.1 mm, about 2.2 mm, about 2.3 mm, about 2.4 mm, or about 2.5). In some embodiments, the longitudinal grooves extend from a proximal end of the central region to a distal end of the device, the proximal region, the central region, or the distal region.

Alignment Markers

In some embodiments, the device may include an alignment marker to facilitate insertion of hardware, such as a screw, through the device. An alignment marker can be any visible indicator and can also include, e.g., a radio-opaque marker. In some embodiments, the shape of the alignment marker is selected from the group consisting of a square, a diamond, a triangle, a cross, a circle, a horseshoe, and a star. In some embodiments, the alignment marker is a bump or raised surface.

Device 100

Device 100 of the disclosure is an implant that can be used for multiple purposes, including in the repair of bone defects. Device 100 is configured for insertion into bone (e.g., into bone hole 875 that is predrilled in the bone prior to insertion of device 100). Once inserted, device 100 can be used to uniformly deliver a biomaterial to the bone, secure the bone structure, and promote bone repair and/or healing.

Device 100 has a unitary cylindrical body that includes proximal region 101, distal region 151, and central region 126 disposed therebetween (see, e.g., FIGS. 1, 15, 19A, 21, 33A, 37, 40, 43). Device 100 also includes internal channel 190 (see, e.g., FIG. 19B) that extends longitudinally through the proximal, central, and distal regions. In some embodiments, device 100 has a length of from about 9 mm to about 110 mm (e.g., from about 10 mm to about 110 mm, from about 20 mm to about 110 mm, from about 25 mm to about 110 mm, from about 30 mm to about 110 mm, from about 35 mm to about 110 mm, from about 40 mm to about 110 m, from about 45 mm to about 110 mm, from about 50 mm to about 110 mm, from about 55 mm to about 110 mm, from about 60 mm to about 110 mm, from about 65 mm to about 110 mm, from about 70 mm to about 110 mm, from about 75 mm to about 110 mm, from about 80 mm to about 110 mm, from about 85 mm to about 110 mm, from about 90 mm to about 110 mm, from about 95 mm to about 110 mm, from about 100 mm to about 110 mm, from about 105 mm to about 110 mm, about 9 mm, about 10 mm, about 11 mm, about 12 mm, about 13 mm, about 14 mm, about 15 mm, about 16 mm, about 17 mm, about 18 mm, about 19 mm, about 20 mm, about 21 mm, about 22 mm, about 23 mm, about 24 mm, about 25 mm, about 26 mm, about 27 mm, about 28 mm, about 29 mm, about 30 mm, about 31 mm, about 32 mm, about 33 mm, about 34 mm, about 35 mm, about 36 mm, about 37 mm, about 38 mm, about 39 mm, about 40 mm, about 41 mm, about 42 mm, about 43 mm, about 44 mm, about 45 mm, about 46 mm, about 47 mm, about 48 mm, about 49 mm, about 50 mm, about 51 mm, about 52 mm, about 53 mm, about 54 mm, about 55 mm, about 56 mm, about 57 mm, about 58 mm, about 59 mm, about 60 mm, about 61 mm, about 62 mm, about 63 mm, about 64 mm, about 65 mm, about 66 mm, about 67 mm, about 68 mm, about 69 mm, about 70 mm, about 71 mm, about 72 mm, about 73 mm, about 74 mm, about 75 mm, about 76 mm, about 77 mm, about 78 mm, about 79 mm, about 80 mm, about 81 mm, about 82 mm, about 83 mm, about 84 mm, about 85 mm, about 86 mm, about 87 mm, about 88 mm, about 89 mm, about 90 mm, about 91 mm, about 92 mm, about 93 mm, about 94 mm, about 95 mm, about 96 mm, about 97 mm, about 98 mm, about 99 mm, about 100 mm, about 101 mm, about 102 mm, about 103 mm, about 104 mm, about 105 mm, about 106 mm, about 107 mm, about 108 mm, about 109 mm, or about 110 mm.

In certain embodiments, device 100 is composed of a material selected from stainless steel or an alloy thereof, titanium or an alloy thereof, magnesium or an alloy thereof, polyetheretherketone (PEEK), hydroxyapatite, tricalcium phosphate, tetracalcium phosphate, dicalcium phosphate, BIOGLASS® 45S5, ceramic composites, copper-based materials or composites, cobalt chrome, xenograft biomaterials, and combinations thereof.

Proximal Region of Device 100

Figure 1:
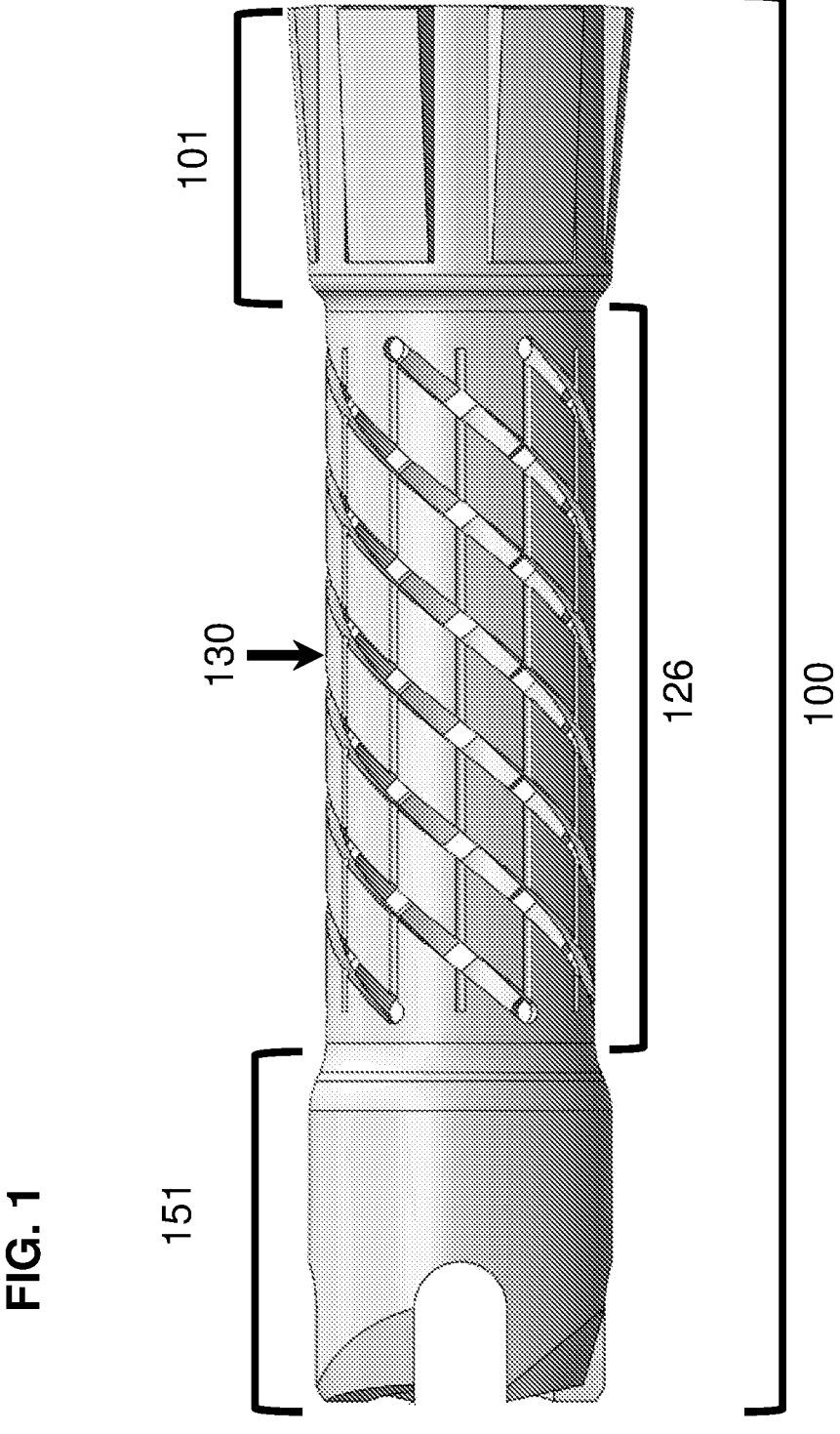
FIG. 1 is a schematic drawing showing a side view of an embodiment of device 100 having proximal region 101, central region 126, and distal region 151. Expandable body 130 of central region 126 is also shown.
Figure 2:
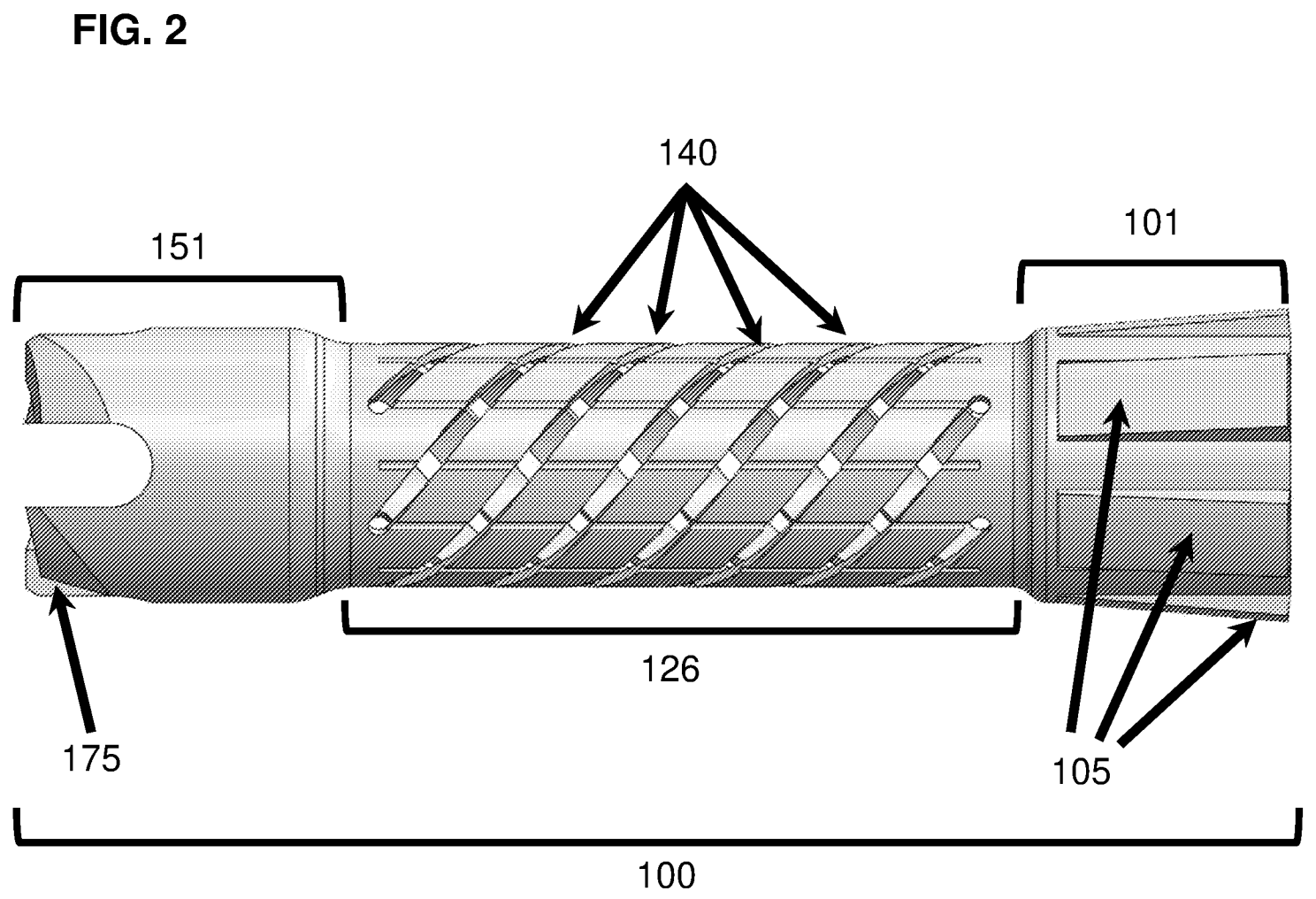
Figure 3:
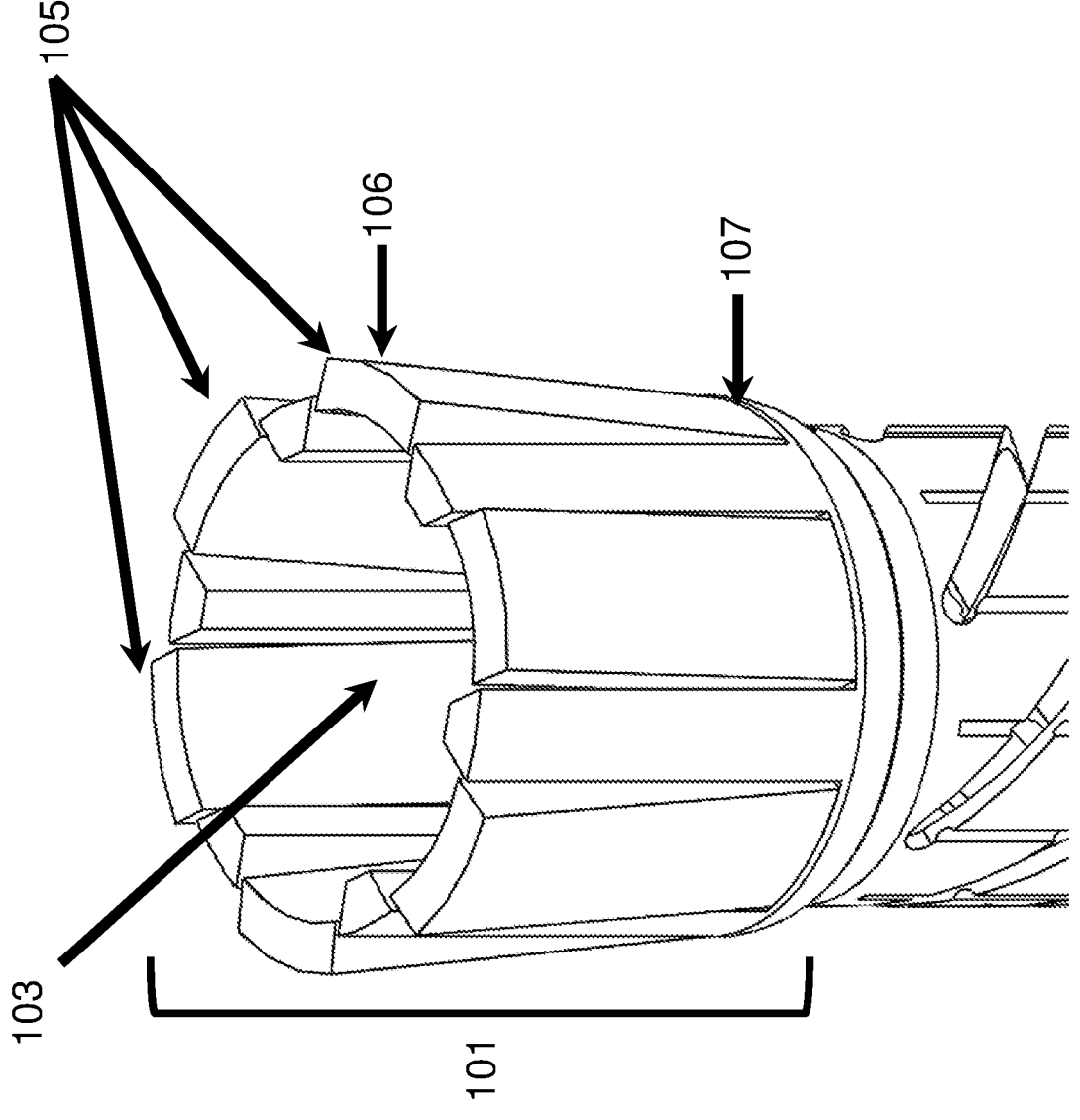
FIG. 3 is a schematic drawing showing an enlarged view of proximal region 101 of device 100. Proximal region 101 is shown with wings 105. Proximal end 106 and distal end 107 of proximal region 101 are also shown. Proximal end 106 of wings 105 is shown angled outwardly in an uncompressed state. Proximal opening 103 is also depicted.

Device 100 includes proximal region 101 that has a proximal end 106, a distal end 107, and proximal opening 103 to internal channel 190 disposed at proximal region 101 (see, e.g., FIG. 1-3). In some embodiments, proximal region 101 has an outer diameter of from about 4 mm to about 25 mm (e.g., about 4 mm, about 5 mm, about 6 mm, about 7 mm, about 8 mm, about 9 mm, about 10 mm, about 11 mm, about 12 mm, about 13 mm, about 14 mm, about 15 mm, about 16 mm, about 17 mm, about 18 mm, about 19 mm, about 20 mm, about 21 mm, about 22 mm, about 23 mm, about 24 mm, or about 25 mm). In some embodiments, proximal region 101 has an inner diameter of from about 3 mm to about 20 mm (e.g., about 3 mm, about 4 mm, about 5 mm, about 6 mm, about 7 mm, about 8 mm, about 9 mm, about 10 mm, about 11 mm, about 12 mm, about 13 mm, about 14 mm, about 15 mm, about 16 mm, about 17 mm, about 18 mm, about 19 mm, or about 20 mm). In some embodiments, proximal region 101 has a length of from about 2 mm to about 30 mm (e.g., from about 2 mm to about 5 mm, from about 2 mm to about 10 mm, from about 5 mm to about 10 mm, from about 5 mm to about 15 mm, from about 10 mm to about 15 mm, from about 10 mm to about 20 mm, from about 15 mm to about 25 mm, from about 20 mm to about 30 mm, about 2 mm, about 3 mm, about 4 mm, about 5 mm, about 6 mm, about 7 mm, about 8 mm, about 9 mm, about 10 mm, about 11 mm, about 12 mm, about 13 mm, about 14 mm, about 15 mm, about 16 mm, about 17 mm, about 18 mm, about 19 mm, about 20 mm, about 21 mm, about 22 mm, about 23 mm, about 24 mm, about 25 mm, about 26 mm, about 27 mm, about 28 mm, about 29 mm, or about 30 mm). In some embodiments, proximal region 101 has a wall thickness of from about 0.6 mm to about 2.5 mm (e.g., about 0.6 mm, about 0.7 mm, about 0.8 mm, about 0.9 mm, about 1 mm, about 1.1 mm, about 1.2 mm, about 1.3 mm, about 1.4 mm, about 1.5 mm, about 1.6 mm, about 1.7 mm, about 1.8 mm, about 1.9 mm, about 2 mm, about 2.1 mm, about 2.2 mm, about 2.3 mm, about 2.4 mm, or about 2.5). In certain embodiments, the outer diameter of proximal region 101 is larger than the outer diameter of central region 126.

Proximal region 101 includes from 3 to 20 (e.g., from 3 to 15, from 4 to 10, from 5 to 8, 3, 4, 5, 6, 7, 8, 9, 10, 11, 12, 13, 14, 15, 16, 17, 18, 19, or 20) wings 105 that radially extend around the outer surface of proximal region 101 (see, e.g., FIG. 2). In some embodiments, wings 105 have proximal end 106 and distal end 107 (see, e.g., FIG. 3). In some embodiments, proximal end 106 of wings 105 is positioned at the same position as proximal end 106 of proximal region 101. In some embodiments, distal end 107 of wings 105 is positioned at a distance of from about 2 mm to about 30 mm (e.g., from about 2 mm to about 5 mm, from about 2 mm to about 10 mm, from about 5 mm to about 10 mm, from about 5 mm to about 15 mm, from about 10 mm to about 15 mm, from about 10 mm to about 20 mm, from about 15 mm to about 25 mm, from about 20 mm to about 30 mm, about 2 mm, about 3 mm, about 4 mm, about 5 mm, about 6 mm, about 7 mm, about 8 mm, about 9 mm, about 10 mm, about 11 mm, about 12 mm, about 13 mm, about 14 mm, about 15 mm, about 16 mm, about 17 mm, about 18 mm, about 19 mm, about 20 mm, about 21 mm, about 22 mm, about 23 mm, about 24 mm, about 25 mm, about 26 mm, about 27 mm, about 28 mm, about 29 mm, or about 30 mm) from proximal opening 103 (along the longitudinal axis of device 100).

In some embodiments, wings 105 have a rectangular shape having a length and a width. In some embodiments, all of wings 105 have substantially equal length and width. In some embodiments, wings 105 have different length and widths. In some embodiments, the length of each wing is from about 5 mm to about 20 mm (e.g., about 5 mm to about 10 mm, about 5 mm to about 15 mm, about 10 mm to about 15 mm, about 10 mm to about 20 mm, about 15 mm to about 20 mm, about 5 mm, about 6 mm, about 7 mm, about 8 mm, about 9 mm, about 10 mm, about 11 mm, about 12 mm, about 13 mm, about 14 mm, about 15 mm, about 16 mm, about 17 mm, about 18 mm, about 19 mm, or about 20 mm). In some embodiments, the width of each wing is from about 1 mm to about 15 mm (e.g., about 1 mm to about 5 mm, about 1 mm to about 10 mm, about 5 mm to about 10 mm, about 5 mm to about 15 mm, about 10 mm to about 15 mm, about 1 mm, about 2 mm, about 3 mm, about 4 mm, about 5 mm, about 6 mm, about 7 mm, about 8 mm, about 9 mm, about 10 mm, about 11 mm, about 12 mm, about 13 mm, about 14 mm, or about 15 mm). In some embodiments, proximal end 106 of wings 105 is configured to radially protrude outwardly from proximal region 101 in an uncompressed (expanded) state (see, e.g., FIG. 70A and FIG. 71) and at an angle of from about 2° to about 10° (e.g., about 2°, about 3°, about 4°, about 5°, about 6°, about 7°, about 8°, about 9°, or about 10°). In some embodiments, proximal end 106 of wings 105 is disconnected from proximal region 101. In some embodiments, distal end 107 of each wing is connected to proximal region 101 and is configured to pivot proximal end 106 of the wing away from proximal region 101. In some embodiments, wings 105 are configured to reversibly deflect inwardly towards internal channel 190 of proximal region 101 thereby substantially eliminating the outward protrusion of proximal end 106 of wings 105 upon compression (see, e.g., FIG. 70B).

In some embodiments, proximal region 101 includes a second set of internal threads 121 disposed along the channel wall. In some embodiments, internal threads 121 of proximal region 101 have a thread pitch of from about 0.25 mm to about 2.5 mm (e.g., about 0.25 mm, about 0.3 mm, about 0.4 mm, about 0.5 mm, about 0.6 mm, about 0.7 mm, about 0.8 mm, about 0.9 mm, about 1 mm, about 1.1 mm, about 1.2 mm, about 1.3 mm, about 1.4 mm, about 1.5 mm, about 1.6 mm, about 1.7 mm, about 1.8 mm, about 1.9 mm, about 2 mm, about 2.1 mm, about 2.2 mm, about 2.3 mm, about 2.4 mm, or about 2.5 mm). In certain embodiments, proximal region 101 of device 100 has alignment marker 125 (e.g., a line, an arrowhead, a colored marking, or textured marking).

Central Region of Device 100

Central region 126 of device 100 includes an expandable body 130 containing a plurality of openings 140, a proximal end, and a distal end. Openings 140 may be slits, helical slits, segmented openings, or perforations that form a mesh or a mesh-like structure. Expandable body 130 is configured to expand to allow for uniform distribution and delivery of biomaterial 550 to the bone surrounding device 100 (see, e.g., FIG. 2). In some embodiments, central region 126 has an outer diameter of from about 1.25 mm to about 25 mm (e.g., about 1.5 mm, about 1.75 mm, about 2 mm, about 3 mm, about 4 mm, about 5 mm, about 6 mm, about 7 mm, about 8 mm, about 9 mm, about 10 mm, about 11 mm, about 12 mm, about 13 mm, about 14 mm, about 15 mm, about 16 mm, about 17 mm, about 18 mm, about 19 mm, about 20 mm, about 21 mm, about 22 mm, about 23 mm, about 24 mm, or about 25 mm). Central region 126 includes an outer diameter that is smaller than the outer diameter of the proximal and distal regions. In some embodiments, central region 126 has an inner diameter of from about 1 mm to about 20 mm (e.g., about 1 mm, about 2 mm, about 3 mm, about 4 mm, about 5 mm, about 6 mm, about 7 mm, about 8 mm, about 9 mm, about 10 mm, about 11 mm, about 12 mm, about 13 mm, about 14 mm, about 15 mm, about 16 mm, about 17 mm, about 18 mm, about 19 mm, or about 20 mm). In some embodiments, central region 126 has a length of from about 5 mm to about 50 mm (e.g., about 5 mm, about 6 mm, about 7 mm, about 8 mm, about 9 mm, about 10 mm, about 11 mm, about 12 mm, about 13 mm, about 14 mm, about 15 mm, about 16 mm, about 17 mm, about 18 mm, about 19 mm, about 20 mm, about 21 mm, about 22 mm, about 23 mm, about 24 mm, about 25 mm, about 26 mm, about 27 mm, about 28 mm, about 29 mm, about 30 mm, about 31 mm, about 32 mm, about 33 mm, about 34 mm, about 35 mm, about 36 mm, about 37 mm, about 38 mm, about 39 mm, about 40 mm, about 41 mm, about 42 mm, about 43 mm, about 44 mm, about 45 mm, about 46 mm, about 47 mm, about 48 mm, about 49 mm, or about 50 mm). In some embodiments, central region 126 has a wall thickness of from about 0.15 mm to about 2 mm (e.g., about 0.15 mm, about 0.2 mm, about 0.3 mm, about 0.4 mmm about 0.5 mm, about 0.6 mm, about 0.7 mm, about 0.8 mm, about 0.9 mm, about 1 mm, about 1.1 mm, about 1.2 mm, about 1.3 mm, about 1.4 mm, about 1.5 mm, about 1.6 mm, about 1.7 mm, about 1.8 mm, about 1.9 mm, or about 2 mm). In certain embodiments, the outer diameter of central region 126 is smaller than the outer diameter of the proximal and distal regions.

Figure 4:
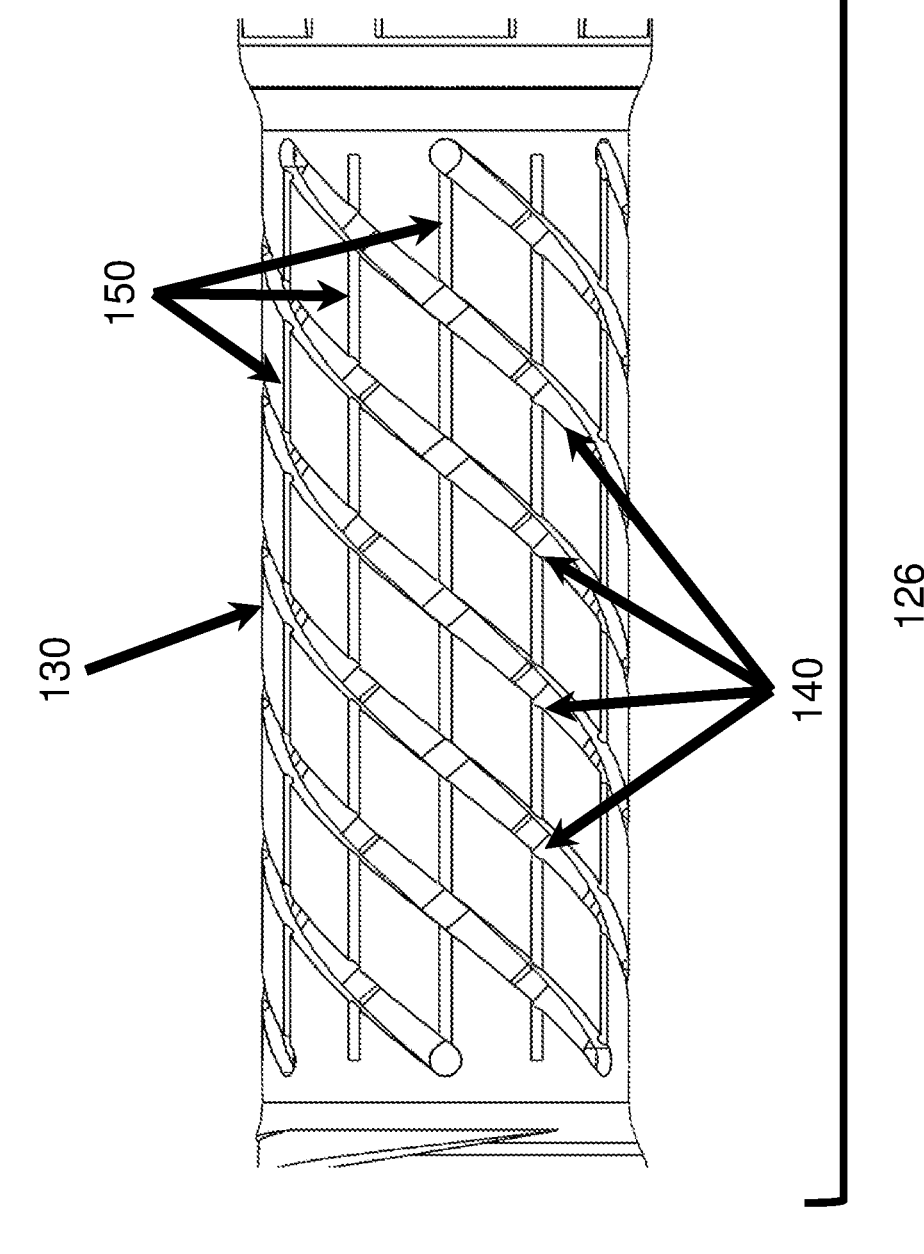
FIG. 4 is a schematic drawing showing an enlarged view of central region 126 of device 100. Slits in central region 126 are also shown wrapping around central region 126. Optional longitudinal grooves 150 along a longitudinal axis of device 100 are also shown.

Central region 126 includes expandable body 130 characterized by having a plurality of openings 140 (e.g., slits, helical slits, segmented openings, or perforations) (see, e.g., FIG. 4). Expandable body 130 may include a helical pattern having from 2 to 20 (e.g., from 2 to 4, from 2 to 6, from 2 to 8, from 2 to 10, from 4 to 8, from 4 to 10, from 4 to 12, from 10 to 16, from 10 to 20, 2, 3, 4, 5, 6, 7, 8, 9, 10, 11, 12, 13, 14, 15, 16, 17, 18, 19, or 20) openings 140. In some embodiments, the openings 140, e.g., helical openings, wrap around central region 126, forming a helical pattern, from the proximal end to the distal end of central region 126 (see, e.g., FIGS. 4, 25B, 27A-27B, 28A-28B, 29A-29B, 30A-30B). In some embodiments, the slits have a length of from about 1 mm to about 20 mm (e.g., about 1 mm, about 2 mm, about 3 mm, about 4 mm, about 5 mm, about 6 mm, about 7 mm, 8 mm, about 9 mm, about 10 mm, about 11 mm, about 12 mm, about 13 mm, about 14 mm, about 15 mm, about 16 mm, about 17 mm, 18 mm, about 19 mm, or about 20 mm). In some embodiments, the slits have a width of from about 0.1 mm to about 2 mm (e.g., about 0.1 mm, about 0.2 mm, about 0.3 mm, about 0.4 mm, about 0.5 mm, about 0.6 mm, about 0.7 mm, about 0.8 mm, about 0.9 mm, about 1 mm, about 1.1 mm, about 1.2 mm, about 1.3 mm, about 1.4 mm, about 1.5 mm, about 1.6 mm, about 1.7 mm, about 1.8 mm, about 1.9 mm, or about 2 mm). In some embodiments, expandable body 130 includes openings 140 having a circular or elliptical shape. In some embodiments, the circular or elliptical openings 140 or perforations, may have a diameter of from about 1 mm to about 5 mm (e.g., about 0.1 mm, about 0.2 mm, about 0.3 mm, about 0.4 mm, about 0.5 mm, about 0.6 mm, about 0.7 mm, about 0.8 mm, about 0.9 mm, about 1 mm, about 1.1 mm, about 1.2 mm, about 1.3 mm, about 1.4 mm, about 1.5 mm, about 1.6 mm, about 1.7 mm, about 1.8 mm, about 1.9 mm, about 2 mm, about 2.1 mm, about 2.2 mm, about 2.3 mm, about 2.4 mm, about 2.5 mm, about 2.6 mm, about 2.7 mm, about 2.8 mm, about 2.9 mm, about 3 mm, about 3.1 mm, about 3.2 mm, about 3.3 mm, about 3.4 mm, about 3.5 mm, about 3.6 mm, about 3.7 mm, about 3.8 mm, about 3.9 mm, about 4 mm, about 4.1 mm, about 4.2 mm, about 4.3 mm, about 4.4 mm, about 4.5 mm, about 4.6 mm, about 4.7 mm, about 4.8 mm, about 4.9 mm, or about 5 mm).

In some embodiments, central region 126 has from 2 to 70 (e.g., from 2 to 4, from 2 to 5, from 2 to 6, from 4 to 8, from 5 to 10, from 6 to 12, from 5 to 15, from 10 to 20, from 20 to 40, from 30 to 60, or from 50 to 70, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, or 70) longitudinal grooves 150 (see, e.g., FIGS. 4 and 26A-26B).

In some embodiments, central region 126 of device 100 is configured to expand thereby providing a volume for receiving biomaterial 550, which can be delivered through expandable body 130 to the bone. In some embodiments, expandable body 130 may expand to a volume of from about 1 ml to about 20 ml (e.g., from about 1 ml to about 2 ml, from about 1 ml to about 3 ml, from about 1 ml to about 4 ml, from about 1 ml to about 5 ml, from about 1 ml to about 10 ml, from about 5 ml to about 10 ml, from about 5 ml to about 15 ml, from about 10 ml to about 15 ml, from about 15 ml to about 20 ml, from about 15 ml to about 20 ml, about 1 ml, about 1.1 ml, about 1.2 ml, about 1.3 ml, about 1.4 ml, about 1.5 ml, about 1.6 ml, about 1.7 ml, about 1.8 ml, about 1.9 ml, about 2 ml, about 2.1 ml, about 2.2 ml, about 2.3 ml, about 2.4 ml, about 2.5 ml, about 2.6 ml, about 2.7 ml, about 2.8 ml, about 2.9 ml, about 3 ml, about 3.1 ml, about 3.2 ml, about 3.3 ml, about 3.4 ml, about 3.5 ml, about 3.6 ml, about 3.7 ml, about 3.8 ml, about 3.9 ml, about 4 ml, about 4.1 ml, about 4.2 ml, about 4.3 ml, about 4.4 ml, about 4.5 ml, about 4.6 ml, about 4.7 ml, about 4.8 ml, about 4.9 ml, about 5 ml, about 5.1 ml, about 5.2 ml, about 5.3 ml, about 5.4 ml, about 5.5 ml, about 5.6 ml, about 5.7 ml, about 5.8 ml, about 5.9 ml, about 6 ml, about 6.1 ml, about 6.2 ml, about 6.3 ml, about 6.4 ml, about 6.5 ml, about 6.6 ml, about 6.7 ml, about 6.8 ml, about 6.9 ml, about 7 ml, about 7.1 ml, about 7.2 ml, about 7.3 ml, about 7.4 ml, about 7.5 ml, about 7.6 ml, about 7.7 ml, about 7.8 ml, about 7.9 ml, about 8 ml, about 8.1 ml, about 8.2 ml, about 8.3 ml, about 8.4 ml, about 8.5 ml, about 8.6 ml, about 8.7 ml, about 8.8 ml, about 8.9 ml, about 9 ml, about 9.1 ml, about 9.2 ml, about 9.3 ml, about 9.4 ml, about 9.5 ml, about 9.6 ml, about 9.7 ml, about 9.8 ml, about 9.9 ml, about 10 ml, about 11 ml, about 11.1 ml, about 11.2 ml, about 11.3 ml, about 11.4 ml, about 11.5 ml, about 11.6 ml, about 11.7 ml, about 11.8 ml, about 11.9 ml, about 12 ml, about 12.1 ml, about 12.2 ml, about 12.3 ml, about 12.4 ml, about 12.5 ml, about 12.6 ml, about 12.7 ml, about 12.8 ml, about 12.9 ml, about 13 ml, about 13.1 ml, about 13.2 ml, about 13.3 ml, about 13.4 ml, about 13.5 ml, about 13.6 ml, about 13.7 ml, about 13.8 ml, about 13.9 ml, about 14 ml, about 14.1 ml, about 14.2 ml, about 14.3 ml, about 14.4 ml, about 14.5 ml, about 14.6 ml, about 14.7 ml, about 14.8 ml, about 14.9 ml, about 15 ml, about 15.1 ml, about 15.2 ml, about 15.3 ml, about 15.4 ml, about 15.5 ml, about 15.6 ml, about 15.7 ml, about 15.8 ml, about 15.9 ml, about 16 ml, about 16.1 ml, about 16.2 ml, about 16.3 ml, about 16.4 ml, about 16.5 ml, about 16.6 ml, about 16.7 ml, about 16.8 ml, about 16.9 ml, about 17 ml, about 17.1 ml, about 17.2 ml, about 17.3 ml, about 17.4 ml, about 17.5 ml, about 17.6 ml, about 17.7 ml, about 17.8 ml, about 17.9 ml, about 18 ml, about 18.1 ml, about 18.2 ml, about 18.3 ml, about 18.4 ml, about 18.5 ml, about 18.6 ml, about 18.7 ml, about 18.8 ml, about 18.9 ml, about 19 ml, about 19.1 ml, about 19.2 ml, about 19.3 ml, about 19.4 ml, about 19.5 ml, about 19.6 ml, about 19.7 ml, about 19.8 ml, about 19.9 ml, or about 20 ml).
Distal Region of Device 100

Figure 5:
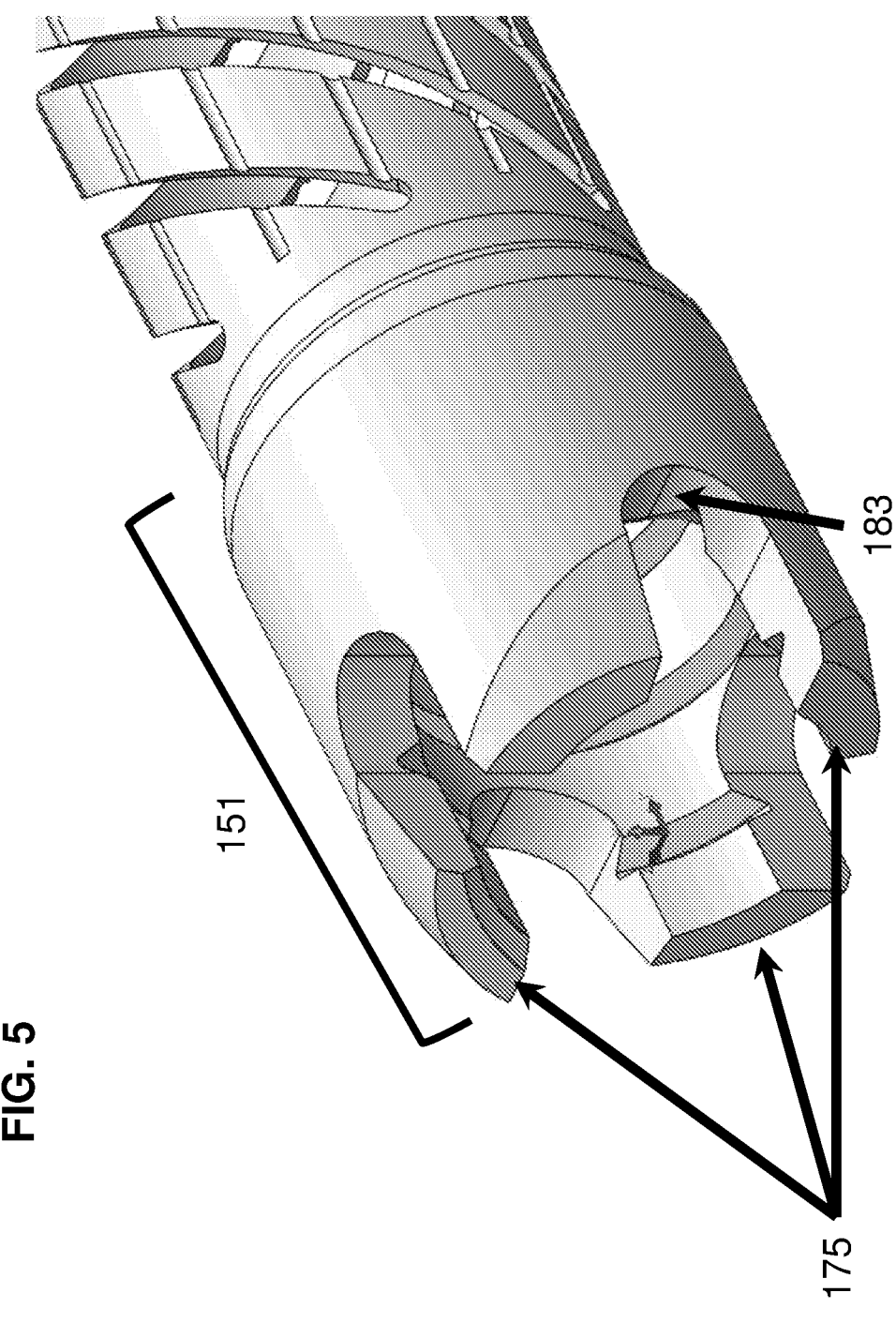
FIG. 5 is a schematic drawing showing an enlarged view of distal region 151 of device 100. In this embodiment, four milling flutes 175 are shown with four notches 183 shown between the flutes.
Figure 6:
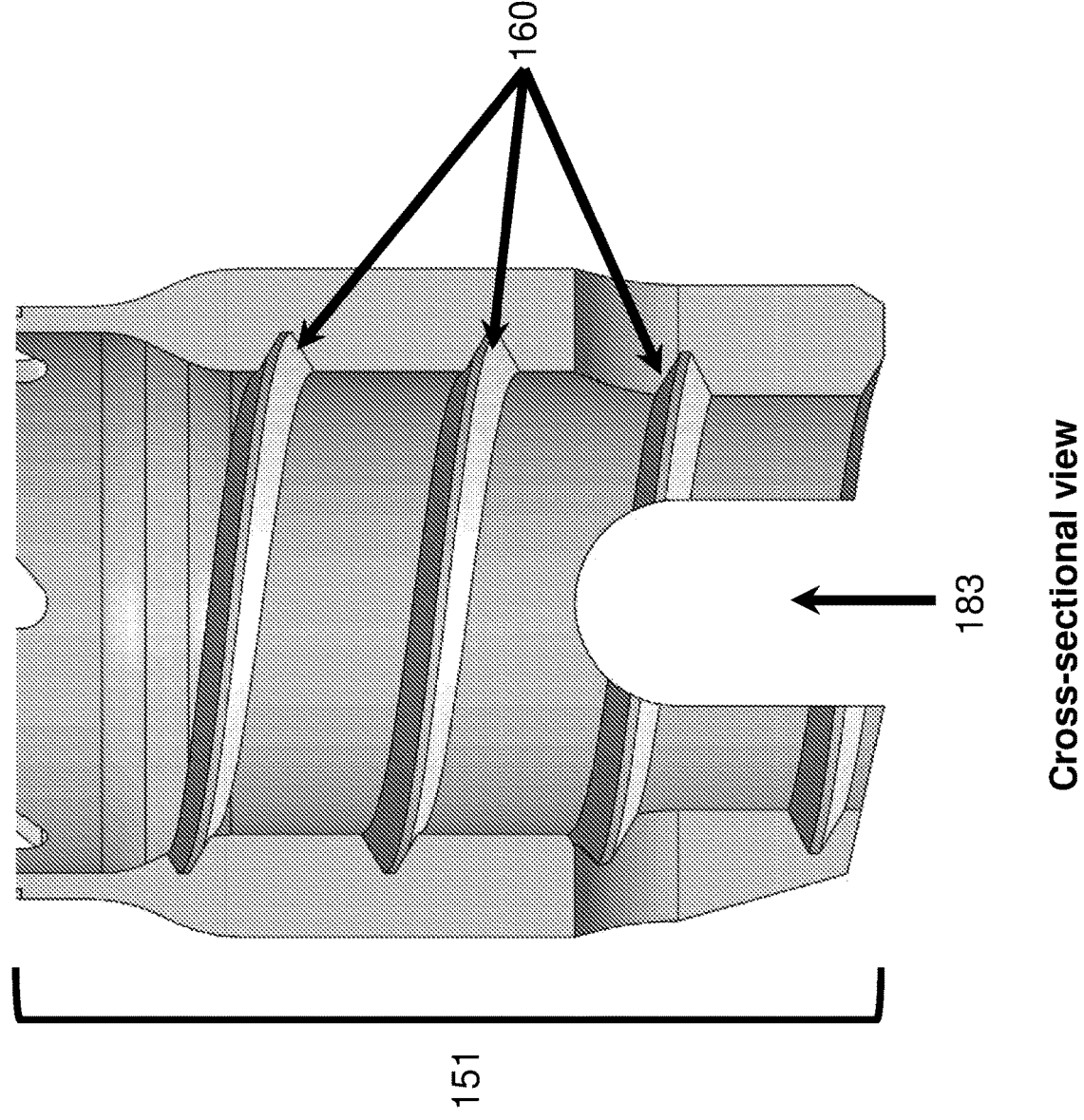
FIG. 6 is a schematic drawing showing a cross-sectional view of distal region 151 of device 100. In this embodiment, notch 183 is shown along with internal threads 160 disposed on an internal surface of distal region 151.

Device 100 includes distal region 151 that includes a proximal end, a distal end, and a distal opening 155 to the channel disposed at the distal end (see, e.g., FIGS. 5 and 6). In some embodiments, distal region 151 has an outer diameter of from about 4 mm to about 25 mm (e.g., about 4 mm, about 5 mm, about 6 mm, about 7 mm, about 8 mm, about 9 mm, about 10 mm, about 11 mm, about 12 mm, about 13 mm, about 14 mm, about 15 mm, about 16 mm, about 17 mm, about 18 mm, about 19 mm, about 20 mm, about 21 mm, about 22 mm, about 23 mm, about 24 mm, or about 25 mm). In some embodiments, distal region 151 has an inner diameter of from about 1 mm to about 20 mm (e.g., about 1 mm, about 2 mm, about 3 mm, about 4 mm, about 5 mm, about 6 mm, about 7 mm, about 8 mm, about 9 mm, about 10 mm, about 11 mm, about 12 mm, about 13 mm, about 14 mm, about 15 mm, about 16 mm, about 17 mm, about 18 mm, about 19 mm, or about 20 mm). In some embodiments, distal region 151 has a length of from about 2 mm to about 30 mm (e.g., from about 2 mm to about 5 mm, from about 2 mm to about 10 mm, from about 5 mm to about 10 mm, from about 5 mm to about 15 mm, from about 10 mm to about 15 mm, from about 10 mm to about 20 mm, from about 15 mm to about 25 mm, from about 20 mm to about 30 mm, about 2 mm, about 3 mm, about 4 mm, about 5 mm, about 6 mm, about 7 mm, about 8 mm, about 9 mm, about 10 mm, about 11 mm, about 12 mm, about 13 mm, about 14 mm, about 15 mm, about 16 mm, about 17 mm, about 18 mm, about 19 mm, about 20 mm, about 21 mm, about 22 mm, about 23 mm, about 24 mm, about 25 mm, about 26 mm, about 27 mm, about 28 mm, about 29 mm, or about 30 mm). In some embodiments, distal region 151 has a wall thickness of from about 0.6 mm to about 2.5 mm (e.g., about 0.6 mm, about 0.7 mm, about 0.8 mm, about 0.9 mm, about 1 mm, about 1.1 mm, about 1.2 mm, about 1.3 mm, about 1.4 mm, about 1.5 mm, about 1.6 mm, about 1.7 mm, about 1.8 mm, about 1.9 mm, about 2 mm, about 2.1 mm, about 2.2 mm, about 2.3 mm, about 2.4 mm, or about 2.5 mm). In certain embodiments, the outer diameter of distal region 151 is larger than the outer diameter of central region 126.

In some embodiments, distal region 151 includes a first set of internal threads 160 disposed along the channel wall (see, e.g., FIGS. 6, 9B, 18B, 19B, 24B, 33B, and 42B). In some embodiments, internal threads 160 of distal region 151 have a thread pitch of from about 0.25 mm to about 2.5 mm (e.g., about 0.25 mm, about 0.3 mm, about 0.4 mm, about 0.5 mm, about 0.6 mm, about 0.7 mm, about 0.8 mm, about 0.9 mm, about 1 mm, about 1.1 mm, about 1.2 mm, about 1.3 mm, about 1.4 mm, about 1.5 mm, about 1.6 mm, about 1.7 mm, about 1.8 mm, about 1.9 mm, about 2 mm, about 2.1 mm, about 2.2 mm, about 2.3 mm, about 2.4 mm, or about 2.5 mm).

The distal end of distal region 151 may have blunt edge 170 (see, e.g., FIGS. 21, 22, and 24-30). In some embodiments, the distal end of distal region 151 has a set of milling flutes 175 (e.g., with sharpened edges) (see, e.g., FIGS. 2 and 5). In some embodiments, the distal end of distal region 151 has 2 to 5 (e.g., 2, 3, 4, or 5) milling flutes 175. In some embodiments, distal region 151 has from 2 to 4 (e.g., 2, 3, or 4) notches 183 (see, e.g., FIGS. 5, 6, 32, 33A-33B, 34A-34B, 37, 38, 39, 41, and 42A-42B) circumferentially disposed around distal region 151 or centrally disposed in distal region 151. In some embodiments, distal region 151 has from 1 to 6 (e.g., 1, 2, 3, 4, 5, or 6) openings 188, fenestrae, or holes (see, e.g., FIGS. 21, 22, 23, and 24A-24B). In some embodiments, openings 188 have a diameter of from about 2 mm to about 5 mm (e.g., about 2 mm, about 2.1 mm, about 2.2 mm, about 2.3 mm, about 2.4 mm, about 2.5 mm, about 2.6 mm, about 2.7 mm, about 2.8 mm, about 2.9 mm, about 3 mm, about 3.1 mm, about 3.2 mm, about 3.3 mm, about 3.4 mm, about 3.5 mm, about 3.6 mm, about 3.7 mm, about 3.8 mm, about 3.9 mm, about 4 mm, about 4.1 mm, about 4.2 mm, about 4.3 mm, about 4.4 mm, about 4.5 mm, about 4.6 mm, about 4.7 mm, about 4.8 mm, about 4.9 mm, or about 5 mm). In some embodiments, distal region 151 has a plurality (e.g., 2, 3, or 4) of bendable tips 180 disposed at the distal end (see, e.g., FIG. 44).

In some embodiments, distal region 151 includes a set of external threads 165 (see, e.g., FIGS. 14A, 40, 41, and 42A-42B). In some embodiments, external threads 165 of distal region 151 have a thread pitch of from about 0.25 mm to about 2.5 mm (e.g., about 0.25 mm, about 0.3 mm, about 0.4 mm, about 0.5 mm, about 0.6 mm, about 0.7 mm, about 0.8 mm, about 0.9 mm, about 1 mm, about 1.1 mm, about 1.2 mm, about 1.3 mm, about 1.4 mm, about 1.5 mm, about 1.6 mm, about 1.7 mm, about 1.8 mm, about 1.9 mm, about 2 mm, about 2.1 mm, about 2.2 mm, about 2.3 mm, about 2.4 mm, or about 2.5 mm).

Device 1100

With reference to FIGS. 74-81, and 91, device 1100 of the disclosure is an implant that can be used for multiple purposes, including in the repair of bone defects. Device 1100 is configured for insertion into bone (e.g., into bone hole 875 that is predrilled in the bone prior to insertion of device 1100). Once inserted, device 1100 can be used to uniformly deliver a biomaterial to the bone, secure the bone structure, and promote bone repair and/or healing.

Device 1100 has a unitary body including from a proximal end to a distal end: proximal region 1101, central region 1126, and distal region 1151, in which central region 1126 joins proximal region 1101 to distal region 1151, and in which: a) the device includes internal 1190 channel extending longitudinally through proximal region 1101, central region 1126, and distal region 1151; b) proximal region 1101 includes a compressible body and opening 1103 to internal channel 1190; c) central region 1126 includes i) plurality of openings 1240 and ii) expandable and/or compressible body 1130 configured to radially expand or compress, in which the expandible and/or compressible body includes plurality of longitudinal segments 1191; and d) distal region 1151 includes opening 1155 to internal channel 1190.

In some embodiments, device 1100 includes a thread or threads, such as internal and/or external threads. In some embodiments, device 1100 includes at least one protrusion, such as internal protrusion 1131 or external protrusion 1132.

Proximal Region of Device 1100

Device 1100 includes proximal region 1101 that has a proximal end, a distal end, and proximal opening 1103 to internal channel 1190 disposed at proximal region 1101 (see, e.g., FIG. 74-77).

In some embodiments, proximal region 1101 has an outer diameter of from about 4 mm to about 25 mm (e.g., from about 4 mm to about 8 mm, from about 4 mm to about 10 mm, from about 4 mm to about 15 mm, from about 5 mm to about 10 mm, from about 10 mm to about 15 mm, from about 10 mm to about 20 mm, from about 15 mm to about 25 mm, from about 20 mm to about 25 mm, about 4 mm, about 5 mm, about 6 mm, about 7 mm, about 8 mm, about 9 mm, about 10 mm, about 11 mm, about 12 mm, about 13 mm, about 14 mm, about 15 mm, about 16 mm, about 17 mm, about 18 mm, about 19 mm, about 20 mm, about 21 mm, about 22 mm, about 23 mm, about 24 mm, or about 25 mm).

In some embodiments, proximal region 1101 has an inner diameter of from about 1 mm to about 20 mm (e.g., from about 1 mm to about 2 mm, from about 1 mm to about 3 mm, from about 1 mm to about 4 mm, from about 1 mm to about 5 mm, from about 1 mm to about 10 mm, from about 5 mm to about 10 mm, from about 5 mm to about 15 mm, from about 10 mm to about 15 mm, from about 15 mm to about 20 mm, from about 15 mm to about 20 mm, about 1 mm, about 2 mm, about 3 mm, about 4 mm, about 5 mm, about 6 mm, about 7 mm, about 8 mm, about 9 mm, about 10 mm, about 11 mm, about 12 mm, about 13 mm, about 14 mm, about 15 mm, about 16 mm, about 17 mm, about 18 mm, about 19 mm, or about 20 mm). In certain embodiments, the outer diameter of proximal region 1101 is smaller than, larger than, or equal to the outer diameter of central region 1126.

In some embodiments, proximal region 1101 has a length of from about 0.1 mm to about 30 mm (e.g., from about 0.1 mm to about 1 mm, from about 0.1 mm to about 5 mm, from about 0.1 mm to about 10 mm, from about 5 mm to about 10 mm, from about 5 mm to about 15 mm, from about 5 mm to about 20 mm, from about 10 mm to about 20 mm, from about 10 mm to about 30 mm, from about 15 mm to about 25 mm, from about 20 mm to about 30 mm, about 2 mm, about 3 mm, about 4 mm, about 5 mm, about 6 mm, about 7 mm, about 8 mm, about 9 mm, about 10 mm, about 11 mm, about 12 mm, about 13 mm, about 14 mm, about 15 mm, about 16 mm, about 17 mm, about 18 mm, about 19 mm, about 20 mm, about 21 mm, about 22 mm, about 23 mm, about 24 mm, about 25 mm, about 26 mm, about 27 mm, about 28 mm, about 29 mm, or about 30 mm). In certain embodiments, the inner diameter of proximal region 1101 is smaller than, larger than, or equal to the inner diameter of central region 1126.

In some embodiments, proximal region 1101 has a wall thickness of from about 0.15 mm to about 2.5 mm (e.g., from about 0.15 mm to about 0.5 mm, from about 0.15 mm to about 1 mm, from about 0.15 mm to about 1.5 mm, from about 0.5 mm to about 1 mm, from about 0.5 mm to about 1.5 mm, from about 1 mm, to about 2 mm, from about 1 mm to about 3 mm, from about 2 mm to about 3 mm, about 0.15 mm, about 0.2 mm, about 0.3 mm, about 0.4 mm, about 0.5 mm about 0.6 mm, about 0.7 mm, about 0.8 mm, about 0.9 mm, about 1 mm, about 1.1 mm, about 1.2 mm, about 1.3 mm, about 1.4 mm, about 1.5 mm, about 1.6 mm, about 1.7 mm, about 1.8 mm, about 1.9 mm, about 2 mm, about 2.1 mm, about 2.2 mm, about 2.3 mm, about 2.4 mm, or about 2.5). In certain embodiments, the wall thickness of proximal region 1101 is smaller than, larger than, or equal to the wall thickness of central region 1126.

In some embodiments, the proximal region 1101 includes from 3 to 20 (e.g., from 3 to 15, from 4 to 10, from 5 to 8, 3, 4, 5, 6, 7, 8, 9, 10, 11, 12, 13, 14, 15, 16, 17, 18, 19, or 20) wings 1105 that radially extend around the outer surface of proximal region 1101 (see, e.g., FIG. 76).

Central Region of Device 1100

Central region 1126 of device 1100 includes i) a first section 1134 including a plurality of segments 1191 separated by a plurality of openings 1140, ii) a second section 1133 including a plurality of openings 1140, iii) a proximal end, and iv) a distal end. In some embodiments, openings 1140 may be slits or perforations. Expandable and/or compressible body 1130 is configured to expand and/or compress to allow for uniform distribution and delivery of biomaterial 550 to the bone surrounding device 1100 (see, e.g., FIG. 81).

In some embodiments, central region 1126 has an outer diameter of from about 1.25 mm to about 25 mm (e.g., from about 1.25 mm to about 2 mm, from about 1.25 mm to about 3 mm, from about 1 mm to about 2 mm, from about 1 mm to about 3 mm, from about 1 mm to about 4 mm, from about 1 mm to about 5 mm, from about 4 mm to about 8 mm, from about 4 mm to about 10 mm, from about 4 mm to about 15 mm, from about 5 mm to about 10 mm, from about 10 mm to about 15 mm, from about 10 mm to about 20 mm, from about 15 mm to about 25 mm, from about 20 mm to about 25 mm, about 1.5 mm, about 1.75 mm, about 2 mm, about 3 mm, about 4 mm, about 5 mm, about 6 mm, about 7 mm, about 8 mm, about 9 mm, about 10 mm, about 11 mm, about 12 mm, about 13 mm, about 14 mm, about 15 mm, about 16 mm, about 17 mm, about 18 mm, about 19 mm, about 20 mm, about 21 mm, about 22 mm, about 23 mm, about 24 mm, or about 25 mm). Central region 1126 includes an outer diameter that is smaller than, larger than, or equal to the outer diameter of the proximal and distal regions.

In some embodiments, central region 1126 has an inner diameter of from about 1 mm to about 20 mm (e.g., from about 1 mm to about 2 mm, from about 1 mm to about 3 mm, from about 1 mm to about 4 mm, from about 1 mm to about 5 mm, from about 1 mm to about 10 mm, from about 5 mm to about 10 mm, from about 5 mm to about 15 mm, from about 10 mm to about 15 mm, from about 15 mm to about 20 mm, about 1 mm, about 2 mm, about 3 mm, about 4 mm, about 5 mm, about 6 mm, about 7 mm, about 8 mm, about 9 mm, about 10 mm, about 11 mm, about 12 mm, about 13 mm, about 14 mm, about 15 mm, about 16 mm, about 17 mm, about 18 mm, about 19 mm, or about 20 mm). Central region 1126 includes an inner diameter that is smaller than, larger than, or equal to the inner diameter of the proximal and distal regions.

In some embodiments, central region 1126 has a length of from about 5 mm to about 110 mm (e.g., from about 10 mm to about 110 mm, from about 20 mm to about 110 mm, from about 25 mm to about 110 mm, from about 30 mm to about 110 mm, from about 35 mm to about 110 mm, from about 40 mm to about 110 m, from about 45 mm to about 110 mm, from about 50 mm to about 110 mm, from about 55 mm to about 110 mm, from about 60 mm to about 110 mm, from about 65 mm to about 110 mm, from about 70 mm to about 110 mm, from about 75 mm to about 110 mm, from about 80 mm to about 110 mm, from about 85 mm to about 110 mm, from about 90 mm to about 110 mm, from about 95 mm to about 110 mm, from about 100 mm to about 110 mm, from about 105 mm to about 110 mm, about 9 mm, about 10 mm, about 11 mm, about 12 mm, about 13 mm, about 14 mm, about 15 mm, about 16 mm, about 17 mm, about 18 mm, about 19 mm, about 20 mm, about 21 mm, about 22 mm, about 23 mm, about 24 mm, about 25 mm, about 26 mm, about 27 mm, about 28 mm, about 29 mm, about 30 mm, about 31 mm, about 32 mm, about 33 mm, about 34 mm, about 35 mm, about 36 mm, about 37 mm, about 38 mm, about 39 mm, about 40 mm, about 41 mm, about 42 mm, about 43 mm, about 44 mm, about 45 mm, about 46 mm, about 47 mm, about 48 mm, about 49 mm, about 50 mm, about 51 mm, about 52 mm, about 53 mm, about 54 mm, about 55 mm, about 56 mm, about 57 mm, about 58 mm, about 59 mm, about 60 mm, about 61 mm, about 62 mm, about 63 mm, about 64 mm, about 65 mm, about 66 mm, about 67 mm, about 68 mm, about 69 mm, about 70 mm, about 71 mm, about 72 mm, about 73 mm, about 74 mm, about 75 mm, about 76 mm, about 77 mm, about 78 mm, about 79 mm, about 80 mm, about 81 mm, about 82 mm, about 83 mm, about 84 mm, about 85 mm, about 86 mm, about 87 mm, about 88 mm, about 89 mm, about 90 mm, about 91 mm, about 92 mm, about 93 mm, about 94 mm, about 95 mm, about 96 mm, about 97 mm, about 98 mm, about 99 mm, about 100 mm, about 101 mm, about 102 mm, about 103 mm, about 104 mm, about 105 mm, about 106 mm, about 107 mm, about 108 mm, about 109 mm, or about 110 mm).

In some embodiments, central region 1126 has a wall thickness of from about 0.15 mm to about 3 mm (e.g., from about 0.15 mm to about 0.5 mm, from about 0.15 mm to about 1 mm, from about 0.15 mm to about 1.5 mm, from about 0.5 mm to about 1 mm, from about 0.5 mm to about 1.5 mm, from about 1 mm, to about 2 mm, from about 1 mm to about 3 mm, from about 2 mm to about 3 mm, about 0.15 mm, about 0.2 mm, about 0.3 mm, about 0.4 mmm about 0.5 mm, about 0.6 mm, about 0.7 mm, about 0.8 mm, about 0.9 mm, about 1 mm, about 1.1 mm, about 1.2 mm, about 1.3 mm, about 1.4 mm, about 1.5 mm, about 1.6 mm, about 1.7 mm, about 1.8 mm, about 1.9 mm, about 2 mm, about 2.1 mm, about 2.2 mm, about 2.3 mm, about 2.4 mm, about 2.5 mm, about 2.6 mm, about 2.7 mm, about 2.8 mm, about 2.9 mm, or about 3 mm). In certain embodiments, the wall thickness of central region 1126 is smaller than, larger than, or equal to the wall thickness of the proximal and distal regions.

In some embodiments, central region 1126 has from 2 to 20 (e.g., from 2 to 4, from 2 to 6, from 2 to 8, from 2 to 10, from 4 to 8, from 4 to 10, from 4 to 12, from 10 to 16, from 10 to 20, 2, 3, 4, 5, 6, 7, 8, 9, 10, 11, 12, 13, 14, 15, 16, 17, 18, 19, or 20) segments 1191 (see, e.g., FIGS. 74-75).

In some embodiments, central region 1126 includes first section 1134 characterized by a plurality of segments 1191 separated by a plurality of openings 1140 (e.g., slits, helical slits, segmented openings, or perforations). As shown in FIG. 74A, first section 1134 includes expandable and/or compressible body 1130 of device 1100.

In some embodiments, central region 1126 includes second section 1133 characterized by a plurality of openings 1140 (e.g., slits, helical slits, segmented openings, or perforations).

In some embodiments, central region 1126 of device 1100 is configured to expand thereby providing a volume for receiving biomaterial 550, which can be delivered through first section 1134 and/or second section 1133 to the bone. In some embodiments, first section 1134 may expand to a volume of from about 1 ml to about 20 ml (e.g., from about 1 ml to about 2 ml, from about 1 ml to about 3 ml, from about 1 ml to about 4 ml, from about 1 ml to about 5 ml, from about 1 ml to about 10 ml, from about 5 ml to about 10 ml, from about 5 ml to about 15 ml, from about 10 ml to about 15 ml, from about 15 ml to about 20 ml, from about 15 ml to about 20 ml, about 1 ml, about 1.1 ml, about 1.2 ml, about 1.3 ml, about 1.4 ml, about 1.5 ml, about 1.6 ml, about 1.7 ml, about 1.8 ml, about 1.9 ml, about 2 ml, about 2.1 ml, about 2.2 ml, about 2.3 ml, about 2.4 ml, about 2.5 ml, about 2.6 ml, about 2.7 ml, about 2.8 ml, about 2.9 ml, about 3 ml, about 3.1 ml, about 3.2 ml, about 3.3 ml, about 3.4 ml, about 3.5 ml, about 3.6 ml, about 3.7 ml, about 3.8 ml, about 3.9 ml, about 4 ml, about 4.1 ml, about 4.2 ml, about 4.3 ml, about 4.4 ml, about 4.5 ml, about 4.6 ml, about 4.7 ml, about 4.8 ml, about 4.9 ml, about 5 ml, about 5.1 ml, about 5.2 ml, about 5.3 ml, about 5.4 ml, about 5.5 ml, about 5.6 ml, about 5.7 ml, about 5.8 ml, about 5.9 ml, about 6 ml, about 6.1 ml, about 6.2 ml, about 6.3 ml, about 6.4 ml, about 6.5 ml, about 6.6 ml, about 6.7 ml, about 6.8 ml, about 6.9 ml, about 7 ml, about 7.1 ml, about 7.2 ml, about 7.3 ml, about 7.4 ml, about 7.5 ml, about 7.6 ml, about 7.7 ml, about 7.8 ml, about 7.9 ml, about 8 ml, about 8.1 ml, about 8.2 ml, about 8.3 ml, about 8.4 ml, about 8.5 ml, about 8.6 ml, about 8.7 ml, about 8.8 ml, about 8.9 ml, about 9 ml, about 9.1 ml, about 9.2 ml, about 9.3 ml, about 9.4 ml, about 9.5 ml, about 9.6 ml, about 9.7 ml, about 9.8 ml, about 9.9 ml, about 10 ml, about 11 ml, about 11.1 ml, about 11.2 ml, about 11.3 ml, about 11.4 ml, about 11.5 ml, about 11.6 ml, about 11.7 ml, about 11.8 ml, about 11.9 ml, about 12 ml, about 12.1 ml, about 12.2 ml, about 12.3 ml, about 12.4 ml, about 12.5 ml, about 12.6 ml, about 12.7 ml, about 12.8 ml, about 12.9 ml, about 13 ml, about 13.1 ml, about 13.2 ml, about 13.3 ml, about 13.4 ml, about 13.5 ml, about 13.6 ml, about 13.7 ml, about 13.8 ml, about 13.9 ml, about 14 ml, about 14.1 ml, about 14.2 ml, about 14.3 ml, about 14.4 ml, about 14.5 ml, about 14.6 ml, about 14.7 ml, about 14.8 ml, about 14.9 ml, about 15 ml, about 15.1 ml, about 15.2 ml, about 15.3 ml, about 15.4 ml, about 15.5 ml, about 15.6 ml, about 15.7 ml, about 15.8 ml, about 15.9 ml, about 16 ml, about 16.1 ml, about 16.2 ml, about 16.3 ml, about 16.4 ml, about 16.5 ml, about 16.6 ml, about 16.7 ml, about 16.8 ml, about 16.9 ml, about 17 ml, about 17.1 ml, about 17.2 ml, about 17.3 ml, about 17.4 ml, about 17.5 ml, about 17.6 ml, about 17.7 ml, about 17.8 ml, about 17.9 ml, about 18 ml, about 18.1 ml, about 18.2 ml, about 18.3 ml, about 18.4 ml, about 18.5 ml, about 18.6 ml, about 18.7 ml, about 18.8 ml, about 18.9 ml, about 19 ml, about 19.1 ml, about 19.2 ml, about 19.3 ml, about 19.4 ml, about 19.5 ml, about 19.6 ml, about 19.7 ml, about 19.8 ml, about 19.9 ml, or about 20 ml).

Distal Region of Device 1100

Device 1100 includes distal region 1151 that includes a proximal end, a distal end, and a distal opening 1155 to the channel disposed at the distal end (see, e.g., FIG. 76).

In some embodiments, distal region 1151 has an outer diameter of from about 4 mm to about 25 mm (e.g., about 4 mm to about 5 mm, about 5 mm to about 15 mm, about 10 mm to about 25 mm, about 4 mm, about 5 mm, about 6 mm, about 7 mm, about 8 mm, about 9 mm, about 10 mm, about 11 mm, about 12 mm, about 13 mm, about 14 mm, about 15 mm, about 16 mm, about 17 mm, about 18 mm, about 19 mm, about 20 mm, about 21 mm, about 22 mm, about 23 mm, about 24 mm, or about 25 mm, about 4 mm, about 5 mm, about 6 mm, about 7 mm, about 8 mm, about 9 mm, about 10 mm, about 11 mm, about 12 mm, about 13 mm, about 14 mm, about 15 mm, about 16 mm, about 17 mm, about 18 mm, about 19 mm, about 20 mm, about 21 mm, about 22 mm, about 23 mm, about 24 mm, or about 25 mm). In certain embodiments, the outer diameter of distal region 1151 is smaller than, larger than, or equal to the outer diameter of central region 1126.

In some embodiments, distal region 1151 has an inner diameter of from about 1 mm to about 20 mm (e.g., from about 1 mm to about 2 mm, from about 1 mm to about 3 mm, from about 1 mm to about 4 mm, from about 1 mm to about 5 mm, from about 2 mm to about 5 mm, from about 4 mm to about 8 mm, from about 5 mm to about 10 mm, from about 8 mm to about 12 mm, from about 10 mm to about 15 mm, from about 10 mm to about 20 mm, from about 15 mm to about 20 mm, about 1 mm, about 2 mm, about 3 mm, about 4 mm, about 5 mm, about 6 mm, about 7 mm, about 8 mm, about 9 mm, about 10 mm, about 11 mm, about 12 mm, about 13 mm, about 14 mm, about 15 mm, about 16 mm, about 17 mm, about 18 mm, about 19 mm, or about 20 mm). In certain embodiments, the inner diameter of distal region 1151 is smaller than, larger than, or equal to the inner diameter of central region 1126.

In some embodiments, distal region 1151 has a length of from about 1 mm to about 30 mm (e.g., from about 0.1 mm to about 1 mm, from about 0.1 mm to about 5 mm, from about 0.1 mm to about 10 mm, from about 5 mm to about 10 mm, from about 5 mm to about 15 mm, from about 5 mm to about 20 mm, from about 10 mm to about 20 mm, from about 10 mm to about 30 mm, from about 15 mm to about 25 mm, from about 20 mm to about 30 mm, about 1 mm, about 2 mm, about 3 mm, about 4 mm, about 5 mm, about 6 mm, about 7 mm, about 8 mm, about 9 mm, about 10 mm, about 11 mm, about 12 mm, about 13 mm, about 14 mm, about 15 mm, about 16 mm, about 17 mm, about 18 mm, about 19 mm, about 20 mm, about 21 mm, about 22 mm, about 23 mm, about 24 mm, about 25 mm, about 26 mm, about 27 mm, about 28 mm, about 29 mm, or about 30 mm).

In some embodiments, distal region 1151 has a wall thickness of from about 0.15 mm to about 3 mm (e.g., from about 0.15 mm to about 0.5 mm, from about 0.15 mm to about 1 mm, from about 0.15 mm to about 1.5 mm, from about 0.5 mm to about 1 mm, from about 0.5 mm to about 1.5 mm, from about 1 mm, to about 2 mm, from about 1 mm to about 3 mm, from about 2 mm to about 3 mm, about 0.15 mm, about 0.2 mm, about 0.3 mm, about 0.4 mmm about 0.5 mm, about 0.6 mm, about 0.7 mm, about 0.8 mm, about 0.9 mm, about 1 mm, about 1.1 mm, about 1.2 mm, about 1.3 mm, about 1.4 mm, about 1.5 mm, about 1.6 mm, about 1.7 mm, about 1.8 mm, about 1.9 mm, about 2 mm, about 2.1 mm, about 2.2 mm, about 2.3 mm, about 2.4 mm, about 2.5 mm, about 2.6 mm, about 2.7 mm, about 2.8 mm, about 2.9 mm, or about 3 mm). In certain embodiments, the wall thickness of distal region 1151 is smaller than, larger than, or equal to the wall thickness of central region 1126.

The distal end of distal region 1151 may have a blunt edge. The distal end of distal region 1151 may have tapered edge 1171.

Device 1200

With reference to FIGS. 82-85, device 1200 of the disclosure is an implant that can be used for multiple purposes, including in the repair of bone defects. Device 1200 is configured for insertion into bone (e.g., into bone hole 875 that is predrilled in the bone prior to insertion of device 1200). Once inserted, device 1200 can be used to uniformly deliver a biomaterial to the bone, secure the bone structure, and promote bone repair and/or healing.

Device 1200 has a unitary body including a proximal end and a distal end, in which: a) the unitary body includes an expandable and/or compressible body configured to radially expand or compress, in which unitary body includes a rolled surface having internal channel 1290 extending longitudinally from proximal end to distal end; b) the unitary body includes plurality of openings 1240; c) internal channel 1290 includes internal protrusion 1231 and/or internal thread; d) the proximal end includes opening 1203 to internal channel 1290; and e) the distal end includes an opening 1255 to internal channel 1290.

In some embodiments, device 1200 includes a thread or threads, such as internal and/or external threads. In some embodiments, device 1200 includes at least one protrusion, such as internal protrusion 1231 or an external protrusion.

Proximal Region of Device 1200

In some embodiments, device 1200 includes proximal region 1201 that has a proximal end, a distal end, and proximal opening 1203 to internal channel 1290 disposed at proximal region 1201 (see, e.g., FIG. 82-83).

In some embodiments, proximal region 1201 has an uncompressed (expanded) or compressed (unexpanded) outer diameter of from about 4 mm to about 25 mm (e.g., from about 4 mm to about 8 mm, from about 4 mm to about 10 mm, from about 4 mm to about 15 mm, from about 5 mm to about 10 mm, from about 10 mm to about 15 mm, from about 10 mm to about 20 mm, from about 15 mm to about 25 mm, from about 20 mm to about 25 mm, about 4 mm, about 5 mm, about 6 mm, about 7 mm, about 8 mm, about 9 mm, about 10 mm, about 11 mm, about 12 mm, about 13 mm, about 14 mm, about 15 mm, about 16 mm, about 17 mm, about 18 mm, about 19 mm, about 20 mm, about 21 mm, about 22 mm, about 23 mm, about 24 mm, or about 25 mm). In certain embodiments, the outer diameter of proximal region 1201 is smaller than, larger than, or equal to the outer diameter of central region 1226.

In some embodiments, proximal region 1201 has an uncompressed (expanded) or compressed (unexpanded) inner diameter of from about 1 mm to about 20 mm (e.g., from about 1 mm to about 2 mm, from about 1 mm to about 3 mm, from about 1 mm to about 4 mm, from about 1 mm to about 5 mm, from about 1 mm to about 10 mm, from about 5 mm to about 10 mm, from about 5 mm to about 15 mm, from about 10 mm to about 15 mm, from about 15 mm to about 20 mm, from about 15 mm to about 20 mm, about 1 mm, about 2 mm, about 3 mm, about 4 mm, about 5 mm, about 6 mm, about 7 mm, about 8 mm, about 9 mm, about 10 mm, about 11 mm, about 12 mm, about 13 mm, about 14 mm, about 15 mm, about 16 mm, about 17 mm, about 18 mm, about 19 mm, or about 20 mm). In certain embodiments, the inner diameter of proximal region 1201 is smaller than, larger than, or equal to the inner diameter of central region 1226.

In some embodiments, proximal region 1201 has a length of from about 0.1 mm to about 30 mm (e.g., from about 0.1 mm to about 1 mm, from about 0.1 mm to about 5 mm, from about 0.1 mm to about 10 mm, from about 5 mm to about 10 mm, from about 5 mm to about 15 mm, from about 5 mm to about 20 mm, from about 10 mm to about 20 mm, from about 10 mm to about 30 mm, from about 15 mm to about 25 mm, from about 20 mm to about 30 mm, about 2 mm, about 3 mm, about 4 mm, about 5 mm, about 6 mm, about 7 mm, about 8 mm, about 9 mm, about 10 mm, about 11 mm, about 12 mm, about 13 mm, about 14 mm, about 15 mm, about 16 mm, about 17 mm, about 18 mm, about 19 mm, about 20 mm, about 21 mm, about 22 mm, about 23 mm, about 24 mm, about 25 mm, about 26 mm, about 27 mm, about 28 mm, about 29 mm, or about 30 mm).

In some embodiments, proximal region 1201 has a wall thickness of from about 0.15 mm to about 2.5 mm (e.g., from about 0.15 mm to about 0.5 mm, from about 0.15 mm to about 1 mm, from about 0.15 mm to about 1.5 mm, from about 0.5 mm to about 1 mm, from about 0.5 mm to about 1.5 mm, from about 1 mm, to about 2 mm, from about 1 mm to about 3 mm, from about 2 mm to about 3 mm, about 0.15 mm, about 0.2 mm, about 0.3 mm, about 0.4 mm, about 0.5 mm about 0.6 mm, about 0.7 mm, about 0.8 mm, about 0.9 mm, about 1 mm, about 1.1 mm, about 1.2 mm, about 1.3 mm, about 1.4 mm, about 1.5 mm, about 1.6 mm, about 1.7 mm, about 1.8 mm, about 1.9 mm, about 2 mm, about 2.1 mm, about 2.2 mm, about 2.3 mm, about 2.4 mm, or about 2.5). In certain embodiments, the wall thickness of proximal region 1201 is smaller than, larger than, or equal to the wall thickness of central region 1226.

In some embodiments, proximal region 1201 does not have openings other than opening 1203. In some embodiments, device 1200 does not have a proximal region 1201.

Central Region of Device 1200

Central region 1226 of device 1200 includes an expandable body 1230 containing a plurality of openings 1240, a proximal end, and a distal end. In some embodiments, openings 1240 may be slits or perforations. Expandable body 1230 is configured to expand to allow for uniform distribution and delivery of biomaterial 550 to the bone surrounding device 1200.

In some embodiments, central region 1226 has an uncompressed (expanded) or compressed (unexpanded) outer diameter of from about 1.25 mm to about 25 mm (e.g., from about 1.25 mm to about 2 mm, from about 1.25 mm to about 3 mm, from about 1 mm to about 2 mm, from about 1 mm to about 3 mm, from about 1 mm to about 4 mm, from about 1 mm to about 5 mm, from about 4 mm to about 8 mm, from about 4 mm to about 10 mm, from about 4 mm to about 15 mm, from about 5 mm to about 10 mm, from about 10 mm to about 15 mm, from about 10 mm to about 20 mm, from about 15 mm to about 25 mm, from about 20 mm to about 25 mm, about 1.25 mm to about 3 mm, about 1.5 mm, about 1.75 mm, about 2 mm, about 3 mm, about 4 mm, about 5 mm, about 6 mm, about 7 mm, about 8 mm, about 9 mm, about 10 mm, about 11 mm, about 12 mm, about 13 mm, about 14 mm, about 15 mm, about 16 mm, about 17 mm, about 18 mm, about 19 mm, about 20 mm, about 21 mm, about 22 mm, about 23 mm, about 24 mm, or about 25 mm). Central region 1226 includes an outer diameter that is smaller than, larger than, or equal to the outer diameter of the proximal and distal regions.

In some embodiments, central region 1226 has an uncompressed (expanded) or compressed (unexpanded) inner diameter of from about 1 mm to about 20 mm (e.g., from about 1 mm to about 2 mm, from about 1 mm to about 3 mm, from about 1 mm to about 4 mm, from about 1 mm to about 5 mm, from about 1 mm to about 10 mm, from about 5 mm to about 10 mm, from about 5 mm to about 15 mm, from about 10 mm to about 15 mm, from about 15 mm to about 20 mm, from about 15 mm to about 20 mm, about 1 mm, about 2 mm, about 3 mm, about 4 mm, about 5 mm, about 6 mm, about 7 mm, about 8 mm, about 9 mm, about 10 mm, about 11 mm, about 12 mm, about 13 mm, about 14 mm, about 15 mm, about 16 mm, about 17 mm, about 18 mm, about 19 mm, or about 20 mm). Central region 1226 includes an inner diameter that is smaller than, larger than, or equal to the inner diameter of the proximal and distal regions.

In some embodiments, central region 1226 has a length of from about 5 mm to about 110 mm (e.g., from about 10 mm to about 110 mm, from about 20 mm to about 110 mm, from about 25 mm to about 110 mm, from about 30 mm to about 110 mm, from about 35 mm to about 110 mm, from about 40 mm to about 110 m, from about 45 mm to about 110 mm, from about 50 mm to about 110 mm, from about 55 mm to about 110 mm, from about 60 mm to about 110 mm, from about 65 mm to about 110 mm, from about 70 mm to about 110 mm, from about 75 mm to about 110 mm, from about 80 mm to about 110 mm, from about 85 mm to about 110 mm, from about 90 mm to about 110 mm, from about 95 mm to about 110 mm, from about 100 mm to about 110 mm, from about 105 mm to about 110 mm, about 9 mm, about 10 mm, about 11 mm, about 12 mm, about 13 mm, about 14 mm, about 15 mm, about 16 mm, about 17 mm, about 18 mm, about 19 mm, about 20 mm, about 21 mm, about 22 mm, about 23 mm, about 24 mm, about 25 mm, about 26 mm, about 27 mm, about 28 mm, about 29 mm, about 30 mm, about 31 mm, about 32 mm, about 33 mm, about 34 mm, about 35 mm, about 36 mm, about 37 mm, about 38 mm, about 39 mm, about 40 mm, about 41 mm, about 42 mm, about 43 mm, about 44 mm, about 45 mm, about 46 mm, about 47 mm, about 48 mm, about 49 mm, about 50 mm, about 51 mm, about 52 mm, about 53 mm, about 54 mm, about 55 mm, about 56 mm, about 57 mm, about 58 mm, about 59 mm, about 60 mm, about 61 mm, about 62 mm, about 63 mm, about 64 mm, about 65 mm, about 66 mm, about 67 mm, about 68 mm, about 69 mm, about 70 mm, about 71 mm, about 72 mm, about 73 mm, about 74 mm, about 75 mm, about 76 mm, about 77 mm, about 78 mm, about 79 mm, about 80 mm, about 81 mm, about 82 mm, about 83 mm, about 84 mm, about 85 mm, about 86 mm, about 87 mm, about 88 mm, about 89 mm, about 90 mm, about 91 mm, about 92 mm, about 93 mm, about 94 mm, about 95 mm, about 96 mm, about 97 mm, about 98 mm, about 99 mm, about 100 mm, about 101 mm, about 102 mm, about 103 mm, about 104 mm, about 105 mm, about 106 mm, about 107 mm, about 108 mm, about 109 mm, or about 110 mm).

In some embodiments, central region 1226 has a wall thickness of from about 0.15 mm to about 3 mm (e.g., from about 0.15 mm to about 0.5 mm, from about 0.15 mm to about 1 mm, from about 0.15 mm to about 1.5 mm, from about 0.5 mm to about 1 mm, from about 0.5 mm to about 1.5 mm, from about 1 mm, to about 2 mm, from about 1 mm to about 3 mm, from about 2 mm to about 3 mm, about 0.15 mm, about 0.2 mm, about 0.3 mm, about 0.4 mmm about 0.5 mm, about 0.6 mm, about 0.7 mm, about 0.8 mm, about 0.9 mm, about 1 mm, about 1.1 mm, about 1.2 mm, about 1.3 mm, about 1.4 mm, about 1.5 mm, about 1.6 mm, about 1.7 mm, about 1.8 mm, about 1.9 mm, about 2 mm, about 2.1 mm, about 2.2 mm, about 2.3 mm, about 2.4 mm, about 2.5 mm, about 2.6 mm, about 2.7 mm, about 2.8 mm, about 2.9 mm, or about 3 mm). In certain embodiments, the wall thickness of central region 1226 is smaller than, larger than, or equal to the wall thickness of the proximal and distal regions.

In some embodiments, central region 1226 of device 1200 is configured to expand thereby providing a volume for receiving biomaterial 550, which can be delivered through expandable body 1230 to the bone. In some embodiments, expandable body 1230 may expand to a volume of from about 1 ml to about 20 ml (e.g., from about 1 ml to about 2 ml, from about 1 ml to about 3 ml, from about 1 ml to about 4 ml, from about 1 ml to about 5 ml, from about 1 ml to about 10 ml, from about 5 ml to about 10 ml, from about 5 ml to about 15 ml, from about 10 ml to about 15 ml, from about 15 ml to about 20 ml, from about 15 ml to about 20 ml, about 1 ml, about 1.1 ml, about 1.2 ml, about 1.3 ml, about 1.4 ml, about 1.5 ml, about 1.6 ml, about 1.7 ml, about 1.8 ml, about 1.9 ml, about 2 ml, about 2.1 ml, about 2.2 ml, about 2.3 ml, about 2.4 ml, about 2.5 ml, about 2.6 ml, about 2.7 ml, about 2.8 ml, about 2.9 ml, about 3 ml, about 3.1 ml, about 3.2 ml, about 3.3 ml, about 3.4 ml, about 3.5 ml, about 3.6 ml, about 3.7 ml, about 3.8 ml, about 3.9 ml, about 4 ml, about 4.1 ml, about 4.2 ml, about 4.3 ml, about 4.4 ml, about 4.5 ml, about 4.6 ml, about 4.7 ml, about 4.8 ml, about 4.9 ml, about 5 ml, about 5.1 ml, about 5.2 ml, about 5.3 ml, about 5.4 ml, about 5.5 ml, about 5.6 ml, about 5.7 ml, about 5.8 ml, about 5.9 ml, about 6 ml, about 6.1 ml, about 6.2 ml, about 6.3 ml, about 6.4 ml, about 6.5 ml, about 6.6 ml, about 6.7 ml, about 6.8 ml, about 6.9 ml, about 7 ml, about 7.1 ml, about 7.2 ml, about 7.3 ml, about 7.4 ml, about 7.5 ml, about 7.6 ml, about 7.7 ml, about 7.8 ml, about 7.9 ml, about 8 ml, about 8.1 ml, about 8.2 ml, about 8.3 ml, about 8.4 ml, about 8.5 ml, about 8.6 ml, about 8.7 ml, about 8.8 ml, about 8.9 ml, about 9 ml, about 9.1 ml, about 9.2 ml, about 9.3 ml, about 9.4 ml, about 9.5 ml, about 9.6 ml, about 9.7 ml, about 9.8 ml, about 9.9 ml, about 10 ml, about 11 ml, about 11.1 ml, about 11.2 ml, about 11.3 ml, about 11.4 ml, about 11.5 ml, about 11.6 ml, about 11.7 ml, about 11.8 ml, about 11.9 ml, about 12 ml, about 12.1 ml, about 12.2 ml, about 12.3 ml, about 12.4 ml, about 12.5 ml, about 12.6 ml, about 12.7 ml, about 12.8 ml, about 12.9 ml, about 13 ml, about 13.1 ml, about 13.2 ml, about 13.3 ml, about 13.4 ml, about 13.5 ml, about 13.6 ml, about 13.7 ml, about 13.8 ml, about 13.9 ml, about 14 ml, about 14.1 ml, about 14.2 ml, about 14.3 ml, about 14.4 ml, about 14.5 ml, about 14.6 ml, about 14.7 ml, about 14.8 ml, about 14.9 ml, about 15 ml, about 15.1 ml, about 15.2 ml, about 15.3 ml, about 15.4 ml, about 15.5 ml, about 15.6 ml, about 15.7 ml, about 15.8 ml, about 15.9 ml, about 16 ml, about 16.1 ml, about 16.2 ml, about 16.3 ml, about 16.4 ml, about 16.5 ml, about 16.6 ml, about 16.7 ml, about 16.8 ml, about 16.9 ml, about 17 ml, about 17.1 ml, about 17.2 ml, about 17.3 ml, about 17.4 ml, about 17.5 ml, about 17.6 ml, about 17.7 ml, about 17.8 ml, about 17.9 ml, about 18 ml, about 18.1 ml, about 18.2 ml, about 18.3 ml, about 18.4 ml, about 18.5 ml, about 18.6 ml, about 18.7 ml, about 18.8 ml, about 18.9 ml, about 19 ml, about 19.1 ml, about 19.2 ml, about 19.3 ml, about 19.4 ml, about 19.5 ml, about 19.6 ml, about 19.7 ml, about 19.8 ml, about 19.9 ml, or about 20 ml).

Distal Region of Device 1200

In some embodiments, device 1200 includes distal region 1251 that includes a proximal end, a distal end, and a distal opening 1255 to the channel disposed at the distal end (see, e.g., FIG. 82).

In some embodiments, distal region 1251 has an uncompressed (expanded) or compressed (unexpanded) outer diameter of from about 4 mm to about 25 mm (e.g., about 4 mm to about 5 mm, about 5 mm to about 15 mm, about 10 mm to about 25 mm, about 4 mm, about 5 mm, about 6 mm, about 7 mm, about 8 mm, about 9 mm, about 10 mm, about 11 mm, about 12 mm, about 13 mm, about 14 mm, about 15 mm, about 16 mm, about 17 mm, about 18 mm, about 19 mm, about 20 mm, about 21 mm, about 22 mm, about 23 mm, about 24 mm, or about 25 mm, about 4 mm, about 5 mm, about 6 mm, about 7 mm, about 8 mm, about 9 mm, about 10 mm, about 11 mm, about 12 mm, about 13 mm, about 14 mm, about 15 mm, about 16 mm, about 17 mm, about 18 mm, about 19 mm, about 20 mm, about 21 mm, about 22 mm, about 23 mm, about 24 mm, or about 25 mm). In certain embodiments, the outer diameter of distal region 1251 is smaller than, larger than, or equal to the outer diameter of central region 1226.

In some embodiments, distal region 1251 has an uncompressed (expanded) or compressed (unexpanded) inner diameter of from about 1 mm to about 20 mm (e.g., from about 1 mm to about 2 mm, from about 1 mm to about 3 mm, from about 1 mm to about 4 mm, from about 1 mm to about 5 mm, from about 2 mm to about 5 mm, from about 4 mm to about 8 mm, from about 5 mm to about 10 mm, from about 8 mm to about 12 mm, from about 10 mm to about 15 mm, from about 10 mm to about 20 mm, from about 15 mm to about 20 mm, about 1 mm, about 2 mm, about 3 mm, about 4 mm, about 5 mm, about 6 mm, about 7 mm, about 8 mm, about 9 mm, about 10 mm, about 11 mm, about 12 mm, about 13 mm, about 14 mm, about 15 mm, about 16 mm, about 17 mm, about 18 mm, about 19 mm, or about 20 mm). In certain embodiments, the inner diameter of distal region 1251 is smaller than, larger than, or equal to the inner diameter of central region 1226.

In some embodiments, distal region 1251 has a length of from about 1 mm to about 30 mm (e.g., from about 0.1 mm to about 1 mm, from about 0.1 mm to about 5 mm, from about 0.1 mm to about 10 mm, from about 5 mm to about 10 mm, from about 5 mm to about 15 mm, from about 5 mm to about 20 mm, from about 10 mm to about 20 mm, from about 10 mm to about 30 mm, from about 15 mm to about 25 mm, from about 20 mm to about 30 mm, about 1 mm, about 2 mm, about 3 mm, about 4 mm, about 5 mm, about 6 mm, about 7 mm, about 8 mm, about 9 mm, about 10 mm, about 11 mm, about 12 mm, about 13 mm, about 14 mm, about 15 mm, about 16 mm, about 17 mm, about 18 mm, about 19 mm, about 20 mm, about 21 mm, about 22 mm, about 23 mm, about 24 mm, about 25 mm, about 26 mm, about 27 mm, about 28 mm, about 29 mm, or about 30 mm).

In some embodiments, distal region 1251 has a wall thickness of from about 0.15 mm to about 3 mm (e.g., from about 0.15 mm to about 0.5 mm, from about 0.15 mm to about 1 mm, from about 0.15 mm to about 1.5 mm, from about 0.5 mm to about 1 mm, from about 0.5 mm to about 1.5 mm, from about 1 mm, to about 2 mm, from about 1 mm to about 3 mm, from about 2 mm to about 3 mm, about 0.15 mm, about 0.2 mm, about 0.3 mm, about 0.4 mmm about 0.5 mm, about 0.6 mm, about 0.7 mm, about 0.8 mm, about 0.9 mm, about 1 mm, about 1.1 mm, about 1.2 mm, about 1.3 mm, about 1.4 mm, about 1.5 mm, about 1.6 mm, about 1.7 mm, about 1.8 mm, about 1.9 mm, about 2 mm, about 2.1 mm, about 2.2 mm, about 2.3 mm, about 2.4 mm, about 2.5 mm, about 2.6 mm, about 2.7 mm, about 2.8 mm, about 2.9 mm, or about 3 mm). In certain embodiments, the wall thickness of distal region 1251 is smaller than, larger than, or equal to the wall thickness of central region 1226.

In some embodiments. The distal end of distal region 1251 may have a blunt edge. The distal end of distal region 1251 may have a tapered edge.

In some embodiments, distal region 1251 does not have openings other than opening 1255. In some embodiments, device 1200 does not have a distal region 1251.

Device 1300

With reference to FIGS. 86-90, device 1300 of the disclosure is an implant that can be used for multiple purposes, including in the repair of bone defects. Device 1300 is configured for insertion into bone (e.g., into bone hole 875 that is predrilled in the bone prior to insertion of device 1300). Once inserted, device 1300 can be used to uniformly deliver a biomaterial to the bone, secure the bone structure, and promote bone repair and/or healing.

Device 1300 has a unitary body including from a proximal end to a distal end: proximal region 1301, central region 1326, and distal region 1351, in which central region 1326 joins proximal region 1301 to distal region 1351, and in which: a) the device includes internal channel 1390 (FIG. 89) extending longitudinally through proximal region 1301, central region 1326, and distal region 1351; b) proximal region 1301 includes a compressible body and opening 1303 to internal channel 1390; c) central region 1326 includes i)

plurality of openings 1340 and ii) an expandable and/or compressible body configured to radially expand or compress, in which the expandable and/or compressible body includes plurality of longitudinal segments 1391 connected by a plurality of expandable arms 1392; and d) distal region 1351 includes opening 1355 to internal channel 1390.

In some embodiments, device 1300 includes a thread or threads, such as internal and/or external threads. In some embodiments, device 1300 includes at least one protrusion, such as internal protrusion 1331 or external protrusion 1332.

Proximal Region of Device 1300

Device 1300 includes proximal region 1301 that has a proximal end, a distal end, and proximal opening 1303 to internal channel 1390 disposed at proximal region 1301 (see, e.g., FIG. 86-88).

In some embodiments, proximal region 1301 has an uncompressed (expanded) or compressed (unexpanded) outer diameter of from about 4 mm to about 25 mm (e.g., from about 4 mm to about 8 mm, from about 4 mm to about 10 mm, from about 4 mm to about 15 mm, from about 5 mm to about 10 mm, from about 10 mm to about 15 mm, from about 10 mm to about 20 mm, from about 15 mm to about 25 mm, from about 20 mm to about 25 mm, about 4 mm, about 5 mm, about 6 mm, about 7 mm, about 8 mm, about 9 mm, about 10 mm, about 11 mm, about 12 mm, about 13 mm, about 14 mm, about 15 mm, about 16 mm, about 17 mm, about 18 mm, about 19 mm, about 20 mm, about 21 mm, about 22 mm, about 23 mm, about 24 mm, or about 25 mm). In certain embodiments, the outer diameter of proximal region 1301 is smaller than, larger than, or equal to the outer diameter of central region 1326.

In some embodiments, proximal region 1301 has an uncompressed (expanded) or compressed (unexpanded) inner diameter of from about 1 mm to about 20 mm (e.g., from about 1 mm to about 2 mm, from about 1 mm to about 3 mm, from about 1 mm to about 4 mm, from about 1 mm to about 5 mm, from about 1 mm to about 10 mm, from about 5 mm to about 10 mm, from about 5 mm to about 15 mm, from about 10 mm to about 15 mm, from about 15 mm to about 20 mm, from about 15 mm to about 20 mm, about 1 mm, about 2 mm, about 3 mm, about 4 mm, about 5 mm, about 6 mm, about 7 mm, about 8 mm, about 9 mm, about 10 mm, about 11 mm, about 12 mm, about 13 mm, about 14 mm, about 15 mm, about 16 mm, about 17 mm, about 18 mm, about 19 mm, or about 20 mm, about 3 mm, about 4 mm, about 5 mm, about 6 mm, about 7 mm, about 8 mm, about 9 mm, about 10 mm, about 11 mm, about 12 mm, about 13 mm, about 14 mm, about 15 mm, about 16 mm, about 17 mm, about 18 mm, about 19 mm, or about 20 mm). In certain embodiments, the inner diameter of proximal region 1301 is smaller than, larger than, or equal to the inner diameter of central region 1326.

In some embodiments, proximal region 1301 has a length of from about 0.1 mm to about 30 mm (e.g., from about 0.1 mm to about 1 mm, from about 0.1 mm to about 5 mm, from about 0.1 mm to about 10 mm, from about 5 mm to about 10 mm, from about 5 mm to about 15 mm, from about 5 mm to about 20 mm, from about 10 mm to about 20 mm, from about 10 mm to about 30 mm, from about 15 mm to about 25 mm, from about 20 mm to about 30 mm, about 2 mm, about 3 mm, about 4 mm, about 5 mm, about 6 mm, about 7 mm, about 8 mm, about 9 mm, about 10 mm, about 11 mm, about 12 mm, about 13 mm, about 14 mm, about 15 mm, about 16 mm, about 17 mm, about 18 mm, about 19 mm, about 20 mm, about 21 mm, about 22 mm, about 23 mm, about 24 mm, about 25 mm, about 26 mm, about 27 mm, about 28 mm, about 29 mm, or about 30 mm).

In some embodiments, proximal region 1301 has a wall thickness of from about 0.15 mm to about 2.5 mm (e.g., from about 0.15 mm to about 0.5 mm, from about 0.15 mm to about 1 mm, from about 0.15 mm to about 1.5 mm, from about 0.5 mm to about 1 mm, from about 0.5 mm to about 1.5 mm, from about 1 mm, to about 2 mm, from about 1 mm to about 3 mm, from about 2 mm to about 3 mm, about 0.15 mm, about 0.2 mm, about 0.3 mm, about 0.4 mm, about 0.5 mm about 0.6 mm, about 0.7 mm, about 0.8 mm, about 0.9 mm, about 1 mm, about 1.1 mm, about 1.2 mm, about 1.3 mm, about 1.4 mm, about 1.5 mm, about 1.6 mm, about 1.7 mm, about 1.8 mm, about 1.9 mm, about 2 mm, about 2.1 mm, about 2.2 mm, about 2.3 mm, about 2.4 mm, or about 2.5). In certain embodiments, the wall thickness of proximal region 1301 is smaller than, larger than, or equal to the wall thickness of central region 1326.

In some embodiments, proximal region 1301 includes from 3 to 20 (e.g., from 3 to 15, from 4 to 10, from 5 to 8, 3, 4, 5, 6, 7, 8, 9, 10, 11, 12, 13, 14, 15, 16, 17, 18, 19, or 20) wings 1305 that radially extend around the outer surface of proximal region 1301.

Central Region of Device 1300

Central region 1326 of device 1300 includes i) an expandable and/or compressible body 1330 including a plurality of segments 1391 separated by a plurality of expandable arms 1392 and openings 1340, ii) a proximal end, and iii) a distal end. Openings 1340 may be slits or perforations. Expandable and/or compressible body 1330 is configured to expand and/or compress to allow for uniform distribution and delivery of biomaterial 550 to the bone surrounding device 1300.

In some embodiments, central region 1326 has an uncompressed (expanded) or compressed (unexpanded) outer diameter of from about 1.25 mm to about 25 mm (e.g., from about 1.25 mm to about 2 mm, from about 1.25 mm to about 3 mm, from about 1 mm to about 2 mm, from about 1 mm to about 3 mm, from about 1 mm to about 4 mm, from about 1 mm to about 5 mm, from about 4 mm to about 8 mm, from about 4 mm to about 10 mm, from about 4 mm to about 15 mm, from about 5 mm to about 10 mm, from about 10 mm to about 15 mm, from about 10 mm to about 20 mm, from about 15 mm to about 25 mm, from about 20 mm to about 25 mm, about 1.5 mm, about 1.75 mm, about 2 mm, about 3 mm, about 4 mm, about 5 mm, about 6 mm, about 7 mm, about 8 mm, about 9 mm, about 10 mm, about 11 mm, about 12 mm, about 13 mm, about 14 mm, about 15 mm, about 16 mm, about 17 mm, about 18 mm, about 19 mm, about 20 mm, about 21 mm, about 22 mm, about 23 mm, about 24 mm, or about 25 mm). Central region 1326 includes an outer diameter that is smaller than, larger than, or equal to the outer diameter of the proximal and distal regions.

In some embodiments, central region 1326 has an uncompressed (expanded) or compressed (unexpanded) inner diameter of from about 1 mm to about 20 mm (e.g., from about 1 mm to about 2 mm, from about 1 mm to about 3 mm, from about 1 mm to about 4 mm, from about 1 mm to about 5 mm, from about 1 mm to about 10 mm, from about 5 mm to about 10 mm, from about 5 mm to about 15 mm, from about 10 mm to about 15 mm, from about 15 mm to about 20 mm, from about 15 mm to about 20 mm, about 1 mm, about 2 mm, about 3 mm, about 4 mm, about 5 mm, about 6 mm, about 7 mm, about 8 mm, about 9 mm, about 10 mm, about 11 mm, about 12 mm, about 13 mm, about 14 mm, about 15 mm, about 16 mm, about 17 mm, about 18 mm, about 19 mm, or about 20 mm). Central region 1326 includes an inner diameter that is smaller than, larger than, or equal to the inner diameter of the proximal and distal regions.

In some embodiments, central region 1326 has a length of from about 5 mm to about 110 mm (e.g., from about 10 mm to about 110 mm, from about 20 mm to about 110 mm, from about 25 mm to about 110 mm, from about 30 mm to about 110 mm, from about 35 mm to about 110 mm, from about 40 mm to about 110 m, from about 45 mm to about 110 mm, from about 50 mm to about 110 mm, from about 55 mm to about 110 mm, from about 60 mm to about 110 mm, from about 65 mm to about 110 mm, from about 70 mm to about 110 mm, from about 75 mm to about 110 mm, from about 80 mm to about 110 mm, from about 85 mm to about 110 mm, from about 90 mm to about 110 mm, from about 95 mm to about 110 mm, from about 100 mm to about 110 mm, from about 105 mm to about 110 mm, about 9 mm, about 10 mm, about 11 mm, about 12 mm, about 13 mm, about 14 mm, about 15 mm, about 16 mm, about 17 mm, about 18 mm, about 19 mm, about 20 mm, about 21 mm, about 22 mm, about 23 mm, about 24 mm, about 25 mm, about 26 mm, about 27 mm, about 28 mm, about 29 mm, about 30 mm, about 31 mm, about 32 mm, about 33 mm, about 34 mm, about 35 mm, about 36 mm, about 37 mm, about 38 mm, about 39 mm, about 40 mm, about 41 mm, about 42 mm, about 43 mm, about 44 mm, about 45 mm, about 46 mm, about 47 mm, about 48 mm, about 49 mm, about 50 mm, about 51 mm, about 52 mm, about 53 mm, about 54 mm, about 55 mm, about 56 mm, about 57 mm, about 58 mm, about 59 mm, about 60 mm, about 61 mm, about 62 mm, about 63 mm, about 64 mm, about 65 mm, about 66 mm, about 67 mm, about 68 mm, about 69 mm, about 70 mm, about 71 mm, about 72 mm, about 73 mm, about 74 mm, about 75 mm, about 76 mm, about 77 mm, about 78 mm, about 79 mm, about 80 mm, about 81 mm, about 82 mm, about 83 mm, about 84 mm, about 85 mm, about 86 mm, about 87 mm, about 88 mm, about 89 mm, about 90 mm, about 91 mm, about 92 mm, about 93 mm, about 94 mm, about 95 mm, about 96 mm, about 97 mm, about 98 mm, about 99 mm, about 100 mm, about 101 mm, about 102 mm, about 103 mm, about 104 mm, about 105 mm, about 106 mm, about 107 mm, about 108 mm, about 109 mm, or about 110 mm).

In some embodiments, central region 1326 has a wall thickness of from about 0.15 mm to about 3 mm (e.g., from about 0.15 mm to about 0.5 mm, from about 0.15 mm to about 1 mm, from about 0.15 mm to about 1.5 mm, from about 0.5 mm to about 1 mm, from about 0.5 mm to about 1.5 mm, from about 1 mm, to about 2 mm, from about 1 mm to about 3 mm, from about 2 mm to about 3 mm, about 0.15 mm, about 0.2 mm, about 0.3 mm, about 0.4 mmm about 0.5 mm, about 0.6 mm, about 0.7 mm, about 0.8 mm, about 0.9 mm, about 1 mm, about 1.1 mm, about 1.2 mm, about 1.3 mm, about 1.4 mm, about 1.5 mm, about 1.6 mm, about 1.7 mm, about 1.8 mm, about 1.9 mm, about 2 mm, about 2.1 mm, about 2.2 mm, about 2.3 mm, about 2.4 mm, about 2.5 mm, about 2.6 mm, about 2.7 mm, about 2.8 mm, about 2.9 mm, or about 3 mm). In certain embodiments, the wall thickness of central region 1326 is smaller than, larger than, or equal to the wall thickness of the proximal and distal regions.

Central region 1326 includes expandable and/or compressible body 1330 characterized by a plurality of segments 1391 separated by a plurality of expandable arms 1392 and plurality of openings 1340 (e.g., slits or perforations).

In some embodiments, central region 1326 has from 2 to 20 (e.g., from 2 to 4, from 2 to 6, from 2 to 8, from 2 to 10, from 4 to 8, from 4 to 10, from 4 to 12, from 10 to 16, from 10 to 20, 2, 3, 4, 5, 6, 7, 8, 9, 10, 11, 12, 13, 14, 15, 16, 17, 18, 19, or 20) segments 1391 (see, e.g., FIGS. 86-88).

In some embodiments, central region 1326 has from 2 to 100 (e.g., 2 to 10, 2 to 20, 10 to 20, 10 to 30, 10 to 50, 20 to 40, 20 to 60, 40 to 80, 50 to 100, 60 to 80, 80 to 100, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100) expandable arms 1392 (see, e.g., FIGS. 86-88).

In some embodiments, central region 1326 has from 2 to 70 (e.g., 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, or 70) external protrusions 1332 (see, e.g., FIGS. 88-89).

In some embodiments, central region 1326 of device 1300 is configured to expand thereby providing a volume for receiving biomaterial 550, which can be delivered through expandable and/or compressible body 1330 to the bone. In some embodiments, expandable and/or compressible body 1330 may expand to a volume of from about 1 ml to about 20 ml (e.g., from about 1 ml to about 2 ml, from about 1 ml to about 3 ml, from about 1 ml to about 4 ml, from about 1 ml to about 5 ml, from about 1 ml to about 10 ml, from about 5 ml to about 10 ml, from about 5 ml to about 15 ml, from about 10 ml to about 15 ml, from about 15 ml to about 20 ml, from about 15 ml to about 20 ml, about 1 ml, about 1.1 ml, about 1.2 ml, about 1.3 ml, about 1.4 ml, about 1.5 ml, about 1.6 ml, about 1.7 ml, about 1.8 ml, about 1.9 ml, about 2 ml, about 2.1 ml, about 2.2 ml, about 2.3 ml, about 2.4 ml, about 2.5 ml, about 2.6 ml, about 2.7 ml, about 2.8 ml, about 2.9 ml, about 3 ml, about 3.1 ml, about 3.2 ml, about 3.3 ml, about 3.4 ml, about 3.5 ml, about 3.6 ml, about 3.7 ml, about 3.8 ml, about 3.9 ml, about 4 ml, about 4.1 ml, about 4.2 ml, about 4.3 ml, about 4.4 ml, about 4.5 ml, about 4.6 ml, about 4.7 ml, about 4.8 ml, about 4.9 ml, about 5 ml, about 5.1 ml, about 5.2 ml, about 5.3 ml, about 5.4 ml, about 5.5 ml, about 5.6 ml, about 5.7 ml, about 5.8 ml, about 5.9 ml, about 6 ml, about 6.1 ml, about 6.2 ml, about 6.3 ml, about 6.4 ml, about 6.5 ml, about 6.6 ml, about 6.7 ml, about 6.8 ml, about 6.9 ml, about 7 ml, about 7.1 ml, about 7.2 ml, about 7.3 ml, about 7.4 ml, about 7.5 ml, about 7.6 ml, about 7.7 ml, about 7.8 ml, about 7.9 ml, about 8 ml, about 8.1 ml, about 8.2 ml, about 8.3 ml, about 8.4 ml, about 8.5 ml, about 8.6 ml, about 8.7 ml, about 8.8 ml, about 8.9 ml, about 9 ml, about 9.1 ml, about 9.2 ml, about 9.3 ml, about 9.4 ml, about 9.5 ml, about 9.6 ml, about 9.7 ml, about 9.8 ml, about 9.9 ml, about 10 ml, about 11 ml, about 11.1 ml, about 11.2 ml, about 11.3 ml, about 11.4 ml, about 11.5 ml, about 11.6 ml, about 11.7 ml, about 11.8 ml, about 11.9 ml, about 12 ml, about 12.1 ml, about 12.2 ml, about 12.3 ml, about 12.4 ml, about 12.5 ml, about 12.6 ml, about 12.7 ml, about 12.8 ml, about 12.9 ml, about 13 ml, about 13.1 ml, about 13.2 ml, about 13.3 ml, about 13.4 ml, about 13.5 ml, about 13.6 ml, about 13.7 ml, about 13.8 ml, about 13.9 ml, about 14 ml, about 14.1 ml, about 14.2 ml, about 14.3 ml, about 14.4 ml, about 14.5 ml, about 14.6 ml, about 14.7 ml, about 14.8 ml, about 14.9 ml, about 15 ml, about 15.1 ml, about 15.2 ml, about 15.3 ml, about 15.4 ml, about 15.5 ml, about 15.6 ml, about 15.7 ml, about 15.8 ml, about 15.9 ml, about 16 ml, about 16.1 ml, about 16.2 ml, about 16.3 ml, about 16.4 ml, about 16.5 ml, about 16.6 ml, about 16.7 ml, about 16.8 ml, about 16.9 ml, about 17 ml, about 17.1 ml, about 17.2 ml, about 17.3 ml, about 17.4 ml, about 17.5 ml, about 17.6 ml, about 17.7 ml, about 17.8 ml, about 17.9 ml, about 18 ml, about 18.1 ml, about 18.2 ml, about 18.3 ml, about 18.4 ml, about 18.5 ml, about 18.6 ml, about 18.7 ml, about 18.8 ml, about 18.9 ml, about 19 ml, about 19.1 ml, about 19.2 ml, about 19.3 ml, about 19.4 ml, about 19.5 ml, about 19.6 ml, about 19.7 ml, about 19.8 ml, about 19.9 ml, or about 20 ml).

Distal Region of Device 1300

Device 1300 includes distal region 1351 that includes a proximal end, a distal end, and a distal opening 1355 to the channel disposed at the distal end (see, e.g., FIG. 86).

In some embodiments, distal region 1351 has an uncompressed (expanded) or compressed (unexpanded) outer diameter of from about 4 mm to about 25 mm (e.g., about 4 mm to about 5 mm, about 5 mm to about 15 mm, about 10 mm to about 25 mm, about 4 mm, about 5 mm, about 6 mm, about 7 mm, about 8 mm, about 9 mm, about 10 mm, about 11 mm, about 12 mm, about 13 mm, about 14 mm, about 15 mm, about 16 mm, about 17 mm, about 18 mm, about 19 mm, about 20 mm, about 21 mm, about 22 mm, about 23 mm, about 24 mm, or about 25 mm, about 4 mm, about 5 mm, about 6 mm, about 7 mm, about 8 mm, about 9 mm, about 10 mm, about 11 mm, about 12 mm, about 13 mm, about 14 mm, about 15 mm, about 16 mm, about 17 mm, about 18 mm, about 19 mm, about 20 mm, about 21 mm, about 22 mm, about 23 mm, about 24 mm, or about 25 mm). In certain embodiments, the outer diameter of distal region 1351 is smaller than, larger than, or equal to the outer diameter of central region 1326.

In some embodiments, distal region 1351 has an uncompressed (expanded) or compressed (unexpanded) inner diameter of from about 1 mm to about 20 mm (e.g., from about 1 mm to about 2 mm, from about 1 mm to about 3 mm, from about 1 mm to about 4 mm, from about 1 mm to about 5 mm, from about 2 mm to about 5 mm, from about 4 mm to about 8 mm, from about 5 mm to about 10 mm, from about 8 mm to about 12 mm, from about 10 mm to about 15 mm, from about 10 mm to about 20 mm, from about 15 mm to about 20 mm, about 1 mm, about 2 mm, about 3 mm, about 4 mm, about 5 mm, about 6 mm, about 7 mm, about 8 mm, about 9 mm, about 10 mm, about 11 mm, about 12 mm, about 13 mm, about 14 mm, about 15 mm, about 16 mm, about 17 mm, about 18 mm, about 19 mm, or about 20 mm). In certain embodiments, the inner diameter of distal region 1351 is smaller than, larger than, or equal to the inner diameter of central region 1326.

In some embodiments, distal region 1351 has a length of from about 1 mm to about 30 mm (e.g., about 1 mm, about 2 mm, about 3 mm, about 4 mm, about 5 mm, about 6 mm, about 7 mm, about 8 mm, about 9 mm, about 10 mm, about 11 mm, about 12 mm, about 13 mm, about 14 mm, about 15 mm, about 16 mm, about 17 mm, about 18 mm, about 19 mm, about 20 mm, about 21 mm, about 22 mm, about 23 mm, about 24 mm, about 25 mm, about 26 mm, about 27 mm, about 28 mm, about 29 mm, or about 30 mm).

In some embodiments, distal region 1351 has a wall thickness of from about 0.15 mm to about 3 mm (e.g., from about 0.15 mm to about 0.5 mm, from about 0.15 mm to about 1 mm, from about 0.15 mm to about 1.5 mm, from about 0.5 mm to about 1 mm, from about 0.5 mm to about 1.5 mm, from about 1 mm, to about 2 mm, from about 1 mm to about 3 mm, from about 2 mm to about 3 mm, about 0.15 mm, about 0.2 mm, about 0.3 mm, about 0.4 mmm about 0.5 mm, about 0.6 mm, about 0.7 mm, about 0.8 mm, about 0.9 mm, about 1 mm, about 1.1 mm, about 1.2 mm, about 1.3 mm, about 1.4 mm, about 1.5 mm, about 1.6 mm, about 1.7 mm, about 1.8 mm, about 1.9 mm, about 2 mm, about 2.1 mm, about 2.2 mm, about 2.3 mm, about 2.4 mm, about 2.5 mm, about 2.6 mm, about 2.7 mm, about 2.8 mm, about 2.9 mm, or about 3 mm). In certain embodiments, the wall thickness of distal region 1351 is smaller than, larger than, or equal to the wall thickness of central region 1326.

In some embodiments, the distal end of distal region 1351 may have a blunt edge. The distal end of distal region 1351 may have a tapered edge.

System for Bone Repair

Figures 18A, 18B:
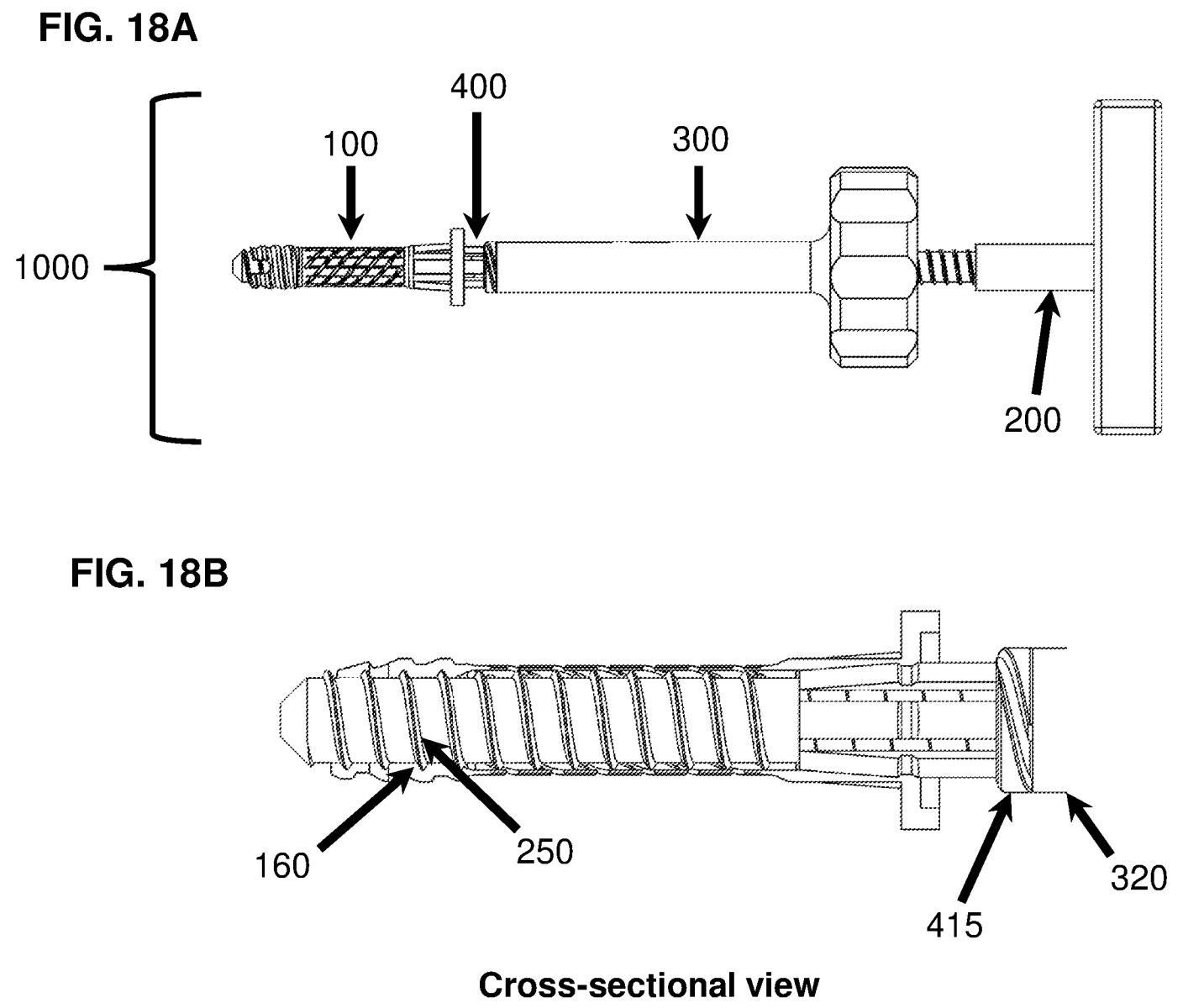

Also featured is system 1000 that includes a device as described herein and one or more of insertion tool 200, pusher 300, and connector 400 (see, e.g., FIGS. 18A and 59).

Insertion Tool

Figure 7:
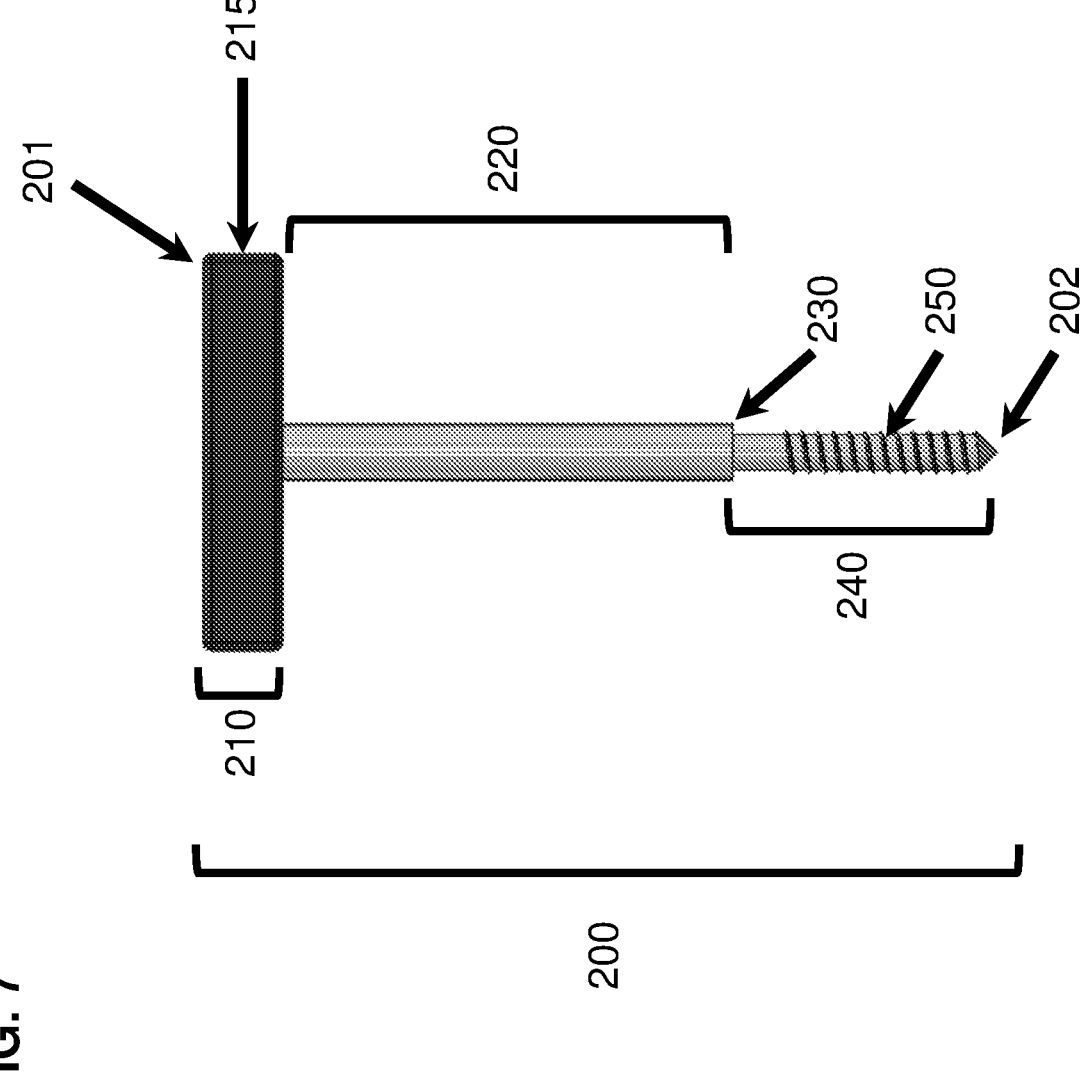
FIG. 7 is a schematic drawing showing an embodiment of insertion tool 200. Handle 215 is shown disposed at proximal region 210 of insertion tool 200. Central region 220 of insertion tool 200 connects proximal region 210 to distal region 240. Lip 230 is positioned in central region 220. External threads 250 in distal region 240 are also shown.

Insertion tool 200 has proximal region 210, distal region 240, and central region 220 that connects proximal region 210 to distal region 240 (see, e.g., FIG. 7). Proximal region 210 includes handle 215 (see, e.g., FIGS. 7, 55, 57, 58). In some embodiments, handle 215 is shaped to be grasped by a hand of a user (e.g., rectangular, circular, elliptical, polygonal, or T-shape). In some embodiments, handle 215 has a length of from about 10 mm to about 100 mm (e.g., about 10 mm, about 11 mm, about 12 mm, about 13 mm, about 14 mm, about 15 mm, about 16 mm, about 17 mm, about 18 mm, about 19 mm, about 20 mm, about 21 mm, about 22 mm, about 23 mm, about 24 mm, about 25 mm, about 26 mm, about 27 mm, about 28 mm, about 29 mm, about 30 mm, about 31 mm, about 32 mm, about 33 mm, about 34 mm, about 35 mm, about 36 mm, about 37 mm, about 38 mm, about 39 mm, about 40 mm, about 41 mm, about 42 mm, about 43 mm, about 44 mm, about 45 mm, about 46 mm, about 47 mm, about 48 mm, about 49 mm, about 50 mm, about 51 mm, about 52 mm, about 53 mm, about 54 mm, about 55 mm, about 56 mm, about 57 mm, about 58 mm, about 59 mm, about 60 mm, about 61 mm, about 62 mm, about 63 mm, about 64 mm, about 65 mm, about 66 mm, about 67 mm, about 68 mm, about 69 mm, about 70 mm, about 71 mm, about 72 mm, about 73 mm, about 74 mm, about 75 mm, about 76 mm, about 77 mm, about 78 mm, about 79 mm, about 80 mm, about 81 mm, about 82 mm, about 83 mm, about 84 mm, about 85 mm, about 86 mm, about 87 mm, about 88 mm, about 89 mm, about 90 mm, about 91 mm, about 92 mm, about 93 mm, about 94 mm, about 95 mm, about 96 mm, about 97 mm, about 98 mm, about 99 mm, or about 100 mm), a width of from about 5 mm to about 25 mm (e.g., about 5 mm, about 6 mm, about 7 mm, about 8 mm, about 9 mm, about 10 mm, about 11 mm, about 12 mm, about 13 mm, about 14 mm, about 15 mm, about 16 mm, about 17 mm, about 18 mm, about 19 mm, about 20 mm, about 21 mm, about 22 mm, about 23 mm, about 24 mm, or about 25 mm), and a height of from about 5 mm to about 25 mm (e.g., about 5 mm, about 6 mm, about 7 mm, about 8 mm, about 9 mm, about 10 mm, about 11 mm, about 12 mm, about 13 mm, about 14 mm, about 15 mm, about 16 mm, about 17 mm, about 18 mm, about 19 mm, about 20 mm, about 21 mm, about 22 mm, about 23 mm, about 24 mm, or about 25 mm). In some embodiments, handle 215 has a cylindrical shape and has a diameter of from about 5 mm to about 25 mm (e.g., about 5 mm, about 6 mm, about 7 mm, about 8 mm, about 9 mm, about 10 mm, about 11 mm, about 12 mm, about 13 mm, about 14 mm, about 15 mm, about 16 mm, about 17 mm, about 18 mm, about 19 mm, about 20 mm, about 21 mm, about 22 mm, about 23 mm, about 24 mm, or about 25 mm).

Figures 8A, 8B:
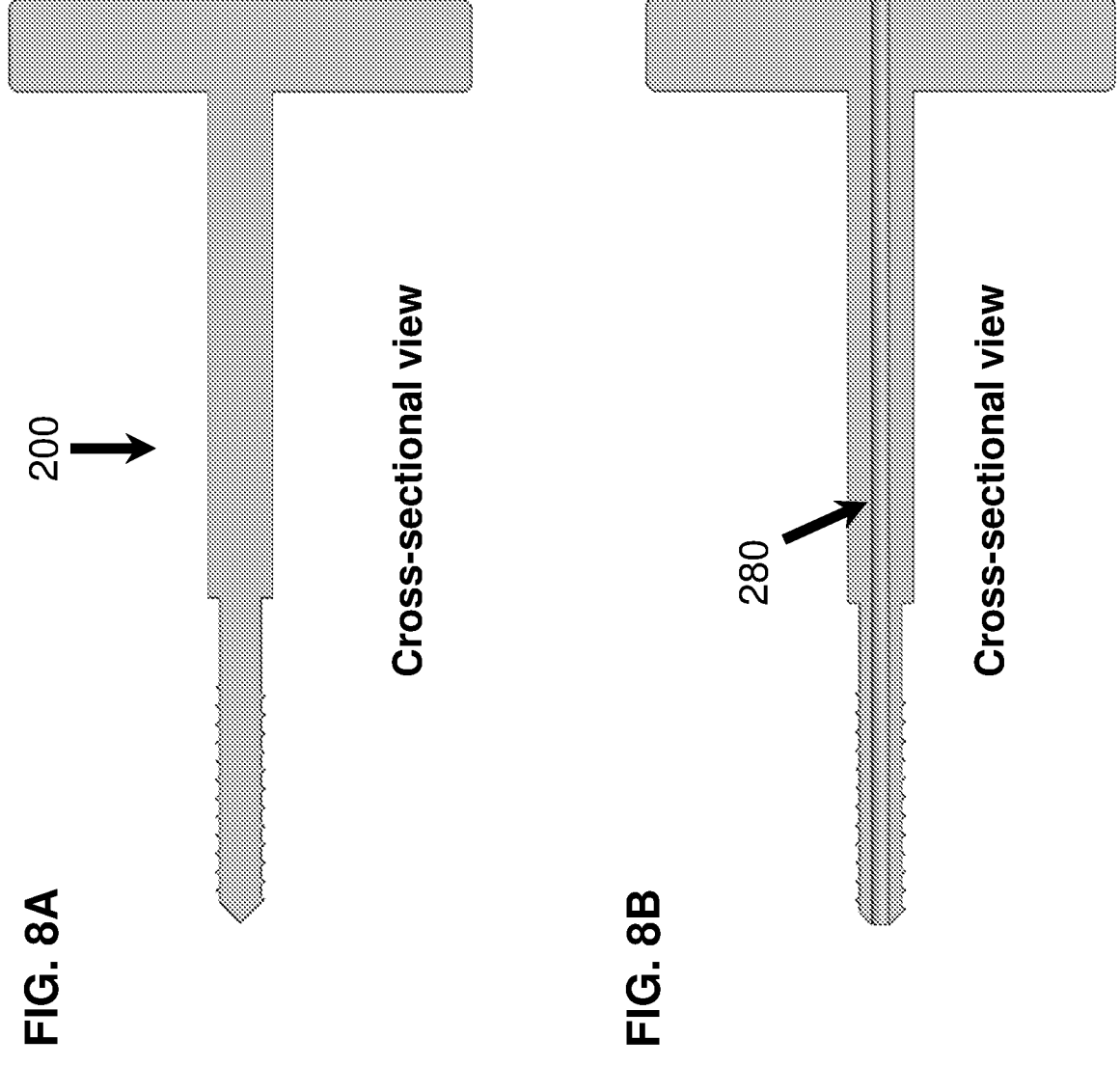
FIG. 8A is a schematic drawing showing a cross-sectional view of an embodiment of insertion tool 200 that does not have an internal channel.
FIG. 8B is a schematic drawing showing a cross-sectional view of an embodiment of insertion tool 200 containing internal channel 280 that traverses longitudinally from a proximal region to insertion to a distal region.
Figures 9A, 9B:
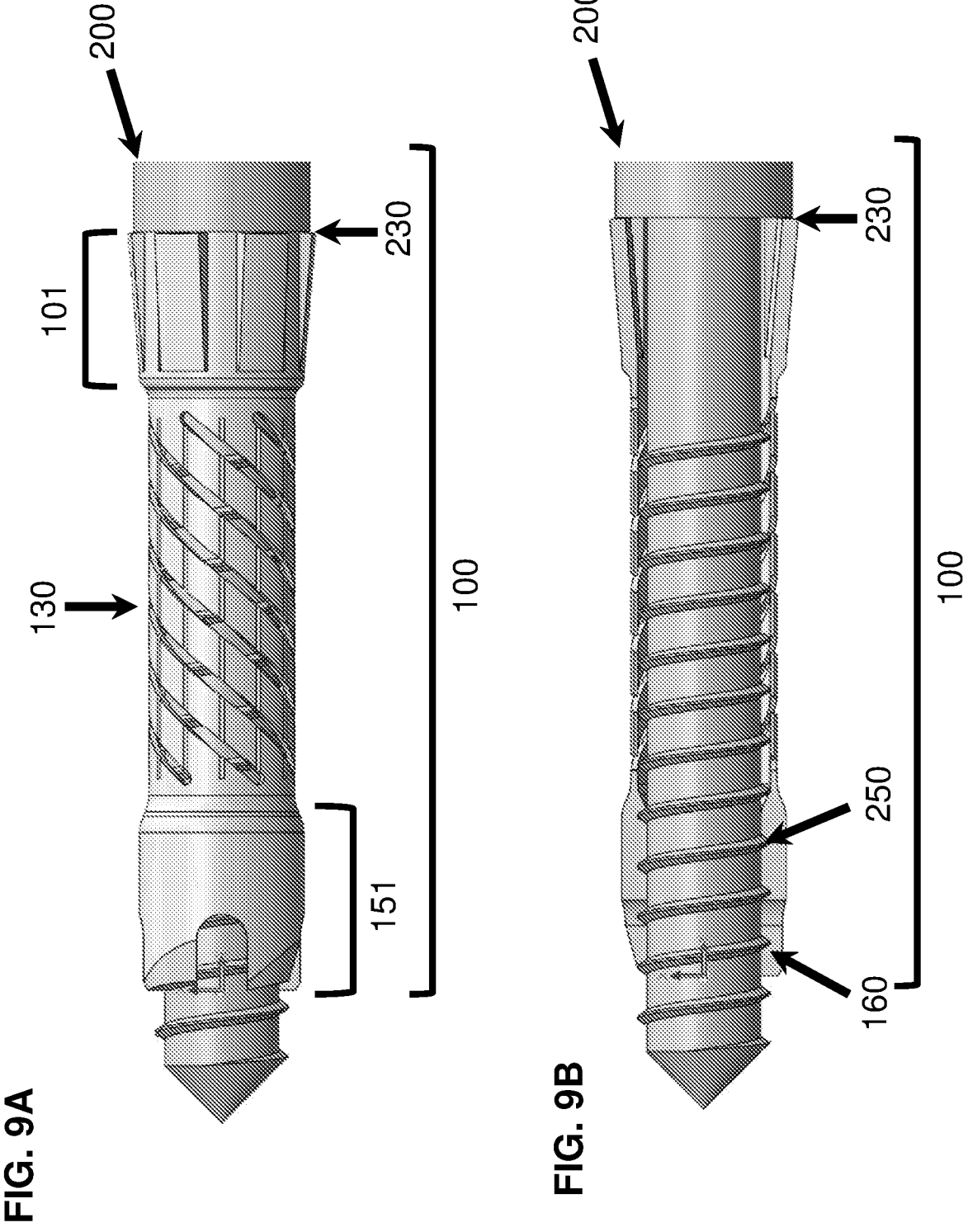
FIG. 9A is a schematic drawing showing a side view of device 100 engaged with a distal region of insertion tool 200. The distal region of Insertion tool 200 is shown traversing internal channel 190 (not shown) of device 100 from proximal region 101 to distal region 151. External threads 250 of insertion tool 200 are engaged with internal threads 160 of distal region 151 of device 100. Lip 230 of insertion tool 200 is shown contacting device 100 at proximal region 101.
FIG. 9B is a schematic drawing showing a cross-sectional view of device 100 of FIG. 9A engaged with insertion tool 200. Insertion tool 200 is shown traversing internal channel 190 (not shown) of device 100 from proximal region 101 to distal region 151 (labels shown in FIG. 9A). External threads 250 of insertion tool 200 are engaged with internal threads 160 of device 100 distal region. Lip 230 of insertion tool 200 is shown contacting device 100 at proximal region 101.
Figure 11:
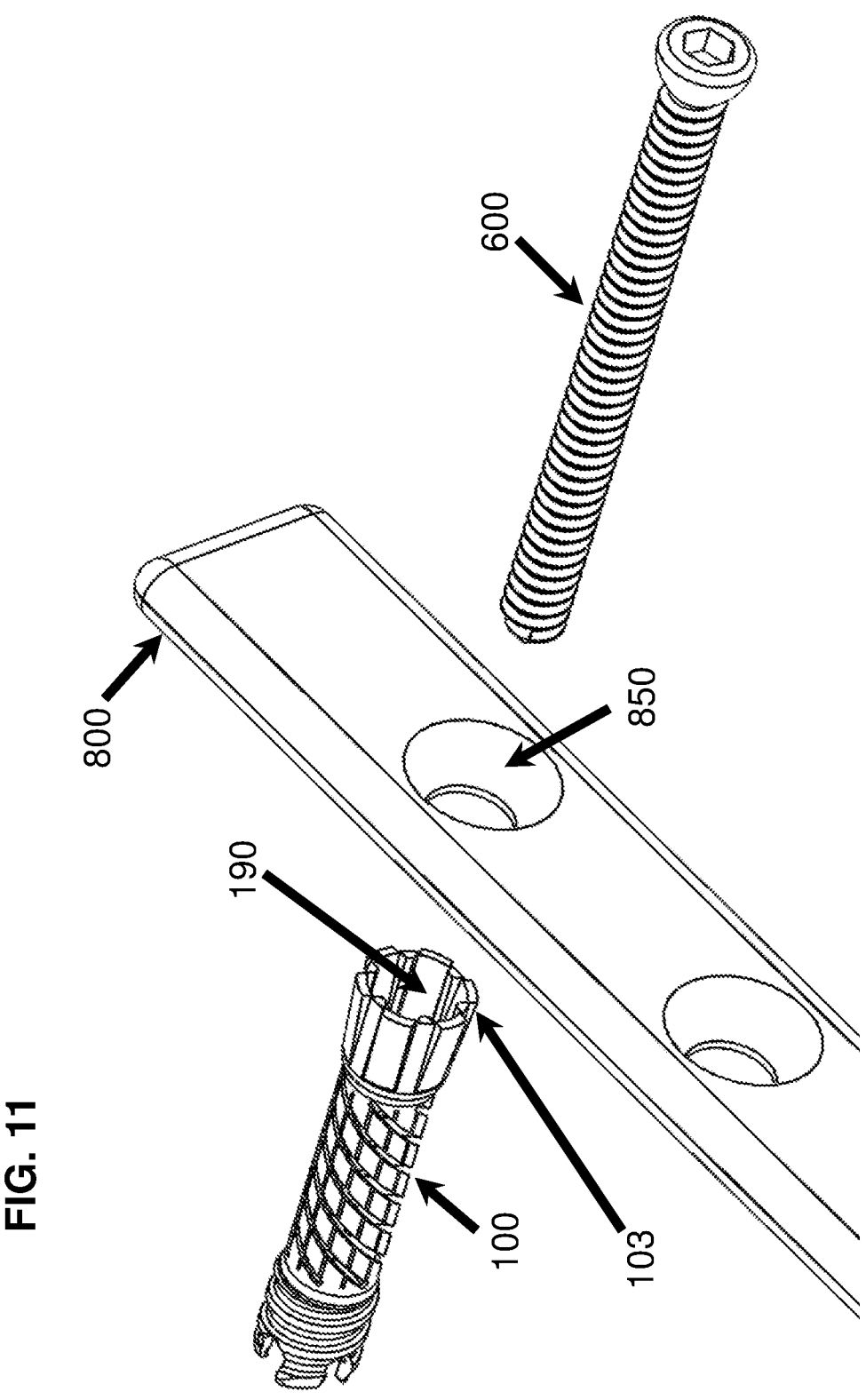
FIG. 11 is a schematic drawing showing a perspective view of screw 600 to be inserted into device 100 with bone plate 800 disposed between screw 600 and device 100. Screw 600 is configured to be inserted into bone plate 800 hole and then into internal channel 190 of device 100 at proximal opening 103.
Figure 12:
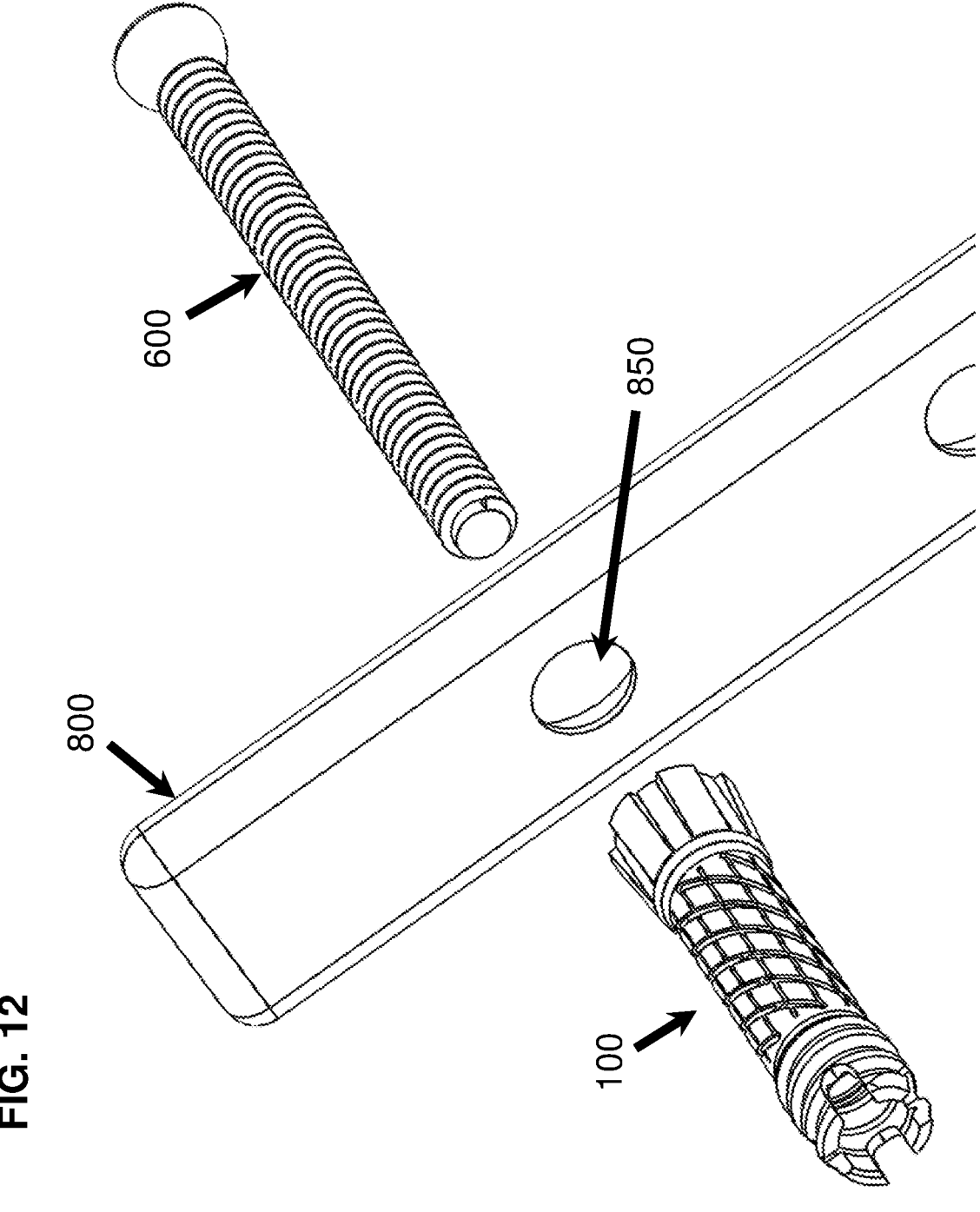
FIG. 12 is a schematic drawing showing a perspective view of screw 600 configured to be inserted into device 100 with bone plate 800 disposed between screw 600 and device 100.
Figure 16:
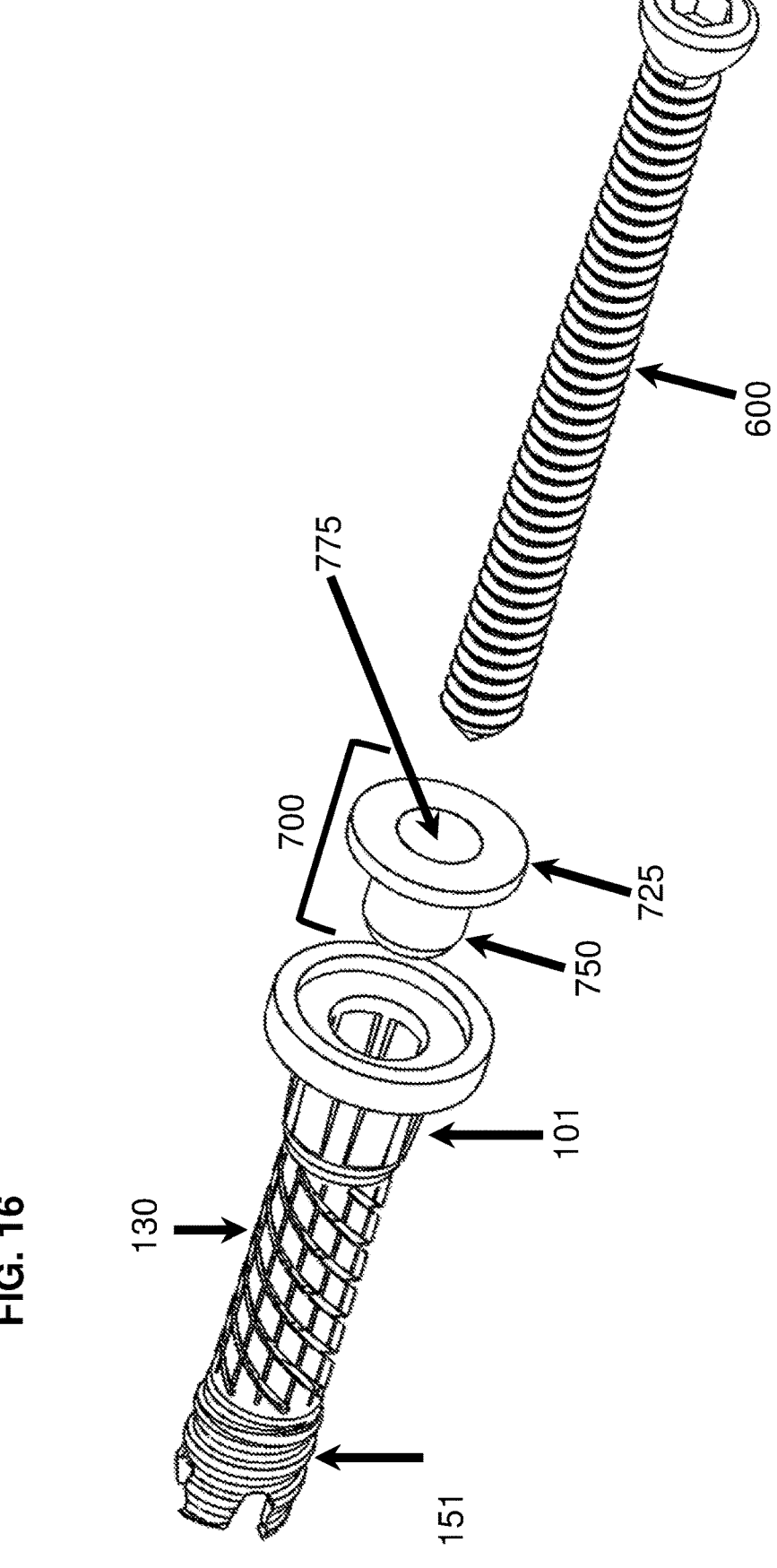
FIG. 16 is a schematic drawing showing a perspective view of device 100, washer 700, and screw 600 of FIG. 15. Proximal region 725, distal region 750, and internal channel 775 of washer 700 are shown. Furthermore, proximal region 101, expandable body 130, and distal region 151 of device 100 are shown.
Figure 17:
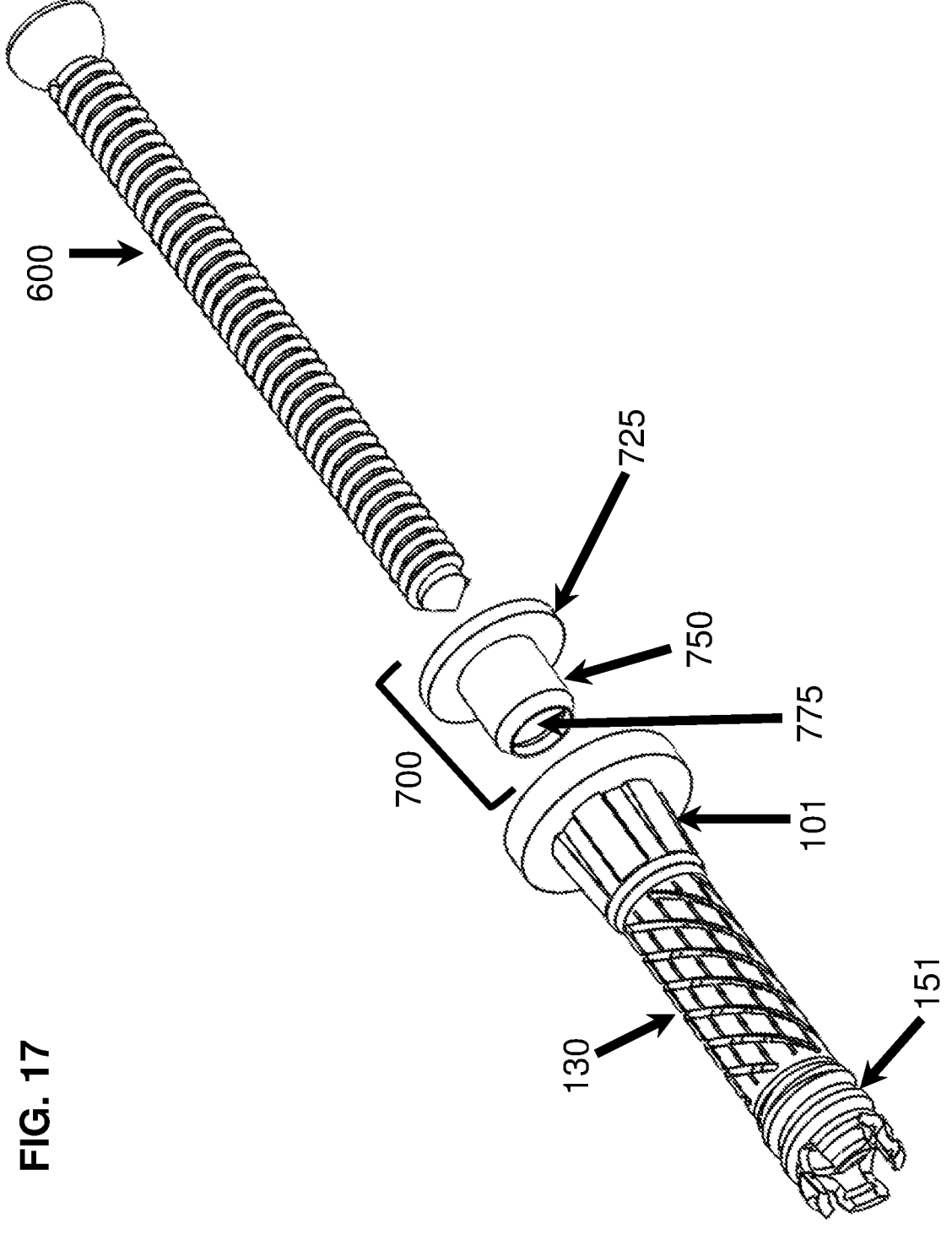
FIG. 17 is a schematic drawing showing a perspective view of device 100, washer 700, and screw 600 of FIG. 15. Proximal region 725, distal region 750, and internal channel 775 of washer 700 are shown. Furthermore, proximal region 101, expandable body 130, and distal region 151 of device 100 are shown.

Central region 220 of insertion tool 200 connects proximal region 210 to distal region 240 of insertion tool 200. Typically, central region 220 of insertion tool 200 is an unthreaded cylindrical shaft with a diameter that ends with lip 230 (see, e.g., FIGS. 7, 9A-9B, 51A, 52, 55). In some embodiments, central region 220 has a length of from about 5 mm to about 100 (e.g., about 5 mm, about 6 mm, about 7 mm, about 8 mm, about 9 mm, about 10 mm, about 11 mm, about 12 mm, about 13 mm, about 14 mm, about 15 mm, about 16 mm, about 17 mm, about 18 mm, about 19 mm, about 20 mm, about 21 mm, about 22 mm, about 23 mm, about 24 mm, about 25 mm, about 26 mm, about 27 mm, about 28 mm, about 29 mm, about 30 mm, about 31 mm, about 32 mm, about 33 mm, about 34 mm, about 35 mm, about 36 mm, about 37 mm, about 38 mm, about 39 mm, about 40 mm, about 41 mm, about 42 mm, about 43 mm, about 44 mm, about 45 mm, about 46 mm, about 47 mm, about 48 mm, about 49 mm, about 50 mm, about 51 mm, about 52 mm, about 53 mm, about 54 mm, about 55 mm, about 56 mm, about 57 mm, about 58 mm, about 59 mm, about 60 mm, about 61 mm, about 62 mm, about 63 mm, about 64 mm, about 65 mm, about 66 mm, about 67 mm, about 68 mm, about 69 mm, about 70 mm, about 71 mm, about 72 mm, about 73 mm, about 74 mm, about 75 mm, about 76 mm, about 77 mm, about 78 mm, about 79 mm, about 80 mm, about 81 mm, about 82 mm, about 83 mm, about 84 mm, about 85 mm, about 86 mm, about 87 mm, about 88 mm, about 89 mm, about 90 mm, about 91 mm, about 92 mm, about 93 mm, about 94 mm, about 95 mm, about 96 mm, about 97 mm, about 98 mm, about 99 mm, or about 100 mm). In some embodiments, insertion tool 200 has internal channel 280 extending from the proximal end 201 of proximal region 210 to distal end 202 of distal region 240 of insertion tool 200 (see, e.g., FIGS. 8A-8B and 52). In some embodiments, central region 220 of insertion tool 200 has an outer diameter and an inner diameter. In some embodiments, the outer diameter of central region 220 is from about 5 mm to about 10 mm (e.g., about 5 mm, about 6 mm, about 7 mm, about 8 mm, about 9 mm, or about 10 mm). In some embodiments, the inner diameter of central region 220 is from about 0.5 mm to about 3 (e.g., about 0.5 mm, about 0.6 mm, about 0.7 mm, about 0.8 mm, about 0.9 mm, about 1 mm, about 1.1 mm, about 1.2 mm, about 1.3 mm, about 1.4 mm, about 1.5 mm, about 1.6 mm, about 1.7 mm, about 1.8 mm, about 1.9 mm, about 2 mm, about 2.1 mm, about 2.2 mm, about 2.3 mm, about 2.4 mm, about 2.5 mm, about 2.6 mm, about 2.7 mm, about 2.8 mm, about 2.9 mm, or about 3 mm). In some embodiments, central region 220 has a set of threads having a thread pitch of from about 0.25 mm to about 2.5 mm (e.g., about 0.25 mm, about 0.3 mm, about 0.4 mm, about 0.5 mm, about 0.6 mm, about 0.7 mm, about 0.8 mm, about 0.9 mm, about 1 mm, about 1.1 mm, about 1.2 mm, about 1.3 mm, about 1.4 mm, about 1.5 mm, about 1.6 mm, about 1.7 mm, about 1.8 mm, about 1.9 mm, about 2 mm, about 2.1 mm, about 2.2 mm, about 2.3 mm, about 2.4 mm, or about 2.5 mm).

In general, distal region 240 of insertion tool 200 is a cylindrical shaft with a reduced diameter relative to the diameter of central region 220 (see, e.g., FIG. 7, 52, 55). In some embodiments, distal region 240 of insertion tool 200 has a length of from about 5 mm to about 100 (e.g., about 5 mm, about 6 mm, about 7 mm, about 8 mm, about 9 mm, about 10 mm, about 11 mm, about 12 mm, about 13 mm, about 14 mm, about 15 mm, about 16 mm, about 17 mm, about 18 mm, about 19 mm, about 20 mm, about 21 mm, about 22 mm, about 23 mm, about 24 mm, about 25 mm, about 26 mm, about 27 mm, about 28 mm, about 29 mm, about 30 mm, about 31 mm, about 32 mm, about 33 mm, about 34 mm, about 35 mm, about 36 mm, about 37 mm, about 38 mm, about 39 mm, about 40 mm, about 41 mm, about 42 mm, about 43 mm, about 44 mm, about 45 mm, about 46 mm, about 47 mm, about 48 mm, about 49 mm, about 50 mm, about 51 mm, about 52 mm, about 53 mm, about 54 mm, about 55 mm, about 56 mm, about 57 mm, about 58 mm, about 59 mm, about 60 mm, about 61 mm, about 62 mm, about 63 mm, about 64 mm, about 65 mm, about 66 mm, about 67 mm, about 68 mm, about 69 mm, about 70 mm, about 71 mm, about 72 mm, about 73 mm, about 74 mm, about 75 mm, about 76 mm, about 77 mm, about 78 mm, about 79 mm, about 80 mm, about 81 mm, about 82 mm, about 83 mm, about 84 mm, about 85 mm, about 86 mm, about 87 mm, about 88 mm, about 89 mm, about 90 mm, about 91 mm, about 92 mm, about 93 mm, about 94 mm, about 95 mm, about 96 mm, about 97 mm, about 98 mm, about 99 mm, or about 100 mm). In some embodiments, distal region 240 has an outer diameter and an inner diameter. In some embodiments, the outer diameter of distal region 240 is from about 2 mm to about 5 (e.g., about 2 mm, about 2.1 mm, about 2.2 mm, about 2.3 mm, about 2.4 mm, about 2.5 mm, about 2.6 mm, about 2.7 mm, about 2.8 mm, about 2.9 mm, about 3 mm, about 3.1 mm, about 3.2 mm, about 3.3 mm, about 3.4 mm, about 3.5 mm, about 3.6 mm, about 3.7 mm, about 3.8 mm, about 3.9 mm, about 4 mm, about 4.1 mm, about 4.2 mm, about 4.3 mm, about 4.4 mm, about 4.5 mm, about 4.6 mm, about 4.7 mm, about 4.8 mm, about 4.9 mm, or about 5 mm). In some embodiments, the inner diameter of distal region 240 is from about 0.5 mm to about 3 (e.g., about 0.5 mm, about 0.6 mm, about 0.7 mm, about 0.8 mm, about 0.9 mm, about 1 mm, about 1.1 mm, about 1.2 mm, about 1.3 mm, about 1.4 mm, about 1.5 mm, about 1.6 mm, about 1.7 mm, about 1.8 mm, about 1.9 mm, about 2 mm, about 2.1 mm, about 2.2 mm, about 2.3 mm, about 2.4 mm, about 2.5 mm, about 2.6 mm, about 2.7 mm, about 2.8 mm, about 2.9 mm, or about 3 mm). Distal region 240 of insertion tool 200 may also include at least one set of external threads 250 (see, e.g., FIGS. 7, 9B, 18B, 52, 55, 57-59). In some embodiments, external threads 250 are configured to engage with internal threads 160 and internal threads 121 of the proximal and distal regions of device 100 (see, e.g., FIGS. 9B, 18B, 19B, 24B, 33B, 42B). In some embodiments, a first set of distal region threads may have a thread pitch of from about 0.25 mm to about 2.5 mm (e.g., about 0.25 mm, about 0.3 mm, about 0.4 mm, about 0.5 mm, about 0.6 mm, about 0.7 mm, about 0.8 mm, about 0.9 mm, about 1 mm, about 1.1 mm, about 1.2 mm, about 1.3 mm, about 1.4 mm, about 1.5 mm, about 1.6 mm, about 1.7 mm, about 1.8 mm, about 1.9 mm, about 2 mm, about 2.1 mm, about 2.2 mm, about 2.3 mm, about 2.4 mm, or about 2.5 mm). In some embodiments, a second set of distal region threads may have a thread pitch of from about 0.25 mm to about 2.5 mm (e.g., about 0.25 mm, about 0.3 mm, about 0.4 mm, about 0.5 mm, about 0.6 mm, about 0.7 mm, about 0.8 mm, about 0.9 mm, about 1 mm, about 1.1 mm, about 1.2 mm, about 1.3 mm, about 1.4 mm, about 1.5 mm, about 1.6 mm, about 1.7 mm, about 1.8 mm, about 1.9 mm, about 2 mm, about 2.1 mm, about 2.2 mm, about 2.3 mm, about 2.4 mm, or about 2.5 mm). In some embodiments, external threads 250 is separated from external threads 260 by unthreaded region 270 of distal region 240 of insertion tool 200 (see, e.g., FIG. 55). In some embodiments, unthreaded region 270 has a length of from about 10 mm to about 100 mm (e.g., about 10 mm, about 11 mm, about 12 mm, about 13 mm, about 14 mm, about 15 mm, about 16 mm, about 17 mm, about 18 mm, about 19 mm, about 20 mm, about 21 mm, about 22 mm, about 23 mm, about 24 mm, about 25 mm, about 26 mm, about 27 mm, about 28 mm, about 29 mm, about 30 mm, about 31 mm, about 32 mm, about 33 mm, about 34 mm, about 35 mm, about 36 mm, about 37 mm, about 38 mm, about 39 mm, about 40 mm, about 41 mm, about 42 mm, about 43 mm, about 44 mm, about 45 mm, about 46 mm, about 47 mm, about 48 mm, about 49 mm, about 50 mm, about 51 mm, about 52 mm, about 53 mm, about 54 mm, about 55 mm, about 56 mm, about 57 mm, about 58 mm, about 59 mm, about 60 mm, about 61 mm, about 62 mm, about 63 mm, about 64 mm, about 65 mm, about 66 mm, about 67 mm, about 68 mm, about 69 mm, about 70 mm, about 71 mm, about 72 mm, about 73 mm, about 74 mm, about 75 mm, about 76 mm, about 77 mm, about 78 mm, about 79 mm, about 80 mm, about 81 mm, about 82 mm, about 83 mm, about 84 mm, about 85 mm, about 86 mm, about 87 mm, about 88 mm, about 89 mm, about 90 mm, about 91 mm, about 92 mm, about 93 mm, about 94 mm, about 95 mm, about 96 mm, about 97 mm, about 98 mm, about 99 mm, or about 100 mm).

In some embodiments, the diameter of central region 220 is larger than the diameter of distal region 240. In some embodiments, the difference in the diameter between central region 220 of insertion tool 200 and distal region 240 of insertion tool 200 produces lip 230 (see, e.g., FIGS. 7, 9A-9B, 51A, 52, 55). In some embodiments, lip 230 has a circumferential height of from about 3 mm to about 7 (e.g., about 3 mm, about 3.1 mm, about 3.2 mm, about 3.3 mm, about 3.4 mm, about 3.5 mm, about 3.6 mm, about 3.7 mm, about 3.8 mm, about 3.9 mm, about 4 mm, about 4.1 mm, about 4.2 mm, about 4.3 mm, about 4.4 mm, about 4.5 mm, about 4.6 mm, about 4.7 mm, about 4.8 mm, about 4.9 mm, about 5 mm, about 5.1 mm, about 5.2 mm, about 5.3 mm, about 5.4 mm, about 5.5 mm, about 5.6 mm, about 5.7 mm, about 5.8 mm, about 5.9 mm, about 6 mm, about 6.1 mm, about 6.2 mm, about 6.3 mm, about 6.4 mm, about 6.5 mm, about 6.6 mm, about 6.7 mm, about 6.8 mm, about 6.9 mm, or about 7 mm) that extends beyond the diameter of the shaft of distal region 240.

In some embodiments, internal channel 280 of insertion tool 200 has a diameter sized to allow guide wire 290 (see, e.g., FIG. 52) to pass through internal channel 280 of insertion tool 200, which can be used to lead insertion tool 200 (and device 100) to bone hole 875.

Pusher

System 1000 can also include pusher 300 (see, e.g., FIGS. 18A-18B and 56-64). Pusher 300 has proximal region 310 and distal region 320. Proximal region 310 of pusher 300 includes handle 315. Typically, handle 315 of pusher 300 is shaped to be grasped by the hand or fingers of a user (e.g., rectangular, circular, elliptical, polygonal, or T-shape). Distal region 320 of pusher 300 is cylindrically shaped. Furthermore, pusher 300 includes internal channel 330 longitudinally extending through proximal region 310 and distal region 320. Internal channel 330 of pusher 300 is configured to fit over shaft 245 of distal region 240 of insertion tool 200. In some embodiments, shaft 245 of distal region 240 of insertion tool 200 is configured to traverse internal channel 330 of pusher 300 from proximal region 310 to distal region 320. In some embodiments, internal channel 330 of pusher 300 includes a set of internal threads 335 configured to match and engage with the at least one set of external threads 250 of distal region 240 of insertion tool 200. In some embodiments internal channel 330 threads of pusher 300 are configured to engage with the second set of external threads 260 of insertion tool 200. In some embodiments, internal channel 330 of pusher 300 has a set of internal threads 335. In some embodiments, internal threads 335 of pusher 300 channel have a thread pitch of from about 0.25 mm to about 2.5 mm (e.g., about 0.25 mm, about 0.3 mm, about 0.4 mm, about 0.5 mm, about 0.6 mm, about 0.7 mm, about 0.8 mm, about 0.9 mm, about 1 mm, about 1.1 mm, about 1.2 mm, about 1.3 mm, about 1.4 mm, about 1.5 mm, about 1.6 mm, about 1.7 mm, about 1.8 mm, about 1.9 mm, about 2 mm, about 2.1 mm, about 2.2 mm, about 2.3 mm, about 2.4 mm, or about 2.5 mm). Alternatively, internal threads 335 are sized to allow for engagement with a corresponding Luer thread (e.g., Luer-lock threads 415 of connector 400). Pusher 300 is configured to be rotatable relative to insertion tool 200. Typically, rotating pusher 300, once pusher 300 is engaged with the second set of external threads 260 of distal region 240 of insertion tool 200, translates pusher 300 longitudinally either towards distal end 202 of insertion tool 200 or the proximal end 201 of insertion tool 200. The direction of rotation, e.g., clockwise or counterclockwise, determines the direction of the longitudinal translation of pusher 300 relative to insertion tool 200. In some embodiments, clockwise rotation of handle 315 of pusher 300 longitudinally translates pusher 300 toward distal end 202 of insertion tool 200. In some embodiments, counterclockwise rotation of handle 315 of pusher 300 longitudinally translates pusher 300 toward distal end 202 of insertion tool 200.
Connector System 1000 may also include connector 400 having a unitary body and a frustoconical shape (see, e.g., FIGS. 18A-18B, 47, 48, 53A-53B). Connector 400 is configured to fluidically connect biomaterial dispenser 500 to device 100, thereby allowing fluid access to device 100. In some embodiments, connector 400 is also sized and configured to apply a force (upon insertion into proximal region of device 100) that causes radial expansion of wings 105 of proximal region 101 of device 100. Connector 400 includes proximal region 410, distal region 430, and internal channel 480 through proximal region to distal region 430. In some embodiments, the first set of threads of insertion tool 200 are configured to longitudinally traverse the internal channel of connector 400. In some embodiments, the internal channel of connector 400 fits over unthreaded region 270 of distal region 240 of insertion tool 200. In some embodiments, proximal region 410 has an outer diameter of from about 7 mm to about 12 mm (e.g., about 7.1 mm, about 7.2 mm, about 7.3 mm, about 7.4 mm, about 7.5 mm, about 7.6 mm, about 7.7 mm, about 7.8 mm, about 7.9 mm, about 8 mm, about 8.1 mm, about 8.2 mm, about 8.3 mm, about 8.4 mm, about 8.5 mm, about 8.6 mm, about 8.7 mm, about 8.8 mm, about 8.9 mm, about 9 mm, about 9.1 mm, about 9.2 mm, about 9.3 mm, about 9.4 mm, about 9.5 mm, about 9.6 mm, about 9.7 mm, about 9.8 mm, about 9.9 mm, about 10 mm, about 10.1 mm, about 10.2 mm, about 10.3 mm, about 10.4 mm, about 10.5 mm, about 10.6 mm, about 10.7 mm, about 10.8 mm, about 10.9 mm, about 11 mm, about 11.1 mm, about 11.2 mm, about 11.3 mm, about 11.4 mm, about 11.5 mm, about 11.6 mm, about 11.7 mm, about 11.8 mm, about 11.9 mm, or about 12 mm) and an inner diameter of from about 4 mm to about 5 mm (e.g., about 4 mm, about 4.1 mm, about 4.2 mm, about 4.3 mm, about 4.4 mm, about 4.5 mm, about 4.6 mm, about 4.7 mm, about 4.8 mm, about 4.9 mm, or about 5 mm). In some embodiments, proximal region 410 includes a set of female Luer-lock threads 415. In some embodiments, the female Luer lock threads have a thread pitch of from about 1 mm to about 3 mm (e.g., about 1 mm, about 1.1 mm, about 1.2 mm, about 1.3 mm, about 1.4 mm, about 1.5 mm, about 1.6 mm, about 1.7 mm, about 1.8 mm, about 1.9 mm, about 2 mm, about 2.1 mm, about 2.2 mm, about 2.3 mm, about 2.4 mm, about 2.5 mm, about 2.6 mm, about 2.7 mm, about 2.8 mm, about 2.9 mm, or about 3 mm). In some embodiments, distal region 430 has a proximal end 450, distal end 460, and is conically shaped (e.g., distal end 460 has a smaller outer diameter than the proximal end 450).

In some embodiments, the proximal end 450 of distal region 430 has an outer diameter of from about 7 mm to about 26 mm (e.g., about 7 mm, about 8 mm, about 9 mm, about 10 mm, about 11 mm, about 12 mm, about 13 mm, about 14 mm, about 15 mm, about 16 mm, about 17 mm, about 18 mm, about 19 mm, about 20 mm, about 21 mm, about 22 mm, about 23 mm, about 24 mm, about 25 mm, or about 26 mm) and an inner diameter of from about 4 mm to about 24.8 mm (e.g., about 4 mm, about 5 mm, about 6 mm, about 7 mm, about 8 mm, about 8.1 mm, about 8.2 mm, about 8.3 mm, about 8.4 mm, about 8.5 mm, about 8.6 mm, about 8.7 mm, about 8.8 mm, about 8.9 mm, about 9 mm, about 9.1 mm, about 9.2 mm, about 9.3 mm, about 9.4 mm, about 9.5 mm, about 9.6 mm, about 9.7 mm, about 9.8 mm, about 9.9 mm, about 10 mm, about 10.1 mm, about 10.2 mm, about 10.3 mm, about 10.4 mm, about 10.5 mm, about 10.6 mm, about 10.7 mm, about 10.8 mm, about 10.9 mm, about 11 mm, about 11.1 mm, about 11.2 mm, about 11.3 mm, about 11.4 mm, about 11.5 mm, about 11.6 mm, about 11.7 mm, about 11.8 mm, about 11.9 mm, about 12 mm, about 12.1 mm, about 12.2 mm, about 12.3 mm, about 12.4 mm, about 12.5 mm, about 12.6 mm, about 12.7 mm, about 12.8 mm, about 12.9 mm, about 13 mm, about 13.1 mm, about 13.2 mm, about 13.3 mm, about 13.4 mm, about 13.5 mm, about 13.6 mm, about 13.7 mm, about 13.8 mm, about 13.9 mm, about 14 mm, about 14.1 mm, about 14.2 mm, about 14.3 mm, about 14.4 mm, about 14.5 mm, about 14.6 mm, about 14.7 mm, about 14.8 mm, about 14.9 mm, about 15 mm, about 15.1 mm, about 15.2 mm, about 15.3 mm, about 15.4 mm, about 15.5 mm, about 15.6 mm, about 15.7 mm, about 15.8 mm, about 15.9 mm, about 6 mm, about 16.1 mm, about 16.2 mm, about 16.3 mm, about 16.4 mm, about 16.5 mm, about 16.6 mm, about 16.7 mm, about 16.8 mm, about 16.9 mm, about 17 mm, about 17.1 mm, about 17.2 mm, about 17.3 mm, about 17.4 mm, about 17.5 mm, about 17.6 mm, about 17.7 mm, about 17.8 mm, about 17.9 mm, about 18 mm, about 18.1 mm, about 18.2 mm, about 18.3 mm, about 18.4 mm, about 18.5 mm, about 18.6 mm, about 18.7 mm, about 18.8 mm, about 18.9 mm, about 19 mm, about 19.1 mm, about 19.2 mm, about 19.3 mm, about 19.4 mm, about 19.5 mm, about 19.6 mm, about 19.7 mm, about 19.8 mm, about 19.9 mm, about 20 mm, about 20.1 mm, about 20.2 mm, about 20.3 mm, about 20.4 mm, about 20.5 mm, about 20.6 mm, about 20.7 mm, about 20.8 mm, about 20.9 mm, about 21 mm, about 21.1 mm, about 21.2 mm, about 21.3 mm, about 21.4 mm, about 21.5 mm, about 21.6 mm, about 21.7 mm, about 21.8 mm, about 21.9 mm, about 22 mm, about 22.1 mm, about 22.2 mm, about 22.3 mm, about 22.4 mm, about 22.5 mm, about 22.6 mm, about 22.7 mm, about 22.8 mm, about 22.9 mm, about 23 mm, about 23.1 mm, about 23.2 mm, about 23.3 mm, about 23.4 mm, about 23.5 mm, about 23.6 mm, about 23.7 mm, about 23.8 mm, about 23.9 mm, about 24 mm, about 24.1 mm, about 24.2 mm, about 24.3 mm, about 24.4 mm, about 24.5 mm, about 24.6 mm, about 24.7 mm, or about 24.8 mm). In some embodiments, distal end 460 of distal region 430 has an outer diameter of from about 1.8 mm to about 18.8 mm (e.g., about 1.8 mm, about 1.9 mm, about 2 mm, about 2.1 mm, about 2.2 mm, about 2.3 mm, about 2.4 mm, about 2.5 mm, about 2.6 mm, about 2.7, about 2.8 mm, about 2.9 mm, about 3 mm, about 3.1 mm, about 3.2 mm, about 3.3 mm, about 3.4 mm, about 3.5 mm, about 3.6 mm, about 3.7, about 3.8 mm, about 3.9 mm, about 4 mm, about 4.1 mm, about 4.2 mm, about 4.3 mm, about 4.4 mm, about 4.5 mm, about 4.6 mm, about 4.7, about 4.8 mm, about 4.9 mm, about 5 mm, about 5.1 mm, about 5.2 mm, about 5.3 mm, about 5.4 mm, about 5.5 mm, about 5.6 mm, about 5.7, about 5.8 mm, about 5.9 mm, about 6 mm, about 6.1 mm, about 6.2 mm, about 6.3 mm, about 6.4 mm, about 6.5 mm, about 6.6 mm, about 6.7, about 6.8 mm, about 6.9 mm, about 7 mm, about 7.1 mm, about 7.2 mm, about 7.3 mm, about 7.4 mm, about 7.5 mm, about 7.6 mm, about 7.7, about 7.8 mm, about 7.9 mm, about 8 mm, about 8.1 mm, about 8.2 mm, about 8.3 mm, about 8.4 mm, about 8.5 mm, about 8.6 mm, about 8.7 mm, about 8.8 mm, about 8.9 mm, about 9 mm, about 9.1 mm, about 9.2 mm, about 9.3 mm, about 9.4 mm, about 9.5 mm, about 9.6 mm, about 9.7 mm, about 9.8 mm, about 9.9 mm, about 10 mm, about 10.1 mm, about 10.2 mm, about 10.3 mm, about 10.4 mm, about 10.5 mm, about 10.6 mm, about 10.7 mm, about 10.8 mm, about 10.9 mm, about 11 mm, about 11.1 mm, about 11.2 mm, about 11.3 mm, about 11.4 mm, about 11.5 mm, about 11.6 mm, about 11.7 mm, about 11.8 mm, about 11.9 mm, about 12 mm, about 12.1 mm, about 12.2 mm, about 12.3 mm, about 12.4 mm, about 12.5 mm, about 12.6 mm, about 12.7 mm, about 12.8 mm, about 12.9 mm, about 13 mm, about 13.1 mm, about 13.2 mm, about 13.3 mm, about 13.4 mm, about 13.5 mm, about 13.6 mm, about 13.7 mm, about 13.8 mm, about 13.9 mm, about 14 mm, about 14.1 mm, about 14.2 mm, about 14.3 mm, about 14.4 mm, about 14.5 mm, about 14.6 mm, about 14.7 mm, about 14.8 mm, about 14.9 mm, about 15 mm, about 15.1 mm, about 15.2 mm, about 15.3 mm, about 15.4 mm, about 15.5 mm, about 15.6 mm, about 15.7 mm, about 15.8 mm, about 15.9 mm, about 6 mm, about 16.1 mm, about 16.2 mm, about 16.3 mm, about 16.4 mm, about 16.5 mm, about 16.6 mm, about 16.7 mm, about 16.8 mm, about 16.9 mm, about 17 mm, about 17.1 mm, about 17.2 mm, about 17.3 mm, about 17.4 mm, about 17.5 mm, about 17.6 mm, about 17.7 mm, about 17.8 mm, about 17.9 mm, about 18 mm, about 18.1 mm, about 18.2 mm, about 18.3 mm, about 18.4 mm, about 18.5 mm, about 18.6 mm, about 18.7 mm, or about 18.8 mm) and an inner diameter of from about 0.6 mm to about 17.6 mm (e.g., about 0.6 mm, about 0.7 mm, about 0.8 mm, about 0.9 mm, about 1 mm, about 1.1 mm, about 1.2 mm, about 1.3 mm, about 1.4 mm, about 1.5 mm, about 1.6 mm, about 1.7 mm, about 1.8 mm, about 1.9 mm, about 2 mm, about 2.1 mm, about 2.2 mm, about 2.3 mm, about 2.4 mm, about 2.5 mm, about 2.6 mm, about 2.7, about 2.8 mm, about 2.9 mm, about 3 mm, about 3.1 mm, about 3.2 mm, about 3.3 mm, about 3.4 mm, about 3.5 mm, about 3.6 mm, about 3.7, about 3.8 mm, about 3.9 mm, about 4 mm, about 4.1 mm, about 4.2 mm, about 4.3 mm, about 4.4 mm, about 4.5 mm, about 4.6 mm, about 4.7, about 4.8 mm, about 4.9 mm, about 5 mm, about 5.1 mm, about 5.2 mm, about 5.3 mm, about 5.4 mm, about 5.5 mm, about 5.6 mm, about 5.7, about 5.8 mm, about 5.9 mm, about 6 mm, about 6.1 mm, about 6.2 mm, about 6.3 mm, about 6.4 mm, about 6.5 mm, about 6.6 mm, about 6.7, about 6.8 mm, about 6.9 mm, about 7 mm, about 7.1 mm, about 7.2 mm, about 7.3 mm, about 7.4 mm, about 7.5 mm, about 7.6 mm, about 7.7, about 7.8 mm, about 7.9 mm, about 8 mm, about 8.1 mm, about 8.2 mm, about 8.3 mm, about 8.4 mm, about 8.5 mm, about 8.6 mm, about 8.7 mm, about 8.8 mm, about 8.9 mm, about 9 mm, about 9.1 mm, about 9.2 mm, about 9.3 mm, about 9.4 mm, about 9.5 mm, about 9.6 mm, about 9.7 mm, about 9.8 mm, about 9.9 mm, about 10 mm, about 10.1 mm, about 10.2 mm, about 10.3 mm, about 10.4 mm, about 10.5 mm, about 10.6 mm, about 10.7 mm, about 10.8 mm, about 10.9 mm, about 11 mm, about 11.1 mm, about 11.2 mm, about 11.3 mm, about 11.4 mm, about 11.5 mm, about 11.6 mm, about 11.7 mm, about 11.8 mm, about 11.9 mm, about 12 mm, about 12.1 mm, about 12.2 mm, about 12.3 mm, about 12.4 mm, about 12.5 mm, about 12.6 mm, about 12.7 mm, about 12.8 mm, about 12.9 mm, about 13 mm, about 13.1 mm, about 13.2 mm, about 13.3 mm, about 13.4 mm, about 13.5 mm, about 13.6 mm, about 13.7 mm, about 13.8 mm, about 13.9 mm, about 14 mm, about 14.1 mm, about 14.2 mm, about 14.3 mm, about 14.4 mm, about 14.5 mm, about 14.6 mm, about 14.7 mm, about 14.8 mm, about 14.9 mm, about 15 mm, about 15.1 mm, about 15.2 mm, about 15.3 mm, about 15.4 mm, about 15.5 mm, about 15.6 mm, about 15.7 mm, about 15.8 mm, about 15.9 mm, about 16 mm, about 16.1 mm, about 16.2 mm, about 16.3 mm, about 16.4 mm, about 16.5 mm, about 16.6 mm, about 16.7 mm, about 16.8 mm, about 16.9 mm, about 17 mm, about 17.1 mm, about 17.2 mm, about 17.3 mm, about 17.4 mm, about 17.5 mm, or about 17.6 mm). In some embodiments, connector 400 has a length from proximal region 410 to distal region 430 of from about 38 mm to about 120 mm (e.g., about 38 mm, about 39 mm, about 40 mm, about 41 mm, about 42 mm, about 43 mm, about 44 mm, about 45 mm, about 46 mm, about 47 mm, about 48 mm, about 49 mm, about 50 mm, about 51 mm, about 52 mm, about 53 mm, about 54 mm, about 55 mm, about 56 mm, about 57 mm, about 58 mm, about 59 mm, about 60 mm, about 61 mm, about 62 mm, about 63 mm, about 64 mm, about 65 mm, about 66 mm, about 67 mm, about 68 mm, about 69 mm, about 70 mm, about 71 mm, about 72 mm, about 73 mm, about 74 mm, about 75 mm, about 76 mm, about 77 mm, about 78 mm, about 79 mm, about 80 mm, about 81 mm, about 82 mm, about 83 mm, about 84 mm, about 85 mm, about 86 mm, about 87 mm, about 88 mm, about 89 mm, about 90 mm, about 91 mm, about 92 mm, about 93 mm, about 94 mm, about 95 mm, about 96 mm, about 97 mm, about 98 mm, about 99 mm, about 100 mm, about 101 mm, about 102 mm, about 103 mm, about 104 mm, about 105 mm, about 106 mm, about 107 mm, about 108 mm, about 109 mm, about 110 mm, about 111 mm, about 112 mm, about 113 mm, about 114 mm, about 115 mm, about 116 mm, about 117 mm, about 118 mm, about 119 mm, or about 120 mm).

In some embodiments, distal region 430 of connector 400 has a plurality (e.g., 2, 3, 4, 5, 6, 7, 8, 9, 10, 11, 12, 13, 14, 15, 16, 17, 18, 19, or 20) of circumferentially disposed, radially extending wedges 440. In some embodiments, wedges 440 extend from proximal end 450 of distal region 430 of connector 400 to distal end 460 of distal region 430 of connector 400. In some embodiments, wedges 440 have a thickness that reduces as wedges 440 extend from the proximal end 450 of distal region 430 to distal end 460 of distal region 430 of connector 400. In some embodiments wedges 440 have a proximal end 445 disposed at proximal end 450 of distal region 430 of connector 400, and distal end 447 disposed at distal end 460 of distal region 430 of connector 400. In some embodiments, proximal end 445 of wedges 440 has a thickness that protrudes from the body of connector 400 by from about 1 mm to about 5 mm (e.g., about 1 mm, about 2 mm, about 3 mm, about 4 mm, or about 5 mm). In some embodiments, the number of wedges 440 is equal to the number of wings 105 at proximal region 101 of device 100. In some embodiments, wedges 440 are configured and sized to fasten distal region 430 of connector 400 into internal channel 190 of proximal region 101 of device 100 and deploy proximal end 106 of wings 105 outwardly from proximal region 101 (see, e.g., FIG. 70A). In some embodiments, distal region 430 also includes alignment marker 420 (e.g., a line, an arrowhead, a colored marker, a textured marker, or a patterned marker). In some embodiments, distal region 430 of connector 400 has circumferential groove 470 (see, e.g., FIGS. 53A-53B). In some embodiments circumferential groove 470 is configured to secure connector 400 to bone plate 800 by press fitting circumferential groove 470 into bone plate 800 hole.

In some embodiments, connector 400 is composed of a material selected from the group consisting of stainless steel or an alloy thereof, titanium or an alloy thereof, magnesium or an alloy thereof, polyetheretherketone (PEEK), hydroxyapatite, tricalcium phosphate, tetracalcium phosphate, dicalcium phosphate, BIOGLASS® 45S5, ceramic composites, copper-based materials or composites, cobalt chrome, and combinations thereof.

Funnel

In some embodiments, the device may be inserted into funnel 1400 or other device in order to compress the device, e.g., for easy insertion into a hole in bone. Funnel 1400 may be aligned with a hole in a bone and the device can be deployed into the hole from funnel 1400. The device may be deployed from funnel 1400 into the hole in the bone with fingers, a pusher, or other tool (e.g., an obturator).

Balloon

In some embodiments, the device may be expanded with balloon 1500. Balloon 1500 may be inserted into the device before or after insertion into the hole. Balloon 1500 may be inflated as to expand devices 100, 1100, 1200, or 1300.

Additional Components

Washer

The devices, systems, and methods may also include a washer 700 (see, e.g., FIG. 15, 16, 17, 19B, 19D, 20B). Washer 700 is configured to adapt internal channel 190 of proximal region 101 of device 100 to screw head 675 facilitating the fastening of screw 600 to device 100 and to the bone. Washer 700 typically has proximal region 725, distal region 750, and an internal channel extending longitudinally through proximal region 725 and distal region 750 of washer 700. In some embodiments, washer 700 has a cylindrical shape. In some embodiments, proximal region of washer 700 has an outer diameter of from about 5 mm to about 30 mm (e.g., about 5 mm, about 6 mm, about 7 mm, about 8 mm, about 9 mm, about 10 mm, about 11 mm, about 12 mm, about 13 mm, about 14 mm, about 15 mm, about 16 mm, about 17 mm, about 18 mm, about 19 mm, about 20 mm, about 21 mm, about 22 mm, about 23 mm, about 24 mm, about 25 mm, about 26 mm, about 27 mm, about 28 mm, about 29 mm, or about 30 mm). In some embodiments, proximal region 725 of washer 700 has an inner diameter of from about 2 mm to about 20 mm (e.g., about 2 mm, about 3 mm, about 4 mm, about 5 mm, about 6 mm, about 7 mm, about 8 mm, about 9 mm, about 10 mm, about 11 mm, about 12 mm, about 13 mm, about 14 mm, about 15 mm, about 16 mm, about 17 mm, about 18 mm, about 19 mm, or about 20 mm). In some embodiments, distal region 750 of washer 700 has an outer diameter configured to fit into internal channel 190 of proximal region 101 of device 100. In some embodiments, the outer diameter of distal region 750 of washer 700 is from about 2.8 mm to about 19.8 mm (e.g., about 2.8 mm, about 2.9 mm, about 3 mm, about 3.1 mm, about 3.2 mm, about 3.3 mm, about 3.4 mm, about 3.5 mm, about 3.6 mm, about 3.7 mm, about 3.8 mm, about 3.9 mm, about 4 mm, about 4.1 mm, about 4.2 mm, about 4.3 mm, about 4.4 mm, about 4.5 mm, about 4.6 mm, about 4.7 mm, about 4.8 mm, about 4.9 mm, about 5 mm, about 5.1 mm, about 5.2 mm, about 5.3 mm, about 5.4 mm, about 5.5 mm, about 5.6 mm, about 5.7, about 5.8 mm, about 5.9 mm, about 6 mm, about 6.1 mm, about 6.2 mm, about 6.3 mm, about 6.4 mm, about 6.5 mm, about 6.6 mm, about 6.7, about 6.8 mm, about 6.9 mm, about 7 mm, about 7.1 mm, about 7.2 mm, about 7.3 mm, about 7.4 mm, about 7.5 mm, about 7.6 mm, about 7.7, about 7.8 mm, about 7.9 mm, about 8 mm, about 8.1 mm, about 8.2 mm, about 8.3 mm, about 8.4 mm, about 8.5 mm, about 8.6 mm, about 8.7 mm, about 8.8 mm, about 8.9 mm, about 9 mm, about 9.1 mm, about 9.2 mm, about 9.3 mm, about 9.4 mm, about 9.5 mm, about 9.6 mm, about 9.7 mm, about 9.8 mm, about 9.9 mm, about 10 mm, about 10.1 mm, about 10.2 mm, about 10.3 mm, about 10.4 mm, about 10.5 mm, about 10.6 mm, about 10.7 mm, about 10.8 mm, about 10.9 mm, about 11 mm, about 11.1 mm, about 11.2 mm, about 11.3 mm, about 11.4 mm, about 11.5 mm, about 11.6 mm, about 11.7 mm, about 11.8 mm, about 11.9 mm, about 12 mm, about 12.1 mm, about 12.2 mm, about 12.3 mm, about 12.4 mm, about 12.5 mm, about 12.6 mm, about 12.7 mm, about 12.8 mm, about 12.9 mm, about 13 mm, about 13.1 mm, about 13.2 mm, about 13.3 mm, about 13.4 mm, about 13.5 mm, about 13.6 mm, about 13.7 mm, about 13.8 mm, about 13.9 mm, about 14 mm, about 14.1 mm, about 14.2 mm, about 14.3 mm, about 14.4 mm, about 14.5 mm, about 14.6 mm, about 14.7 mm, about 14.8 mm, about 14.9 mm, about 15 mm, about 15.1 mm, about 15.2 mm, about 15.3 mm, about 15.4 mm, about 15.5 mm, about 15.6 mm, about 15.7 mm, about 15.8 mm, about 15.9 mm, about 6 mm, about 16.1 mm, about 16.2 mm, about 16.3 mm, about 16.4 mm, about 16.5 mm, about 16.6 mm, about 16.7 mm, about 16.8 mm, about 16.9 mm, about 17 mm, about 17.1 mm, about 17.2 mm, about 17.3 mm, about 17.4 mm, about 17.5 mm, about 17.6 mm, about 17.7 mm, about 17.8 mm, about 17.9 mm, about 18 mm, about 18.1 mm, about 18.2 mm, about 18.3 mm, about 18.4 mm, about 18.5 mm, about 18.6 mm, about 18.7 mm, about 18.8 mm, about 18.9 mm, about 19 mm, about 19.1 mm, about 19.2 mm, about 19.3 mm, about 19.4 mm, about 19.5 mm, about 19.6 mm, about 19.7 mm, or about 19.8 mm). In some embodiments, distal region 750 of washer 700 has an inner diameter of from about 2 mm to about 18 mm (e.g., about 2 mm, about 3 mm, about 4 mm, about 5 mm, about 6 mm, about 7 mm, about 8 mm, about 9 mm, about 10 mm, about 11 mm, about 12 mm, about 13 mm, about 14 mm, about 15 mm, about 16 mm, about 17 mm, or about 18 mm).

In some embodiments, the outer diameter of proximal region 725 of washer 700 is larger than the outer diameter of distal region 750 of washer 700. In some embodiments, internal channel 775 of washer 700 is shaped to engage with the head of screw 600 (e.g., washer 700 channel has a conical shape to engage with a conical screw head).

Biomaterial Dispenser and Biomaterial

The devices, systems, and methods herein described are configured to deliver biomaterial 550 to bone using, e.g., a biomaterial dispenser 500. In some embodiments, biomaterial dispenser 500 includes tube 525 connected to a syringe, a vial, a reservoir, or any suitable fluid container configured to hold and dispense a biomaterial. Tube 525, in some embodiments, includes a male Luer-lock plug disposed at one end of tube 525 configured to connect to the female Luer-lock threads 415 of proximal region of connector 400 (see, e.g., FIGS. 45, 46, 65-67).

Biomaterial 550 can be a polymeric adhesive, a bone void filler material, a cement, a phosphoserine-based bioadhesive, a cohesiveness agent, an osteogenic agent, a medicinal agent, or a pharmaceutical agent (see, e.g., FIGS. 66-69). In some embodiments, biomaterial 550 is selected from a calcium phosphate-based bone cement, a non-self-hardening calcium phosphate based bone void filler, a flowable xenograft bone void filler, polymethacrylate (PMMA), polymethylmethacrylate (PMMA), calcium sulfate, a metal alloy, a polysaccharide, a nucleic acid, a carbohydrate, a protein, a polypeptide, a poly(α-hydroxy acid), a poly(lactone), a poly(amino acid), a poly(anhydride), a poly(orthoester), a poly(anhydride-co-imide), a poly(orthocarbonate), a poly (α-hydroxy alkanoate), a poly(dioxanone), a poly(phospho-ester), poly(L-lactide) (PLLA), poly(D,L-lactide) (PDLLA), polyglycolide (PGA), poly(lactide-co-glycolide (PLGA), poly(L-lactide-co-D, L-lactide), poly(D,L-lactide-co-trim-ethylene carbonate), polyhydroxybutyrate (PHB), poly(ε-caprolactone), poly(δ-valerolactone), poly(γ-butyrolactone), poly(caprolactone), polyacrylic acid, polycarboxylic acid, poly(allylamine hydrochloride), poly(diallyldimethylammo-nium chloride), poly(ethyleneimine), polypropylene fumarate, polyvinyl alcohol, polyvinylpyrrolidone, polyeth-ylene, carbon fibers, poly(ethylene glycol), poly(ethylene oxide), poly(vinyl alcohol), poly(vinylpyrrolidone), poly (ethyloxazoline), poly(ethylene oxide)-co-poly(propylene oxide), a block copolymer, poly(ethylene terephthalate) polyamide, a homo-polymer or a co-polymer including one or more monomers selected from the group consisting of acrolein potassium, (meth)acrylamide, (meth)acrylic acid and salts thereof, (meth)acrylate, acrylonitrile, ethylene, ethylene glycol, ethyleneimine, ethyleneoxide, styrene sulfonate, vinyl acetate, vinyl alcohol, vinyl chloride, vinylpyrrolidone, a polyphenolic complexing agent selected from a gallotannin, an ellagitannin, a taragallotannin, a caffetannin, a proanthocyanidin, catechin, epicatechin, chlo-rogenic acid, and arbutin, alginic acid, arabic gum, guar gum, xantham gum, gelatin, chitin, chitosan, chitosan acetate, chitosan lactate, chondroitin sulfate, N,O-car-boxymethyl chitosan, a dextran, fibrin glue, glycerol, hyaluronic acid, sodium hyaluronate, a cellulose, a glu-cosamine, a proteoglycan, a starch, lactic acid, a pluronic, sodium glycerophosphate, collagen, glycogen, a keratin, silk, transforming growth factors-beta (TGF-β), an activin, an inhibin, a bone morphogenetic proteins (BMP), an anti-biotic, an enzyme inhibitor, an antihistamine, an anti-inflam-matory agent, a muscle relaxant, an anti-spasmodics, an analgesic, a prostaglandin, an anti-depressant, a trophic factor, or a hormone. In some embodiments, biomaterial 550 is configured to harden upon delivery to the bone.

Implantable Devices

Screw

Figures 20A, 20B:
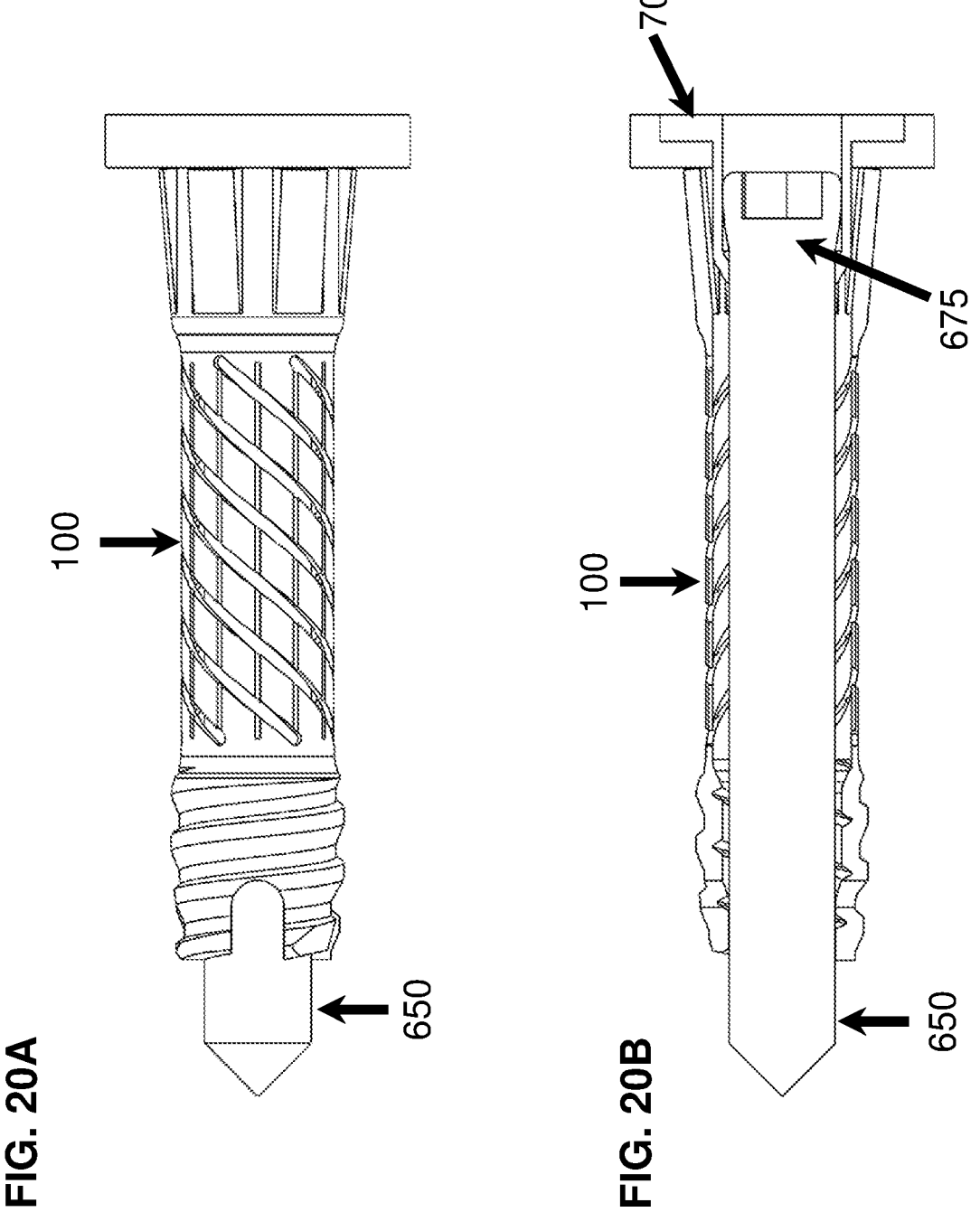
FIG. 20A is a schematic drawing showing a side view of device 100 with screw 600 having threadless body 650 inserted through internal channel 190 of device 100. Screw head 675 is in contact with washer 700.
FIG. 20B is a schematic drawing showing a cross-sectional view of device 100 of FIG. 20A showing a screw with threadless body 650 inserted through internal channel 190 of device 100. Shown is screw head 675 in contact with washer 700.
Figure 21:
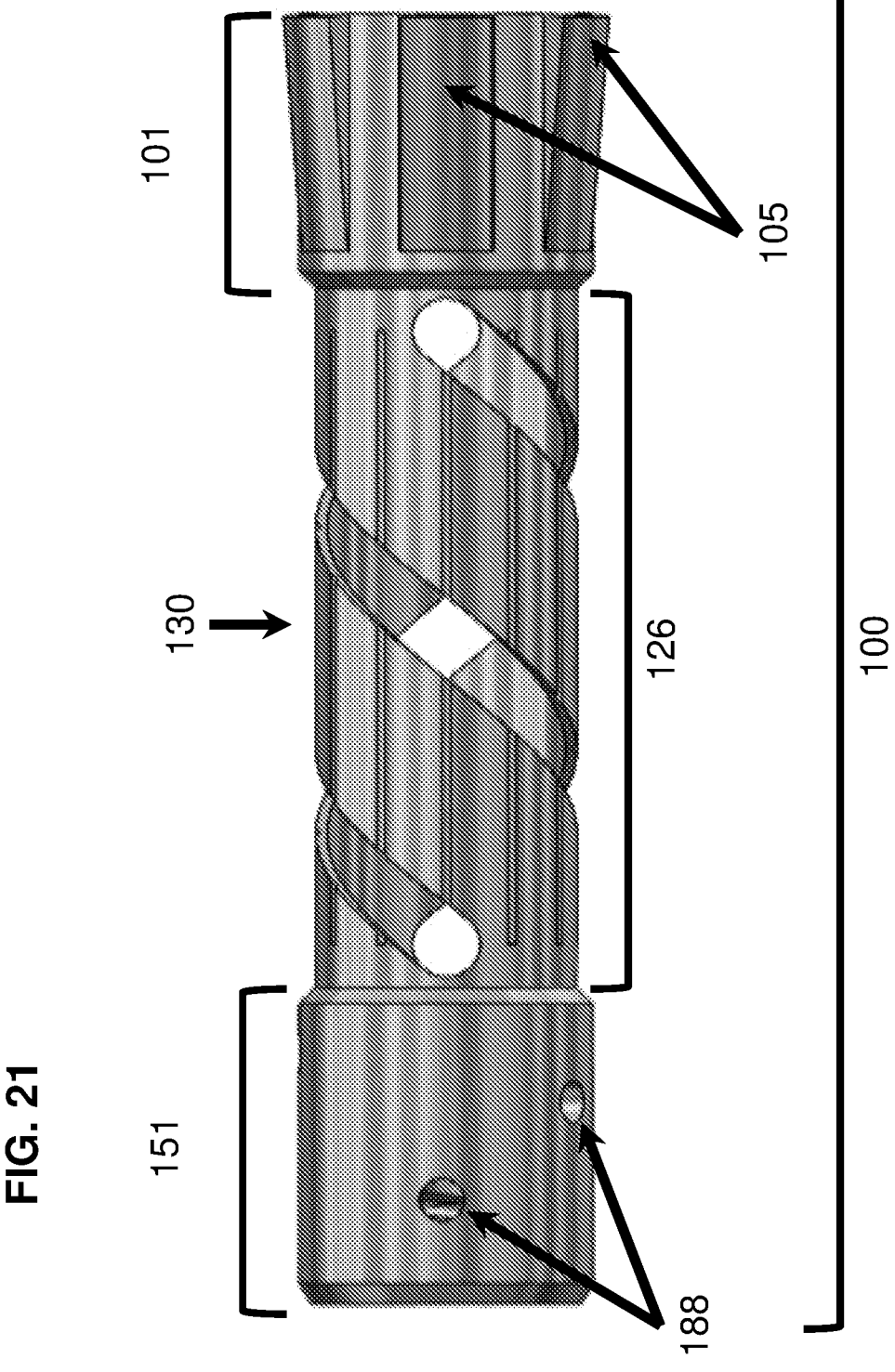
FIG. 21 is a schematic drawing showing a side view of an embodiment of device 100 including proximal region 101, central region 126, distal region 151, and distal region openings 188.
Figure 22:
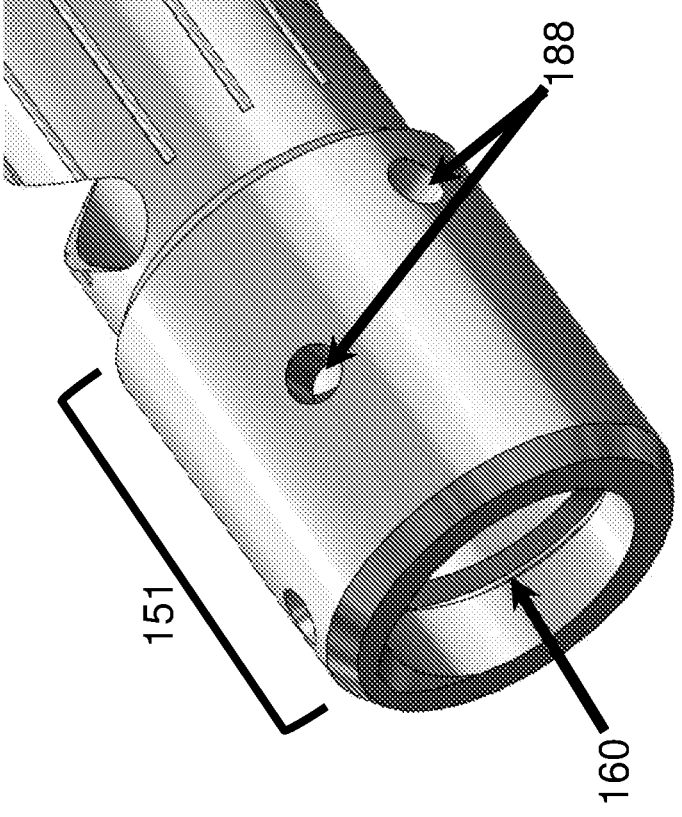
FIG. 22 is a schematic drawing showing a perspective view of distal region 151 of device 100 of FIG. 21 showing a plurality of openings 188 at distal region 151.
Figure 23:
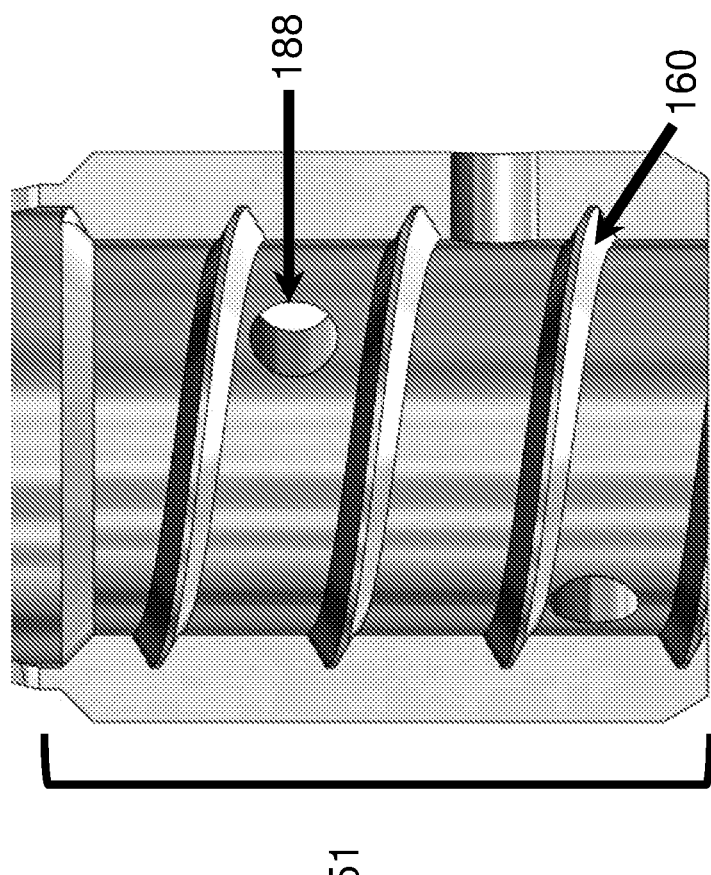
FIG. 23 is a schematic drawing showing a cross-sectional view of distal region 151 of device 100 of FIG. 21 showing a plurality of openings 188 at distal region 151.
Figures 24A, 24B:
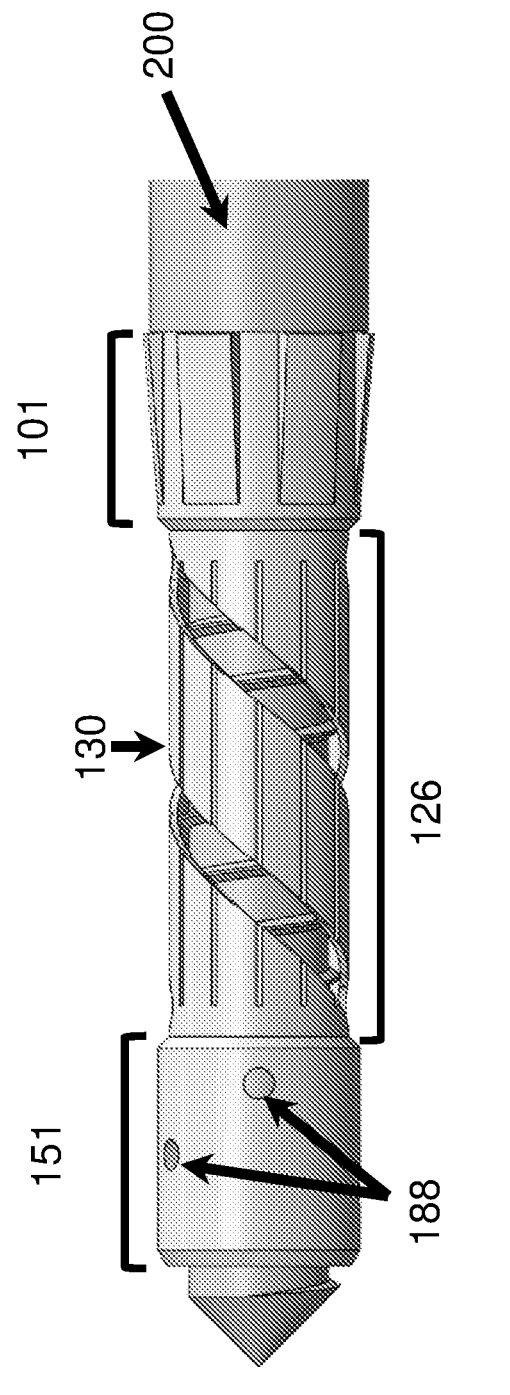
FIG. 24A is a schematic drawing showing a side view of an embodiment of device 100 engaged with insertion tool 200 (only distal region of insertion tool 200 is shown). Distal region 240 of Insertion tool 200 is shown traversing internal channel 190 of device 100 from proximal region 101 to distal region 151. External threads 250 of distal region 240 of insertion tool 200 are engaged with internal threads 160 of distal region 151 of device 100. Distal region 151 of device 100 is shown with a plurality of openings 188.
FIG. 24B is a schematic drawing showing a cross-sectional view of device 100 of FIG. 24A engaged with insertion tool 200. Insertion tool 200 is shown traversing internal channel 190 of device 100 from proximal region 101 to distal region 151. External threads 250 of insertion tool 200 are engaged with internal threads 160 of distal region 151 of device 100.

The devices, systems, and methods herein described are configured to treat a bone defect using any standard screw (e.g., a bone screw; see, e.g., FIGS. 10, 11, 12, 14B, 14C, 15-17, 19C, 19D, 68, 69). Examples of suitable bone screws include those that are compliant with American Society for Testing and Materials (ASTM) standard F543-17, Standard Specification and Test Methods for Metallic Medical Bone Screws, ASTM International; and International Organization for Standardization (ISO) 5835:1991, herein incorporated by reference in their entirety. Screw 600 (e.g., a bone screw) is used to distribute a biomaterial to the bone surrounding device 100 (upon insertion of screw 600 into interior chan-nel 190 of device 100 following delivery of biomaterial 550 to interior channel 190 of device 100) and can be used to secure device 100 to the bone. In some embodiments, screw 600 has a diameter or from about 1 mm to about 20 mm (e.g., about 1 mm, about 2 mm, about 3 mm, about 4 mm, about 5 mm, about 6 mm, about 7 mm, about 8 mm, about 9 mm, about 10 mm, about 11 mm, about 12 mm, about 13 mm, about 14 mm, about 15 mm, about 16 mm, about 17 mm, about 18 mm, about 19 mm, or about 20 mm). In certain embodiments, screw 600 has a length of from about 5 mm to about 300 mm (about 5 mm, about 6 mm, about 7 mm, about 8 mm, about 9 mm, about 10 mm, about 11 mm, about 12 mm, about 13 mm, about 14 mm, about 15 mm, about 16 mm, about 17 mm, about 18 mm, about 19 mm, about 20 mm, about 21 mm, about 22 mm, about 23 mm, about 24 mm, about 25 mm, about 26 mm, about 27 mm, about 28 mm, about 29 mm, about 30 mm, about 31 mm, about 32 mm, about 33 mm, about 34 mm, about 35 mm, about 36 mm, about 37 mm, about 38 mm, about 39 mm, about 40 mm, about 41 mm, about 42 mm, about 43 mm, about 44 mm, about 45 mm, about 46 mm, about 47 mm, about 48 mm, about 49 mm, about 50 mm, about 51 mm, about 52 mm, about 53 mm, about 54 mm, about 55 mm, about 56 mm, about 57 mm, about 58 mm, about 59 mm, about 60 mm, about 61 mm, about 62 mm, about 63 mm, about 64 mm, about 65 mm, about 66 mm, about 67 mm, about 68 mm, about 69 mm, about 70 mm, about 71 mm, about 72 mm, about 73 mm, about 74 mm, about 75 mm, about 76 mm, about 77 mm, about 78 mm, about 79 mm, about 80 mm, about 81 mm, about 82 mm, about 83 mm, about 84 mm, about 85 mm, about 86 mm, about 87 mm, about 88 mm, about 89 mm, about 90 mm, about 91 mm, about 92 mm, about 93 mm, about 94 mm, about 95 mm, about 96 mm, about 97 mm, about 98 mm, about 99 mm, about 100 mm, about 101 mm, about 102 mm, about 103 mm, about 104 mm, about 105 mm, about 106 mm, about 107 mm, about 108 mm, about 109 mm, about 110 mm, about 111 mm, about 112 mm, about 113 mm, about 114 mm, about 115 mm, about 116 mm, about 117 mm, about 118 mm, about 119 mm, about 120 mm, about 121 mm, about 122 mm, about 123 mm, about 124 mm, about 125 mm, about 126 mm, about 127 mm, about 128 mm, about 129 mm, about 130 mm, about 131 mm, about 132 mm, about 133 mm, about 134 mm, about 135 mm, about 136 mm, about 137 mm, about 138 mm, about 139 mm, about 140 mm, about 141 mm, about 142 mm, about 143 mm, about 144 mm, about 145 mm, about 146 mm, about 147 mm, about 148 mm, about 149 mm, about 150 mm, about 151 mm, about 152 mm, about 153 mm, about 154 mm, about 155 mm, about 156 mm, about 157 mm, about 158 mm, about 159 mm, about 160 mm, about 161 mm, about 162 mm, about 163 mm, about 164 mm, about 165 mm, about 166 mm, about 167 mm, about 168 mm, about 169 mm, about 170 mm, about 171 mm, about 172 mm, about 173 mm, about 174 mm, about 175 mm, about 176 mm, about 177 mm, about 178 mm, about 179 mm, about 180 mm, about 181 mm, about 182 mm, about 183 mm, about 184 mm, about 185 mm, about 186 mm, about 187 mm, about 188 mm, about 189 mm, about 190 mm, about 191 mm, about 192 mm, about 193 mm, about 194 mm, about 195 mm, about 196 mm, about 197 mm, about 198 mm, about 199 mm, about 200 mm, about 201 mm, about 202 mm, about 203 mm, about 204 mm, about 205 mm, about 206 mm, about 207 mm, about 208 mm, about 209 mm, about 210 mm, about 211 mm, about 212 mm, about 213 mm, about 214 mm, about 215 mm, about 216 mm, about 217 mm, about 218 mm, about 219 mm, about 220 mm, about 221 mm, about 222 mm, about 223 mm, about 224 mm, about 225 mm, about 226 mm, about 227 mm, about 228 mm, about 229 mm, about 230 mm, about 231 mm, about 232 mm, about 233 mm, about 234 mm, about 235 mm, about 236 mm, about 237 mm, about 238 mm, about 239 mm, about 240 mm, about 241 mm, about 242 mm, about 243 mm, about 244 mm, about 245 mm, about 246 mm, about 247 mm, about 248 mm, about 249 mm, about 250 mm, about 251 mm, about 252 mm, about 253 mm, about 254 mm, about 255 mm, about 256 mm, about 257 mm, about 258 mm, about 259 mm, about 260 mm, about 261 mm, about 262 mm, about 263 mm, about 264 mm, about 265 mm, about 266 mm, about 267 mm, about 268 mm, about 269 mm, about 270 mm, about 271 mm, about 272 mm, about 273 mm, about 274 mm, about 275 mm, about 276 mm, about 277 mm, about 278 mm, about 279 mm, about 280 mm, about 281 mm, about 282 mm, about 283 mm, about 284 mm, about 285 mm, about 286 mm, about 287 mm, about 288 mm, about 289 mm, about 290 mm, about 291 mm, about 292 mm, about 293 mm, about 294 mm, about 295 mm, about 296 mm, about 297 mm, about 298 mm, about 299 mm, or about 300 mm). In some embodiments, screw 600 has a length suitable for traversing the length of internal channel 190 of device 100 and fastening to bone distally disposed relative to the distal end of device 100 (see, e.g., FIGS. 13C, 14C, 14D). In some embodiments, screw 600 has threadless body 650 (see, e.g., FIGS. 20A-20B). In some embodiments, screw 600 has threads 625 having a thread pitch of from about 0.25 mm to about 2.5 mm (e.g., about 0.25 mm, about 0.3 mm, about 0.4 mm, about 0.5 mm, about 0.6 mm, about 0.7 mm, about 0.8 mm, about 0.9 mm, about 1 mm, about 1.1 mm, about 1.2 mm, about 1.3 mm, about 1.4 mm, about 1.5 mm, about 1.6 mm, about 1.7 mm, about 1.8 mm, about 1.9 mm, about 2 mm, about 2.1 mm, about 2.2 mm, about 2.3 mm, about 2.4 mm, or about 2.5 mm). In some embodiments, screw head 675 is shaped and sized to mate with washer 700 internal channel (see, e.g., FIGS. 19D and 20B). In some embodiments, screw head 675 is shaped and sized to mate with hole 850 of bone plate 800 (see, e.g., FIG. 13D). In some embodiments, screw 600 is made of a material suitable for implantation into the body (e.g., a bone) of a subject. In some embodiments, screw material is selected from the group consisting of stainless steel or an alloy thereof, titanium or an alloy thereof, magnesium or an alloy thereof, polyetheretherketone (PEEK), hydroxyapatite, tricalcium phosphate, tetracalcium phosphate, dicalcium phosphate, BIOGLASS® 45S5, ceramic composites, copper-based materials or composites, cobalt chrome, and combinations thereof.

Other Devices

The devices, systems, and methods herein described are configured to treat a bone defect using any implantable device configured to be implanted into a calcified substrate. Implantable devices include but are not limited to, e.g., suture anchors, dental implants, vertebral implants, bone rods, bone plates, nails, intramedullary pins, intramedullary pina, nail devices, spinal attachment devices, and bone screws, such as those described herein.

Extraction Tool

The devices, systems, and methods herein described also may be used for bone repair in combination with extraction tool 900 (see, e.g., FIGS. 31A-31B, 32, 33A-33B, 34A-34B, 35, 36, 38, 39). Extraction tool 900 is generally configured to remove device 100 from the bone. In some embodiments, extraction tool 900 includes, from a proximal to a distal end, proximal region 910, central region 920, and distal region 930. In some embodiments, proximal region includes grip handle 915, central region 920 includes pivot joint 925, distal region 930 includes a pair of nubs 935, and two members pivotally coupled by pivot joint 925. In some embodiments, the two members each have a nub disposed at distal region 930 to form the pair of nubs 935. In some embodiments, the nubs 935 are shaped and sized to fit into the one or more notches 183 of distal region 151 of device 100. In some embodiments, nubs 935 are protrusions shaped as hooks, pins, fins, bumps, or columnar projections.

Bone Plate

In some embodiments, the devices, systems, and methods herein described are configured for use in bone repair or implant fixation in combination with bone plate 800 (e.g., a standard bone plate known in the art; see e.g., ISO 9269; ASTM F382; Uhtoff, H. K., Poitras, P., and Backman, D. S.

"Internal plate fixation of fractures: short history and recent developments." J. Orthop. Sci. 2006 March; 11(2): 118-126; Kottmeier, S. A., Jones, C. B., Tornetta, 3$^{rd}$, P., Russell, T. A., Locked and minimally invasive plating: a paradigm shift? Metadiaphyseal site-specific concerns and controversies." AAOS Instr. Course Lect. 2013; 62:41-59; herein incorporated in their entirety by reference (see, e.g., FIGS. 10-12, 13A-13D, 61-69, 71, 72A-72B, 73A-73B)). In some embodiments, bone plate 800 includes two or more bone plate holes 850. In some embodiments, bone plate 800 may include from 1 to 50 (e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50) bone plate holes 850. In some embodiments, bone plate 800 holes are shaped and sized to mate with screw head 675.

Methods of Use

Also featured are methods of delivering a biomaterial to a bone in connection with methods of repairing a bone defect (e.g., a bone fracture, a bone cancer, osteoporosis, a metabolic bone disease, a stress fracture, scoliosis) or installing hardware (e.g., an implant). The methods, devices, and systems ensure the biomaterial is uniformly distributed to the bone. The devices, systems, and methods herein described are useful for implant fixation by installing at least one of the devices described herein, e.g., using the systems, kits, and/or methods described herein, which can be used to anchor or stabilize the implant (e.g., hardware) to bone.

Insertion of the Device

The treatment of a bone defect or condition with a device of the disclosure, e.g., any one or more of device 100, 1100, 1200, or 1300 herein described, includes inserting the device, e.g., device 100, 1100, 1200, or 1300 into the bone. If desired, device 100, 1100, 1200, or 1300 can be used in combination with bone plate 800 to repair the bone defect and/or condition. Alternatively, device 100, 1100, 1200, or 1300 can be used alone in the treatment of the bone defect and/or condition. Device 100, 1100, 1200, or 1300 may be used for repair of bone trauma or a bone defect that may have resulted from surgery or disease. The damaged or fragmented bone tissue may be reconstructed using device 100, 1100, 1200, or 1300 by delivering a biomaterial (e.g., a bone cement, which may also include a therapeutic agent, such as an osteogenic agent) to the damaged bone tissue, for example, for immediate repair of, or restoration of anatomical shape of, the bone. Device 100, 1100, 1200, or 1300 can also be used for bone augmentation (e.g., improving bone quality surrounding a bone defect). Devices 100, 1100, 1200, or 1300 may further provide mechanical support for bone fragments at the site of damage and simultaneously allow blood and bone forming cells from adjacent tissues to penetrate device 100, 1100, 1200, or 1300 for improved healing. For example, device 100, 1100, 1200, or 1300 can be used in orthopedic and spine surgery, as well as in fixation of fragmented pieces of bone and cosmetic surgeries, including the repair of bone defects and in reconstructions of bony tissues, including jaw bones. In the presence of long bones weakened by diseases, or when parts of the cortical bone are lost, device 100, 1100, 1200, or 1300 can be used to reinforce the long bones and cover openings where cortical bone is lost.

Device 100, 1100, 1200, or 1300 may also be used with bones of reduced quality (e.g., osteoporotic bone) or in revision surgeries (e.g., they can be used to replace previously inserted implants). Device 100, 1100, 1200, or 1300 can be used, for example, in osteosynthesis to internally stabilize and/or join bones, e.g., fractured (broken) bones.

Device 100, 1100, 1200, or 1300 may also be used to treat a bone defect in a patient with a fracture requiring compression. In particular, device 100, 1100, 1200, or 1300 may be used to provide compressive fixation in a patient. Device 100, 1100, 1200, or 1300 may also be used to provide fixation of a bone plate or an implant to bone.

The devices, systems, and kits can be used in a method of treating a patient having a bone defect (e.g., subarticular fracture, a defect of the spine or vertebra, or a defect of the radius, ulna, fibula, clavicle, humerus, pelvis, femur, patella, tibia, talus, calcaneus, navicular, cuneiforms, metatarsals, metacarpals, phalanges, scapula, ankle, maxilla, or mandible) by positioning device 100 in proximity to the bone defect (e.g., positioning device 100, 1100, 1200, or 1300 so that it contacts the intraosseous space of a bone). The method of treatment includes use of device 100, 1100, 1200, or 1300 to deliver uniformly distributed biomaterial into and/or around the site of damaged bone tissue.

Particular bone defects that may be treated using devices 100, 1100, 1200, or 1300 include, e.g., any bone deficient region, such as a void, gap, recess, or other discontinuity in a bone. The bone defect may be due to, for example, disease or trauma. Device 100, 1100, 1200, or 1300 can be applied, for example, in the repair of periodontal defects, in craniofacial or maxillofacial surgery or reconstruction, in hand surgery, in joint reconstruction, in fracture repair, in orthopedic surgical procedures, and in spinal fusion. Non-limiting examples of bone fractures include, e.g., stable fractures, transverse fractures, oblique fractures, spiral fractures, comminuted fractures and open and displaced fractures. Exemplary large bones that may require fracture fixation include, e.g., the femur, tibia, fibula, humerus, ulna, radius, 7$^{th}$ and 8$^{th}$ ribs, innominate bone (hip bone), sacrum, sacroiliac joint, and sternum.

The method of treating a patient having a bone defect (e.g., subarticular fracture, a defect of the spine or vertebra, or a defect of the radius, ulna, fibula, clavicle, humerus, pelvis, femur, patella, tibia, talus, calcaneus, navicular, cuneiforms, metatarsals, metacarpals, phalanges, scapula, ankle, teeth, or mandible) includes the following: a) positioning a device of the disclosure, e.g., device 100, 1100, 1200, or 1300, in proximity to the bone defect (e.g., positioning device 100 so that it contacts the intraosseous space of a bone, and/or, in the treatment of a fracture, spans the fracture line); b) introducing biomaterial 550 (e.g., a bone void filler material, a cement, or a pharmaceutical agent) c) allowing the flowable medium to be extruded through an expandable body of the device (e.g., expandable body 130; e.g., the flowable medium is extruded through substantially all or a plurality of expandable body openings 140, e.g., in substantially equal volumes), d) optionally inserting a screw or other device into the interior channel of the device (e.g., interior channel 190 of device 100) to distribute biomaterial out of interior channel and into surrounding bone, and e) allowing the biomaterial to harden, thereby fixing the device (and bone screw, if present) in place.

For vertebral fixation, device 100, 1100, 1200, or 1300 may be placed within a pedicle, used to anchor an interbody device, used to anchor spinal fusion plates and spacer replacement, used in an osteoporotic vertebra, or positioned in proximity to the spinous processes of adjacent vertebrae.

Prior to inserting device 100, 1100, 1200, or 1300 into the bone, the method includes drilling a hole into the bone to provide access to the interior of the bone. The hole may be drilled using any suitable tool known in the art. Bone hole 875 is typically drilled according to the size of device 100, 1100, 1200, or 1300 to be inserted into the hole. The size of device 100, 1100, 1200, or 1300 to be inserted into the bone may, in some embodiments, be determined by the volume of biomaterial needed to treat the bone defect. In some embodiments, the size and/or degree of damage to a bone is used to determine the size of device 100, 1100, 1200, or 1300 to be inserted. In some embodiments a subject's age, body weight, bone defect location, the type of bone affected by the bone defect, and/or other medical conditions can be used to determine the size of device 100, 1100, 1200, or 1300 to insert. Typically, the length of the hole is at most about one third the diameter of the bone in which device 100, 1100, 1200, or 1300 is to be inserted. When a larger amount of biomaterial is required, two or more (e.g., 2, 3, 4, 5, 6, 7, 8, 9, or 10) devices 100, 1100, 1200, or 1300 may be inserted into the bone near and/or around the defect area. In some embodiments, the bone defect and/or condition requires two or more of device 100, 1100, 1200, or 1300 to be inserted to ensure adequate stabilization and/or bone healing.

Inserting device 100, 1100, 1200, or 1300 includes engaging device 100, 1100, 1200, or 1300 with the components of system 1000 (if used), placing device 100, 1100, 1200, or 1300 into bone hole 875, and securing proximal region 101, 1101, 1201, or 1301 of device 100, 1100, 1200, or 1300 in the bone.

In some embodiments, device 100, 1100, 1200, or 1300 is compressed using funnel 1400. Following compression, device 100, 1100, 1200, or 1300 can be inserted using, for example, funnel 1400. Funnel 1400 may be aligned with the hole, and device 100, 1100, 1200, or 1300 inserted into the whole with a finger, with pusher 300, or a pushing alternative (e.g., an obturator or other device). Funnel 1500 may be advantageous in that device 100, 1100, 1200, or 1300 may be able to be pre-loaded into funnel 1500.

Alternatively, device 100 can be inserted using, for example, insertion tool 200, as described herein. If used, insertion tool 200 may include one or more threads that engage with the one or more sets of internal threads of internal channel 190 of device 100. Engaging insertion tool 200 with internal threads 160 of internal channel 190 of device 100 includes twisting insertion tool 200 into internal channel 190 until insertion tool 200 is sufficiently coupled to device 100 to allow for device 100 to be placed inside the hole.

Device 100, after engagement with insertion tool 200, may be placed in the hole by twisting insertion tool 200 until device 100 is placed (e.g., threaded) in the hole. A guide wire 290 may be passed through internal channel 280 of insertion tool 200 and through interior channel 190 of device 100 to help guide device 100 to bone hole 875, thereby facilitating the placement of device 100 in bone hole 875. During the insertion of device 100 into the bone, wings 105 of proximal region 101 of the device may compress or deflect inwardly toward interior channel 190 at proximal region 101 of device 100. Once device 100 is placed in the hole, the method may further include rotating device 100 until wings 105 of proximal region 101 expand, thereby securing (e.g., fixedly engaging) proximal region 101 of device 100 to the bone.

Securing proximal region 101 of device 100 in the hole includes expanding and friction fitting proximal end 106 of wings 105 disposed at proximal region 101 of device 100 upon placing device 100 in the hole. In some embodiments, proximal end 106 of wings 105 is deployed and expanded outwardly from proximal region 101 of device 100 by inserting and fastening connector 400 into internal channel 190 of device 100 at proximal region 101 (see, e.g., FIG. 70A). If used to deploy wings 105, connector 400 may be fastened to internal channel 190 of device 100 at proximal region 101 by pressing distal region 430 of connector into internal channel 190 of device 100 at proximal region 101. Typically, connector 400 includes a plurality of wedges 440 that slot connector 400 into internal channel 190 of device 100 at proximal region 101 relative to wings 105 of proximal region 101 of device 100. Connector 400 may include alignment marker 420. Similarly, proximal region 101 of device 100 may include alignment marker 125. When present, the two alignment markers are aligned to facilitate the fastening of connector 400 to internal channel 190 of device 100 at proximal region 101 (see, e.g., FIGS. 49 and 50).

Device 100 may also be inserted without using system 1000. If so, device 100 may first be coupled to connector 400 by inserting and fastening distal region 430 of connector 400 to internal channel 190 of device 100 at the proximal end 106, followed by placing device 100 in bone hole 875. If device 100 is to be used with a bone plate, the method may include passing device 100 and connector 400 through hole 850 of bone plate 800 and securing connector 400 to bone plate 800 by pressing circumferential groove 470 of connector 400 into hole 850 of bone plate 800 (see, e.g., FIG. 54) until circumferential groove 470 fixedly engages with bone plate 800. Proximal end 106 of wings 105 of proximal region 101 of device 100 reversibly deflect toward proximal region 101 when placing device 100 through hole 850 of bone plate 800 (see, e.g., FIGS. 70B, 72A-72B). Consequently, proximal end 106 of wings 105 return to an uncompressed (expanded) state after insertion of device 100 through bone plate 800 and into the bone (see, e.g., FIGS. 73A-73B).

Securing proximal region 101 of device 100 in the hole rotationally anchors proximal region 101 of device 100 in the hole (e.g., by friction fit), thereby allowing distal region 151 and central region 126 of device 100 to rotate independently from proximal region 101, thereby resulting in radial expansion of expandable body 130 of device 100.

Radial Expansion of Expandable Body 130

As herein described, device 100 includes central region 126 having expandable body 130 configured to radially expand. Radial expansion of expandable body 130 enlarges openings 140 of central region 126, thereby facilitating flow of biomaterial to the bone through device 100.

Device 100, 1100, 1200, or 1300 can be expanded following deployment of device 100, 1100, 1200, or 1300 from funnel 1400.

Device 100, 1100, 1200, or 1300 can be expanded using, for example, balloon 1500 (see, e.g., FIG. 80A-80C). Balloon 1500 may be inserted into device 100, 1100, 1200, or 1300 following insertion into the hole. Following insertion, balloon 1500 may be inflated to expand device 100, 1100, 1200, or 1300.

Alternatively, to expand expandable body 130 of device 100 proximal region 101 is first rotationally anchored as herein described. Insertion tool 200, having a set of external threads 250 configured to engage with a set of internal threads of device 100, is then inserted into (or is already present in) internal channel 190 of device 100. The external threads 250 of insertion tool 200 engage with the first set of internal threads of internal channel 190 of device 100 at distal region 151. Insertion tool 200 is then twisted in a first direction (e.g., clockwise) and the twisting of insertion tool 200, being engaged with device 100, applies a torque to distal region 151 of device 100 (see, e.g., FIG. 63) as distal region 151 rotates relative to proximal region 101, which is fixed. In some embodiments, the torque applied is from about 0.1 N·m to about 10 N·m (e.g., from about 0.1 N·m to about 9 N·m, from about 0.1 N·m to about 8 N·m, from about 0.1 N·m to about 7 N·m, from about 0.1 N·m to about 6 N·m, from about 0.1 N·m to about 5 N·m, from about 0.1 N·m to about 4 N·m, from about 0.1 N·m to about 3 N·m, from about 0.1 N·m to about 2 N·m, from about 0.1 N·m to about 1 N·m, about 0.1 N·m, about 0.2 N·m, about 0.3 N·m, about 0.4 N·m, about 0.5 N·m, about 0.6 N·m, about 0.7 N·m, about 0.8 N·m, about 0.9 N·m, about 1 N·m, about 1.1 N·m, about 1.2 N·m, about 1.3 N·m, about 1.4 N·m, about 1.5 N·m, about 1.6 N·m, about 1.7 N·m, about 1.8 N·m, about 1.9 N·m, about 2 N·m, about 2.1 N·m, about 2.2 N·m, about 2.3 N·m, about 2.4 N·m, about 2.5 N·m, about 2.6 N·m, about 2.7 N·m, about 2.8 N·m, about 2.9 N·m, about 3 N·m, about 3.1 N·m, about 3.2 N·m, about 3.3 N·m, about 3.4 N·m, about 3.5 N·m, about 3.6 N·m, about 3.7 N·m, about 3.8 N·m, about 3.9 N·m, about 4 N·m, about 4.1 N·m, about 4.2 N·m, about 4.3 N·m, about 4.4 N·m, about 4.5 N·m, about 4.6 N·m, about 4.7 N·m, about 4.8 N·m, about 4.9 N·m, about 5 N·m, about 5.1 N·m, about 5.2 N·m, about 5.3 N·m, about 5.4 N·m, about 5.5 N·m, about 5.6 N·m, about 5.7 N·m, about 5.8 N·m, about 5.9 N·m, about 6 N·m, about 6.1 N·m, about 6.2 N·m, about 6.3 N·m, about 6.4 N·m, about 6.5 N·m, about 6.6 N·m, about 6.7 N·m, about 6.8 N·m, about 6.9 N·m, about 7 N·m, about 7.1 N·m, about 7.2 N·m, about 7.3 N·m, about 7.4 N·m, about 7.5 N·m, about 7.6 N·m, about 7.7 N·m, about 7.8 N·m, about 7.9 N·m, about 8 N·m, about 8.1 N·m, about 8.2 N·m, about 8.3 N·m, about 8.4 N·m, about 8.5 N·m, about 8.6 N·m, about 8.7 N·m, about 8.8 N·m, about 8.9 N·m, about 9 N·m, about 9.1 N·m, about 9.2 N·m, about 9.3 N·m, about 9.4 N·m, about 9.5 N·m, about 9.6 N·m, about 9.7 N·m, about 9.8 N·m, about 9.9 N·m, or about 10 N·m). In some embodiments, applying torque, as herein described, compresses distal region 151 and central region 126 of device 100 expanding expandable body 130 by a displacement of from about 0.1 mm to about 10 mm (e.g., from about 0.1 mm to about 9 mm, from about 0.1 mm to about 8 mm, from about 0.1 mm to about 7 mm, from about 0.1 mm to about 6 mm, from about 0.1 mm to about 5 mm, from about 0.1 mm to about 4 mm, from about 0.1 mm to about 3 mm, from about 0.1 mm to about 2 mm, from about 0.1 mm to about 1 mm, about 0.1 mm, about 0.2 mm, about 0.3 mm, about 0.4 mm, about 0.5 mm, about 0.6 mm, about 0.7 mm, about 0.8 mm, about 0.9 mm, about 1 mm, about 1.1 mm, about 1.2 mm, about 1.3 mm, about 1.4 mm, about 1.5 mm, about 1.6 mm, about 1.7 mm, about 1.8 mm, about 1.9 mm, about 2 mm, about 2.1 mm, about 2.2 mm, about 2.3 mm, about 2.4 mm, about 2.5 mm, about 2.6 mm, about 2.7 mm, about 2.8 mm, about 2.9 mm, about 3 mm, about 3.1 mm, about 3.2 mm, about 3.3 mm, about 3.4 mm, about 3.5 mm, about 3.6 mm, about 3.7 mm, about 3.8 mm, about 3.9 mm, about 4 mm, about 4.1 mm, about 4.2 mm, about 4.3 mm, about 4.4 mm, about 4.5 mm, about 4.6 mm, about 4.7 mm, about 4.8 mm, about 4.9 mm, about 5 mm, about 5.1 mm, about 5.2 mm, about 5.3 mm, about 5.4 mm, about 5.5 mm, about 5.6 mm, about 5.7 mm, about 5.8 mm, about 5.9 mm, about 6 mm, about 6.1 mm, about 6.2 mm, about 6.3 mm, about 6.4 mm, about 6.5 mm, about 6.6 mm, about 6.7 mm, about 6.8 mm, about 6.9 mm, about 7 mm, about 7.1 mm, about 7.2 mm, about 7.3 mm, about 7.4 mm, about 7.5 mm, about 7.6 mm, about 7.7 mm, about 7.8 mm, about 7.9 mm, about 8 mm, about 8.1 mm, about 8.2 mm, about 8.3 mm, about 8.4 mm, about 8.5 mm, about 8.6 mm, about 8.7 mm, about 8.8 mm, about 8.9 mm, about 9 mm, about 9.1 mm, about 9.2 mm, about 9.3 mm, about 9.4 mm, about 9.5 mm, about 9.6 mm, about 9.7 mm, about 9.8 mm, about 9.9 mm, or about 10 mm). The extent of the displacement of expandable body 130 is determined by the number of openings 140, the slit width, and the magnitude of the torque applied to distal region 151 of device 100. In some embodiments, the displacement of expandable body 130 is determined by the amount of biomaterial required to be delivered to the bone.

Delivery of Biomaterial

Following expansion of device 100, 1100, 1200, or 1300 in the hole, biomaterial may be delivered to device 100, 1100, 1200, or 1300.

Following the expansion of expandable body 130, insertion tool 200, if used, is withdrawn from internal channel 190 of device 100 and expandable body 130 maintains an expanded configuration.

In some embodiments, biomaterial is delivered to device 100, 1100, 1200, or 1300 using a needle. In some embodiments the needle is a 14 to 27 gauge needle, e.g., an 18 or 20 gauge needle.

Alternatively, connector 400 is either connected to device 100, 1100, 1200, or 1300 for the first time, or kept fastened to internal channel 190 of device 100 at proximal region 101 and biomaterial dispenser 500 is coupled to the Luer-lock threads 415 of proximal region of connector 400. For example, a male Luer-lock plug of biomaterial dispenser 500 is fastened to the female Luer-lock threads. Subsequently, biomaterial 550 is uniformly delivered to the bone surrounding device 100 by flowing biomaterial 550 from biomaterial dispenser 500 (e.g., a syringe, a vial, a container, or a reservoir), through the internal channel of connector 400, through internal channel 190 of device 100, and to the bone via expandable body 130 (see, e.g., FIG. 65). In some embodiments, openings 188 disposed at distal region 151 of device 100 contribute to the delivery of biomaterial 550 to the bone. In some embodiments, biomaterial 550 is introduced at a flow rate of from about 0.5 ml/min to about 10 ml/min (e.g., about 0.5 ml/min, about 0.6 ml/min, about 0.7 ml/min, about 0.8 ml/min, about 0.9 ml/min, about 1 ml/min, about 1.1 ml/min, about 1.2 ml/min, about 1.3 ml/min, about 1.4 ml/min, about 1.5 ml/min, about 1.6 ml/min, about 1.7 ml/min, about 1.8 ml/min, about 1.9 ml/min, about 2 ml/min, about 2.1 ml/min, about 2.2 ml/min, about 2.3 ml/min, about 2.4 ml/min, about 2.5 ml/min, about 2.6 ml/min, about 2.7 ml/min, about 2.8 ml/min, about 2.9 ml/min, about 3 ml/min, about 3.1 ml/min, about 3.2 ml/min, about 3.3 ml/min, about 3.4 ml/min, about 3.5 ml/min, about 3.6 ml/min, about 3.7 ml/min, about 3.8 ml/min, about 3.9 ml/min, about 4 ml/min, about 4.1 ml/min, about 4.2 ml/min, about 4.3 ml/min, about 4.4 ml/min, about 4.5 ml/min, about 4.6 ml/min, about 4.7 ml/min, about 4.8 ml/min, about 4.9 ml/min, about 5 ml/min, about 5.1 ml/min, about 5.2 ml/min, about 5.3 ml/min, about 5.4 ml/min, about 5.5 ml/min, about 5.6 ml/min, about 5.7 ml/min, about 5.8 ml/min, about 5.9 ml/min, about 6 ml/min, about 6.1 ml/min, about 6.2 ml/min, about 6.3 ml/min, about 6.4 ml/min, about 6.5 ml/min, about 6.6 ml/min, about 6.7 ml/min, about 6.8 ml/min, about 6.9 ml/min, about 7 ml/min, about 7.1 ml/min, about 7.2 ml/min, about 7.3 ml/min, about 7.4 ml/min, about 7.5 ml/min, about 7.6 ml/min, about 7.7 ml/min, about 7.8 ml/min, about 7.9 ml/min, about 8 ml/min, about 8.1 ml/min, about 8.2 ml/min, about 8.3 ml/min, about 8.4 ml/min, about 8.5 ml/min, about 8.6 ml/min, about 8.7 ml/min, about 8.8 ml/min, about 8.9 ml/min, about 9 ml/min, about 9.1 ml/min, about 9.2 ml/min, about 9.3 ml/min, about 9.4 ml/min, about 9.5 ml/min, about 9.6 ml/min, about 9.7 ml/min, about 9.8 ml/min, about 9.9 ml/min, or about 10 ml/min). In some embodiments, the volume of biomaterial introduced to the bone is from about 1 ml to about 20 ml (e.g., from about 1 ml to about 2 ml, from about 1 ml to about 3 ml, from about 1 ml to about 4 ml, from about 1 ml to about 5 ml, from about 1 ml to about 10 ml, from about 5 ml to about 10 ml, from about 5 ml to about 15 ml, from about 10 ml to about 15 ml, from about 15 ml to about 20 ml, from about 15 ml to about 20 ml, about 1 ml, about 1.1 ml, about 1.2 ml, about 1.3 ml, about 1.4 ml, about 1.5 ml, about 1.6 ml, about 1.7 ml, about 1.8 ml, about 1.9 ml, about 2 ml, about 2.1 ml, about 2.2 ml, about 2.3 ml, about 2.4 ml, about 2.5 ml, about 2.6 ml, about 2.7 ml, about 2.8 ml, about 2.9 ml, about 3 ml, about 3.1 ml, about 3.2 ml, about 3.3 ml, about 3.4 ml, about 3.5 ml, about 3.6 ml, about 3.7 ml, about 3.8 ml, about 3.9 ml, about 4 ml, about 4.1 ml, about 4.2 ml, about 4.3 ml, about 4.4 ml, about 4.5 ml, about 4.6 ml, about 4.7 ml, about 4.8 ml, about 4.9 ml, about 5 ml, about 5.1 ml, about 5.2 ml, about 5.3 ml, about 5.4 ml, about 5.5 ml, about 5.6 ml, about 5.7 ml, about 5.8 ml, about 5.9 ml, about 6 ml, about 6.1 ml, about 6.2 ml, about 6.3 ml, about 6.4 ml, about 6.5 ml, about 6.6 ml, about 6.7 ml, about 6.8 ml, about 6.9 ml, about 7 ml, about 7.1 ml, about 7.2 ml, about 7.3 ml, about 7.4 ml, about 7.5 ml, about 7.6 ml, about 7.7 ml, about 7.8 ml, about 7.9 ml, about 8 ml, about 8.1 ml, about 8.2 ml, about 8.3 ml, about 8.4 ml, about 8.5 ml, about 8.6 ml, about 8.7 ml, about 8.8 ml, about 8.9 ml, about 9 ml, about 9.1 ml, about 9.2 ml, about 9.3 ml, about 9.4 ml, about 9.5 ml, about 9.6 ml, about 9.7 ml, about 9.8 ml, about 9.9 ml, about 10 ml, about 11 ml, about 11.1 ml, about 11.2 ml, about 11.3 ml, about 11.4 ml, about 11.5 ml, about 11.6 ml, about 11.7 ml, about 11.8 ml, about 11.9 ml, about 12 ml, about 12.1 ml, about 12.2 ml, about 12.3 ml, about 12.4 ml, about 12.5 ml, about 12.6 ml, about 12.7 ml, about 12.8 ml, about 12.9 ml, about 13 ml, about 13.1 ml, about 13.2 ml, about 13.3 ml, about 13.4 ml, about 13.5 ml, about 13.6 ml, about 13.7 ml, about 13.8 ml, about 13.9 ml, about 14 ml, about 14.1 ml, about 14.2 ml, about 14.3 ml, about 14.4 ml, about 14.5 ml, about 14.6 ml, about 14.7 ml, about 14.8 ml, about 14.9 ml, about 15 ml, about 15.1 ml, about 15.2 ml, about 15.3 ml, about 15.4 ml, about 15.5 ml, about 15.6 ml, about 15.7 ml, about 15.8 ml, about 15.9 ml, about 16 ml, about 16.1 ml, about 16.2 ml, about 16.3 ml, about 16.4 ml, about 16.5 ml, about 16.6 ml, about 16.7 ml, about 16.8 ml, about 16.9 ml, about 17 ml, about 17.1 ml, about 17.2 ml, about 17.3 ml, about 17.4 ml, about 17.5 ml, about 17.6 ml, about 17.7 ml, about 17.8 ml, about 17.9 ml, about 18 ml, about 18.1 ml, about 18.2 ml, about 18.3 ml, about 18.4 ml, about 18.5 ml, about 18.6 ml, about 18.7 ml, about 18.8 ml, about 18.9 ml, about 19 ml, about 19.1 ml, about 19.2 ml, about 19.3 ml, about 19.4 ml, about 19.5 ml, about 19.6 ml, about 19.7 ml, about 19.8 ml, about 19.9 ml, or about 20 ml). In some embodiments, biomaterial 550 hardens or solidifies after from about 60 s to about 600 s (e.g., about 60 s, about 70 s, about 80 s, about 90 s, about 100s, about 110s, about 120 s, about 130 s, about 140 s, about 150s, about 160 s, about 170s, about 180 s, about 190 s, about 200 s, about 210 s, about 220 s, about 230 s, about 240 s, about 250 s, about 260s, about 270s, about 280s, about 290s, about 300s, about 310s, about 320s, about 330s, about 340s, about 350s, about 360s, about 370s, about 380s, about 390s, about 400s, about 410s, about 420 s, about 430 s, about 440 s, about 450 s, about 460 s, about 470 s, about 480 s, about 490 s, about 500s, about 510s, about 520 s, about 530 s, about 540 s, about 550s, about 560s, about 570 s, about 580 s, about 590 s, or about 600 s) of being introduced into the bone. In some embodiments, the hardening of biomaterial 550 secures device 100 to the bone.

In some embodiments, biomaterial 550 is expelled or distributed through expandable body 130 by inserting screw 600 extending the length of internal channel 190 of device 100. In some embodiments, a distal end of screw 600 is fastened to the bone cortex distally disposed from distal region 151 of device 100. In some embodiments, tightening screw 600 in the distal bone cortex causes bone compression (e.g., when used in combination with a bone plate or a washer to apply pressure to the bone cortex opposite of the screw tip). In some embodiments, inserting screw 600 promotes the uniform distribution of biomaterial 550 throughout device 100 and into the bone surrounding device 100.

Securing a Bone Plate to the Bone

Device 100, 1100, 1200, or 1300 can also be used to secure bone plate 800 to the bone. In some embodiments, bone plate 800 is secured to the bone by inserting screw 600 through hole 850 of bone plate 800 and into an internal channel (e.g., internal channel 190 of device 100) using any suitable screw driving tool known in the art. Afterwards, the distal end of screw 600 is fastened to the cortex distally disposed from a distal region of device 100, 1100, 1200, or 1300 (e.g., distal region 151 of device 100). In some embodiments, bone plate 800 includes two or more bone plate holes 850. In some embodiments, bone plate 800 is secured by using more than one of device 100, 1100, 1200, or 1300. Typically, one of device 100, 1100, 1200, or 1300 is inserted into each bone plate hole 850 (e.g., when a 4-hole bone plate is used, four devices are inserted into the bone, one in each bone plate hole 850). Alternatively, two or more bone plate holes at each end of the bone plate may be secured to bone using device 100, 1100, 1200, or 1300 (e.g., a bone plate with 5 holes can be secured to bone by placing device 100, 1100, 1200, or 1300 at the first hole and a second of device 100, 1100, 1200, or 1300 at a fifth hole opposite the first hole). Device 100, 1100, 1200, or 1300 may also be used to secure a bone plate to bone unilaterally, e.g., by referencing the midpoint of the plate length. Bone plate 800 includes at least one hole providing access to an internal channel of device 100, 1100, 1200, or 1300 (e.g., internal channel 190 of device 100; see, e.g., FIG. 13B). In some embodiments, securing bone plate 800 to bone further involves placing washer 700 into an internal channel of device 100, 1100, 1200, or 1300 (e.g., internal channel 190 at proximal region 101 of device 100), which can facilitate bone compression.

Securing the Device to the Bone Using a Washer

The methods described herein may also involve the use of washer 700 placed into a proximal region of device 100, 1100, 1200, or 1300 (e.g., proximal region 101 of device 100). Washer 700 can be inserted into device 100, 1100, 1200, or 1300 prior to insertion of screw 600 through an internal channel (e.g., internal channel 190 of device 100). After placement of washer 700 into device 100, 1100, 1200, or 1300, screw 600 can be inserted through the interior channel (e.g., internal channel 190 of device 100) and the distal tip of screw 600 can be fastened to the distal bone cortex until screw head 675 presses against the internal channel of washer 700, thereby securing washer 700 and device 100, 1100, 1200, or 1300 to the bone. The use of washer 700 may also improve bone compression, if desired.

Insertion of the Device Using the System

Device 100 may also be inserted into bone using system 1000, as described herein. Prior to engaging insertion tool 200 with device 100, the method includes assembling the components of system 1000, including device 100, insertion tool 200, pusher 300, and connector 400, as herein described (see, e.g., FIG. 18A). First pusher 300, having proximal region 310 and distal region 320, is connected to insertion tool 200 by threading the threaded internal channel of pusher 300 along shaft 245 of distal region 240 of insertion tool 200 until the threaded internal channel of pusher 300 engages the second set of external threads 260 of insertion tool 200 and until proximal region of pusher 300 is adjacent to central region 220 of insertion tool 200. Then the internal channel of connector 400 is slid along shaft 245 of distal region 240 of insertion tool 200 until connector 400 overlaps with unthreaded region 270 of distal region 240 of insertion tool 200, in which connector 400 is positioned distal to pusher 300. Afterwards, shaft 245 of distal region 240 of insertion tool 200 is inserted through internal channel 190 of device 100 until the first set of threads of insertion tool 200 engage internal threads 160 of distal region 151 of device 100.

Following assembly of the system, device 100 can be inserted into the bone by twisting handle 215 of the insertion device until device 100 is fully inserted into the bone. Thereafter, connector 400 can be inserted into internal channel 190 of proximal region 101 of device 100 by twisting handle 315 of pusher 300 until distal region 320 of pusher 300 engages proximal region of connector 400. Twisting pusher 300 translates pusher 300 along shaft 245 of insertion tool 200, causing pusher 300 to push connector 400 along shaft 245 of distal region 240 of insertion tool 200 until distal region 430 of connector 400 engages internal channel 190 of proximal region 101 of device 100.

The method further includes securing proximal region 101 of device 100 to the bone using the system as herein described. Securing proximal region 101 of device 100 in bone hole 875, in some embodiments, includes expanding and friction fitting proximal end 106 of wings 105 disposed at proximal region 101 of device 100 upon placing device 100 in the hole. In some embodiments, proximal end 106 of wings 105 is deployed and expanded outwardly from proximal region 101 of device 100 by inserting and fastening connector 400 into internal channel 190 of device 100 at proximal region 101. In some embodiments, connector 400 is engaged to internal channel 190 of device 100 at proximal region 101 by pressing distal region 430 of connector 400 into internal channel 190 of device 100 at proximal region 101. Connector 400 is engaged to internal channel 190 of proximal region 101 of device 100, by twisting handle 315 of pusher 300 in a first direction (e.g., clockwise) until distal region 320 of pusher 300 engages proximal region of connector 400. In general, twisting pusher 300 handle translates connector 400 along shaft 245 of distal region 240 of insertion tool 200 until distal region 430 of connector 400 engages internal channel 190 of proximal region 101 of device 100.

Connector 400 includes a plurality of wedges 440 that are configured to interconnect with the plurality of wings 105 of proximal region 101 of device 100. Wedges 440 on distal region 430 of connector 400 are configured to expand proximal end 106 of wings 105 into the cortical bone upon insertion into proximal region 101 of device 100, thereby rotationally anchoring proximal region 101 of device 100, which allows distal region 151 and central region 126 of device 100 to rotate independently from proximal region 101.

Connector 400 may also include alignment marker 420, which can be used to align connector 400 with device 100. Device 100 may also include alignment marker 125. If both device 100 and connector 400 include alignment markers, they can be used to ensure proper alignment of device 100 with connector 400 to facilitate the fastening of connector 400 to internal channel 190 of device 100 at proximal region 101.

In some embodiments, proximal region 101 of device 100 is fastened to distal region 430 of connector 400 prior to insertion into the bone. In some embodiments, bone plate 800 is included in the insertion process by 1) passing device 100 fastened to connector 400 through bone plate 800 hole and 2) securing connector 400 to bone plate 800 by pressing circumferential groove 470 of connector 400 into bone plate 800 hole (see, e.g., FIG. 54). In some embodiments, proximal end 106 of wings 105 of proximal region 101 of device 100 reversibly deflects toward proximal region 101 when placing device 100 in bone hole 875 and/or in hole 850 of bone plate 800. In some embodiments, proximal end 106 of wings 105 returns to the starting protruded configuration after insertion of device 100 in the bone (see, e.g., FIGS. 71 and 73A-73B).

Securing proximal region 101 of device 100 in the hole rotationally anchors proximal region 101 of device 100 in the hole allowing distal region 151 and central region 126 of device 100 to rotate and deflect independently of proximal region 101.

Radial Expansion of the Expandable Body of the Device Using the System

To expand expandable body 130 of device 100 proximal region 101 is first rotationally anchored to bone, e.g., by using pusher 300 and connector. Then, insertion tool 200 is twisted in a first direction (e.g., clockwise) and the twisting of insertion tool 200, when engaged with device 100, applies a torque to distal region 151 of device 100. In some embodiments, the torque applied is from about 0.1 N·m to about 10 N·m (e.g., from about 0.1 N·m to about 9 N·m, from about 0.1 N·m to about 8 N·m, from about 0.1 N·m to about 7 N·m, from about 0.1 N·m to about 6 N·m, from about 0.1 N·m to about 5 N·m, from about 0.1 N·m to about 4 N·m, from about 0.1 N·m to about 3 N·m, from about 0.1 N·m to about 2 N·m, from about 0.1 N·m to about 1 N·m, about 0.1 N·m, about 0.2 N·m, about 0.3 N·m, about 0.4 N·m, about 0.5 N·m, about 0.6 N·m, about 0.7 N·m, about 0.8 N·m, about 0.9 N·m, about 1 N·m, about 1.1 N·m, about 1.2 N·m, about 1.3 N·m, about 1.4 N·m, about 1.5 N·m, about 1.6 N·m, about 1.7 N·m, about 1.8 N·m, about 1.9 N·m, about 2 N·m, about 2.1 N·m, about 2.2 N·m, about 2.3 N·m, about 2.4 N·m, about 2.5 N·m, about 2.6 N·m, about 2.7 N·m, about 2.8 N·m, about 2.9 N·m, about 3 N·m, about 3.1 N·m, about 3.2 N·m, about 3.3 N·m, about 3.4 N·m, about 3.5 N·m, about 3.6 N·m, about 3.7 N·m, about 3.8 N·m, about 3.9 N·m, about 4 N·m, about 4.1 N·m, about 4.2 N·m, about 4.3 N·m, about 4.4 N·m, about 4.5 N·m, about 4.6 N·m, about 4.7 N·m, about 4.8 N·m, about 4.9 N·m, about 5 N·m, about 5.1 N·m, about 5.2 N·m, about 5.3 N·m, about 5.4 N·m, about 5.5 N·m, about 5.6 N·m, about 5.7 N·m, about 5.8 N·m, about 5.9 N·m, about 6 N·m, about 6.1 N·m, about 6.2 N·m, about 6.3 N·m, about 6.4 N·m, about 6.5 N·m, about 6.6 N·m, about 6.7 N·m, about 6.8 N·m, about 6.9 N·m, about 7 N·m, about 7.1 N·m, about 7.2 N·m, about 7.3 N·m, about 7.4 N·m, about 7.5 N·m, about 7.6 N·m, about 7.7 N·m, about 7.8 N·m, about 7.9 N·m, about 8 N·m, about 8.1 N·m, about 8.2 N·m, about 8.3 N·m, about 8.4 N·m, about 8.5 N·m, about 8.6 N·m, about 8.7 N·m, about 8.8 N·m, about 8.9 N·m, about 9 N·m, about 9.1 N·m, about 9.2 N·m, about 9.3 N·m, about 9.4 N·m, about 9.5 N·m, about 9.6 N·m, about 9.7 N·m, about 9.8 N·m, about 9.9 N·m, or about 10 N·m). In some embodiments, applying torque, as herein described, compresses distal region 151, thereby causing expandable body 130 of central region 126 of device 100 to expand by a displacement of from about 0.1 mm to about 10 mm (e.g., from about 0.1 mm to about 9 mm, from about 0.1 mm to about 8 mm, from about 0.1 mm to about 7 mm, from about 0.1 mm to about 6 mm, from about 0.1 mm to about 5 mm, from about 0.1 mm to about 4 mm, from about 0.1 mm to about 3 mm, from about 0.1 mm to about 2 mm, from about 0.1 mm to about 1 mm, about 0.1 mm, about 0.2 mm, about 0.3 mm, about 0.4 mm, about 0.5 mm, about 0.6 mm, about 0.7 mm, about 0.8 mm, about 0.9 mm, about 1 mm, about 1.1 mm, about 1.2 mm, about 1.3 mm, about 1.4 mm, about 1.5 mm, about 1.6 mm, about 1.7 mm, about 1.8 mm, about 1.9 mm, about 2 mm, about 2.1 mm, about 2.2 mm, about 2.3 mm, about 2.4 mm, about 2.5 mm, about 2.6 mm, about 2.7 mm, about 2.8 mm, about 2.9 mm, about 3 mm, about 3.1 mm, about 3.2 mm, about 3.3 mm, about 3.4 mm, about 3.5 mm, about 3.6 mm, about 3.7 mm, about 3.8 mm, about 3.9 mm, about 4 mm, about 4.1 mm, about 4.2 mm, about 4.3 mm, about 4.4 mm, about 4.5 mm, about 4.6 mm, about 4.7 mm, about 4.8 mm, about 4.9 mm, about 5 mm, about 5.1 mm, about 5.2 mm, about 5.3 mm, about 5.4 mm, about 5.5 mm, about 5.6 mm, about 5.7 mm, about 5.8 mm, about 5.9 mm, about 6 mm, about 6.1 mm, about 6.2 mm, about 6.3 mm, about 6.4 mm, about 6.5 mm, about 6.6 mm, about 6.7 mm, about 6.8 mm, about 6.9 mm, about 7 mm, about 7.1 mm, about 7.2 mm, about 7.3 mm, about 7.4 mm, about 7.5 mm, about 7.6 mm, about 7.7 mm, about 7.8 mm, about 7.9 mm, about 8 mm, about 8.1 mm, about 8.2 mm, about 8.3 mm, about 8.4 mm, about 8.5 mm, about 8.6 mm, about 8.7 mm, about 8.8 mm, about 8.9 mm, about 9 mm, about 9.1 mm, about 9.2 mm, about 9.3 mm, about 9.4 mm, about 9.5 mm, about 9.6 mm, about 9.7 mm, about 9.8 mm, about 9.9 mm, or about 10 mm). The extent of the displacement of expandable body 130 is determined by the number of openings 140, the slit width, and the magnitude of the torque applied to distal region 151 of device 100. In some embodiments, the displacement of expandable body 130 is determined by the amount of biomaterial required to be delivered to the bone.

Following the expansion of expandable body 130, pusher 300 is decoupled from connector 400 by twisting pusher 300 in a second direction (e.g., counterclockwise) until pusher 300 retreats to the starting position (e.g., where handle 315 of pusher 300 engages central region 220 of insertion tool 200). Then, insertion tool 200 is twisted in a second direction (e.g., counterclockwise) until external threads 250 of insertion tool 200 are unthreaded from internal threads 160 of device 100. In some embodiments, expandable body 130 maintains an expanded form after the uncoupling of pusher 300 and insertion tool from device 100. In some embodiments, the first direction is clockwise, and the second direction is counterclockwise. In some embodiments, the first direction is counterclockwise, and the second direction is clockwise.

Delivery of Biomaterial Using the System and/or the Connector

Delivery of biomaterial 550 includes keeping connector 400 fastened to internal channel 190 of device 100 at proximal region 101 after uncoupling pusher 300 and insertion tool from device 100. Alternatively, connector 400 can be engaged with device 100 independent of the use of system 1000.

Biomaterial dispenser 500 can be coupled to Luer-lock threads 415 of proximal region 410 of connector 400. For example, a male Luer-lock plug of biomaterial dispenser 500 is fastened to the female Luer-lock threads. Subsequently, biomaterial 550 is uniformly delivered to the bone surrounding device 100 by flowing biomaterial 550 from biomaterial dispenser 500 along, e.g., tube 525 (which can be part of, for example, a syringe, a vial, a container, or a reservoir), through internal channel 480 of connector 400 and internal channel 190 of device 100 until biomaterial 550 enters expandable body 130 and flows into the bone. In some embodiments, openings 188 disposed at distal region 151 of device 100 contribute to the delivery of biomaterial 550 to the bone. In some embodiments, biomaterial 550 is introduced at a flow rate of from about 0.5 ml/min to about 10 ml/min (e.g., about 0.5 ml/min, about 0.6 ml/min, about 0.7 ml/min, about 0.8 ml/min, about 0.9 ml/min, about 1 ml/min, about 1.1 ml/min, about 1.2 ml/min, about 1.3 ml/min, about 1.4 ml/min, about 1.5 ml/min, about 1.6 ml/min, about 1.7 ml/min, about 1.8 ml/min, about 1.9 ml/min, about 2 ml/min, about 2.1 ml/min, about 2.2 ml/min, about 2.3 ml/min, about 2.4 ml/min, about 2.5 ml/min, about 2.6 ml/min, about 2.7 ml/min, about 2.8 ml/min, about 2.9 ml/min, about 3 ml/min, about 3.1 ml/min, about 3.2 ml/min, about 3.3 ml/min, about 3.4 ml/min, about 3.5 ml/min, about 3.6 ml/min, about 3.7 ml/min, about 3.8 ml/min, about 3.9 ml/min, about 4 ml/min, about 4.1 ml/min, about 4.2 ml/min, about 4.3 ml/min, about 4.4 ml/min, about 4.5 ml/min, about 4.6 ml/min, about 4.7 ml/min, about 4.8 ml/min, about 4.9 ml/min, about 5 ml/min, about 5.1 ml/min, about 5.2 ml/min, about 5.3 ml/min, about 5.4 ml/min, about 5.5 ml/min, about 5.6 ml/min, about 5.7 ml/min, about 5.8 ml/min, about 5.9 ml/min, about 6 ml/min, about 6.1 ml/min, about 6.2 ml/min, about 6.3 ml/min, about 6.4 ml/min, about 6.5 ml/min, about 6.6 ml/min, about 6.7 ml/min, about 6.8 ml/min, about 6.9 ml/min, about 7 ml/min, about 7.1 ml/min, about 7.2 ml/min, about 7.3 ml/min, about 7.4 ml/min, about 7.5 ml/min, about 7.6 ml/min, about 7.7 ml/min, about 7.8 ml/min, about 7.9 ml/min, about 8 ml/min, about 8.1 ml/min, about 8.2 ml/min, about 8.3 ml/min, about 8.4 ml/min, about 8.5 ml/min, about 8.6 ml/min, about 8.7 ml/min, about 8.8 ml/min, about 8.9 ml/min, about 9 ml/min, about 9.1 ml/min, about 9.2 ml/min, about 9.3 ml/min, about 9.4 ml/min, about 9.5 ml/min, about 9.6 ml/min, about 9.7 ml/min, about 9.8 ml/min, about 9.9 ml/min, or about 10 ml/min). In some embodiments, the volume of biomaterial introduced to the bone is from about 1 ml to about 20 ml (e.g., from about 1 ml to about 2 ml, from about 1 ml to about 3 ml, from about 1 ml to about 4 ml, from about 1 ml to about 5 ml, from about 1 ml to about 10 ml, from about 5 ml to about 10 ml, from about 5 ml to about 15 ml, from about 10 ml to about 15 ml, from about 15 ml to about 20 ml, from about 15 ml to about 20 ml, about 1 ml, about 1.1 ml, about 1.2 ml, about 1.3 ml, about 1.4 ml, about 1.5 ml, about 1.6 ml, about 1.7 ml, about 1.8 ml, about 1.9 ml, about 2 ml, about 2.1 ml, about 2.2 ml, about 2.3 ml, about 2.4 ml, about 2.5 ml, about 2.6 ml, about 2.7 ml, about 2.8 ml, about 2.9 ml, about 3 ml, about 3.1 ml, about 3.2 ml, about 3.3 ml, about 3.4 ml, about 3.5 ml, about 3.6 ml, about 3.7 ml, about 3.8 ml, about 3.9 ml, about 4 ml, about 4.1 ml, about 4.2 ml, about 4.3 ml, about 4.4 ml, about 4.5 ml, about 4.6 ml, about 4.7 ml, about 4.8 ml, about 4.9 ml, about 5 ml, about 5.1 ml, about 5.2 ml, about 5.3 ml, about 5.4 ml, about 5.5 ml, about 5.6 ml, about 5.7 ml, about 5.8 ml, about 5.9 ml, about 6 ml, about 6.1 ml, about 6.2 ml, about 6.3 ml, about 6.4 ml, about 6.5 ml, about 6.6 ml, about 6.7 ml, about 6.8 ml, about 6.9 ml, about 7 ml, about 7.1 ml, about 7.2 ml, about 7.3 ml, about 7.4 ml, about 7.5 ml, about 7.6 ml, about 7.7 ml, about 7.8 ml, about 7.9 ml, about 8 ml, about 8.1 ml, about 8.2 ml, about 8.3 ml, about 8.4 ml, about 8.5 ml, about 8.6 ml, about 8.7 ml, about 8.8 ml, about 8.9 ml, about 9 ml, about 9.1 ml, about 9.2 ml, about 9.3 ml, about 9.4 ml, about 9.5 ml, about 9.6 ml, about 9.7 ml, about 9.8 ml, about 9.9 ml, about 10 ml, about 11 ml, about 11.1 ml, about 11.2 ml, about 11.3 ml, about 11.4 ml, about 11.5 ml, about 11.6 ml, about 11.7 ml, about 11.8 ml, about 11.9 ml, about 12 ml, about 12.1 ml, about 12.2 ml, about 12.3 ml, about 12.4 ml, about 12.5 ml, about 12.6 ml, about 12.7 ml, about 12.8 ml, about 12.9 ml, about 13 ml, about 13.1 ml, about 13.2 ml, about 13.3 ml, about 13.4 ml, about 13.5 ml, about 13.6 ml, about 13.7 ml, about 13.8 ml, about 13.9 ml, about 14 ml, about 14.1 ml, about 14.2 ml, about 14.3 ml, about 14.4 ml, about 14.5 ml, about 14.6 ml, about 14.7 ml, about 14.8 ml, about 14.9 ml, about 15 ml, about 15.1 ml, about 15.2 ml, about 15.3 ml, about 15.4 ml, about 15.5 ml, about 15.6 ml, about 15.7 ml, about 15.8 ml, about 15.9 ml, about 16 ml, about 16.1 ml, about 16.2 ml, about 16.3 ml, about 16.4 ml, about 16.5 ml, about 16.6 ml, about 16.7 ml, about 16.8 ml, about 16.9 ml, about 17 ml, about 17.1 ml, about 17.2 ml, about 17.3 ml, about 17.4 ml, about 17.5 ml, about 17.6 ml, about 17.7 ml, about 17.8 ml, about 17.9 ml, about 18 ml, about 18.1 ml, about 18.2 ml, about 18.3 ml, about 18.4 ml, about 18.5 ml, about 18.6 ml, about 18.7 ml, about 18.8 ml, about 18.9 ml, about 19 ml, about 19.1 ml, about 19.2 ml, about 19.3 ml, about 19.4 ml, about 19.5 ml, about 19.6 ml, about 19.7 ml, about 19.8 ml, about 19.9 ml, or about 20 ml). In some embodiments, biomaterial 550 hardens or solidifies after from about 60 s to about 600 s (e.g., about 60 s, about 70 s, about 80 s, about 90 s, about 100 s, about 110 s, about 120 s, about 130 s, about 140 s, about 150 s, about 160 s, about 170 s, about 180 s, about 190 s, about 200 s, about 210 s, about 220 s, about 230 s, about 240 s, about 250 s, about 260 s, about 270 s, about 280 s, about 290 s, about 300 s, about 310 s, about 320 s, about 330 s, about 340 s, about 350 s, about 360 s, about 370 s, about 380 s, about 390 s, about 400 s, about 410 s, about 420 s, about 430 s, about 440s, about 450 s, about 460 s, about 470 s, about 480 s, about 490 s, about 500 s, about 510 s, about 520 s, about 530 s, about 540 s, about 550 s, about 560 s, about 570 s, about 580 s, about 590 s, or about 600 s) of being introduced into the bone. In some embodiments, the hardening of biomaterial 550 secures device 100 to the bone.

In some embodiments, biomaterial 550 is expelled through expandable body 130 by inserting screw 600 extending the length of internal channel 190 of device 100. In some embodiments, a distal end of screw 600 is fastened to the bone cortex distally disposed from distal region 151 of device 100. In some embodiments, tightening screw 600 in the distal bone cortex causes bone compression. In some embodiments, inserting screw 600 promotes the uniform distribution of biomaterial 550 throughout device 100 and into the bone surrounding device 100.

Extraction of Device

The methods of bone repair may, in some cases, require removal of device 100, 1100, 1200, or 1300 after insertion. In such cases, device 100, 1100, 1200, or 1300 can be removed using extraction tool 900, as described herein.

For example, the extraction tool can be used to remove device 100 from bone by inserting the distal region of extraction tool 900 into internal channel 190 of device 100, followed by engaging the pair of nubs 935 of extraction tool 900 with the notches 183, elongated slits 185 (see, e.g., FIG. 43), or openings 188 (see, e.g., FIG. 23 and FIG. 24A) of distal region 151 of device 100. If necessary, the method may include first removing screw 600 from device 100 prior to inserting extraction tool 900 into device 100. Extracting device 100 includes the step of twisting extraction tool 900 clockwise to remove device 100 (e.g., to unthread or release device 100) from the bone. Extraction tool 900 may also be used to remove device 100 from bone by twisting in a counterclockwise direction. The direction of twisting may depend upon whether device 100 includes exterior threads (e.g., at the distal end) and, if so, the twisting may depend upon the orientation of the threads of device 100.

Fabrication of the Device

Device 100, 1100, 1200, or 1300 may be fabricated as a unitary body or as separate parts subsequently combined to form device 100, 1100, 1200, or 1300 (e.g., proximal region 101, central region 126, and distal region 151 of device 100 may be manufactured separately and later combined to form the unitary body).

Device 100, 1100, 1200, or 1300 can be fabricated using, for example, additive manufacturing techniques. Device 100, 1100, 1200, or 1300 may also be fabricated using laser cutting and wire electrical discharge machining (EDM). When device 100, 1100, 1200, or 1300 is composed of a metal or metal alloy material, a four axis CNC lathe or a Swiss lathe system may be used to fabricate device 100, 1100, 1200, or 1300 from solid or tubular stock material. When device 100, 1100, 1200, or 1300 is composed of a non-metallic material, molding or additive manufacturing may be used. For example, device 100, 1100, 1200, or 1300 could be manufactured using 3D printing techniques and materials (see, e.g., Dhandapani et al., Bioact. Mater. 5:458-467, 2020 (incorporated herein by reference)), e.g., 3D printing using coral-cultured powder (calcium carbonate).

Proximal region 101 of device 100 may be cut to produce the plurality of wings 105 disposed therein. Wings 105 may also be produced by removing material from proximal region 101 of device 100 by a laser cutting machine, a cutting wire, a water-jet machine, or a lathe or milling machine. In some embodiments, the material removed from proximal region 101 is shaped as linear slits. In some embodiments, the linear slits produced by removing material from proximal region 101 of device 100 have a slit width of from about 0.1 mm to about 0.2 mm. Similar methods could be used to manufacture wings for device 1100, 1200, and 1300.

Insertion tool 200, pusher 300, connector 400, and extraction tool 900 may all be fabricated using standard CNC lathe milling, gun drilling, and/or molded handle type technologies known in the art. Extraction tool 900 may be milled or EDM machined as separate components (e.g., each member separately fabricated) and subsequently joined.

Kits

The disclosure also provides kits that include the device alone or the device with one or more of the components described herein (e.g., one or more of the components of the system described herein). For example, the kit may include device 100, 1100, 1200, or 1300, and one or more of insertion tool 200, extraction tool 900, pusher 300, connector 400, washer 700, bone plate 800, screw 600, and biomaterial 550, as herein described. The kit may also include a biomaterial dispenser (e.g., as a single unit or one or more components thereof, such as tubing and/or connection materials (e.g., pumps, reservoirs, syringes, vials, etc.)). The kit may also include a biomaterial, either in ready to use form or in a container ready to be prepared for use. The biomaterial may be provided as a prefilled container as part of a biomaterial dispenser. In some embodiments, the kit may include funnel 1400. In some embodiments, the kit may include device 100, 1100, 1200, or 1200 pre-loaded into funnel 1400.

The kit may also include any of the components described above, each in a quantity of 1 to 100 (e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100). One or more of the components of the kit may be supplied in sterile condition. The kit may also include a package insert that instructs a user of the kit, such as a physician, to perform the methods disclosed herein. The devices described herein can also be sterilized prior to use in a method of bone repair, as needed.

EXAMPLES

The following examples are put forth so as to provide those of ordinary skill in the art with a description of how the compositions and methods described herein may be used, made, and evaluated, and are intended to be purely exemplary of the disclosure and are not intended to limit the scope of what the inventors regard as their invention.

Example 1. Effect of Central Region Configuration on the Displacement of the Expandable Body Determination of expandable body displacement relative to number of central region openings 140 and opening width was performed using computer modeling. Furthermore, the effect of longitudinal grooves 150 on expandable body displacement was also characterized. First, a device having proximal region 101, central region 126, and distal region 151 underwent rotational fixation at proximal region 101 of device 100 (see, e.g., FIG. 25A-25B). Anchoring proximal region 101 promotes independent rotational motion of the distal and central regions of device 100 relative to proximal region 101. The displacement was determined by calculating the difference in the width of expandable body 130 before (see, e.g., FIG. 25A) and after (see, e.g., FIG. 25B) expanding expandable body 130. A torque of 0.1 N·m was applied to distal region 151 of a device (see, e.g., FIG. 25B) containing two helical openings 140 and a displacement of 2.809 mm was measured.

Furthermore, the effect of incorporating longitudinal grooves 150 in expandable body 130 was determined by applying a torque of 5 N·m to a device having longitudinal grooves 150 and comparing the displacement of expandable body 130 in response to the torque to the displacement of a device devoid of longitudinal grooves 150 in response to an equal torque. Greater displacement was observed in device 100 containing longitudinal grooves 150, with a measured displacement of 5.092 mm (see, e.g., FIG. 26B), compared to device 100 devoid of longitudinal grooves 150, with a measured displacement of 5.048 mm (see, e.g., FIG. 26A).

Next, the effect of expandable body opening size and number on the displacement was determined. Torque of 0.1 N·m was applied to all devices studied. In a device with four helical openings 140 and an opening width of 0.75 mm (see, e.g., FIGS. 27A-27B) a displacement of 3.894 mm was observed. In a device with six helical openings 140 and an opening width of 0.5 mm (see, e.g., FIGS. 28A-28B) a displacement of 3.964 mm was observed. In a device with twelve helical openings 140 and an opening width of 0.25 mm (see, e.g., FIGS. 29A-29B) a displacement of 4.065 mm was observed.

Finally, a comparison between a device having two helical openings 140 and a device having twelve helical openings 140 in expandable body 130 was performed. Torque of 5 N·m was applied to both devices (see, e.g., FIGS. 30A-30B). Device 100 with twelve helical openings 140 and an opening width of 0.25 mm had a displacement of 5.348 mm while device 100 with two helical openings 140 and an opening width of 1.5 mm had a displacement of 5.092 mm.

Example 2. Treatment of a Tibial Oblique Fracture with a Bone Plate

The devices, systems, and methods herein described may be used to treat a tibial shaft fracture, including device 100, 1100, 1200, or 1300.

For example, a surgeon treats a patient with an oblique diaphyseal tibial fracture, diagnosed using X-ray radiography, using device 100 and system 1000 as herein described. The fracture site is first prepared for implantation of a pre-contoured bone plate having from one to ten bone plate holes 850. The desired number of holes is to be drilled into the two main fracture fragments of the tibia (such as, e.g., five holes on each fragment if ten holes are used). One of device 100, as herein described, is prepared to be implanted into each of bone hole. Each of device 100 has proximal region 101, distal region 151, and expandable body 130 disposed therebetween. Furthermore, each of device 100 has internal threads at distal region 151, expandable body 130 with four helical slits, and proximal region 101 with six wings 105.

System 1000, described herein, may be used to insert device 100 into the bone. System 1000 may include connector 400 having circumferential groove 470 and insertion tool 200 (see, e.g., FIG. 55), which are connected to pusher 300 (see, e.g., FIGS. 18A and FIGS. 56-57). Each of device 100 is to be implanted into bone hole 875 according to the following sequence. First, insertion tool 200 is connected to a first of device 100 to be implanted. Insertion tool 200 is connected to device 100 by first inserting distal region 240 through the internal channel of connector 400 and then by threading external threads 250 of insertion tool 200 into internal threads 160 of device 100 (see, e.g., FIG. 18B). Device 100 is then completely inserted into bone hole 875 (see, e.g., FIG. 61). Connector 400 is then pushed into internal channel 190 of device 100 with pusher 300, by twisting handle 315 of pusher 300 clockwise (see, e.g., FIG. 58), until circumferential groove 470 is secured to bone plate 800 (see, e.g., FIG. 62 and FIG. 54). Handle 215 of insertion tool 200 is then rotated clockwise causing a torque to be applied to distal region 151 of device 100 which in turn compresses device 100 longitudinally and radially expands expandable body 130 (see, e.g., FIG. 63). Thereafter, insertion tool 200 is disengaged from device 100 by rotating counterclockwise and separated from device 100 and connector 400 (see, e.g., FIG. 64). Biomaterial dispenser 500 including a syringe filled with a bone cement is connected to proximal region 410 of connector 400 via Luer lock threads 415 (see, e.g., FIG. 65). A 5-10 ml volume of the bone cement is injected into interior channel 190 of device 100 and the bone cement flows into the surrounding bone tissue (see, e.g., FIG. 66). Then biomaterial dispenser 500 and connector 400 are removed from device 100 (see, e.g., FIG. 67). Screw 600 is then inserted into interior channel 190 of device 100 and fastened to the bone tissue beyond distal region 151 of device 100 (see, e.g., FIG. 68 and FIG. 69). Screw 600 is fastened until screw head 675 presses against bone plate 800 (see, e.g., FIG. 13D). The process is repeated for each of device 100 that is to be inserted into bone and the surgery proceeds to completion. The bone cement, delivered using device 100 as herein described, provides effective fracture healing due to the uniform distribution of biomaterial 550 in the bone tissue.

Example 3. Bone Tissue Regeneration Using the Device

The devices, systems, and methods herein described may be used for bone tissue regeneration, including device 100, 1100, 1200, or 1300.

For example, device 100 may be implanted using system 1000 and methods herein described in order to regenerate a bone tissue by driving bone growth and tissue restoration. A surgeon treats a patient in need of bone tissue regeneration, using device 100 and system 1000 as herein described. The bone site is first prepared for implantation of four devices as herein described. Four holes are drilled into the bone site. Four devices are prepared to be implanted into four of bone hole 875. Each device has proximal region 101, distal region 151, and expandable body 130 disposed therebetween. Furthermore, device 100 has internal threads at distal region 151, expandable body 130 with six slits, and proximal region 101 with six wings 105. The system also includes washer 700 (see, e.g., FIGS. 15-17, FIG. 19B, and FIG. 19D), connector 400 (see, e.g., FIGS. 47-48), and insertion tool 200 (see, e.g., FIG. 55) connected to pusher 300 (see, e.g., FIGS. 18A and FIGS. 56-57). Each of the four devices is implanted into one of bone hole 875 according to the following sequence. First, insertion tool 200 is connected to a first of device 100 to be implanted. Insertion tool 200 is connected to device 100 by first inserting distal region 240 through the channel of connector 400 and then by threading external threads 250 of insertion tool 200 into internal threads 160 of device 100 (see, e.g., FIGS. 51A-51B and FIG. 60). Device 100 is then completely inserted into bone hole 875 (see, e.g., FIG. 61). Connector 400 is then pushed into internal channel 190 of device 100 with pusher 300, by twisting pusher 300 handle clockwise (see, e.g., FIG. 58). If a bone plate is used, connector 400 may include a circumferential groove 470. Circumferential groove 470 of connector 400 can be used to secure connector 400 to bone plate 800 (see, e.g., FIG. 62 and FIG. 54). Insertion tool 200 handle is then rotated clockwise causing a torque to be applied to distal region 151 of device 100 which in turn compresses device 100 longitudinally and radially expands expandable body 130 (see, e.g., FIG. 63). Then insertion tool 200 is disengaged from device 100 by rotating counterclockwise and pulled out from the channel of device 100 and connector 400 (see, e.g., FIG. 64). Biomaterial dispenser 500, which may include, e.g., a syringe filled with an osteogenic composition, is connected to proximal region of connector 400 via Luer lock threads 415 (see, e.g., FIG. 65). A 5 ml volume of the osteogenic composition is injected into interior channel 190 of device 100 and flows into the surrounding bone tissue through expandable body 130 (see, e.g., FIG. 66). Thereafter, biomaterial dispenser 500 and connector 400 are removed from device 100 (see, e.g., FIG. 67). Washer 700 and screw 600 are then inserted into interior channel 190 of device 100 (see, e.g., FIGS. 19A-19D). Screw 600 is fastened to the bone tissue beyond distal region 151 of device 100. Screw 600 is fastened until screw head 675 presses against washer 700 (see, e.g., FIG. 19D). The process is repeated for each of the devices until the surgery is completed. The osteogenic composition, delivered using device 100 herein described, provides effective bone tissue growth and tissue restoration due to the uniform distribution of the osteogenic composition in the bone tissue.

Example 4. Extraction of the Device

A surgeon can use extraction tool 900 (see, e.g., FIGS. 31A-31B) to remove device 100, 1100, 1200, or 1300 from one of bone hole 875, if necessary, including after healing of a fracture in the bone is complete.

For example, as a first step, screw 600 is unfastened, with a standard screwdriver, from the cortical bone distally located from distal region 151 of device 100. Then, the surgeon drills out the interior diameter of device 100 to allow clearance for extraction tool 900. The surgeon then inserts the distal region of extraction tool 900 into internal channel 190 of device 100 until the pair of nubs 935 reach distal region 151 of device 100 (see, e.g., FIG. 34A-34B). The surgeon joins the two members of extraction tool 900 to engage the pair of nubs 935 with a pair of notches 183 in distal region 151 of device 100 (see, e.g., FIGS. 35-39). Maintaining the two members joined, the surgeon twists extraction tool 900 to unfasten device 100 from the bone. If necessary, expandable body 130 of device 100 can be retracted or collapsed by twisting device 100 counterclockwise. Alternatively, expandable body 130 is readily collapsible and can be deformed when the force of extraction is applied by extraction tool 900 on device 100.

If desired, the bone defect can be re-filled with a biocompatible substance or a different implant, or the defect may be repaired by inserting a different one of device 100 into bone hole 875 and by, e.g., following the procedure set forth in, e.g., Example 3.

Example 5. Use of Device in Spinal Surgery

A surgeon can use device 100, 1100, 1200, or 1300 to treat a subject in need of spinal fracture repair. The bone site is first prepared for implantation of device 100, 1100, 1200, or 1300. If desired more than one of device 100, 1100, 1200, or 1300, such two of device 100, may be implanted, as is herein described.

Two holes are first drilled into the bone site. Two of device 100 are prepared to be implanted, one of device 100 per bone hole. Each of device 100 has proximal region 101, distal region 151, and expandable body 130 disposed therebetween. Furthermore, device 100 has internal threads at distal region 151, expandable body 130 with six slits, and proximal region 101 with six wings 105. Device 100 may be inserted into the bone using, e.g., system 1000, which may also include connector 400 (see, e.g., FIGS. 47-48), insertion tool 200 (see, e.g., FIG. 55), and pusher 300 (see, e.g., FIGS. 18A and FIGS. 56-57). Each of device 100 is implanted into one of bone hole 875 according to the following sequence. First, insertion tool 200 is connected to a first of device 100 to be implanted. Insertion tool 200 is connected to device 100 by first inserting distal region 240 through the channel of connector 400 and then by threading external threads 250 of insertion tool 200 into internal threads 160 of device 100 (see, e.g., FIGS. 51A-51B and FIG. 60). Device 100 is then completely inserted into bone hole 875 (see, e.g., FIG. 61). Connector 400 is then pushed into internal channel 190 of device 100 with pusher 300, by twisting pusher 300 handle clockwise (see, e.g., FIG. 58). If a bone plate is used, connector 400 may include a circumferential groove 470. Circumferential groove 470 of connector 400 can be used to secure connector 400 to bone plate 800 (see, e.g., FIG. 62 and FIG. 54). Insertion tool 200 handle is then rotated clockwise causing a torque to be applied to distal region 151 of device 100 which in turn compresses device 100 longitudinally and radially expands expandable body 130 (see, e.g., FIG. 63). Then insertion tool 200 is disengaged from device 100 by rotating counterclockwise and pulled out from the channel of device 100 and connector 400 (see, e.g., FIG. 64). Biomaterial dispenser 500, which may include, e.g., a syringe filled with an osteogenic composition, is connected to proximal region of connector 400 via Luer lock threads 415 (see, e.g., FIG. 65). A 2-7.5 ml volume of an osteogenic composition is injected into interior channel 190 of device 100 and flows into the surrounding bone tissue through expandable body 130 (see, e.g., FIG. 66). Thereafter, biomaterial dispenser 500 and connector 400 are removed from device 100 (see, e.g., FIG. 67). Washer 700 (see, e.g., FIGS. 15-17, FIG. 19B, and FIG. 19D) and screw 600 are then inserted into interior channel 190 of device 100 (see, e.g., FIGS. 19A-19D). Screw 600 does not fasten to the bone tissue beyond distal region 151 of device 100. Screw 600 is fastened until screw head 675 presses against washer 700 (see, e.g., FIG. 19D). The process is repeated for each of device 100 to be inserted into bone until the surgery is completed. The osteogenic composition, delivered using device 100 herein described, provides effective bone tissue growth and tissue restoration due to the uniform distribution of the osteogenic composition in the bone tissue.

Example 6. Use of Device in Bone Augmentation

A surgeon can treat a subject in need of bone augmentation (e.g., to improve the quality of bone tissue, in particular, bone tissue surrounding an insertion site of device 100, 1100, 1200, or 1300).

For example, the subject may have a periarticular fracture (e.g., tibial plateau with a defect) in need of bone augmentation. The bone site is first prepared for implantation of three of device 100 as herein described. Three holes are predrilled into the bone near the subarticular defect. Three of device 100 are prepared to be implanted, one of device 100 to be placed into each bone hole. Each of device 100 has proximal region 101, distal region 151, and expandable body 130 disposed therebetween. Furthermore, device 100 has internal threads at distal region 151, expandable body 130 with three slits, and proximal region 101 with three wings 105.

Device 100 can be inserted into the bone using, e.g., system 1000 described herein. System 1000 may include connector 400 (see, e.g., FIGS. 47-48), insertion tool 200 (see, e.g., FIG. 55), and pusher 300 (see, e.g., FIGS. 18A and FIGS. 56-57). Each of device 100 is implanted into its respective bone hole according to the following sequence. First, insertion tool 200 is connected to a first of device 100 to be implanted. Insertion tool 200 is connected to device 100 by first inserting distal region 240 through the channel of connector 400 and then by threading external threads 250 of insertion tool 200 into internal threads 160 of device 100 (see, e.g., FIGS. 51A-51B and FIG. 60). Device 100 is then completely inserted into bone hole 875 (see, e.g., FIG. 61). Connector 400 is then pushed into internal channel 190 of device 100 with pusher 300, by twisting pusher 300 handle clockwise (see, e.g., FIG. 58). If a bone plate is used, connector 400 may include a circumferential groove 470. Circumferential groove 470 of connector 400 can be used to secure connector 400 to bone plate 800 (see, e.g., FIG. 62 and FIG. 54). Insertion tool 200 handle is then rotated clockwise causing a torque to be applied to distal region 151 of device 100 which in turn compresses device 100 longitudinally and radially expands expandable body 130 (see, e.g., FIG. 63). Then insertion tool 200 is disengaged from device 100 by rotating counterclockwise and pulled out from the channel of device 100 and connector 400 (see, e.g., FIG. 64). Biomaterial dispenser 500, which may include, e.g., a syringe filled with an osteogenic composition, is connected to proximal region of connector 400 via Luer lock threads 415 (see, e.g., FIG. 65). A 5-10 ml volume of the osteogenic composition is injected into interior channel 190 of device 100 and flows into the surrounding bone tissue through expandable body 130 (see, e.g., FIG. 66). Thereafter, biomaterial dispenser 500 and connector 400 are removed from device 100 (see, e.g., FIG. 67).

Next, washer 700 (see, e.g., FIGS. 15-17, FIG. 19B, and FIG. 19D) and screw 600 can be inserted into interior channel 190 of device 100 (see, e.g., FIGS. 19A-19D). Screw 600 can be fastened to the unfractured bone tissue beyond distal region 151 of device 100. Screw 600 can be fastened until screw head 675 presses against washer 700 (see, e.g., FIG. 19D), which promotes compression of the bone tissue.

The process is repeated for each of device 100 to be inserted until the subarticular defect is filled with biomaterial and the fracture fragment is fixed to the opposite unfractured bone cortex. The osteogenic composition, delivered using device 100 herein described, provides effective bone tissue growth and tissue restoration due to the uniform distribution of the osteogenic composition in the bone tissue.

OTHER EMBODIMENTS

All publications, patents, and patent applications mentioned in the above specification are hereby incorporated by reference. Various modifications and variations of the described method and system of the invention will be apparent to those skilled in the art without departing from the scope and spirit of the invention. Although the invention has been described in connection with specific embodiments, it should be understood that the invention as claimed should not be unduly limited to such specific embodiments. Indeed, various modifications of the described modes for carrying out the invention that are obvious to those skilled in the art are intended to be within the scope of the invention. This application is intended to cover any variations, uses, or adaptations of the invention following, in general, the principles of the invention and including such departures from the present disclosure come within known customary practice within the art to which the invention pertains and may be applied to the essential features herein before set forth.

Other embodiments are within the claims.

The invention claimed is:

1. A device comprising a unitary body comprising from a proximal end to a distal end: a proximal region, a central region, and a distal region, wherein the central region joins the proximal region to the distal region, and wherein:
a) the device comprises an internal channel extending longitudinally through the proximal, central, and distal regions;
b) the proximal region comprises an opening to the internal channel and a plurality of circumferentially disposed and compressible wings;
c) the central region comprises an internal or external thread and a compressible body configured to radially compress during insertion and to return to an uncompressed state upon removal of the radial pressure; and
d) the distal region comprises an opening to the internal channel and internal threads.

2. The device of claim 1, wherein:
i) the proximal region comprises an inner diameter of from about 1 mm to about 20 mm and an outer diameter of from about 4 mm to about 25 mm;
ii) the central region comprises an inner diameter of from 1 mm to about 20 mm and an outer diameter of from about 1.25 mm to about 25 mm;

iii) the distal region comprises an inner diameter of from 1 mm to about 20 mm and an outer diameter of from about 4 mm to about 25 mm; or
iv) wherein the proximal region, the central region, and the distal region comprise an inner diameter of from 1 mm to about 20 mm and an outer diameter of from about 1.25 mm to about 25 mm.

3. The device of claim 2, wherein the outer diameter of the proximal and/or distal regions is smaller than the outer diameter of the central region.

4. The device of claim 1, wherein the device comprises:
A) a length of from about 9 mm to about 110 mm;
B) 1 to 70 longitudinal grooves; and/or
C) a plurality of longitudinal segments.

5. The device of claim 1, wherein the internal or external thread of the central region is broken by a slit.

6. The device of claim 5, wherein the slit is a helical slit, a segmented slit, a longitudinal slit, or a circumferential slit.

7. The device of claim 4, wherein for B), the longitudinal grooves:
a) comprise a depth of from about 0.15 mm to about 2.5 mm; and/or
b) extend from a proximal end of the central region to a distal end of the central region.

8. The device of claim 4, wherein for C):
a) the proximal region, central region, and/or distal region comprises the plurality of segments;
b) the plurality of segments extends from the proximal end, through the central region, to the distal end;
c) the plurality of segments comprises a polygonal, circular, triangular, elliptical, cylindrical, or amorphous shape;
d) the device comprises from 2 to 10 segments;
e) each of the segments are the same size;
f) each of the segments is separated by at least one opening, wherein the opening has a maximum width of about 0.1 mm to about 50 mm;
g) each of the segments comprises a length of about 9 mm to about 110 mm; or
h) each of the segments comprises a width of about 0.1 mm to about 50 mm.

9. The device of claim 8:
i) wherein for a), the plurality of segments comprises longitudinal segments; or
ii) wherein for c), the plurality of segments comprises a rectangular shape.

10. The device of claim 1, wherein the proximal region comprises:
A) a length of from about 2 mm to about 30 mm;
B) a wall thickness of from about 0.15 mm to about 3.0 mm;
C) an internal or external protrusion; or
D) an internal or external thread.

11. The device of claim 10, wherein for B), the wall thickness of the proximal region is from about 0.3 mm to about 0.6 mm.

12. The device of claim 10, wherein for C):
a) the internal or external protrusion comprises one or more of a bump, a spike, a tab, a fin, a ridge, or a raised surface;
b) the internal or external protrusion extends from a proximal end to a distal end of the proximal region;
c) a plurality of internal or external protrusions extends from a proximal end to a distal end of the proximal region; or
d) the device comprises from 1 to 500 internal or external protrusions.

13. The device of claim 10, wherein for D), the internal or external thread:

a) comprises a thread pitch of from about 0.25 mm to about 2.5 mm;

b) is formed from protrusions, grooves, waves, or a mesh;

c) comprises a continuous thread or non-continuous thread; or d) is broken by a slit.

14. The device of claim 13:

i) wherein for b), the protrusions, grooves, or waves are at from about 1 to about 180 points per 360°;

ii) wherein for c), the non-continuous thread comprises a gap, wherein the gap has a length from about 0.5 mm to about 30 mm; or iii) wherein for d), the slit is a helical slit, a segmented slit, a longitudinal slit, or a circumferential slit.

15. The device of claim 1, wherein the central region comprises:

A) a length of from about 5 mm to about 110 mm;

B) a wall thickness of from about 0.15 mm to about 2 mm;

C) an internal or external protrusion; or

D) a first section comprising the compressible body, wherein the central region further comprises a second section comprising a plurality of openings.

16. The device of claim 15, wherein for B), the wall thickness of the central region is from about 0.8 mm to about 0.9 mm.

17. The device of claim 15, wherein for C):

a) the internal or external protrusion of the central region comprises a bump, a spike, a tab, a fin, a ridge, or a raised surface;

b) the internal or external protrusion extends from a proximal end to a distal end of the central region;

c) a plurality of internal or external protrusions extends from a proximal end to a distal end of the central region: or d) the device comprises from 1 to 500 internal or external protrusions.

18. The device of claim 1, wherein the internal or external thread of the central region:

a) comprises a thread pitch of from about 0.25 mm to about 2.5 mm;

b) is formed from protrusions, grooves, waves, or a mesh; or c) comprises a continuous thread or non-continuous thread.

19. The device of claim 18:

i) wherein for b), the protrusions, grooves, or waves are at from about 1 to about 180 points per 360°; or ii) wherein for c), the non-continuous thread comprises a gap, wherein the gap has a length from about 0.5 mm to about 30 mm.

20. The device of claim 15, wherein for D):

a) the central region comprises from a proximal end to a distal end: the first section and the second section;

b) the first section comprises a length of from about 5 mm to about 100 mm; or c) the second section comprises a length of from about 5 mm to about 100 mm.

21. The device of claim 1, wherein the distal region comprises:

A) a length of from about 2 mm to about 30 mm;

B) a wall thickness of from about 0.15 mm to about 2.5 mm;

C) a distal end;

D) from 2 to 4 notches and/or elongated slits;

E) from 1 to 500 openings;

F) an internal or external protrusion;

G) an external thread; or

H) a plurality of bendable tips disposed at the proximal end and/or the distal end.

22. The device of claim 21:

a) wherein for B), the wall thickness of the distal region is from about 0.4 mm to about 0.5 mm;

b) wherein for D), the slits comprise a helical slit, a segmented slit, a longitudinal slit, or a circumferential slit; or c) wherein for E), the diameter of each opening is from about 0.01 mm to about 5 mm.

23. The device of claim 21, wherein for C), the distal end of the distal region comprises:

a) a blunt and/or tapered edge; or b) from 2 to 5 milling flutes, wherein optionally the distal region comprises 3 milling flutes.

24. The device of claim 21, wherein for F):

a) the internal or external protrusion comprises one or more of a bump, a spike, a tab, a fin, a ridge, or a raised surface;

b) the internal or external protrusion extends from a proximal end to a distal end of the distal region;

c) a plurality of internal or external protrusions extends from a proximal end to a distal end of the distal region; or d) the device comprises from 1 to 500 internal or external protrusions.

25. The device of claim 21, wherein for G), the external thread:

a) comprises a thread pitch of from about 0.25 mm to about 2.5 mm;

b) is formed from protrusions, grooves, waves, or a mesh;

c) comprises a continuous thread or non-continuous thread; or d) is broken by a slit.

26. The device of claim 25:

i) wherein for b), the protrusions, grooves, or waves are at from about 1 to about 180 points per 360°;

ii) wherein for c), the non-continuous thread comprises a gap, wherein the gap has a length from about 0.5 mm to about 30 mm; or iii) wherein for d), the slit is a helical slit, a segmented slit, a longitudinal slit, or a circumferential slit.

27. The device of claim 1, wherein each of the wings comprises:

A) a rectangular, round, elliptical, triangular, jagged, or parabolic shape, comprising a length and a width;

B) a proximal end disconnected from the proximal region and configured to protrude outwardly from the proximal region; and C) a distal end connected to the proximal region and configured to pivot the proximal end of the wing away from the proximal region.

28. The device of claim 27:

a) wherein each of the wings comprises a length of from about 5 mm to about 20 mm and/or a width of from 1 mm to 15 mm; and/or b) wherein the device comprises 3 to 20 wings.

29. The device of claim 28, wherein for b), the device comprises 4 to 8 wings.

30. The device of claim 29, wherein the device comprises 8 wings.

31. The device of claim 27, wherein for B), the proximal end of each of the wings:

a) protrudes outwardly from the proximal region at an angle of from about 2° to 10°, and b) is configured to reversibly deflect towards the proximal region to substantially eliminate the outward protrusion of the proximal end upon compression.

32. The device of claim 1, wherein the compressible body comprises a plurality of openings.

33. The device of claim 32, wherein the plurality of openings comprises slits or perforations.

34. The device of claim 33, wherein the plurality of openings comprises helical slits, segmented slits, longitudinal slits, circumferential slits, circular perforations, elliptical perforations, triangular perforations, polygonal perforations, or amorphous perforations.

35. The device of claim 32, wherein:

A) the openings extend into the proximal region and/or the distal region;

B) the device comprises 2 to 500 openings;

C) the openings comprise a width of from about 0.01 mm to about 20 mm and a length of from about 0.01 mm to about 20 mm;

D) the openings comprise perforations and wherein the perforations comprise a circular, elliptical, triangular, polygonal, or amorphous shape comprising a diameter of from about 0.1 mm to about 5 mm;

E) the openings comprise perforations, wherein a plurality of the perforations are connected by at least one slit; or F) the openings comprise perforations, wherein the perforations form a mesh or mesh-like structure.

36. The device of claim 35, wherein for E):

a) the slit is a helical slit, a segmented slit, a longitudinal slit, or a circumferential slit; or b) the slit connects 2 to 100 perforations.

37. The device of claim 35, wherein for F), the mesh or mesh-like structure:

a) is woven, perforated, crimped, welded, molded, sintered, or 3D-printed;

b) comprises a percent porosity from about 5% to about 90%; or c) comprises a wire gauge from 5 to 50.

38. The device of claim 1, wherein the internal threads of the distal region have a thread pitch of from about 0.25 mm to about 2.5 mm.

39. The device of claim 1, wherein the device is made from or comprises a material selected from the group consisting of stainless steel or an alloy thereof, titanium or an alloy thereof, magnesium or an alloy thereof, polyetheretherketone (PEEK), hydroxyapatite, tricalcium phosphate, tetracalcium phosphate, dicalcium phosphate, BIOGLASS® 45S5, ceramic composites, copper-based materials or composites, cobalt chrome, xenograft biomaterials, and combinations thereof.

40. The device of claim 1, wherein the proximal region, the central region, and the distal region are fabricated separately and combined to form the unitary body.

41. The device of claim 1, wherein:

A) the proximal region comprises:

a) a length of from about 5 mm to about 10 mm; and b) a wall thickness of from about 0.3 mm to about 0.5 mm;

c) an inner diameter of from about 1 mm to about 20 mm; and d) an outer diameter of from about 4 mm to about 25 mm;

B) the central region comprises:

a) a length of from about 14 mm to about 26 mm;

b) a wall thickness of from about 0.8 mm to about 0.9 mm;

c) an inner diameter of from about 1 mm to about 20 mm; and d) an outer diameter of from about 1.25 mm to about 25 mm; and C) the distal region comprises:

a) a length of from about 15 mm to about 30 mm;

b) a wall thickness of from about 0.4 mm to about 0.5 mm;

c) an inner diameter of from 1 mm to about 20 mm; and d) an outer diameter of from about 4 mm to about 25 mm.

42. The device of claim 41, wherein:

A) the proximal region further comprises:

e) a first plurality of openings, wherein each of the openings of the first plurality of openings comprises:

i) a width of from about 1.5 mm to about 2 mm; and ii) a length of from about 2 mm to about 5 mm;

f) a second plurality of openings, wherein each of the openings of the second plurality of openings comprises:

i) a width of from about 1 mm to about 1.5 mm; and ii) a length of from about 1 mm to about 1.5 mm;

B) the central region further comprises:

e) a plurality of slits, wherein each of the plurality of slits comprises a width of about 1.4 mm;

f) an internal thread, wherein the internal thread comprises a pitch of from about 1.2 mm to about 1.3 mm; and C) the distal region further comprises:

e) a third plurality of openings, wherein each of the openings of the third plurality of openings comprises:

i) a width of from about 1.5 mm to about 2 mm; and ii) a length of from about 2 mm to about 5 mm;

D) each of the wings of the plurality of circumferentially disposed and compressible wings comprises a width of about 1 mm to about 2 mm;

E) the outer diameter of the proximal region is from about 4 mm to about 5 mm, and wherein the inner diameter of the proximal region is from about 3 mm to about 4 mm;

F) the outer diameter of the central region is from about 5 mm to about 6 mm, and wherein the inner diameter of the central region is from about 3 mm to about 4 mm; and G) the outer diameter of the distal region is from about 4 mm to about 5 mm, and wherein the inner diameter of the distal region is from about 3 mm to about 4 mm.

43. The device of claim 42, wherein:

i) the length of the proximal region is about 7 mm;

ii) the length of the central region is from about 18 mm to about 19 mm; and iii) the length of the distal region is from about 19 mm to about 20 mm.

44. The device of claim 42, wherein:

i) the length of the proximal region is from about 8 mm to about 9 mm;

ii) the length of the central region is from about 21 mm to about 22 mm; and iii) the length of the distal region is from about 25 mm to about 26 mm.

45. A system comprising the device of claim 1, wherein the device is connected to a connector or pre-loaded in a cylinder.

46. A kit comprising the device of claim 1.

47. A method of bone repair comprising inserting the device of claim 1 into a bone and, optionally, introducing a biomaterial to the internal channel of the device, whereby hardening of the biomaterial secures the device in the bone.

* * * * *